United States Patent
McGrath, Jr. et al.

(10) Patent No.: US 11,606,966 B2
(45) Date of Patent: Mar. 21, 2023

(54) NUTRITIONAL FORMULA

(71) Applicant: Building Block Nutritionals, LLC, Charlottesville, VA (US)

(72) Inventors: James W. McGrath, Jr., Port Charlotte, FL (US); Paul B. Manning, Troy, VA (US); Eugene R. Scavola, Charlottesville, VA (US)

(73) Assignee: Building Block Nutritionals, LLC, Charlottesville, VA (US)

( * ) Notice: Subject to any disclaimer, the term of this patent is extended or adjusted under 35 U.S.C. 154(b) by 0 days.

(21) Appl. No.: 17/347,977

(22) Filed: Jun. 15, 2021

(65) Prior Publication Data

US 2021/0386107 A1    Dec. 16, 2021

Related U.S. Application Data

(60) Provisional application No. 63/039,316, filed on Jun. 15, 2020.

(51) Int. Cl.

| | | |
|---|---|---|
| A23L 33/00 | (2016.01) |
| A61K 38/40 | (2006.01) |
| A61K 47/14 | (2017.01) |
| A61K 47/26 | (2006.01) |
| A61K 47/12 | (2006.01) |
| A61K 9/00 | (2006.01) |
| A61P 3/02 | (2006.01) |
| A23L 33/19 | (2016.01) |
| A23L 33/12 | (2016.01) |
| A23L 33/125 | (2016.01) |
| A23L 33/155 | (2016.01) |
| A23L 33/16 | (2016.01) |
| A23L 2/395 | (2006.01) |
| A23L 2/58 | (2006.01) |
| A23L 2/60 | (2006.01) |
| A23L 2/66 | (2006.01) |
| A61K 38/38 | (2006.01) |

(52) U.S. Cl.
CPC .............. *A23L 33/40* (2016.08); *A23L 2/395* (2013.01); *A23L 2/58* (2013.01); *A23L 2/60* (2013.01); *A23L 2/66* (2013.01); *A23L 33/12* (2016.08); *A23L 33/125* (2016.08); *A23L 33/155* (2016.08); *A23L 33/16* (2016.08); *A23L 33/19* (2016.08); *A61K 9/0095* (2013.01); *A61K 38/38* (2013.01); *A61K 38/40* (2013.01); *A61K 47/12* (2013.01); *A61K 47/14* (2013.01); *A61K 47/26* (2013.01); *A61P 3/02* (2018.01); *A23V 2002/00* (2013.01)

(58) Field of Classification Search
None
See application file for complete search history.

(56) References Cited

U.S. PATENT DOCUMENTS

| | | |
|---|---|---|
| 9,181,325 B2 | 11/2015 | Bertelsen et al. |
| 2006/0286252 A1 | 12/2006 | Rangavajla et al. |
| 2012/0171328 A1 | 7/2012 | Banavara et al. |
| 2014/0037818 A1 | 2/2014 | Sorensen et al. |
| 2015/0189905 A1 | 7/2015 | Banavara et al. |
| 2015/0237902 A1 | 8/2015 | Rosado Loria et al. |
| 2016/0015068 A1 | 1/2016 | Ao et al. |
| 2019/0247469 A1 | 8/2019 | McGrath et al. |

FOREIGN PATENT DOCUMENTS

| | | |
|---|---|---|
| CN | 102283289 A | 12/2011 |
| CN | 102422900 A | 4/2012 |
| CN | 104489101 A | 4/2015 |
| CN | 105638908 A | 6/2016 |
| EP | 2208424 A | 7/2010 |
| JP | S53-079060 A | 7/1978 |
| JP | S56-36494 A | 4/1981 |
| JP | H05-236883 A | 9/1993 |
| JP | H05-268879 A | 10/1993 |
| JP | H07-508417 A | 9/1995 |
| JP | 2004-519229 A | 7/2004 |
| JP | 2007-505610 A | 3/2007 |
| JP | 2014-508157 A | 4/2014 |

(Continued)

OTHER PUBLICATIONS

Good Start Gentle (https://medical.gerber.com/products/formulas/good-start-gentle 2014).*
International Search Report and Written Opinion for Application No. PCT/US2021/037403, dated Sep. 15, 2021.
Agostoni et al., Neurodevelopmental quotient of healthy term infants at 4 months and feeding practice: the role of long-chain polyunsaturated fatty acids. Pediatr Res. Aug. 1995;38(2):262-6. doi: 10.1203/00006450-199508000-00021.
Auestad et al., Visual acuity, erythrocyte fatty acid composition, and growth in term infants fed formulas with long chain polyunsaturated fatty acids for one year. Ross Pediatric Lipid Study. PediatrRes. Jan. 1997;41(1):1-10. doi: 10.1203/00006450-199701000-00001.
Ballard et al., Human milk composition: nutrients and bioactive factors. Pediatr Clin North Am. Feb. 2013;60(1):49-74. doi: 10.1016/j.pcl.2012.10.002. Author Manuscript. 24 pages.

(Continued)

*Primary Examiner* — Julie Ha
*Assistant Examiner* — Tara L Martinez
(74) *Attorney, Agent, or Firm* — Wolf, Greenfield & Sacks, P.C.

(57) ABSTRACT

The present disclosure provides a nutritional formula comprising alpha-lactalbumin enriched whey protein concentrate; lactoferrin; oleic acid-palmitic acid-oleic acid triglyceride; lactose; lutein; docosahexanoic acid; arachidonic acid; galactooligosaccharides; and fructooligosaccharides. The provided nutritional formulas may be useful in providing nutrition and/or promoting postnatal development of a subject (e.g., promoting postnatal development of an infant's gastrointestinal tract, promoting proper gastrointestinal function, nutrient absorption, proper immune system development, etc.). Also provided are powder forms, reconstituted formulas, kits, methods, and uses that include or involve a nutritional formula described herein.

28 Claims, 5 Drawing Sheets

(56) References Cited

FOREIGN PATENT DOCUMENTS

| RU | 2013125292 A | 12/2014 |
|---|---|---|
| RU | 2575610 C2 | 2/2016 |
| WO | WO 2011/051557 A1 | 5/2011 |
| WO | WO 2012/092157 A2 | 7/2012 |
| WO | WO 2015/154265 A1 | 10/2015 |
| WO | WO 2016/010664 A1 | 1/2016 |
| WO | WO 2017/102710 A1 | 6/2017 |
| WO | WO 2018/009647 A1 | 1/2018 |

OTHER PUBLICATIONS

Birch et al., A randomized controlled trial of early dietary supply of long-chain polyunsaturated fatty acids and mental development in term infants. Dev Med Child Neurol. Mar. 2000;42(3):174-81. doi: 10.1017/s0012162200000311.

Bode, Human milk oligosaccharides: every baby needs a sugar mama. Glycobiology. Sep. 2012;22(9):1147-62. doi: 10.1093/glycob/cws074. Epub Apr. 18, 2012.

Brenna et al., Docosahexaenoic and arachidonic acid concentrations in human breast milk worldwide. Am J Clin Nutr. Jun. 2007;85(6):1457-64. doi: 10.1093/ajcn/85.6.1457.

Capeding et al., Lutein-fortified infant formula fed to healthy term infants: evaluation of growth effects and safety. Nutr J. May 21, 2010;9:22. doi: 10.1186/1475-2891-9-22.

Cheng et al., actors affecting the lactoferrin concentration in bovine milk. J Dairy Sci. Mar. 2008;91(3):970-6. doi: 10.3168/jds.2007-0689.

Clandinin et al., Extrauterine fatty acid accretion in infant brain: implications for fatty acid requirements. Early Hum Dev. Jun. 1980;4(2):131-8. doi: 10.1016/0378-3782(80)90016-x.

Clandinin et al., Intrauterine fatty acid accretion rates in human brain: implications for fatty acid requirements. Early Hum Dev. Jun. 1980;4(2):121-9. doi: 10.1016/0378-3782(80)90015-8.

Coppa et al., Oligosaccharides in human milk during different phases of lactation. Acta Paediatr Suppl. Aug. 1999;88(430):89-94. doi: 10.1111/j.1651-2227.1999.tb01307.x.

Dupont et al., Alpha-lactalbumin-enriched and probiotic-supplemented infant formula in infants with colic: growth and gastrointestinal tolerance. Eur J Clin Nutr. Jul. 2010;64(7):765-7. doi: 10.1038/ejcn.2010.81. Epub Jun. 2, 2010.

Innis et al., Evidence that palmitic acid is absorbed as sn-2 monoacylglycerol from human milk by breast-fed infants. Lipids. Aug. 1994;29(8):541-5. doi: 10.1007/BF02536625.

Innis, Dietary triacylglycerol structure and its role in infant nutrition. Adv Nutr. May 2011;2(3):275-83. doi: 10.3945/an.111.000448. Epub Apr. 30, 2011.

Johnston et al., Growth and tolerance of formula with lactoferrin in infants through one year of age: double-blind, randomized, controlled trial. BMC Pediatr. Nov. 7, 2015;15:173. doi: 10.1186/S12887-015-0488-3.

Kennedy et al., Double-blind, randomized trial of a synthetic triacylglycerol in formula-fed term infants: effects on stool biochemistry, stool characteristics, and bone mineralization. Am J Clin Nutr. Nov. 1999;70(5):920-7. doi: 10.1093/ajcn/70.5.920.

King, Jr, et al., A double-blind, placebo-controlled, pilot study of bovine lactoferrin supplementation in bottle-fed infants. J Pediatr Gastroenterol Nutr. Feb. 2007;44(2):245-51. doi: 10.1097/01.mpg.0000243435.54958.68.

Krinsky et al., Carotenoid actions and their relation to health and disease. Mol Aspects Med. Dec. 2005;26(6):459-516. doi: 10.1016/j.mam.2005.10.001. Epub Nov. 23, 2005.

Landrum et al., Lutein, zeaxanthin, and the macular pigment. Arch Biochem Biophys. Jan. 1, 2001;385(1):28-40. doi: 10.1006/abbi.2000.2171.

Lien et al., Growth and safety in term infants fed reduced-protein formula with added bovine alpha-lactalbumin. J Pediatr Gastroenterol Nutr. Feb. 2004;38(2):170-6. doi: 10.1097/00005176-200402000-00013.

Lien, The role of fatty acid composition and positional distribution in fat absorption in infants. J Pediatr. Nov. 1994;125(5 Pt 2):S62-8. doi: 10.1016/s0022-3476(06)80738-9.

Litmanovitz et al., Reduced crying in term infants fed high beta-palmitate formula: a double-blind randomized clinical trial. BMC Pediatr. Jun. 19, 2014;14:152. doi: 10.1186/1471-2431-14-152.

Lönnderal, Infant formula and infant nutrition: bioactive proteins of human milk and implications for composition of infant formulas. Am J Clin Nutr. Mar. 2014;99(3):712S-7S. doi: 10.3945/ajcn.113.071993. Epub Jan. 22, 2014.

Lönnerdal, Digestibility and absorption of protein in infants. In: Protein Metabolism During Infancy. Protein Metabol During Infancy. Raiha et al. Eds. 1994. pp. 53-65.

Mitchell et al., Protein efficiency ratios and net protein ratios of selected protein foods. Plant Foods Hum Nutr. 1989;39(1):53-8. doi: 10.1007/BF01092401.

Moro et al., Dosage-related bifidogenic effects of galacto- and fructooligosaccharides in formula-fed term infants. J Pediatr Gastroenterol Nutr. Mar. 2002;34(3):291-5. doi: 10.1097/00005176-200203000-00014.

Neuringer et al., Biochemical and functional effects of prenatal and postnatal omega 3 fatty acid deficiency on retina and brain in rhesus monkeys. Proc Natl Acad Sci U S A. Jun. 1986;83(11):4021-5. doi: 10.1073/pnas.83.11.4021.

O'Connor et al., Growth and development in preterm infants fed long-chain polyunsaturated fatty acids: a prospective, randomized controlled trial. Pediatrics. Aug. 2001;108(2):359-71. doi: 10.1542/peds.108.2.359.

Ochoa et al., Effect of lactoferrin on enteric pathogens. Biochimie. Jan. 2009;91(1):30-4. doi: 10.1016/j.biochi.2008.04.006. Epub Apr. 18, 2008.

Roberfroid, Prebiotics: the concept revisited. J Nutr. Mar. 2007;137(3 Suppl 2):830S-7S. doi: 10.1093/jn/137.3.830S.

Scalabrin et al., New prebiotic blend of polydextrose and galacto-oligosaccharides has a bifidogenic effect in young infants. J Pediatr Gastroenterol Nutr. Mar. 2012;54(3):343-52. doi: 10.1097/MPG.0b013e318237ed95.

Schack et al., Considerable variation in the concentration of osteopontin in human milk, bovine milk, and infant formulas. J Dairy Sci. Nov. 2009;92(11):5378-85. doi: 10.3168/jds.2009-2360.

Tadesse, The effect of continued feeding of physiological amounts of lactose on the level of intestinal lactase and other disaccharidase enzyme activities in the rat. Exp Physiol. Mar. 1990;75(2):231-8. doi: 10.1113/expphysiol.1990.sp003397.

Trabulsi et al., Effect of an α-lactalbumin-enriched infant formula with lower protein on growth. Eur J Clin Nutr. Feb. 2011;65(2):167-74. doi: 10.1038/ejcn.2010.236. Epub Nov. 10, 2010.

Yao et al., Effects of term infant formulas containing high sn-2 palmitate with and without oligofructose on stool composition, stool characteristics, and bifidogenicity. J Pediatr Gastroenterol Nutr. Oct. 2014;59(4):440-8. doi: 10.1097/MPG.0000000000000443.

Ziegler et al., Term infants fed formula supplemented with selected blends of prebiotics grow normally and have soft stools similar to those reported for breast-fed infants. J Pediatr Gastroenterol Nutr. Mar. 2007;44(3):359-64. doi: 10.1097/MPG.0b013e31802fca8c.

Partial Supplementary European Search Report, in connection with Application No. EP 17824875.3, dated Dec. 13, 2019.

Extended European Search Report, in connection with Application No. EP 17824875.3, dated Mar. 16, 2020.

International Search Report and Written Opinion, in connection with Application No. PCT/US2017/040879, dated Jan. 17, 2019.

International Preliminary Report on Patentability, in connection with Application No. PCT/US2017/040879, dated Sep. 28, 2017.

[No Author Listed] Database GNPD: Accession No. 1480298. Baby Milk Stage 1. Feb. 9, 2011. Retrieved from https://www.gnpd.com. 4 pages.

[No Author Listed] Database GNPD: Accession No. 2170047. Baby Formula Kit. Sep. 13, 2013. Retrieved from https://www.gnpd.com. 7 pages.

[No Author Listed] Database WPI Week 201539. Thomson Scientific. AN 2015-342709. CN 104 489 101 A (Ausnutria Dairy China Co LTD). Apr. 8, 2015. 2 pages.

(56) References Cited

OTHER PUBLICATIONS

[No Author Listed] Database WPI Week 201670. Thomson Scientific. AN 2016-38070M. CN 105 638 908 A (Univ Northeast Agricultural). Jun. 8, 2016. 2 pages.

Gopal et al., Oligosaccharides and glycoconjugates in bovine milk and colostrum. *Br J Nutr*. 2000;84 Suppl 1:S69-S74. doi:10.1017/s0007114500002270.

Moreau et al., A Comparison of the Levels of Lutein and Zeaxanthin in Corn Germ Oil, Corn Fiber Oil and Corn Kernel Oil. *J Am Oil Chem Soc*. Oct. 9, 2007;84:1039-44. doi: 10.1007/sl 1749-007-1137-2.

O'Connor, N.R., Infant formula. *Am Fam Physician*. Apr. 1, 2009;79(7):565-70.

U.S. Appl. No. 16/315,132, filed Jan. 3, 2019, McGrath et al.

EP 17824875.3, Dec. 13, 2019, Partial Supplementary European Search Report.

EP 17824875.3, Mar. 16, 2020, Extended European Search Report.

PCT/US2017/040879, Sep. 28, 2017, International Serach Report and Written Opinion.

PCT/US2017/040879, Jan. 17, 2019, International Preliminary Report on Patentability.

Raninen et al., Dietary fiber type reflects physiological functionality: comparison of grain fiber, inulin, and polydextrose. Nutr Rev. Jan. 2011;69(1):9-21. doi: 10.1111/j.1753-4887.2010.00358.x.

\* cited by examiner

NUTRITIONAL FORMULA

RELATED APPLICATIONS

This application claims priority under 35 U.S.C. § 119(e) to U.S. Provisional Application, U.S. Ser. No. 63/039,316, filed Jun. 15, 2020, which is incorporated herein by reference.

BACKGROUND OF THE INVENTION

The focal point of infant nutrition is the developing gastrointestinal tract and its response to the infant's feeding. The tolerance of the infant formula along with the postnatal development of gastrointestinal functions, nutrient absorption, immune system development, gut epithelia interactions, and micro flora maintenance during digestion provide for the healthy development of the infant. Sufficient intake of protein and of essential amino acids is important for normal growth of infants. The consumption of inadequate amounts of even a single essential amino acid may produce less desirable effects with regard to infant growth. Thus, the presence of an appropriate amount of protein and of essential amino acids in a bioavailable matrix is important in the development of new or revised infant formulas. Triglycerides are an important source of lipids in infant formulas and provide approximately 50% of calories. Triglycerides consist of a glycerol backbone with a fatty acid esterified at each of the three glycerol —OH groups. The positions of the fatty acids on the glycerol backbone are designated as SN-1, SN-2, and SN-3. The outer fatty acids (positions SN-1 and SN-3) are readily hydrolyzed by the pancreatic lipase-colipase enzyme system resulting in two free fatty acids and an SN-2 monoglyceride. SN-2 monoglycerides are well absorbed, while the absorption of free fatty acids is dependent on their structure. Monounsaturated and polyunsaturated fatty acids are readily absorbed as are saturated fatty acids 12 carbons in length or less. Long chain saturated free fatty acids, especially palmitic acid (C16:0) and stearic acid (C18:0), form insoluble calcium soaps and are poorly absorbed, resulting in loss of fatty acids, calcium and calories (Innis, 2011). Human milk triglycerides have relatively high levels of palmitic acid, with this fatty acid being primarily in the SN-2 position. It is important to develop a nutritional formula which provides these types of nutritional, nutraceutical, and gastrointestinal benefits. It would be beneficial to develop a nutritional formula with improved tolerance, while providing for nutrition, and promoting postnatal development of an infant's gastrointestinal tract, nutrient absorption, and healthy immune system development in a subject.

SUMMARY OF THE INVENTION

The nutritional formula disclosed therein includes skim milk solids and demineralized whey, which, without wishing to be bound by any particular theory, support the ease of digestion and full absorption of milk proteins. The inventors posit that oleic acid-palmitic acid-oleic acid triglyceride, wherein palmitic acid is at the SN-2 position of the glycerol backbone of the triglyceride ("OPO SN-2 oil"), improves the efficiency of fatty acid absorption, improves the digestibility, reduces calcium loss to the infant's stool, reduces the incidence of constipation, and improves calcium absorption. The inventors also posit that lactoferrin helps support the infant immune system, intestinal development, and iron absorption. In addition, the inventors believe that the combination of lutein and docosahexaenoic acid may promote retinal health and vision development. Docosahexaenoic acid is susceptible to damage by oxidation and degradation, while lutein is an antioxidant. The inventors accordingly believe that lutein may reduce oxidative degradation of docosahexaenoic acid concentrated in the retina, and thus further promote retinal health and vision development. Docosahexaenoic acid and arachidonic acid improve the tolerance and acceptance of the nutritional formula. Prebiotics are thought to modulate the gut flora, affect diverse gastrointestinal activities, and influence inflammatory processes.

A nutritional formula of the present invention provides a subject (e.g., infant) with nutrients similar to those provided by human breast milk while maintaining and promoting gastrointestinal function in the subject (e.g., infant). Specifically, the addition of alpha-lactalbumin is thought to facilitate the absorption of essential minerals, and alpha-lactalbumin provides a well-balanced supply of essential amino acids to the subject (e.g., a growing infant).

Previous nutritional formulations included beta-casein enriched milk protein, mildly hydrolyzed milk protein, osteopontin and/or polydextrose, for example, both osteopontin and polydextrose; or beta-casein enriched milk protein, mildly hydrolyzed milk protein, and polydextrose. In contrast, nutritional formulations disclosed herein do not include beta-casein enriched milk protein, mildly hydrolyzed milk protein, polydextrose, or osteopontin. In some embodiments, the nutritional formulations of the present invention provides nutrition to a subject (e.g., infant), similar to the nutrition provided by human breast milk. In one aspect, the present invention provides a nutritional formula comprising proteins (not including beta-casein enriched milk protein, mildly hydrolyzed milk protein, or osteopontin), lipids, carbohydrates, lutein, polyunsaturated fatty acids, and prebiotics (e.g., galactooligosaccharides and fructooligosaccharides, but not polydextrose). The invention provides powder forms of the nutritional formula, reconstituted formulas, methods of preparing the nutritional formula, methods of administering the nutritional formula, and kits useful for the preparation and administration of the nutritional formula to a subject (e.g., infant). The present invention also provides methods of preparing the nutritional formula. The nutritional formulas described herein are useful in methods, uses, and uses in the manufacture of a medicament for providing nutrition and/or promoting postnatal development of a subject (e.g., promoting development of an infant's gastrointestinal tract, promoting proper gastrointestinal function (e.g., intestinal microbiota), promoting nutrient (e.g., calcium) absorption, promoting immune system development; and/or improving bone strength, sleep (e.g., sleep patterns), decreased crying (duration, frequency), decreased fussiness, etc) by administering to (feeding) the subject a nutritional formula described herein.

Specifically, the nutritional formula of the present invention includes ingredients for providing nutrition, including, but not limited to, alpha-lactalbumin enriched whey protein concentrate; lactoferrin; oleic acid-palmitic acid-oleic acid triglyceride, wherein palmitic acid is at the SN-2 position of the glycerol backbone of the triglyceride; lactose (e.g., wherein the lactose is a decreased amount of lactose, compared to the amount of lactose in standard cow's milk (approximately 55 g/L)); lutein; docosahexanoic acid; arachidonic acid; prebiotics selected from galactooligosaccharides and fructooligosaccharides; and combinations thereof. The nutritional formula of the present invention may also include one or more of the following: linoleic acid, alpha-linolenic acid, vitamins, minerals, nucleotides, biotin, choline, inositol, taurine, and L-carnitine.

Exemplary nutritional formulas disclosed herein include, but are not limited to, a nutritional formula comprising alpha-lactalbumin enriched whey protein concentrate; lactoferrin; oleic acid-palmitic acid-oleic acid triglyceride, wherein palmitic acid is at the SN-2 position of the glycerol backbone of the triglyceride; lactose (e.g., wherein the lactose is a decreased amount of lactose, compared to the amount of lactose in standard cow's milk (approximately 55 g/L)); lutein; docosahexanoic acid; arachidonic acid; galactooligosaccharides; and fructooligosaccharides, and powder forms and reconstituted formulas thereof. The nutritional formula further comprises, in certain embodiments, vitamins, minerals, nucleotides, and combinations (e.g. or a combination) thereof. In certain embodiments, the nutritional formulas disclosed herein also include one or more of the following: linoleic acid, alpha-linolenic acid, vitamins, minerals, nucleotides, biotin, choline, inositol, taurine, and L-carnitine.

In another aspect, described herein are reconstituted formulas of a powder form of a nutritional formula described herein, reconstituted with water to form a ready-to-feed liquid. In some embodiments, the reconstituted formulas disclosed herein are useful in methods, uses, and uses in the manufacture of a medicament for providing nutrition and/or promoting postnatal development of a subject (e.g., promoting development of an infant's gastrointestinal tract, promoting proper gastrointestinal function (e.g., intestinal microbiota), promoting nutrient (e.g., calcium) absorption, promoting immune system development; and/or improving bone strength, sleep (e.g., sleep patterns), decreased crying (duration, frequency), decreased fussiness, etc.).

In another aspect, described herein are methods of providing nutrition (e.g., feeding) to a subject (e.g., an infant) comprising administering (feeding) the nutritional formula described herein to the subject. In another aspect, described herein are methods of providing nutrition to (e.g., feeding) a subject (e.g., an infant) comprising preparing (e.g., reconstituting) a powdered form of the nutritional formula described herein with water to form a ready-to-feed liquid, and administering (feeding) the reconstituted formula to a subject. In another aspect, described herein is the nutritional formula provided herein for providing nutrition as well as promoting development of an infant's gastrointestinal tract, promoting proper gastrointestinal function (e.g., intestinal microbiota), nutrient (e.g., calcium) absorption, promoting proper immune system development; and/or improving bone strength, sleep (e.g., sleep patterns), decreased crying (duration, frequency), decreased fussiness, etc). In another aspect, described herein are uses of the nutritional formulas described herein for methods, uses, and uses in the manufacture of a medicament for providing nutrition as well as promoting postnatal development of the gastrointestinal tract, for example, promoting development of an infant's gastrointestinal tract, promoting proper gastrointestinal function (e.g., intestinal microbiota), promoting nutrient (e.g., calcium) absorption, promoting proper immune system development; and/or improving bone strength, sleep (e.g., sleep patterns), decreased crying (duration, frequency), and/or decreased fussiness.

In certain embodiments, the subject being administered a nutritional formula described herein is a human (e.g., an infant not more than about thirty-six (36) months of age, an infant not more than about thirty months of age, an infant not more than about two years of age, an infant not more than about eighteen months of age, an infant not more than about one year of age, an infant not more than about six months of age, or a newborn). In certain embodiments, the subject being administered a nutritional formula described herein is a non-human animal.

In still another aspect, described herein are kits including a container (e.g., a ridged or flexible container) with a nutritional formula described herein. A kit described herein may include a single serving or multiple servings (e.g., one or more packages, wherein each package comprises approximately 1.0 g to 100 g or 50 g to 100 g, of the powdered nutritional formula described herein) of the nutritional formula or reconstituted formula disclosed herein. A kit described herein may include a single serving or multiple servings (e.g., one or more packages, wherein each package comprises approximately 9 g to 100 g, 18 g to 100 g, 36 g to 100 g, 5.0 g to 100 g, or 4.5 g to 100 g, of the powdered nutritional formula described herein) of the nutritional formula or reconstituted formula. in certain embodiments, a package (e.g., service) comprises enough powdered formula to produce approximately 2 oz to 10 oz, approximately 10 oz to 20 oz, approximately 20 oz to 30 oz, approximately 30 oz to 40 oz, approximately 40 oz to 50 oz, approximately 50 oz to 60 oz, approximately 60 oz to 70 oz, approximately 70 oz to 80 oz, approximately 80 oz to 90 oz, approximately 90 oz to 100 oz, approximately 100 oz to 110 oz, approximately 2 oz to approximately 90 oz, 4 oz to approximately 90 oz, 8 oz to approximately 90 oz, or 1 oz to approximately 90 oz, of the reconstituted formula. The embodiment of the kit with a flexible package may contain a restriction at the opening end below the tare strip to form a pour spout with an opening smaller than the diameter of a baby (e.g., infant) bottle. The package of the kit may be a unit of use package. The kits may have added benefits, for example, the added benefit of reducing the contamination of the powder during the reconstitution of the formula. In certain embodiments, a package (e.g., service) comprises enough powdered formula to produce approximately 0.01 L-0.025 L, 0.025 L-0.05 L, or 0.05 L-0.1 L, of the reconstituted formula. The described kits may be useful in providing nutrition and/or in methods, uses, and uses in the manufacture of a medicament for promoting postnatal development of a subject (e.g., promoting development of an infant's gastrointestinal tract, promoting proper gastrointestinal function (e.g., intestinal microbiota), promoting nutrient (e.g., calcium) absorption, promoting immune system development; and/or improving bone strength, sleep (e.g., sleep patterns), decreased crying (duration, frequency), decreased fussiness, etc). In certain embodiments, a kit described herein further includes instructions for using the kit, for example, preparing (e.g., reconstituting) the powdered formula, administering the formula to a subject (e.g., infant). In still another aspect, described herein are devices (e.g., bottles) for administering to (e.g., feeding) a subject the nutritional formula or reconstituted formula.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Examples, and the Claims.

Definitions

Definitions of specific terms are described in more detail below.

The term "nutritional formula" as used herein refers to a nutritional composition that is designed for the administration/consumption of sufficient fats, proteins, carbohydrates, vitamins, minerals, prebiotics, and other nutrients to a subject. The nutritional formula may be the sole source of nutrition when provided in sufficient quantity. The nutritional formula is suitable for consumption by a subject as described herein, including, but not limited to, infants. The nutritional formula may come in different forms, including but not limited to powders, liquids, and liquid concentrates. The terms "consume," "feed," "administer," and conjugations or derivatives thereof refer to ingesting a nutritional formula or facilitating another's ingestion of a nutritional formula, and can be used interchangeably.

The term "formula" encompasses any form of the nutritional formula described herein, including, but not limited to, powder and liquid forms, liquid concentrates, and forms having both liquid and dry components. Additionally, the powder can be reconstituted from a dehydrated powder form to yield a liquid form suitable for the administration of the formula to a subject, including an infant.

The term "ready-to-feed" used herein refers to a liquid formula suitable for administration to a subject (e.g., infant), including reconstituted powders, diluted formulas of a concentrated nutritional formula, and manufactured liquids.

As used herein, concentrations expressed as micrograms per liter ("mcg/L"), milligrams per liter ("mg/L"), and grams per liter ("g/L") refer to ingredient concentrations within the nutritional formulation of the present disclosure (e.g., invention) calculated on a reconstituted, ready-to-feed, or fed basis, unless otherwise specified.

The term "about X," or "approximately X," where X is a number or percentage, refers to a number or percentage that is between 99.5% and 100.5%, between 99% and 101%, between 98% and 102%, between 97% and 103%, between 96% and 104%, between 95% and 105%, between 92% and 108%, or between 90% and 110%, inclusive, of X.

As used herein, a "subject" is a mammal. In certain embodiments, the mammal is an animal. In certain embodiments, the animal is a human. In certain embodiments, the human is an adult, adolescent, child, toddler, infant, or newborn of either sex. An "infant" or "newborn" refers to a human not more than about two years of age. The term "infant" also includes an infant from about 0 to about 4 months of age, from about 4 to about 8 months of age, from about 8 to about 12 months of age, from about 12 to about 16 months of age, from about 16 to about 18 months of age, from about 18 to about 24 months of age, from about 24 to about 30 months of age, from about 30 months to about 36 months of age, and preterm infants that are less than about 37 weeks gestational age. A "newborn" is an infant that is not more than about 4 weeks of age, and includes an infant from about 0 to about 1 week of age, from about 1 to about 2 weeks of age, from about 2 to about 3 weeks of age, and from about 3 to about 4 weeks of age. In certain embodiments, the animal is non-human. In certain embodiments, the non-human animal is a cow, sheep, buffalo, goat, camel, donkey, horse, or any other non-human animal that produces milk. In certain embodiments, the animal is a non-human mammal. In certain embodiments, the animal is a non-human primate.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. In certain embodiments, proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

"Whey protein concentrate" is a concentrated form of whey protein. The term whey protein concentrate encompasses whey protein of any size, structure, or function, and from any source or any composition. In nutrition, whey protein concentrate may be used to increase dietary protein intake. In general, whey protein concentrate contains from about 20% to about 90% protein by weight.

"Demineralized whey" or "reduced-minerals whey" refers to, with reference to a purification process, whey protein in which the minerals and salts (organic and inorganic) have been removed. In some embodiments, between 25-90% of the minerals in the whey protein in the demineralized whey are removed. In some embodiments, up to 25% of the minerals in the whey protein in the demineralized whey are removed. In some embodiments, up to 50% of the minerals in the whey protein in the demineralized whey are removed. In some embodiments, up to 60% of the minerals in the whey protein in the demineralized whey are removed. In some embodiments, up to 75% of the minerals in the whey protein in the demineralized whey are removed. In some embodiments, up to 80% of the minerals in the whey protein in the demineralized whey are removed. In some embodiments, up to 90% of the minerals in the whey protein in the demineralized whey are removed.

The term "skimmed milk powder" refers to a product that results from the removal of fat and water from pasteurized milk. The term skimmed milk powder also encompasses "skim milk powder." In skimmed milk powder, the fat content or protein content or both in the milk can be altered by the removal or addition of milk constituents. Milk retentate, milk permeate, and lactose can be used to adjust the skimmed milk powder protein content. Skimmed milk powder retains the original whey protein to casein ratio present in the milk. The production of skimmed milk powder often involves, but is not limited to, the evaporation of moisture from the milk until a dry powder with a low moisture content is obtained. The milk used to produce the skimmed milk powder as described herein can be obtained from any source. As described herein, skimmed milk powder can be obtained from any source, most typically from bovine (cow) milk.

"Alpha-lactalbumin" or "α-lactalbumin" is the most abundant protein in human breast milk, constituting between about 20% to about 25% of the total protein content. The alpha-lactalbumin protein binds divalent cations, such as $Ca^{2+}$ and $Zn^{2+}$, in addition to aiding in the absorption of essential dietary minerals. Upon digestion within the gastrointestinal tract, alpha-lactalbumin derived peptides may exhibit antibacterial and immune stimulatory properties to protect the subject against infection. As described herein, the alpha-lactalbumin can be obtained from any source, most typically from bovine milk.

The term "enriched" refers to a protein fraction having a high amount of a specified protein. In some embodiments, a protein fraction enriched with a specified protein has at least 30% of the specified protein. In some embodiments, a protein fraction enriched with a specified protein has at least 40% of the specified protein. In some embodiments, a protein fraction enriched with a specified protein has at least 50% of the specified protein. In some embodiments, a protein fraction enriched with a specified protein has at least 60% of the specified protein. In some embodiments, a protein fraction enriched with a specified protein has at least 65% of the specified protein. In some embodiments, a protein fraction enriched with a specified protein has at least 70% of the specified protein. In some embodiments, a protein fraction enriched with a specified protein has at least 80% of the specified protein. In some embodiments, a protein fraction enriched with a specified protein has at least 90% of the specified protein. "Alpha-lactalbumin enriched whey protein concentrate" or "alpha-lactalbumin enhanced whey protein concentrate" refers to a whey protein concentrate enriched with alpha-lactalbumin. A whey protein concentrate enriched with alpha-lactalbumin contains more alpha-lactalbumin than a non-enriched whey protein concentrate. A whey protein concentrate enriched with alpha-lactalbumin typically contains more than 15% by weight of alpha-lactalbumin, preferably more than 20% by weight of alpha-lactalbumin. A whey protein concentrate enriched with alpha-lactalbumin may contain 25%, 30%, 35% or more alpha-lactalbumin by weight, and preferably contains 28% alpha-lactalbumin by weight or more.

"Lactoferrin," sometimes referred to as "lactotransferrin," is a protein produced during the late stages of pregnancy and is found in breast milk colostrum and mature breast milk. Lactoferrin is found in the milk of many mammals, including in cow milk and in human breast milk. Lactoferrin is classified as a glycoprotein, in which normally about 1 to about 4 glycans are attached to amino acid side chains throughout the protein. Lactoferrin aids in intestinal development and iron absorption, as well as providing immune system support. As described herein, the lactoferrin can be obtained from any source, most typically from bovine milk.

A "triglyceride" is comprised of three fatty acid chains connected to a glycerol molecule through an ester bond. The term "fat" refers to all fatty acid, triglyceride, lipid, and oil molecules of any size, structure, or function. Typically, a fat is a hydrophobic molecule that is insoluble in water. An "oil" is generally a mixture of one or more unsaturated fatty acid chains. A "lipid" is any molecule of a class of organic compounds that are fatty acids or their derivatives, and are insoluble in water but soluble in organic compounds, and include many natural oils, waxes, and steroids. Fats may include fatty acid chains that are either saturated or unsaturated. A saturated fat contains no double bonds between carbon atoms in the chain. An unsaturated fat contains one or more double bonds between carbon atoms in the chain, and the double bond or bonds can be in the cis or trans configuration. Fats containing one or more trans double bonds are called trans fats. Fat containing one or more cis double bonds are called cis fats. Further, a monounsaturated fatty acid contains at least one double bond between carbons in the aliphatic chain. A polyunsaturated fat that contains at least one aliphatic chains with at least two or more double bonds between carbons in the chain. Sources of fat and oils, including saturated, unsaturated, and polyunsaturated fat, include, but are not limited to, canola, sunflower, sesame, peanut, walnut, chia, palm, coconut, avocado, olive, safflower, seaweed, sardine, soybean, tuna, salmon, and whole grain wheat.

The term "unsaturated bond" refers to a double or triple bond.

The term "saturated" refers to a moiety that does not contain a double or triple bond, i.e., the moiety only contains single bonds.

A "fatty acid" is an aliphatic carbon chain connected to a carboxylic acid. The term fatty acid refers to fatty acids of any size, structure, or function. The aliphatic carbon chain may be either unsaturated or saturated. In some embodiments, the fatty acid is not connected to a glycerol backbone. A saturated fatty acid contains no double bonds between carbons in the chain. An unsaturated fatty acids contains one or more double bonds between carbons in the chain, and the double bond or bonds can be cis or trans. A monounsaturated fatty acid contains at least one double bond between carbons in the aliphatic chain. A polyunsaturated fatty acid contains at least two or more double bonds between carbons in the aliphatic chain. Fatty acids are generally straight-chained carbons and not branched carbon chains, wherein the number of carbon atoms present in the aliphatic chain is from 4 to about 28 carbon atoms. Fatty acid chains differ in length, wherein short-chain fatty acids (SCFA) are fatty acids with aliphatic chains of fewer than about 6 carbon atoms, wherein medium-chain fatty acids (MCFA) are fatty acids with aliphatic chains of about 6 to about 12 carbon atoms, wherein long-chain fatty acids (LCFA) are fatty acids with aliphatic chains of about 13 to about 21 carbon atoms, and wherein very long-chain fatty acids (VLCFA) are fatty acids with aliphatic chains of about 22 or more carbon atoms. Non-limiting examples of fatty acids include saturated fatty acids, including but not limited to, caprylic acid, capric acid, lauric acid, stearic acid, arachidonic acid, behenic acid, lignoceric acid, cerotic acid, butyric acid, caproic acid, myristic acid, pentadecanoic acid, palmitic acid, heptadecanoic acid, and arachidic acid; and unsaturated fatty acids, including but not limited to, myristoleic acid, palmitoleic acid, sapienic acid, oleic acid, elaidic acid, vaccenic acid, linoleic acid, linoelaidic acid, α-linolenic acid, γ-linoleneic acid, homogamma-linolenic acid, arachidonic acid, eicosapentaenoic acid, erucic acid, docosahexaenoic acid, pentadecenoic acid, heptadecenoic acid, octadecatetraenoic acid, eicosenoic acid, eicosadienoic acid, eicosatrienoic acid, heneicosapentaenoic acid, behenic acid, docosadienoic acid, docosatrienoic aicd, docosatetraenoic acic, docosapentaenoic acid, lignoceric acid, and nervonic acid; and others.

Unsaturated fatty acids can be further classified according to the location of the double bond in the aliphatic carbon chain. The placement of the double bond is described by the number of the first carbon in the double bond, counting from the terminal methyl (—CH$_3$) of the aliphatic chain according to the formula below:

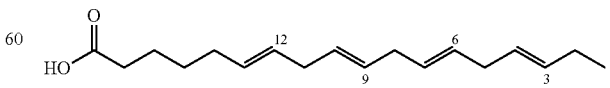

An "omega-3 fatty acid," "ω-3 fatty acid," or "n-3 fatty acid" contains a double bond at carbon 3. An "omega-6 fatty acid," "ω-6 fatty acid," or "n-6 fatty acid" contains a double bond at carbon 6. An "omega-9 fatty acid," "ω-9 fatty acid,"

or "n-9 fatty acid" contains a double bond at carbon 9. An "omega-12 fatty acid," "ω-12 fatty acid," or "n-12 fatty acid" contains a double bond at carbon 12.

"Oleic acid" or "C18:1" is a naturally occurring fatty acid in a variety of animal and vegetable oils. The term oleic acid as described herein encompasses fatty acids under the IUPAC nomenclature "(9E)-octadec-9-enoic acid." Oleic acid includes salts or esters of oleic acid, and oleic acid can be obtained from any source. Oleic acid is further classified as an omega-9 cis monounsaturated fatty acid with one double bond at carbon 9 and a total of 18 carbons in the aliphatic chain (18:1 cis-9). Oleic acid has the chemical formula $CH_3(CH_2)_7CH\!=\!CH(CH_2)_7COOH$, and the structure

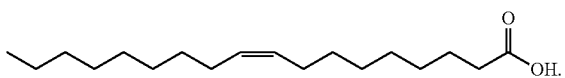

"Palmitic acid" or "C16:0" is the most common fatty acid found in animals, plants, and microorganisms, such as algae and fungi. The term palmitic acid as described herein encompasses all fatty acids under the IUPAC nomenclature "hexadecanoic acid." Palmitic acid includes salts or esters of palmitic acid, and palmitic acid can be obtained from any source. Palmitic acid is further classified as a saturated fatty acid and consists of a 16 carbon aliphatic chain (16:0). Palmitic acid has the chemical formula $CH_3(CH_2)_{14}COOH$, and the structure

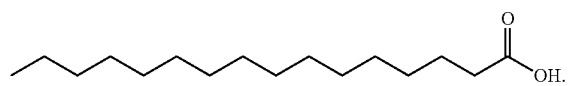 [SMILES: CCCCCCCCCCCCCCCC(=O)O]

"OPO SN-2 oil," "SN2 palmitate," "SN-2 palmitate," "OPO" or "oleic acid-palmitic acid-oleic acid triglyceride" refers to an oleic acid-palmitic acid-oleic acid triglyceride, wherein palmitic acid is at the SN-2 position of the glycerol backbone of the triglyceride, and oleic acid is at the SN-1 and SN-3 positions of the glycerol backbone of the triglyceride. In some embodiments, the oleic acid-palmitic acid-oleic acid triglyceride is of Formula (I):

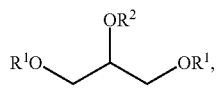

wherein $R^1$ is oleic acid (C18:1), and $R^2$ is palmitic acid (C16:0). In some embodiments, the SN-2 position of the glycerol backbone of the triglyceride is the second position on the glycerol backbone of the triglyceride. OPO SN-2 oil may refer to the oleic acid-palmitic acid-oleic acid triglyceride of Formula (I). Optionally, OPO SN-2 oil comprises OPO triglyceride in an amount of about 50% to about 100% of the triglycerides.

"Linoleic acid" or "C18:2" is a fatty acid found in many foods, including many nuts, fatty seeds (such as, but not limited to, flax seeds, hemp seeds, poppy seeds, sesame seeds, and others), and their derived vegetable oils. Linoleic acid is one of two essential fatty acids for humans, meaning that it must be obtained through a human's diet. The term linoleic acid as described herein encompasses all fatty acids under the IUPAC nomenclature "(9Z,12Z)-octadeca-9,12-dienoic acid," including, but not limited to, "cis,cis-9,12-octadecadienoic acid," "18:2 (n-6)", and "18:2 cis-9,12". Linoleic acid includes salts or esters of linoleic acid, and linoleic acid can be derived from any source. Linoleic acid is further classified as an omega-6 cis polyunsaturated fatty acid with two double bonds at carbons 9 and 12, respectively, and a total of 18 carbons in the aliphatic chain (18:2 cis,cis-9,12). Linoleic acid has the chemical formula $CH_3(CH_2)_4CH\!=\!CH(CH_2)CH\!=\!CH(CH_2)_7COOH$, and the structure

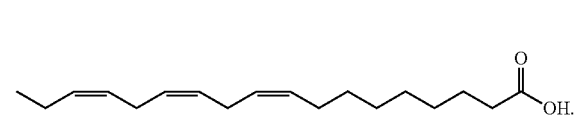 [SMILES: CC/C=C\C/C=C\C/C=C\CCCCCCCC(=O)O]

"α-linolenic acid" or "alpha-linolenic acid," sometimes referred to as "ALA," is a fatty acid found in many seeds and oils, including flaxseed, walnuts, chia, hemp, and many common vegetable oils. Alpha-linolenic acid is an essential fatty acid for humans, meaning that it must be obtained through a human's diet. The term alpha-linolenic acid, as described herein, encompasses all fatty acids under the IUPAC nomenclature "(9Z,12Z,15Z)-octadeca-9,12,15-trienoic acid," including, but not limited to, "ALA," "LNA" "linolenic acid," "cis,cis,cis-9,12,15-octadecatrienoic acid," "all-cis-9,12,15-octadecatrienoic acid," "(9Z,12Z,15Z)-9,12,15-octadecatrienoic acid" and "Industrene 120." Alpha-linolenic acid includes salts or esters of alpha-linolenic acid, and alpha-linoleic acid can be derived from any source. Alpha-linolenic acid is further classified as an omega-3 cis polyunsaturated fatty acid with three double bonds at carbons 9, 12, and 15, respectively, and a total of 18 carbons in the aliphatic chain (18:3 cis,cis,cis-9,12,15). Alpha-linolenic acid has the chemical formula $CH_3CH_2(CH\!=\!CH)CH_2(CH\!=\!CH)(CH_2)_7COOH$, and the structure The term "aliphatic" refers to alkyl, alkenyl, alkynyl, and carbocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$) group. In certain embodiments, the alkyl group is a substituted $C_{1-10}$ alkyl group.

"Microencapsulated," "microencapsulation," or "microcapsule" refers to any substance, particle, or droplet surrounded by a coating of any material to give small capsules or the process of producing such capsules. Optionally, the coating material may include a carbohydrate (e.g., ethyl cellulose or sodium alginate), alcohol (e.g., polyvinyl alcohol), protein (e.g., sodium alginate), and combinations, or a combination thereof. The term microencapsulated may refer to any food ingredient, enzyme, cell, or other material that may be incorporated into the relevant composition, mixture, ingredient, or product. Microencapsulation may be used to enclose any solid, liquid, or gaseous substance. Optionally, the microcapsule may be used to enclose any substance permanently or temporarily. The term microencapsulation covers all physical, chemical, and physiochemical techniques used in the process of generating microcapsules, including pan coating, air-suspension coating, centrifugal extrusion, vibrational nozzle, spray-drying, ionotropic gelation, coacervation-phase separation, interfacial polycondensation, interfacial cross-linking, in-situ polymerization, matrix polymerization, or the combination of techniques described herein.

"Docosahexaenoic acid" or "DHA" is an omega-3 fatty acid comprising a 22 carbon chain and 6 cis double bonds. The terms docosahexaenoic acid and DHA also encompass "cervonic acid," "all-cis-docosa-4,7,10,13,16,19-hexaenoic acid," "22:6(n-3)," and any fatty acid that can be classified under the IUPAC nomenclature "(4Z,7Z,10Z,13Z,16Z,19Z)-docosa-4,7,10,13,16,19-hexaenoic acid" and "doconexent". The terms docosahexaenoic acid and DHA may refer to any docosahexaenoic acid of any size, structure, or function. The docosahexaenoic acid defined herein may be derived from any source, including milk or oil. In certain embodiments, the milk is maternal milk. In certain embodiments, the oil is fish oil, algae oil, microalgae oil, fungal oil, and/or any combination thereof. In certain embodiments, the docosahexaenoic acid is sourced from *Crypthecodinium cohnii* oil. In certain embodiments, the docosahexaenoic acid is sourced from fish oil. Docosahexaenoic acid has the chemical formula $CH_3CH_2(CH=CH)CH_2(CH=CH)CH_2(CH=CH)CH_2(CH=CH)CH_2(CH=CH)CH_2(CH=CH)(CH_2)_2COOH$, and the structure

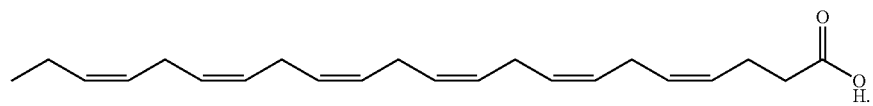 [SMILES: CC/C=C\C/C=C\C/C=C\C/C=C\C/C=C\C/C=C\CCC(=O)O]

"Arachidonic acid" or "ARA" is a polyunsaturated omega-6 fatty acid comprising a 20 carbon aliphatic chain and 4 cis double bonds. The terms arachidonic acid and ARA also encompass "(5Z,8Z,11Z,14Z)-Icosa-5,8,11,14-tetraenoic acid," "5,8,11,14-all-cis-eicosatetraenoic acid," "all-cis-5,8,11,14-eicosatetraenoic acid," "arachidonate," and any fatty acid that can be classified under the IUPAC nomenclature "(5Z,8Z,11Z,14Z)-5,8,11,14-eicosatetraenoic acid." Arachidonic acid has the chemical formula $CH_3(CH_2)_4(CH=CH)CH_2(CH=CH)CH_2(CH=CH)CH_2(CH=CH)(CH_2)_3COOH$, and the structure

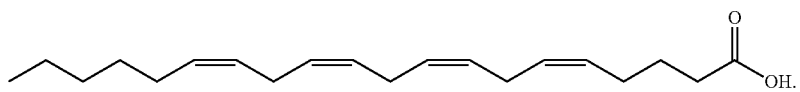 [SMILES: CCCCC/C=C\C/C=C\C/C=C\C/C=C\CCCC(=O)O]

The arachidonic acid may be from any source, including milk and/or oil. In certain embodiments, the milk is bovine milk. In certain embodiments, the oil is fish oil, algae oil, is found in high quantities in green leafy vegetables such as spinach, kale, and yellow carrots. Lutein has the chemical structure

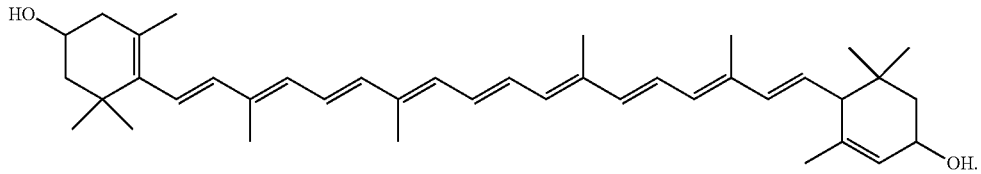 [SMILES: CC1=CC(O)CC(C)(C)C1/C=C/C(C)=C/C=C/C(C)=C/C=C/C=C(C)/C=C/C=C(C)/C=C/C1=C(C)CC(O)CC1(C)C]

microalgae oil, fungal oil, and/or any combination thereof. In certain embodiments, the arachidonic acid is sourced from *Mortierella alpina* oil.

A "carbohydrate," "saccharide," "sugar," or "starch" is a molecule comprised of carbon, hydrogen, and oxygen atoms. The term carbohydrate refers to all carbohydrate, saccharide, sugar, or starch molecules of any size, structure, or function. A carbohydrate can be a monosaccharide. Two or more monosaccharides may be joined by one or more glycosidic bonds to produce higher order carbohydrates. A disaccharide is a carbohydrate comprised of two monosaccharides, an oligosaccharide is comprised of about 3 to about 10 monosaccharides, and a polysaccharide is comprised of about 10 or more monosaccharides. In certain embodiments, the carbohydrate is lactose, maltodextrin, corn syrup, corn syrup solids, or any combination thereof. In certain embodiments, the carbohydrate is lactose, maltodextrin, or any combination thereof. In certain embodiments, the carbohydrate is lactose.

"Lactose" is a disaccharide carbohydrate. Lactose contains a galactose moiety and a glucose moiety linked by a glycosidic bond. The term lactose refers to any lactose of any size, structure, or function. The term lactose also encompasses "milk sugar," "4-O-β-D-galactopyranosyl-D-glucose," and any carbohydrate classified under the IUPAC nomenclature "β-D-galactopyranosyl-(1→4)-D-glucose."

"Maltodextrin" is a polysaccharide comprising D-glucose units connected in chains of any length. Optionally, the maltodextrin chain is between about 2 to about 17 glucose units long, and may exists as a mixture of chain lengths between about 2 to about 17 glucose units long. The term maltodextrin encompasses any maltodextrin of any size, structure, or function, and derived from any source.

An "antioxidant" is a molecule that can prevent the oxidation of another molecule. The term antioxidant refers to all antioxidants of any size, structure, or function. An antioxidant functions to prevent chain reactions produced by free radicals, or any atom, ion, or molecule with an unpaired electron, that arise through a variety of natural, biological, and metabolic oxidation reactions. Antioxidants may be sulfur-containing compounds, such as glutathione, an enzyme, or a dietary antioxidant. Typical dietary antioxidants may include vitamin A, vitamin C, vitamin E, lutein, β-carotene, or others. In certain embodiments, the nutritional formula includes vitamin A, vitamin C, vitamin E, lutein, and/or β-carotene.

"Lutein" is a xanthophyll, a division of the carotenoid group. The term lutein also encompasses "luteine," "trans-lutein," "(1R)-4-[(1E,3E,5E,7E,9E,11E,13E,15E,17E)-18-[(1R,4R)-4-hydroxy-2,6,6-trimethylcyclohex-2-en-1-yl]-3,7,12,16-tetramethyloctadeca-1,3,5,7,9,11,13,15,17-nonaenyl]-3,5,5-trimethylcyclohex-3-en-1-ol," and "β,ε-carotene-3,3'-diol." Lutein is synthesized only by plants and "Prebiotic" or "prebiotics" refers to a compound that may induce the growth and beneficial activity of host microorganisms, such as bacteria, fungi, or others. A prebiotic refers to all prebiotics of any size, structure, or function. A prebiotic may be from plant or animal sources. In nutrition, a prebiotic is commonly a compound comprising dietary fiber, wherein the dietary fiber contains a soluble portion and an insoluble portion, and the fiber aids in digestion. A prebiotic commonly alters and effects the microorganisms living in the gastrointestinal tract of the host, and often influences microorganisms or microflora in the gut and elsewhere in the body. Prebiotics suitable for nutritional formulas include, but are not limited to, galactooligosaccharides, inulin, and fructooligosaccharides. Preferably, the nutritional composition contains galactooligosaccharides, fructooligosaccharides, or any combination thereof. Optionally, the nutritional formula includes galactooligosaccharides, fructooligosaccharides, and one or more additional prebiotics. In some embodiments, the nutritional composition contains galactooligosaccharides and fructooligosaccharides.

A "vitamin" is an organic or inorganic compound that is required by an organism. The term vitamin refers to a vitamin or nutrient of any size, structure, or function. The term vitamin may also refer to a vitamin within a complex or coenzyme. Vitamins include compounds required by an organism that the organism cannot synthesize for itself and must be obtained from the organism's diet. Vitamins also include compounds required by an organism that may be synthesized by the organism itself, may be obtained from the organism's diet, or may be both synthesized by the organism and obtained from the organism's diet. Vitamins required by humans may include, but are not limited to, vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin $D_2$, vitamin $D_3$, vitamin E, vitamin $K_1$, folic acid, inositol, biotin, niacin, and similarly named derivatives or variants of these named vitamins (e.g., a variant of vitamin E).

A "dietary mineral," "mineral," "trace mineral," "dietary element," or "mineral nutrient" is any element required by living organisms. The term mineral or dietary mineral refers to a dietary mineral, dietary element, or mineral nutrient of any size, structure, or function. A dietary mineral does not include carbon, hydrogen, oxygen, or nitrogen due to their presence in common organic molecules. Dietary minerals important for humans include, but are not limited to, sulfur, potassium, chloride, sodium, calcium, phosphorous, magnesium, zinc, iron, manganese, copper, iodine, selenium, molybdenum, cobalt, and bromine. A dietary mineral may be provided in the form of a salt. Non-limiting examples of salts containing dietary minerals include sodium chloride, calcium phosphate, calcium carbonate, calcium citrate, potassium chloride, potassium citrate, potassium iodide, sodium citrate, sodium selenite, magnesium phosphate, magnesium chloride, magnesium oxide, iron (II) sulfate, zinc sulfate, copper sulfate, and manganese (II) sulfate. In some embodiments, the nutritional composition includes dicalcium phosphate, calcium carbonate, L-choline bitartrate, potassium chloride, magnesium chloride, sodium citrate, L-carnitine, potassium iodide, potassium citrate, dimagnesium phosphate, sodium selenite, trisodium citrate, tripotassium citrate, iron (II) sulfate, zinc sulfate, copper sulfate, and manganese (II) sulfate.

A "nucleotide" is an organic molecule that serves as the basic subunit of nucleic acids, such as deoxyribonucleic acids (DNA) and ribonucleic acids (RNA). The term nucleotide refers to a nucleotide of any size, structure, or function. Nucleotides are typically comprised of a nitrogenous base (nucleobase), a 5- or 6-carbon sugar unit, and at least one phosphate group. Nucleotides serve as energy storage molecules in the cell, commonly in the form of nucleotide triphosphates, and are central to metabolism. The primary nucleobases are cytosine, guanine, adenine, thymine, and uracil. When a nucleobase is connected to a sugar and at least one phosphate group, the nucleotide base is formed. Common nucleotides include cytidine 5'-monophosphate (CMP), uridine 5'-monophosphate (UMP), guanosine 5'-monophosphate (GMP), and adenosine 5'-monophosphate (AMP), thymidine 5'-monophosphate (TMP), and salts thereof, as well as diphosphate and triphosphate analogs, among others.

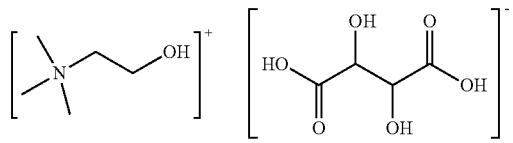

"L-carnitine" is an amino acid derivative. L-carnitine is involved in lipid and fat metabolism in mammals and other eukaryotes. The term L-carnitine encompasses "3-hydroxy-4-(trimethylazaniumyl)butanoate." L-carnitine can be from any food, plant, or animal source. In certain embodiments, L-carnitine is from a plant source. In certain embodiments, L-carnitine is from an animal source. L-carnitine comprises exclusively, or is enriched for the L-enantiomer of carnitine.

"Beta-carotene" is a carotene, a class of terpenoids or isoprenoids. Beta-carotene is an organic pigment that has an orange or red color and is abundant in many plants and fruits. Generally, beta-carotene has about 40 carbons. The term beta-carotene also encompasses "betacarotene," "β-carotene," "Food Orange 5," "Provitamin A," "1,1'-(3,7,12,16-Tetramethyl-1,3,5,7,9,11,13,15,17-octadecanonaene-1,18-diyl)bis[2,6,6-trimethylcyclohexene]," and "1,3,3-trimethyl-2-[3,7,12,16-tetramethyl-18-(2,6,6-trimethylcyclohex-1-en-1-yl)octadeca-1,3,5,7,9,11,13,15,17-nonaen-1-yl]cyclohex-1-ene." Beta-carotene can be derived from any food, plant, or animal source. In certain embodiments, beta-carotene is from a plant source. In certain embodiments, beta-carotene is from an animal source. Beta-carotene has the chemical structure

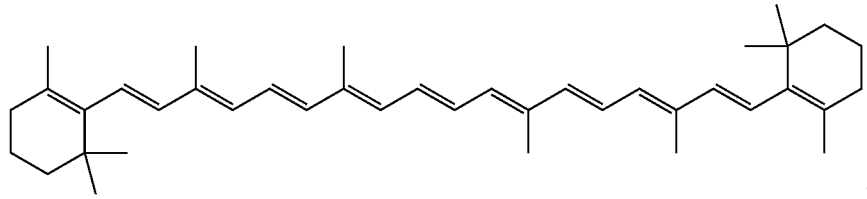 [SMILES: CC1=C(/C=C/C(C)=C/C=C/C(C)=C/C=C/C=C(C)/C=C/C=C(C)/C=C/C2=C(C)CCCC2(C)C)C(C)(C)CCC1]

"Lecithin" is a term used to define any fatty acid or substance that occurs naturally in a plant or animal tissue. Lecithin is a yellow-brown amphiphilic substance. In certain embodiments, lecithin may be used for smoothing food textures, dissolving powders, homogenizing liquid mixtures, repelling sticking materials, and/or as an emulsifier. The term lecithin encompasses any lecithin of any size, structure, or function, and from any source. In certain embodiments, the sources of lecithin include, but are not limited to, soy, soya, soybeans, eggs, milk, marine sources, rapeseed, cottonseed, and sunflower. In certain embodiments, the lecithin source is soya lecithin.

"L-choline bitartrate" is a water soluble nutrient. L-choline bitartrate is a salt or monoester of choline and tartaric acid. L-choline bitartrate encompasses any salt containing an N,N,N-trimethylethanolammonium cation and tartaric acid anion. In certain embodiments, choline bitartrate is a mixture of D/L-choline bitartrate. L-choline bitartrate contains only the L-enantiomer of choline bitartrate. In certain embodiments, L-choline bitartrate is conditioned (e.g., combined) with silica to improve flow characteristics and handling qualities. In certain embodiments, L-choline bitartrate is conditioned or coated with silica. In certain embodiments, L-choline bitartrate has the structure:

"Taurine" or "2-aminoethanesulfonic acid" is an organic compound that serves a variety of biological roles, such as conjugation of bile acids, antioxidation, osmoregulation, membrane stabilization, calcium signaling modulation, development and function of skeletal muscle, development and function of the retina, and development and function of the central nervous system. "Taurine" is also referred to as "2-aminoethanesulfonic acid." Taurine may be obtained from any source. In certain embodiments, taurine is from an animal source. Taurine has the chemical structure

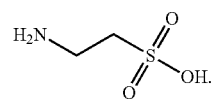

An "effective amount" of a nutritional formula described herein refers to an amount sufficient to provide nutrition to a subject or to have a biological effect on a subject. An effective amount of a nutritional formula described herein may vary depending on such factors as the desired biological endpoint (e.g., promoting to a certain degree the postnatal development of the gastrointestinal tract, promoting proper gastrointestinal function (e.g., intestinal microbiota), promoting nutrient (e.g., calcium) absorption, and/or promoting proper immune system development; improving bone strength, sleep (e.g., sleep patterns), decreased crying (duration, frequency), decreased fussiness, etc), the mode of administration, and the age and health of the subject. In certain embodiments, an effective amount is a nutraceutically effective amount. In certain embodiments, an effective amount is the amount of a nutritional formula described herein in a single serving. In certain embodiments, an effective amount is the amount of a nutritional formula described herein in a single feeding. In certain embodiments, an effective amount is the combined amounts of a nutritional formula described herein in multiple servings. In certain embodiments, an effective amount is the combined amounts of a nutritional formula described herein in multiple servings (e.g., feedings).

A "nutraceutically effective amount" of a nutritional formula described herein is an amount sufficient to provide a nutraceutical benefit in the health (e.g., gastrointestinal development, nutritional health, nutrient absorption, immune system development, etc.), of a subject. A nutraceutically effective amount of a nutritional formula means an amount of a nutraceutical agent, alone or in combination with other therapies, which provides a nutritional benefit in the health of the subject. The term "nutraceutically effective amount" can encompass an amount that improves overall health, reduces or avoids symptoms, signs, or causes of poor health of the subject, and/or enhances the nutraceutical/nutritional efficacy of another nutritional formula.

BRIEF DESCRIPTION OF THE FIGURES

The accompanying drawings are not intended to be drawn to scale. In the Drawings, for purposes of clarity, not every component may be labeled in every drawing.

DETAILED DESCRIPTION OF CERTAIN EMBODIMENTS OF THE INVENTION

Figure 1A:
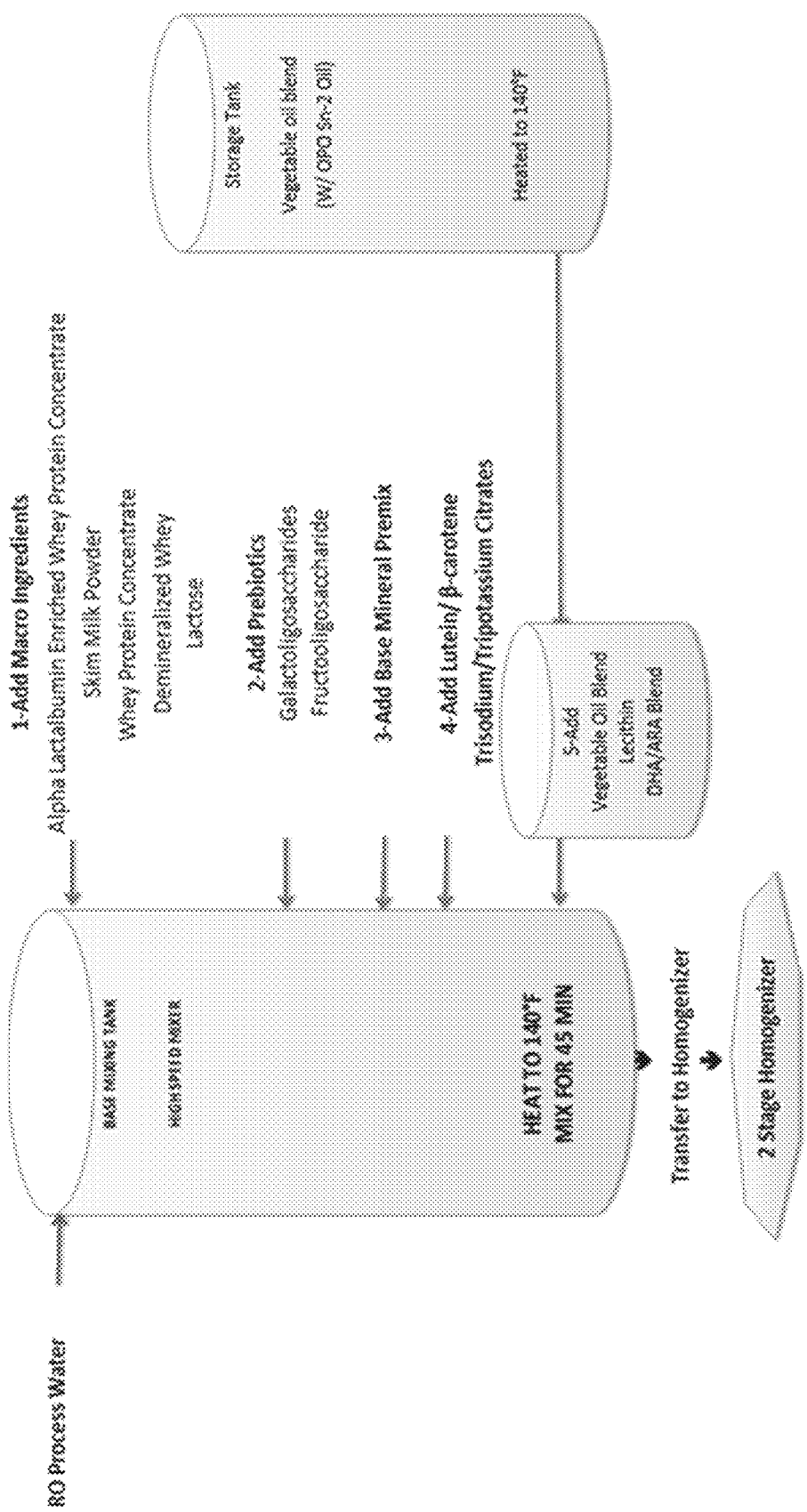
FIGS. 1A and 1B show the manufacturing process for the preparation of infant formula in which the formula is prepared through homogenization and pasteurization.

The present disclosure provides, in one aspect, a nutritional formula comprising alpha-lactalbumin enriched whey protein concentrate; lactoferrin; oleic acid-palmitic acid-oleic acid triglyceride, wherein palmitic acid is at the SN-2 position of the glycerol backbone of the triglyceride; lactose; lutein; docosahexanoic acid; arachidonic acid; galactooligosaccharides; and fructooligosaccharides. In certain embodiments, the nutritional formula also comprises additional proteins, nucleotides, vitamins, minerals, and saccharides. The invention provides powdered forms of the nutritional formulas, reconstituted formulas, methods of preparing the nutritional formula, methods of administering the nutritional formula, and kits useful for the preparation and administration of the nutritional formula to a subject (e.g., infant). The nutritional formulas described herein are useful in providing nutrition and/or promoting postnatal development of a subject (e.g., promoting development of an infant's gastrointestinal tract, promoting proper gastrointestinal function (e.g., intestinal microbiota), promoting nutrient (e.g., calcium) absorption, promoting immune system development; improving bone strength, sleep (e.g., sleep patterns), decreased crying (duration, frequency), decreased fussiness, etc.)). Provided are methods of providing nutrition to (e.g., feeding) a subject, by feeding the subject the nutritional formulas described herein. Also provided are methods of providing nutrition to (e.g., feeding) a subject, by administering to the subject a nutritional formula described herein, reconstituted with water. Also provided are kits, methods, and uses including a nutritional formula described herein.

Nutritional Formulas and Reconstituted Formulations

In one aspect, the present disclosure provides a nutritional formula comprising:
a) alpha-lactalbumin enriched whey protein concentrate;
b) lactoferrin;
c) oleic acid-palmitic acid-oleic acid triglyceride, wherein palmitic acid is at the SN-2 position of the glycerol backbone of the triglyceride;
d) lactose;
e) lutein;
f) docosahexanoic acid;
g) arachidonic acid;
h) galactooligosaccharides; and
i) fructooligosaccharides.

The amounts of each of the components of the nutritional formula are provided herein as values in grams per liter (g/L) of reconstituted, ready-to-use nutritional formula. In certain embodiments, the amount of each component of the nutritional formula in grams per 100 grams of nutritional formula can be calculated by dividing the value in grams per liter (g/L) of reconstituted, ready-to-use nutritional formula by 1.35. In certain embodiments, the nutritional formula also comprises additional proteins, nucleotides, vitamins, minerals, and saccharides.

In certain embodiments, the nutritional formula includes both 1) a whey protein concentrate that is not alpha-lactalbumin enriched (e.g., does not comprise additional added alpha-lactalbumin); and 2) a whey protein concentrate that is alpha-lactalbumin enriched. In certain embodiments, the nutritional formula includes approximately 24.4 grams of a whey protein concentrate that is not alpha-lactalbumin enriched, per liter (g/L) of reconstituted, ready-to-use nutritional formula, which is equivalent to approximately 18.1 grams per 100 grams of nutritional formula. In certain embodiments, the amount of each of the component of the nutritional formula in grams per liter (g/L) of reconstituted, ready-to-use nutritional formula includes each component in the form of salts, triturated forms, spray dried forms, lyophilized forms, other forms, and/or combinations thereof.

The nutritional formula also includes an additional whey protein concentrate that is not alpha-lactalbumin enriched, in that no additional alpha-lactalbumin is added to the whey protein concentrate. In certain embodiments, the whey protein concentrate is sourced from a non-human animal (e.g., a cow). In certain embodiments, the whey protein concentrate can be obtained from Arla Foods Ingredients Group. In certain embodiments, none of the whey protein concentrate is alpha-lactalbumin enriched (e.g., the amount of alpha-lactalbumin in the whey protein concentrate is not above 1%, 2%, 3%, 4%, 5%, 6%, 7%, 8%, 10%, 12%, 15%, 18%, or 20% by weight of the whey protein concentrate). In certain embodiments, the whey protein concentrate that is not alpha-lactalbumin enriched is present in the weight range from approximately 3 grams to approximately 4 grams per liter (g/L), approximately 4 grams to approximately 5 grams per liter (g/L), approximately 5 grams to approximately 6 grams per liter (g/L), approximately 6 grams to approximately 7 grams per liter (g/L), approximately 7 grams to approximately 8 grams per liter (g/L), approximately 8 grams to approximately 8.5 grams per liter (g/L), approximately 8.5 grams to approximately 9.0 grams per liter (g/L), approximately 9.0 grams to approximately 9.5 grams per liter (g/L), approximately 9.5 grams to approximately 10.0 grams per liter (g/L), or approximately 10.0 grams to approximately 11.0 grams per liter (g/L), of reconstituted, ready-to-use nutritional formula. In certain embodiments, the whey protein concentrate that is not alpha-lactalbumin enriched is present in the weight range from approximately 5 grams to approximately 6 grams per liter (g/L), approximately 6 grams to approximately 7 grams per liter (g/L), approximately 7 grams to approximately 8 grams per liter (g/L), approximately 8 grams to approximately 8.25 grams per liter (g/L), approximately 8.25 grams to approximately 8.5 grams per liter (g/L), approximately 8.5 grams to approximately 9.0 grams per liter (g/L), approximately 9.0 grams to approximately 9.5 grams per liter (g/L), or approximately 9.5 grams to approximately 10.0 grams per liter (g/L), of reconstituted, ready-to-use nutritional formula. In certain embodiments, the whey protein concentrate that is not alpha-lactalbumin enriched is present in the weight range from approximately 8 grams per liter (g/L), approximately 8.1 grams per liter (g/L), or approximately 8.2 grams per liter (g/L), of reconstituted, ready-to-use nutritional formula.

The nutritional formula also includes alpha-lactalbumin enriched whey protein concentrate. In certain embodiments, the alpha-lactalbumin enriched whey protein concentrate is sourced from a non-human animal (e.g., a cow). In certain embodiments, the alpha-lactalbumin enriched whey protein concentrate is obtained from Arla Foods Ingredients Group. In certain embodiments, approximately 30-50%, approximately 30-35%, approximately 35-40%, approximately 30-40%, approximately 40-50%, approximately 40-45%, approximately 45-50%, approximately 50-55%, or approximately 55-60%, of the whey protein concentrate is alpha-lactalbumin. In certain embodiments, 40-60% of the whey protein concentrate is alpha-lactalbumin. In certain embodiments, approximately 40% of the whey protein concentrate is alpha-lactalbumin. In certain embodiments, approximately 43% of the whey protein concentrate is alpha-lactalbumin. In certain embodiments, approximately 46% of the whey protein concentrate is alpha-lactalbumin. In certain embodiments, approximately 50% of the whey protein concentrate is alpha-lactalbumin. In certain embodiments, approximately 60% of the whey protein concentrate is alpha-lactalbumin. In certain embodiments, the alpha-lactalbumin enriched whey protein concentrate is present in the weight range from approximately 0.25 grams to approximately 5.0 grams per liter (g/L) of reconstituted, ready-to-use nutritional formula. In certain embodiments, the alpha-lactalbumin enriched whey protein concentrate is present in the weight range from approximately 0.25 grams to approximately 5.0 grams per liter (g/L) of reconstituted, ready-to-use nutritional formula. In certain embodiments, the alpha-lactalbumin enriched whey protein concentrate is present in the weight range from approximately 0.25 grams to approximately 0.5 grams per liter (g/L), approximately 0.5 grams to approximately 0.75 grams per liter (g/L), approximately 0.5 grams to approximately 1.0 grams per liter (g/L), approximately 1.0 grams to approximately 1.5 grams per liter (g/L), approximately 1.5 grams to approximately 1.75 grams per liter (g/L), approximately 1.75 grams to approximately 2.0 grams per liter (g/L), approximately 1.75 grams to approximately 3.0 grams per liter (g/L), approximately 2.0 grams to approximately 3.0 grams per liter (g/L), approximately 2.0 grams to approximately 2.25 grams per liter (g/L), approximately 2.25 grams to approximately 2.5 grams per liter (g/L), approximately 2.5 grams to approximately 2.75 grams per liter (g/L), approximately 2.75 grams to approximately 3.0 grams per liter (g/L), approximately 3.0 grams to approximately 3.25 grams per liter (g/L), approximately 3.25 grams to approximately 3.5 grams per liter (g/L), approximately 3.5 grams to approximately 3.75 grams per liter (g/L), approximately 3.75 grams to approximately 4.0 grams per liter (g/L), approximately 4.0 grams to approximately 4.25 grams per liter (g/L), approximately 4.25 grams to approximately 4.5 grams per liter (g/L), approximately 4.5 grams to approximately 4.75 grams per liter (g/L), approximately 4.75 grams to approximately 5.0 grams per liter (g/L), approximately 1.75 grams to approximately 5.0 grams per liter (g/L), or approximately 5.0 grams to approximately 5.25 grams per liter (g/L), of reconstituted, ready-to-use nutritional formula. In certain embodiments, the alpha-lactalbumin enriched whey protein concentrate is present in the weight range from approximately 0.5 grams to approximately 4.0 grams per liter (g/L) of reconstituted, ready-to-use nutritional formula. In certain embodiments, the alpha-lactalbumin enriched whey protein concentrate is present in the weight range from approximately 2.0 grams to approximately 2.5 grams per liter (g/L), approximately 2.5 grams to approximately 3.0 grams per liter (g/L), approximately 3.0 grams to approximately 5.0 grams per liter (g/L), approximately 0.5 grams to approximately 4.2 grams per liter (g/L), or approximately 3.0 grams to approximately 3.5 grams per liter (g/L), of reconstituted, ready-to-use nutritional formula. In certain embodiments, the alpha-lactalbumin enriched whey protein concentrate is present in the weight range from approximately 2.5 grams to approximately 3.0 grams per liter (g/L) of reconstituted, ready-to-use nutritional formula. In certain embodiments, the alpha-lactalbumin enriched whey protein concentrate is present in the weight range from approximately 2.0 grams to approximately 2.5 grams per liter (g/L), approximately 2.5 grams to approximately 2.6 grams per liter (g/L), approximately 2.6 grams to approximately 2.7 grams per liter (g/L), approximately 2.7 grams to approximately 2.8 grams per liter (g/L), approximately 2.8 grams to approximately 2.9 grams per liter (g/L), approximately 2.6 grams to approximately 2.9 grams per liter (g/L), or approximately 3.0 grams to approximately 3.5 grams per liter (g/L), of reconstituted, ready-to-use nutritional formula. In certain embodiments, the alpha-lactalbumin enriched whey protein concentrate is present in the weight range from approximately 2.6 grams to approximately 2.9 grams per liter (g/L) of reconstituted, ready-to-use nutritional formula. In certain embodiments, the alpha-lactalbumin enriched whey protein concentrate is present in the weight range from approximately 0.5 grams to approximately 4.0 grams of alpha-lactalbumin enriched whey protein concentrate per L of reconstituted, ready-to-use nutritional formula; approximately 2.5 grams to approximately 3.0 grams of alpha-lactalbumin enriched whey protein concentrate per L of reconstituted, ready-to-use nutritional formula; or approximately 2.6 grams to approximately 2.9 grams per liter (g/L) of reconstituted, ready-to-use nutritional formula. In certain embodiments, the alpha-lactalbumin enriched whey protein concentrate is present in the weight range from approximately 2.5 grams to approximately 3.0 grams per liter (g/L) of reconstituted, ready-to-use nutritional formula. In certain embodiments, the nutritional formula includes approximately 2.8 grams of alpha-lactalbumin enriched whey protein concentrate per liter (g/L) of reconstituted, ready-to-use nutritional formula. In certain embodiments, the nutritional formula includes approximately 2.715 grams of alpha-lactalbumin enriched whey protein concentrate per liter (g/L) of reconstituted, ready-to-use nutritional formula. In certain embodiments, the nutritional formula includes approximately 2.7 grams of alpha-lactalbumin enriched whey protein concentrate per liter (g/L) of reconstituted, ready-to-use nutritional formula. In certain embodiments, the nutritional formula includes approximately 2.7 grams of alpha-lactalbumin enriched whey protein concentrate per liter (g/L) of reconstituted, ready-to-use nutritional formula. In certain embodiments, the nutritional formula includes approximately 2.661 grams of alpha-lactalbumin enriched whey protein concentrate per liter (g/L) of reconstituted, ready-to-use nutritional formula. In certain embodiments, the nutritional formula includes approximately 2.6 grams of alpha-lactalbumin enriched whey protein concentrate per liter (g/L) of reconstituted, ready-to-use nutritional formula. In certain embodiments, the nutritional formula includes approximately 2.577 grams of alpha-lactalbumin enriched whey protein concentrate per liter (g/L) of reconstituted, ready-to-use nutritional formula. In certain embodiments, the nutritional formula includes approximately 2.5 grams of alpha-lactalbumin enriched whey protein concentrate per liter (g/L) of reconstituted, ready-to-use nutritional formula. In certain embodiments, the nutritional formula includes approximately 3.6 grams of alpha-lactalbumin per liter (g/L) of reconstituted, ready-to-use nutritional formula. In certain embodiments, the nutritional formula includes approximately 3.592 grams of alpha-lactalbumin enriched whey protein concentrate per liter (g/L) of reconstituted, ready-to-use nutritional formula. In certain embodiments, the nutritional formula includes approximately 3.5 grams of alpha-lactalbumin enriched whey protein concentrate per liter (g/L) of reconstituted, ready-to-use nutritional formula. In certain embodiments, the nutritional formula includes approximately 3.479 grams of alpha-lactalbumin enriched whey protein concentrate per liter (g/L) of reconstituted, ready-to-use nutritional formula. In certain embodiments, the nutritional formula includes approximately 3.4 grams of alpha-lactalbumin enriched whey protein concentrate per liter (g/L) of reconstituted, ready-to-use nutritional formula. In certain embodiments, the nutritional formula includes approximately 1.4 grams of alpha-lactalbumin enriched whey protein concentrate per liter (g/L) of reconstituted, ready-to-use nutritional formula. In certain embodiments, the nutritional formula includes approximately 1.385 grams of alpha-lactalbumin enriched whey protein concentrate per liter (g/L) of reconstituted, ready-to-use nutritional formula. In certain embodiments, the nutritional formula includes approximately 1.3 grams of alpha-lactalbumin enriched whey protein concentrate per liter (g/L) of reconstituted, ready-to-use nutritional formula.

As part of the alpha-lactalbumin enriched whey protein concentrate, the nutritional formula includes alpha-lactalbumin. The alpha-lactalbumin may be obtained from any source. In certain embodiments, the source of alpha-lactalbumin within the formula is demineralized whey, whey protein concentrate, skimmed milk powder, or alpha-lactalbumin enriched whey protein concentrate. In certain embodiments, the alpha-lactalbumin is present in the weight range of 0.25 grams to approximately 5.0 grams per liter (g/L) of reconstituted, ready-to-use nutritional formula. In certain embodiments, the alpha-lactalbumin is present in the weight range from approximately 0.25 grams to approximately 4.5 grams per liter (g/L) of reconstituted, ready-to-use nutritional formula. In certain embodiments, the alpha-lactalbumin is present in the weight range from approximately 0.25 grams to approximately 4.0 grams per liter (g/L) of reconstituted, ready-to-use nutritional formula. In certain embodiments, the alpha-lactalbumin is present in the weight range from approximately 0.25 grams to approximately 0.5 grams per liter (g/L), approximately 0.5 grams to approximately 0.75 grams per liter (g/L), approximately 0.5 grams to approximately 1.0 grams per liter (g/L), approximately 1.0 grams to approximately 1.5 grams per liter (g/L), approximately 1.5 grams to approximately 1.75 grams per liter (g/L), approximately 1.75 grams to approximately 2.0 grams per liter (g/L), approximately 2.0 grams to approximately 2.25 grams per liter (g/L), approximately 2.25 grams to approximately 2.5 grams per liter (g/L), approximately 2.5 grams to approximately 2.75 grams per liter (g/L), approximately 2.75 grams to approximately 3.0 grams per liter (g/L), approximately 3.0 grams to approximately 3.25 grams per liter (g/L), approximately 3.25 grams to approximately 3.5 grams per liter (g/L), approximately 3.5 grams to approximately 3.75 grams per liter (g/L), approximately 3.75 grams to approximately 4.0 grams per liter (g/L), or approximately 4.0 grams to approximately 4.25 grams per liter (g/L), of reconstituted, ready-to-use nutritional formula. In certain embodiments, the alpha-lactalbumin is present in the weight range from approximately 3.25 grams to approximately 3.75 grams per liter (g/L) of reconstituted, ready-to-use nutritional formula. In certain embodiments, the alpha-lactalbumin is present in the weight range from approximately 0.25 grams to approximately 3.5 grams per liter (g/L) of reconstituted, ready-to-use nutritional formula. In certain embodiments, the alpha-lactalbumin is present in the weight range from approximately 0.25 grams to approximately 3.0 grams per liter (g/L) of reconstituted, ready-to-use nutritional formula. In certain embodiments, the alpha-lactalbumin is present in the weight range from approximately 0.5 grams to approximately 3.0 grams per liter (g/L) of reconstituted, ready-to-use nutritional formula. In certain embodiments, the alpha-lactalbumin is present in the weight range from approximately 0.25 grams to approximately 2.5 grams per liter (g/L) of reconstituted, ready-to-use nutritional formula. In certain embodiments, the alpha-lactalbumin is present in the weight range from approximately 0.25 grams to approximately 2.0 grams per liter (g/L) of reconstituted, ready-to-use nutritional formula. In certain embodiments, the alpha-lactalbumin is present in the weight range from approximately 0.25 grams to approximately 1.5 grams per liter (g/L) of reconstituted, ready-to-use nutritional formula. In certain embodiments, the alpha-lactalbumin is present in the weight range from approximately 0.5 grams to approximately 1.5 grams per liter (g/L) of reconstituted, ready-to-use nutritional formula. In certain embodiments, the alpha-lactalbumin is present in the weight range from approximately 0.25 grams to approximately 1.0 grams per liter (g/L) of reconstituted, ready-to-use nutritional formula. In certain embodiments, the alpha-lactalbumin is present in the weight range from approximately 0.25 grams to approximately 0.5 grams per liter (g/L) of reconstituted, ready-to-use nutritional formula. In certain embodiments, the alpha-lactalbumin is present in the weight range from approximately 0.25 grams to approximately 0.5 grams per liter (g/L), approximately 0.5 grams to approximately 1.0 grams per liter (g/L), approximately 1.0 grams to approximately 1.2 grams per liter (g/L), approximately 1.2 grams to approximately 1.25 grams per liter (g/L), or approximately 1.25 grams to approximately 1.5 grams per liter (g/L), of reconstituted, ready-to-use nutritional formula. In certain embodiments, the alpha-lactalbumin is present in the weight range from approximately 0.5 grams to approximately 1.2 grams per liter (g/L), approximately 1.2 grams to approximately 1.5 grams per liter (g/L), or approximately 0.75 grams to approximately 1.5 grams per liter (g/L), of reconstituted, ready-to-use nutritional formula. In certain embodiments, the alpha-lactalbumin is present in the weight range from approximately 0.5 grams to approximately 1.2 grams per liter (g/L), of reconstituted, ready-to-use nutritional formula. In certain embodiments, the nutritional formula includes approximately 1.2 grams of alpha-lactalbumin per liter (g/L) of reconstituted, ready-to-use nutritional formula, approximately 1.16 grams of alpha-lactalbumin per liter (g/L) of reconstituted, ready-to-use nutritional formula or approximately 1.165 grams of alpha-lactalbumin per liter (g/L) of reconstituted, ready-to-use nutritional formula. In certain embodiments, the nutritional formula includes approximately 1.165 grams of alpha-lactalbumin per liter (g/L) of reconstituted, ready-to-use nutritional formula. In certain embodiments, the nutritional formula comprises approximately 0.5 grams to approximately 1.2 grams of alpha-lactalbumin per 100 grams of nutritional formula in powdered form. In certain embodiments, the nutritional formula comprises approximately 0.5 grams to approximately 0.6 grams, approximately 0.6 grams to approximately 0.7 grams, approximately 0.7 grams to approximately 0.8 grams, approximately 0.8 grams to approximately 0.9 grams, approximately 0.9 grams to approximately 1.1 grams, or approximately 1.1 grams to approximately 1.2 grams of alpha-lactalbumin per 100 grams of nutritional formula in powdered form.

The nutritional formula includes demineralized whey. In certain embodiments, the demineralized whey is present in the weight range from approximately 20.0 grams to approximately 21.0 grams per liter (g/L), approximately 21.0 grams to approximately 22.0 grams per liter (g/L), approximately 22.0 grams to approximately 23.0 grams per liter (g/L), approximately 23.0 grams to approximately 23.5 grams per liter (g/L), approximately 23.5 grams to approximately 24.0 grams per liter (g/L), approximately 24.0 grams to approximately 24.5 grams per liter (g/L), approximately 24.0 grams to approximately 25.0 grams per liter (g/L), approximately 25.0 grams to approximately 26.0 grams per liter (g/L), approximately 26.0 grams to approximately 27.0 grams per liter (g/L), approximately 27.0 grams to approximately 28.0 grams per liter (g/L), approximately 28.0 grams to approximately 29.0 grams per liter (g/L), approximately 29.0 grams to approximately 30.0 grams per liter (g/L), or approximately 30.0 grams to approximately 31.0 grams per liter (g/L), of reconstituted, ready-to-use nutritional formula. In certain embodiments, the demineralized whey is present in the weight range from approximately 22.0 grams to approximately 23.0 grams per liter (g/L), approximately 23.0 grams to approximately 23.5 grams per liter (g/L), approximately 23.5 grams to approximately 24.0 grams per liter (g/L), approximately 24.0 grams to approximately 24.5 grams per liter (g/L), approximately 24.0 grams to approximately 25.0 grams per liter (g/L), or approximately 25.0 grams to approximately 26.0 grams per liter (g/L), of reconstituted, ready-to-use nutritional formula. In certain embodiments, the demineralized whey is present in the weight range from approximately 20.0 grams to approximately 30.0 grams of demineralized whey per L of reconstituted, ready-to-use nutritional formula. In certain embodiments, the demineralized whey is present in the weight range from approximately 20.0 grams to approximately 25.0 grams or approximately 25.0 grams to approximately 30.0 grams of demineralized whey per L of reconstituted, ready-to-use nutritional formula.

The nutritional formula includes skimmed milk powder. In certain embodiments, the skimmed milk powder is produced from skimmed milk protein. In certain embodiments, the skimmed milk protein is sourced from a non-human animal (e.g., a cow). In certain embodiments, 0.1-5% or 5% or less of the skimmed milk powder is water by weight. In certain embodiments, 0.1-1.5%, 0.1-0.5%, 0.5-1%, 1-1.5%, or 1.5% or less of the skimmed milk powder is milkfat by weight. In certain embodiments, 34-60% or 34% or more of the skimmed milk powder is milk protein. In certain embodiments, the skimmed milk powder is present in the weight range from approximately 5 grams to approximately 50 grams per liter (g/L) of reconstituted, ready-to-use nutritional formula. In certain embodiments, the skimmed milk powder is present in the weight range from approximately 5.0 grams to approximately 10.0 grams per liter (g/L), approximately 5.0 grams to approximately 10.0 grams per liter (g/L), approximately 10.0 grams to approximately 12.0 grams per liter (g/L), approximately 12.0 grams to approximately 14.0 grams per liter (g/L), approximately 14.0 grams to approximately 16.0 grams per liter (g/L), approximately 16.0 grams to approximately 16.5 grams per liter (g/L), approximately 16.5 grams to approximately 17.0 grams per liter (g/L), approximately 17.0 grams to approximately 17.5 grams per liter (g/L), approximately 17.5 grams to approximately 18.0 grams per liter (g/L), approximately 18.0 grams to approximately 18.5 grams per liter (g/L), or approximately 18.5 grams to approximately 19.0 grams per liter (g/L), of reconstituted, ready-to-use nutritional formula. In certain embodiments, the skimmed milk powder is present in the weight range from approximately 16.5 grams to approximately 18.5 grams of skimmed milk powder per L of reconstituted, ready-to-use nutritional formula. In certain embodiments, the skimmed milk powder is present in the weight range from approximately 16.0 grams to approximately 19.0 grams of skimmed milk powder per L (g/L) or approximately 16.0 grams to approximately 20.0 grams of skimmed milk powder per L (g/L), of reconstituted, ready-to-use nutritional formula. In certain embodiments, the skimmed milk powder is present in the weight range from approximately 10 grams to approximately 20 grams per liter (g/L) of reconstituted, ready-to-use nutritional formula. In certain embodiments, the skimmed milk powder is present in the weight range from approximately 5 grams to approximately 15 grams per liter (g/L) of reconstituted, ready-to-use nutritional formula. In certain embodiments, the skimmed milk powder is present in the weight range from approximately 5 grams to approximately 10 grams per liter (g/L) of reconstituted, ready-to-use nutritional formula. In certain embodiments, the nutritional formula includes approximately 17.0 grams of skimmed milk powder per liter (g/L), approximately 17.25 grams of skimmed milk powder per liter (g/L), or approximately 17.5 grams of skimmed milk powder per liter (g/L), of reconstituted, ready-to-use nutritional formula. In certain embodiments, the nutritional formula includes approximately 18 grams of skimmed milk powder per liter (g/L) of reconstituted, ready-to-use nutritional formula. In certain embodiments, the nutritional formula includes approximately 17.550 grams of skimmed milk powder per liter (g/L) of reconstituted, ready-to-use nutritional formula. In certain embodiments, the nutritional formula includes approximately 17 grams of skimmed milk powder per liter (g/L) of reconstituted, ready-to-use nutritional formula. In certain embodiments, the nutritional formula includes approximately 16.780 grams of skimmed milk powder per liter (g/L) of reconstituted, ready-to-use nutritional formula. In certain embodiments, the nutritional formula includes approximately 16 grams of skimmed milk powder per liter (g/L) of reconstituted, ready-to-use nutritional formula.

The nutritional formula also includes lactoferrin. In certain embodiments, the lactoferrin is from a non-human animal (e.g., a cow). In certain embodiments, the lactoferrin can be obtained from IOI Loders Croklaan (Netherlands), Loders Croklaan B.V. (Netherlands), Milei GmbH (Germany), or Kerry (Ireland). In certain embodiments, the lactoferrin is MLF-2M. In certain embodiments, MLF-2M is obtained from Milei GmbH (Germany). In certain embodiments, lactoferrin is present in the weight range of approximately 0.0002 grams to approximately 0.064 grams per liter (g/L) of reconstituted, ready-to-use nutritional formula. In certain embodiments, lactoferrin is present in the weight range of approximately 0.0002 grams to approximately 0.002 grams per liter (g/L), approximately 0.002 grams to approximately 0.02 grams per liter (g/L), approximately 0.02 grams to approximately 0.04 grams per liter (g/L), approximately 0.04 grams to approximately 0.05 grams per liter (g/L), approximately 0.05 grams to approximately 0.06 grams per liter (g/L), approximately 0.06 grams to approximately 0.08 grams per liter (g/L), approximately 0.08 grams to approximately 0.1 grams per liter (g/L), approximately 0.1 grams to approximately 0.13 grams per liter (g/L), or approximately 0.13 grams to approximately 0.135 grams per liter (g/L), of reconstituted, ready-to-use nutritional formula. In certain embodiments, lactoferrin is present in the weight range of approximately 0.05 grams to approximately 0.135 grams per liter (g/L) of reconstituted, ready-to-use nutritional formula. In certain embodiments, lactoferrin is present in the weight range of approximately 0.01 grams to approximately 1.5 grams per liter (g/L) of reconstituted, ready-to-use nutritional formula. In certain embodiments, lactoferrin is present in the weight range of approximately 0.01 grams to approximately 1.0 grams per liter (g/L) of reconstituted, ready-to-use nutritional formula. In certain embodiments, the lactoferrin is present in the weight range from approximately 0.05 grams to approximately 1.0 grams per liter (g/L) of reconstituted, ready-to-use nutritional formula. In certain embodiments, lactoferrin is present in the weight range of approximately 0.01 grams to approximately 0.5 grams per liter (g/L) of reconstituted, ready-to-use nutritional formula. In certain embodiments, the lactoferrin is present in the weight range from approximately 0.01 grams to approximately 0.02 grams per liter (g/L), approximately 0.02 grams to approximately 0.03 grams per liter (g/L), approximately 0.03 grams to approximately 0.04 grams per liter (g/L), approximately 0.04 grams to approximately 0.05 grams per liter (g/L), approximately 0.05 grams to approximately 0.06 grams per liter (g/L), approximately 0.06 grams to approximately 0.07 grams per liter (g/L), approximately 0.07 grams to approximately 0.08 grams per liter (g/L), approximately 0.08 grams to approximately 0.09 grams per liter (g/L), approximately 0.09 grams to approximately 0.1 grams per liter (g/L), approximately 0.1 grams to approximately 0.13 grams per liter (g/L), or approximately 0.13 grams to approximately 0.15 grams per liter (g/L), of reconstituted, ready-to-use nutritional formula. In certain embodiments, the lactoferrin is present in the weight range from approximately 0.01 grams to approximately 0.02 grams per liter (g/L), approximately 0.02 grams to approximately 0.03 grams per liter (g/L), approximately 0.03 grams to approximately 0.04 grams per liter (g/L), approximately 0.04 grams to approximately 0.05 grams per liter (g/L), approximately 0.05 grams to approximately 0.06 grams per liter (g/L), approximately 0.06 grams to approximately 0.07 grams per liter (g/L), approximately 0.07 grams to approximately 0.08 grams per liter (g/L), approximately 0.08 grams to approximately 0.09 grams per liter (g/L), approximately 0.09 grams to approximately 0.1 grams per liter (g/L), approximately 0.1 grams to approximately 0.13 grams per liter (g/L), or approximately 0.13 grams to approximately 0.15 grams per liter (g/L), approximately 0.13 grams to approximately 0.16 grams per liter (g/L), or approximately 0.16 grams to approximately 0.17 grams per liter (g/L), or approximately 0.02 grams to approximately 0.17 grams per liter (g/L), of reconstituted, ready-to-use nutritional formula. In certain embodiments, the lactoferrin is present in the weight range from approximately 0.05 grams to approximately 0.2 grams per liter (g/L) of reconstituted, ready-to-use nutritional formula. In certain embodiments, lactoferrin is present in the weight range of approximately 0.01 grams to approximately 0.1 grams per liter (g/L) of reconstituted, ready-to-use nutritional formula. In certain embodiments, lactoferrin is present in the weight range of approximately 0.01 grams to approximately 0.05 grams per liter (g/L) of reconstituted, ready-to-use nutritional formula. In certain embodiments, the nutritional formula includes approximately 0.14 grams of lactoferrin per liter (g/L) of reconstituted, ready-to-use nutritional formula. In certain embodiments, the nutritional formula includes approximately 0.135 grams of lactoferrin per liter (g/L) of reconstituted, ready-to-use nutritional formula. In certain embodiments, the nutritional formula includes approximately 0.13 grams of lactoferrin per liter (g/L) of reconstituted, ready-to-use nutritional formula. In certain embodiments, the nutritional formula includes approximately 0.07 grams of lactoferrin per liter (g/L) of reconstituted, ready-to-use nutritional formula. In certain embodiments, the lactoferrin is present in the weight range from approximately 0.02 grams to approximately 1.0 grams per liter (g/L), approximately 0.02 grams to approximately 0.05 grams per liter (g/L), approximately 0.05 grams to approximately 0.10 grams per liter (g/L), approximately 0.02 grams to approximately 0.10 grams per liter (g/L), approximately 0.1 grams to approximately 0.2 grams per liter (g/L), or approximately 0.02 grams to approximately 0.2 grams per liter (g/L), per liter (g/L) of reconstituted, ready-to-use nutritional formula. In certain embodiments, the nutritional formula includes approximately 0.06 grams of lactoferrin per liter (g/L) or approximately 0.07 grams of lactoferrin per liter (g/L) of reconstituted, ready-to-use nutritional formula. In certain embodiments, the lactoferrin is present in the weight range from approximately 0.02 grams to approximately 1.0 grams per liter (g/L), of reconstituted, ready-to-use nutritional formula. In certain embodiments, the nutritional formula includes approximately 0.065 grams of lactoferrin per liter (g/L) of reconstituted, ready-to-use nutritional formula. In certain embodiments, the nutritional formula includes approximately 0.064 grams of lactoferrin per liter (g/L) of reconstituted, ready-to-use nutritional formula. In certain embodiments, the nutritional formula includes approximately 0.063 grams of lactoferrin per liter (g/L) of reconstituted, ready-to-use nutritional formula. In certain embodiments, the nutritional formula includes approximately 0.06 grams of lactoferrin per liter (g/L) of reconstituted, ready-to-use nutritional formula. In certain embodiments, the nutritional formula includes approximately 0.063 grams, 0.133 grams, or 0.162 grams of lactoferrin per liter (g/L) of reconstituted, ready-to-use nutritional formula.

In one aspect, the present nutritional formula includes a vegetable oil blend. In certain embodiments, the vegetable oil blend includes soybean oil, soya lecithin, coconut oil, sunflower (non-high Oleic) oil, and combinations, or a combination thereof. In certain embodiments, the vegetable oil blend includes soybean oil. In certain embodiments, the vegetable oil blend includes soya lecithin. In certain embodiments, the vegetable oil blend includes coconut oil. In certain embodiments, the vegetable oil blend includes oleic acid-palmitic acid-oleic acid triglyceride, wherein palmitic acid is at the SN-2 position of the glycerol backbone of the triglyceride. In certain embodiments, the oleic acid-palmitic acid-oleic acid triglyceride is of Formula (I):

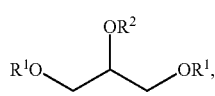

wherein $R^1$ is oleic acid (C18:1), and $R^2$ is palmitic acid (C16:0). In certain embodiments, the SN-2 position of the glycerol backbone of the triglyceride is the second position on the glycerol backbone of the triglyceride. In certain embodiments, the oleic acid-palmitic acid-oleic acid triglyceride is vegetable-derived. In certain embodiments, the oleic acid-palmitic acid-oleic acid triglyceride is from a vegetable oil blend. In certain embodiments, the oleic acid-palmitic acid-oleic acid triglyceride is approximately 30% to 50% of a vegetable oil blend. In certain embodiments, the oleic acid-palmitic acid-oleic acid triglyceride is from high oleic sunflower oil (e.g., high amounts of oleic acid, for example, 80% or more oleic acid, in the sunflower oil), palm oil, and combinations, or a combination thereof. In certain embodiments, the oleic acid-palmitic acid-oleic acid triglyceride is from sunflower oil. In certain embodiments, the oleic acid-palmitic acid-oleic acid triglyceride is from high oleic sunflower oil. In certain embodiments, the oleic acid-palmitic acid-oleic acid triglyceride is from palm oil. In certain embodiments, the vegetable oil blend comprising oleic acid-palmitic acid-oleic acid triglyceride is Betapol DP9100. Betapol DP9100 can be obtained from IOI Loders Croklaan (Netherlands), Loders Croklaan B.V. (Netherlands), and/or Kerry (Ireland). In certain preferred embodiments, the vegetable oil blend comprising oleic acid-palmitic acid-oleic acid triglyceride is an INFAT® fat blend, which can be obtained from Advanced Lipids (Sweden).

In certain embodiments, the nutritional formula includes the vegetable oil blend in the following weight range, in grams per liter (g/L) of reconstituted, ready-to-use nutritional formula: approximately 20 grams to approximately 45 grams of the vegetable oil blend per L of reconstituted, ready-to-use nutritional formula. In certain embodiments, the nutritional formula includes approximately 20 grams to approximately 22 grams of the vegetable oil blend per L (g/L), approximately 22 grams to approximately 25 grams of the vegetable oil blend per L (g/L), approximately 25 grams to approximately 27 grams of the vegetable oil blend per L (g/L), approximately 27 grams to approximately 30 grams of the vegetable oil blend per L (g/L), approximately 30 grams to approximately 32 grams of the vegetable oil blend per L (g/L), approximately 32 grams to approximately 35 grams of the vegetable oil blend per L (g/L), approximately 35 grams to approximately 37 grams of the vegetable oil blend per L (g/L), approximately 37 grams to approximately 40 grams of the vegetable oil blend per L (g/L), approximately 40 grams to approximately 42 grams of the vegetable oil blend per L (g/L), or approximately 42 grams to approximately 45 grams of the vegetable oil blend per L (g/L), of reconstituted, ready-to-use nutritional formula, wherein the triglyceride is vegetable-derived. In certain embodiments, the nutritional formula includes approximately 20 grams to approximately 25 grams of the vegetable oil blend per L (g/L), approximately 25 grams to approximately 30 grams of the vegetable oil blend per L (g/L), approximately 30 grams to approximately 40 grams of the vegetable oil blend per L (g/L), approximately 40 grams to approximately 42 grams of the vegetable oil blend per L (g/L), or approximately 30.0 grams to approximately 42.0 grams of the vegetable oil blend per L (g/L), of reconstituted, ready-to-use nutritional formula. In certain embodiments, the nutritional formula includes approximately 30.0 grams to approximately 42.0 grams of the vegetable oil blend per L (g/L), of reconstituted, ready-to-use nutritional formula, wherein the triglyceride is vegetable-derived. In certain embodiments, the nutritional formula includes approximately 30.0 grams to approximately 42.0 grams of a vegetable oil blend comprising oleic acid-palmitic acid-oleic acid triglyceride; in which approximately 3.0 grams to approximately 7.0 grams of the vegetable oil blend is oleic acid-palmitic acid-oleic acid triglyceride per L of reconstituted, ready-to-use nutritional formula. In certain embodiments, the nutritional formula includes approximately 30.0 grams to approximately 42.0 grams of a vegetable oil blend comprising oleic acid-palmitic acid-oleic acid triglyceride; in which approximately 3.0 grams to approximately 7.0 grams of the vegetable oil blend is oleic acid-palmitic acid-oleic acid triglyceride per L of reconstituted, ready-to-use nutritional formula, wherein the triglyceride is vegetable-derived. In certain embodiments, the nutritional formula includes approximately 25 grams to approximately 40 grams of the vegetable oil blend per L of reconstituted, ready-to-use nutritional formula. In certain embodiments, the nutritional formula includes approximately 30 grams to approximately 40 grams of the vegetable oil blend per L of reconstituted, ready-to-use nutritional formula. In certain embodiments, the nutritional formula includes approximately 35 grams to approximately 40 grams of the vegetable oil blend per L of reconstituted, ready-to-use nutritional formula. In certain embodiments, the nutritional formula includes approximately 37 grams of the vegetable oil blend per L of reconstituted, ready-to-use nutritional formula. In certain embodiments, the nutritional formula includes approximately 36.519 grams of the vegetable oil blend per L of reconstituted, ready-to-use nutritional formula. In certain embodiments, the nutritional formula includes approximately 30 grams, approximately 31 grams, approximately 32 grams, approximately 33 grams, approximately 34 grams, approximately 35 grams, approximately 36 grams, approximately 37 grams, approximately 38 grams, approximately 39 grams, or approximately 40 grams, of the vegetable oil blend per L (g/L) of reconstituted, ready-to-use nutritional formula. In certain embodiments, the nutritional formula includes approximately 36 grams of the vegetable oil blend per L (g/L) of reconstituted, ready-to-use nutritional formula. In certain embodiments, the nutritional formula includes approximately 36.315 grams of the vegetable oil blend per L (g/L) of reconstituted, ready-to-use nutritional formula. In certain embodiments, the nutritional formula includes approximately 35 grams of the vegetable oil blend per L of reconstituted, ready-to-use nutritional formula.

The nutritional formula includes oleic acid-palmitic acid-oleic acid triglyceride as part of the vegetable oil blend. In certain embodiments, the nutritional formula includes oleic acid-palmitic acid-oleic acid triglyceride in the following weight range, in grams per liter (g/L) of reconstituted, ready-to-use nutritional formula: approximately 0.1 grams to approximately 1.5 grams of oleic acid-palmitic acid-oleic acid triglyceride or approximately 1.0 grams to approximately 14.0 grams of oleic acid-palmitic acid-oleic acid triglyceride per L of reconstituted, ready-to-use nutritional formula. In certain embodiments, the nutritional formula includes approximately 0.1 grams to approximately 0.5 grams of oleic acid-palmitic acid-oleic acid triglyceride per L (g/L), approximately 0.5 grams to approximately 1.0 grams of oleic acid-palmitic acid-oleic acid triglyceride per L (g/L), approximately 1.0 grams to approximately 1.5 grams of oleic acid-palmitic acid-oleic acid triglyceride per L (g/L), approximately 1.5 grams to approximately 2.0 grams of oleic acid-palmitic acid-oleic acid triglyceride per L (g/L), approximately 2.0 grams to approximately 2.5 grams of oleic acid-palmitic acid-oleic acid triglyceride per L (g/L), approximately 2.5 grams to approximately 3.0 grams of oleic acid-palmitic acid-oleic acid triglyceride per L (g/L), approximately 3.0 grams to approximately 3.5 grams of oleic acid-palmitic acid-oleic acid triglyceride per L (g/L), approximately 3.5 grams to approximately 4.0 grams of oleic acid-palmitic acid-oleic acid triglyceride per L (g/L), approximately 4.0 grams to approximately 4.25 grams of oleic acid-palmitic acid-oleic acid triglyceride per L (g/L), approximately 4.25 grams to approximately 4.50 grams of oleic acid-palmitic acid-oleic acid triglyceride per L (g/L), approximately 4.50 grams to approximately 4.75 grams of oleic acid-palmitic acid-oleic acid triglyceride per L (g/L), approximately 4.75 grams to approximately 5.0 grams of oleic acid-palmitic acid-oleic acid triglyceride per L (g/L), approximately 5.0 grams to approximately 5.25 grams of oleic acid-palmitic acid-oleic acid triglyceride per L (g/L), approximately 5.25 grams to approximately 5.5 grams of oleic acid-palmitic acid-oleic acid triglyceride per L (g/L), approximately 5.5 grams to approximately 5.75 grams of oleic acid-palmitic acid-oleic acid triglyceride per L (g/L), approximately 5.75 grams to approximately 6.0 grams of oleic acid-palmitic acid-oleic acid triglyceride per L (g/L), approximately 6.0 grams to approximately 6.25 grams of oleic acid-palmitic acid-oleic acid triglyceride per L (g/L), approximately 6.25 grams to approximately 6.5 grams of oleic acid-palmitic acid-oleic acid triglyceride per L (g/L), approximately 6.75 grams to approximately 7.0 grams of oleic acid-palmitic acid-oleic acid triglyceride per L (g/L), of reconstituted, ready-to-use nutritional formula. In certain embodiments, the nutritional formula includes approximately 1.0 grams to approximately 1.5 grams of oleic acid-palmitic acid-oleic acid triglyceride per L (g/L), approximately 1.5 grams to approximately 2.0 grams of oleic acid-palmitic acid-oleic acid triglyceride per L (g/L), approximately 2.0 grams to approximately 2.5 grams of oleic acid-palmitic acid-oleic acid triglyceride per L (g/L), approximately 2.5 grams to approximately 3.0 grams of oleic acid-palmitic acid-oleic acid triglyceride per L (g/L), approximately 3.0 grams to approximately 3.5 grams of oleic acid-palmitic acid-oleic acid triglyceride per L (g/L), approximately 3.5 grams to approximately 4.0 grams of oleic acid-palmitic acid-oleic acid triglyceride per L (g/L), approximately 4.0 grams to approximately 4.25 grams of oleic acid-palmitic acid-oleic acid triglyceride per L (g/L), approximately 4.25 grams to approximately 4.50 grams of oleic acid-palmitic acid-oleic acid triglyceride per L (g/L), approximately 4.50 grams to approximately 4.75 grams of oleic acid-palmitic acid-oleic acid triglyceride per L (g/L), approximately 4.75 grams to approximately 5.0 grams of oleic acid-palmitic acid-oleic acid triglyceride per L (g/L), approximately 5.0 grams to approximately 5.25 grams of oleic acid-palmitic acid-oleic acid triglyceride per L (g/L), approximately 5.25 grams to approximately 5.5 grams of oleic acid-palmitic acid-oleic acid triglyceride per L (g/L), approximately 5.5 grams to approximately 5.75 grams of oleic acid-palmitic acid-oleic acid triglyceride per L (g/L), approximately 5.75 grams to approximately 6.0 grams of oleic acid-palmitic acid-oleic acid triglyceride per L (g/L), of reconstituted, ready-to-use nutritional formula.

In certain embodiments, the nutritional formula includes approximately 1.0 grams to approximately 2.0 grams of oleic acid-palmitic acid-oleic acid triglyceride per L (g/L), approximately 2.0 grams to approximately 3.0 grams of oleic acid-palmitic acid-oleic acid triglyceride per L (g/L), approximately 3.0 grams to approximately 4.0 grams of oleic acid-palmitic acid-oleic acid triglyceride per L (g/L), approximately 4.0 grams to approximately 5.0 grams of oleic acid-palmitic acid-oleic acid triglyceride per L (g/L), approximately 5.0 grams to approximately 6.0 grams of oleic acid-palmitic acid-oleic acid triglyceride, approximately 6.0 grams to approximately 7.0 grams of oleic acid-palmitic acid-oleic acid triglyceride, approximately 7.0 grams to approximately 8.0 grams of oleic acid-palmitic acid-oleic acid triglyceride, approximately 8.0 grams to approximately 9.0 grams of oleic acid-palmitic acid-oleic acid triglyceride, approximately 9.0 grams to approximately 10.0 grams of oleic acid-palmitic acid-oleic acid triglyceride, approximately 10.0 grams to approximately 11.0 grams of oleic acid-palmitic acid-oleic acid triglyceride, approximately 11.0 grams to approximately 12.0 grams of oleic acid-palmitic acid-oleic acid triglyceride, approximately 12.0 grams to approximately 13.0 grams of oleic acid-palmitic acid-oleic acid triglyceride, approximately 13.0 grams to approximately 14.0 grams of oleic acid-palmitic acid-oleic acid triglyceride, approximately 14.0 grams to approximately 14.5 grams of oleic acid-palmitic acid-oleic acid triglyceride, or approximately 14.5 grams to approximately 15.0 grams of oleic acid-palmitic acid-oleic acid triglyceride, per L (g/L), of reconstituted, ready-to-use nutritional formula, wherein the palmitic acid is at the SN-2 position of a glycerol backbone of the triglyceride. In certain embodiments, the nutritional formula includes approximately 2.0 grams to approximately 3.0 grams of oleic acid-palmitic acid-oleic acid triglyceride per L (g/L), approximately 3.0 grams to approximately 4.0 grams of oleic acid-palmitic acid-oleic acid triglyceride per L (g/L), approximately 4.0 grams to approximately 5.0 grams of oleic acid-palmitic acid-oleic acid triglyceride per L (g/L), of reconstituted, ready-to-use nutritional formula. In certain embodiments, the nutritional formula includes approximately 0.1 grams to approximately 1.25 grams of oleic acid-palmitic acid-oleic acid triglyceride per L of reconstituted, ready-to-use nutritional formula. In certain embodiments, the nutritional formula includes approximately 0.1 grams to approximately 1.0 grams of oleic acid-palmitic acid-oleic acid triglyceride per L of reconstituted, ready-to-use nutritional formula. In certain embodiments, the nutritional formula includes approximately 0.1 grams to approximately 0.75 grams of oleic acid-palmitic acid-oleic acid triglyceride per L of reconstituted, ready-to-use nutritional formula. In certain embodiments, the nutritional formula includes approximately 0.3 grams to approximately 0.6 grams of oleic acid-palmitic acid-oleic acid triglyceride per L of reconstituted, ready-to-use nutritional formula. In certain embodiments, the nutritional formula includes approximately 0.4 grams to approximately 0.6 grams of oleic acid-palmitic acid-oleic acid triglyceride per L of reconstituted, ready-to-use nutritional formula. In certain embodiments, the nutritional formula includes approximately 0.6 grams of oleic acid-palmitic acid-oleic acid triglyceride per L of reconstituted, ready-to-use nutritional formula. In certain embodiments, the nutritional formula includes approximately 0.5 grams of oleic acid-palmitic acid-oleic acid triglyceride per L of reconstituted, ready-to-use nutritional formula. In certain embodiments, the nutritional formula includes oleic acid-palmitic acid-oleic acid triglyceride in the following weight range, in grams per liter (g/L) of reconstituted, ready-to-use nutritional formula: approximately 0.5 grams to approximately 5.0 grams of oleic acid-palmitic acid-oleic acid triglyceride per L of reconstituted, ready-to-use nutritional formula. In certain embodiments, the nutritional formula includes approximately 0.5 grams to approximately 4.5 grams of oleic acid-palmitic acid-oleic acid triglyceride per L of reconstituted, ready-to-use nutritional formula. In certain embodiments, the nutritional formula includes approximately 0.5 grams to approximately 4.0 grams of oleic acid-palmitic acid-oleic acid triglyceride per L of reconstituted, ready-to-use nutritional formula. In certain embodiments, the nutritional formula includes approximately 0.5 grams to approximately 3.5 grams of oleic acid-palmitic acid-oleic acid triglyceride per L of reconstituted, ready-to-use nutritional formula. In certain embodiments, the nutritional formula includes approximately 0.5 grams to approximately 3.0 grams of oleic acid-palmitic acid-oleic acid triglyceride per L of reconstituted, ready-to-use nutritional formula. In certain embodiments, the nutritional formula includes approximately 0.5 grams to approximately 2.5 grams of oleic acid-palmitic acid-oleic acid triglyceride per L of reconstituted, ready-to-use nutritional formula. In certain embodiments, the nutritional formula includes approximately 0.5 grams to approximately 2.0 grams of oleic acid-palmitic acid-oleic acid triglyceride per L of reconstituted, ready-to-use nutritional formula. In certain embodiments, the nutritional formula includes approximately 0.5 grams to approximately 1.5 grams of oleic acid-palmitic acid-oleic acid triglyceride per L of reconstituted, ready-to-use nutritional formula. In certain embodiments, the nutritional formula includes approximately 0.5 grams to approximately 1.0 grams of oleic acid-palmitic acid-oleic acid triglyceride per L of reconstituted, ready-to-use nutritional formula. In certain embodiments, the nutritional formula includes approximately 5.0 grams of oleic acid-palmitic acid-oleic acid triglyceride per L of reconstituted, ready-to-use nutritional formula. In certain embodiments, the nutritional formula includes approximately 4.5 grams of oleic acid-palmitic acid-oleic acid triglyceride per L of reconstituted, ready-to-use nutritional formula. In certain embodiments, the nutritional formula includes approximately 4.0 grams of oleic acid-palmitic acid-oleic acid triglyceride per L of reconstituted, ready-to-use nutritional formula. In certain embodiments, the nutritional formula includes approximately 1.0 grams to approximately 6.0 grams, or approximately 6.0 grams to approximately 14.0 grams of oleic acid-palmitic acid-oleic acid triglyceride, per L of reconstituted, ready-to-use nutritional formula, wherein the palmitic acid is at the SN-2 position of a glycerol backbone of the triglyceride. In certain embodiments, the nutritional formula includes approximately 1.0 grams to approximately 14.0 grams, approximately 1.0 grams to approximately 14.5 grams, approximately 2.0 grams to approximately 17.5 grams, approximately 2.0 grams to approximately 14.5 grams, or approximately 14.5 grams to approximately 17.5 grams, of oleic acid-palmitic acid-oleic acid triglyceride per L of reconstituted, ready-to-use nutritional formula, wherein the palmitic acid is at the SN-2 position of a glycerol backbone of the triglyceride. In certain embodiments, the nutritional formula includes approximately 3.0 grams to approximately 7.0 grams of oleic acid-palmitic acid-oleic acid triglyceride per L, of reconstituted, ready-to-use nutritional formula, wherein the palmitic acid is at the SN-2 position of a glycerol backbone of the triglyceride, wherein the triglyceride is vegetable-derived. In certain embodiments, the nutritional formula includes approximately 2.0 grams to approximately 5.0 grams of oleic acid-palmitic acid-oleic acid triglyceride per L of reconstituted, ready-to-use nutritional formula. In certain embodiments, the nutritional formula includes approximately 1.0 grams to approximately 6.0 grams of oleic acid-palmitic acid-oleic acid triglyceride per L, approximately 2.0 grams to approximately 5.0 grams of oleic acid-palmitic acid-oleic acid triglyceride per L, or approximately 3.0 grams to approximately 7.0 grams of oleic acid-palmitic acid-oleic acid triglyceride per L, of reconstituted, ready-to-use nutritional formula, wherein the palmitic acid is at the SN-2 position of a glycerol backbone of the triglyceride. In certain embodiments, the nutritional formula includes approximately 4.8 grams of oleic acid-palmitic acid-oleic acid triglyceride per L (g/L) of reconstituted, ready-to-use nutritional formula. In certain embodiments, the nutritional formula includes approximately 4.84 grams of oleic acid-palmitic acid-oleic acid triglyceride per L (g/L) of reconstituted, ready-to-use nutritional formula. In certain embodiments, the nutritional formula includes approximately 4.9 grams of oleic acid-palmitic acid-oleic acid triglyceride per L of reconstituted, ready-to-use nutritional formula. In certain embodiments, the nutritional formula includes approximately 5.0 grams of oleic acid-palmitic acid-oleic acid triglyceride per L of reconstituted, ready-to-use nutritional formula.

The present nutritional formula also includes carbohydrates. In certain embodiments, the carbohydrates include lactose. In certain embodiments, the nutritional formula includes a decreased amount of lactose, compared to the amount of lactose present in standard full-fat milk (approximately 55 g/L), for example, milk from a mammal, e.g., cow's milk. In certain embodiments, the nutritional formula includes the following weight range of lactose, in grams per liter (g/L) of reconstituted, ready-to-use nutritional formula: approximately 60 grams to approximately 80 grams of lactose per L of reconstituted, ready-to-use nutritional formula. In certain embodiments, the nutritional formula includes approximately 35 grams of lactose per L (g/L) to approximately 80 grams of lactose per L (g/L), approximately 35 grams of lactose per L (g/L) to approximately 40 grams of lactose per L (g/L), approximately 40 grams of lactose per L (g/L) to approximately 45 grams of lactose per L (g/L), approximately 35 grams of lactose per L (g/L) to approximately 45 grams of lactose per L (g/L), approximately 40 grams of lactose per L (g/L) to approximately 50 grams of lactose per L (g/L), approximately 50 grams of lactose per L (g/L) to approximately 60 grams of lactose per L (g/L), approximately 60 grams of lactose per L (g/L) to approximately 70 grams of lactose per L (g/L), approximately 70 grams of lactose per L (g/L) to approximately 80 grams of lactose per L (g/L), or approximately 80 grams of lactose per L (g/L) to approximately 90 grams of lactose per L (g/L), of reconstituted, ready-to-use nutritional formula. In certain embodiments, the nutritional formula includes approximately 35 grams of lactose per L (g/L) to approximately 80 grams of lactose per L (g/L), approximately 35 grams of lactose per L (g/L) to approximately 40 grams of lactose per L (g/L), approximately 40 grams of lactose per L (g/L) to approximately 45 grams of lactose per L (g/L), approximately 35 grams of lactose per L (g/L) to approximately 45 grams of lactose per L (g/L), approximately 40 grams of lactose per L (g/L) to approximately 50 grams of lactose per L (g/L), approximately 50 grams of lactose per L (g/L) to approximately 60 grams of lactose per L (g/L), approximately 60 grams of lactose per L (g/L) to approximately 65 grams of lactose per L (g/L), approximately 65 grams of lactose per L (g/L) to approximately 68 grams of lactose per L (g/L), approximately 68 grams of lactose per L (g/L) to approximately 70 grams of lactose per L (g/L), approximately 60 grams of lactose per L (g/L) to approximately 70 grams of lactose per L (g/L), approximately 70 grams of lactose per L (g/L) to approximately 80 grams of lactose per L (g/L), approximately 65 grams of lactose per L (g/L) to approximately 80 grams of lactose per L (g/L), approximately 80 grams of lactose per L (g/L) to approximately 90 grams of lactose per L (g/L), approximately 90 grams of lactose per L (g/L) to approximately 95 grams of lactose per L (g/L), approximately 95 grams of lactose per L (g/L) to approximately 98 grams of lactose per L (g/L), or approximately 98 grams of lactose per L (g/L) to approximately 99 grams of lactose per L (g/L), of reconstituted, ready-to-use nutritional formula. In certain embodiments, the nutritional formula includes approximately 60 grams of lactose per L (g/L) to approximately 65 grams of lactose per L (g/L), approximately 65 grams of lactose per L (g/L) to approximately 70 grams of lactose per L (g/L), approximately 70 grams of lactose per L (g/L) to approximately 72 grams of lactose per L (g/L), approximately 72 grams of lactose per L (g/L) to approximately 75 grams of lactose per L (g/L), approximately 75 grams of lactose per L (g/L) to approximately 80 grams of lactose per L (g/L), or approximately 70 grams of lactose per L (g/L) to approximately 80 grams of lactose per L (g/L), of reconstituted, ready-to-use nutritional formula. In certain embodiments, the nutritional formula includes approximately 70 grams to approximately 80 grams of lactose per L of reconstituted, ready-to-use nutritional formula. In certain embodiments, the nutritional formula includes approximately 60 grams to approximately 75 grams of lactose per L of reconstituted, ready-to-use nutritional formula. In certain embodiments, the nutritional formula includes approximately 65 grams to approximately 75 grams of lactose per L of reconstituted, ready-to-use nutritional formula. In certain embodiments, the nutritional formula includes approximately 70 grams to approximately 75 grams of lactose per L of reconstituted, ready-to-use nutritional formula. In certain embodiments, the nutritional formula includes approximately 60 grams to approximately 70 grams of lactose per L of reconstituted, ready-to-use nutritional formula. In certain embodiments, the nutritional formula includes approximately 60 grams to approximately 65 grams of lactose per L of reconstituted, ready-to-use nutritional formula. In certain embodiments, the nutritional formula includes approximately 37 grams or approximately 37.1 grams of lactose per L of reconstituted, ready-to-use nutritional formula. In certain embodiments, the nutritional formula includes approximately 72 grams or approximately 73 grams of lactose per L of reconstituted, ready-to-use nutritional formula. In certain embodiments, the nutritional formula includes approximately 74 grams of lactose per L of reconstituted, ready-to-use nutritional formula. In certain embodiments, the nutritional formula includes approximately 73.71 grams of lactose per L of reconstituted, ready-to-use nutritional formula. In certain embodiments, the nutritional formula includes approximately 73 grams of lactose per L of reconstituted, ready-to-use nutritional formula. In certain embodiments, the nutritional formula includes approximately 74 grams of lactose per L of reconstituted, ready-to-use nutritional formula. In certain embodiments, the nutritional formula includes approximately 72.9 grams of lactose per L of reconstituted, ready-to-use nutritional formula. In certain embodiments, the nutritional formula includes approximately 67.0 grams, approximately 72.9 grams, or approximately 97 grams of lactose per L of reconstituted, ready-to-use nutritional formula. In certain embodiments, the nutritional formula includes approximately 67.0 grams of lactose per L of reconstituted, ready-to-use nutritional formula. In certain embodiments, the nutritional formula includes approximately 72 grams of lactose per L of reconstituted, ready-to-use nutritional formula. In certain embodiments, the nutritional formula includes approximately 97 grams of lactose per L of reconstituted, ready-to-use nutritional formula. In certain embodiments, the nutritional formula includes less than approximately 55 grams of lactose per L, less than approximately 54 grams of lactose per L, less than approximately 53 grams of lactose per L, less than approximately 52 grams of lactose per L, less than approximately 50 grams of lactose per L, or less than approximately 45 grams of lactose per L, of reconstituted, ready-to-use nutritional formula. In certain embodiments, the nutritional formula includes approximately 40 grams of lactose per L of reconstituted, ready-to-use nutritional formula. In certain embodiments, the nutritional formula comprises at most 40 grams of lactose, at most 45 grams of lactose, at most 50 grams of lactose, at most 55 grams of lactose, at most 60 grams of lactose, at most 70 grams of lactose, at most 80 grams of lactose, at most 85 grams of lactose, or at most 90 grams of lactose, per L of reconstituted, ready-to-use nutritional formula. In certain embodiments, the nutritional formula comprises at most 40 grams of lactose, at most 45 grams of lactose, at most 50 grams of lactose, at most 55 grams of lactose, at most 60 grams of lactose, at most 65 grams of lactose, at most 68 grams of lactose, at most 69 grams of lactose, at most 70 grams of lactose, at most 72 grams of lactose, at most 80 grams of lactose, at most 85 grams of lactose, at most 90 grams of lactose, at most 95 grams of lactose, or at most 98 grams of lactose, per L of reconstituted, ready-to-use nutritional formula. In certain embodiments, the nutritional formula comprises at most 85 grams of lactose per L of reconstituted, ready-to-use nutritional formula. In certain embodiments, the nutritional formula comprises at most 98 grams of lactose per L of reconstituted, ready-to-use nutritional formula.

In certain embodiments, the carbohydrates in the nutritional formula include maltodextrin. In certain embodiments, the nutritional formula includes at least approximately 0.00001 grams of maltodextrin per L of reconstituted, ready-to-use nutritional formula. In certain embodiments, the nutritional formula includes approximately 0.00001 to 0.05 grams (e.g., 10 micrograms to 50 mg) of maltodextrin per L of reconstituted, ready-to-use nutritional formula. In certain embodiments, the nutritional formula includes approximately 0.00001 to 0.00005 grams (e.g., 10 to 50 micrograms) of maltodextrin per L of reconstituted, ready-to-use nutritional formula. In certain embodiments, the nutritional formula includes approximately 0.00003 grams (e.g., 30 micrograms) of maltodextrin per L of reconstituted, ready-to-use nutritional formula. In certain embodiments, the nutritional formula includes approximately 0.0000344 grams (e.g., 34.4 micrograms) of maltodextrin per L of reconstituted, ready-to-use nutritional formula. In certain embodiments, the nutritional formula includes approximately 0.0005 to 0.05 grams (e.g., 0.5 to 50 mg) of maltodextrin per L of reconstituted, ready-to-use nutritional formula. In certain embodiments, the nutritional formula includes approximately 0.01 grams (e.g., 10 mg) of maltodextrin per L of reconstituted, ready-to-use nutritional formula. In certain embodiments, the nutritional formula includes approximately 0.01138 grams (e.g., 11.38 mg) of maltodextrin per L of reconstituted, ready-to-use nutritional formula.

In certain embodiments, the nutritional formula includes one or more antioxidants. In certain embodiments, the antioxidants include selenium, and vitamins (e.g., vitamin C, vitamin E) and carotenoids, such as beta-carotene, lycopene, and/or lutein. In certain embodiments, the nutritional formula includes lutein. In certain embodiments, the nutritional formula includes the following weight range of lutein, in grams per liter (g/L) of reconstituted, ready-to-use nutritional formula: approximately 60 micrograms to approximately 0.05 grams of lutein, approximately 0.04 grams to approximately 0.05 grams of lutein, approximately 0.043 grams to approximately 0.05 grams of lutein, approximately 0.05 grams to approximately 0.075 grams of lutein, approximately 0.075 grams to approximately 0.1 grams of lutein, approximately 0.1 grams to approximately 0.15 grams of lutein, approximately 0.15 grams to approximately 0.2 grams of lutein, approximately 0.2 grams to approximately 0.25 grams of lutein, approximately 0.25 grams to approximately 0.28 grams of lutein, approximately 0.28 grams to approximately 0.3 grams of lutein, or approximately 0.043 grams to approximately 0.28 grams of lutein, per L of reconstituted, ready-to-use nutritional formula. In certain embodiments, the nutritional formula includes the following weight range of lutein, in grams per liter (g/L) of reconstituted, ready-to-use nutritional formula: approximately 60 micrograms to approximately 0.05 grams of lutein, approximately 0.01 grams to approximately 0.015 grams of lutein, approximately 0.015 grams to approximately 0.017 grams of lutein, approximately 0.017 grams to approximately 0.018 grams of lutein, approximately 0.018 grams to approximately 0.02 grams of lutein, approximately 0.04 grams to approximately 0.05 grams of lutein, approximately 0.043 grams to approximately 0.05 grams of lutein, approximately 0.05 grams to approximately 0.075 grams of lutein, approximately 0.075 grams to approximately 0.1 grams of lutein, approximately 0.1 grams to approximately 0.15 grams of lutein, approximately 0.15 grams to approximately 0.2 grams of lutein, approximately 0.2 grams to approximately 0.205 grams of lutein, approximately 0.205 grams to approximately 0.21 grams of lutein, approximately 0.21 grams to approximately 0.22 grams of lutein, approximately 0.2 grams to approximately 0.23 grams of lutein, approximately 0.23 grams to approximately 0.25 grams of lutein, approximately 0.2 grams to approximately 0.25 grams of lutein, approximately 0.25 grams to approximately 0.28 grams of lutein, approximately 0.28 grams to approximately 0.3 grams of lutein, or approximately 0.043 grams to approximately 0.28 grams of lutein, per L of reconstituted, ready-to-use nutritional formula. In certain embodiments, the nutritional formula includes approximately 0.0025 grams to approximately 0.05 grams of lutein per L of reconstituted, ready-to-use nutritional formula. In certain embodiments, the nutritional formula includes approximately 0.0025 grams to approximately 0.025 grams of lutein per L of reconstituted, ready-to-use nutritional formula. In certain embodiments, the nutritional formula includes approximately 0.015 grams to approximately 0.020 grams of lutein per L of reconstituted, ready-to-use nutritional formula. In certain embodiments, the nutritional formula includes approximately 0.017 grams of lutein per L of reconstituted, ready-to-use nutritional formula. In certain embodiments, the nutritional formula includes approximately 0.0169 grams of lutein per L of reconstituted, ready-to-use nutritional formula. In certain embodiments, the nutritional formula includes approximately 60 micrograms to approximately 100 micrograms of lutein per L of reconstituted, ready-to-use nutritional formula. In certain embodiments, the nutritional formula includes approximately 70 micrograms to approximately 100 micrograms of lutein per L of reconstituted, ready-to-use nutritional formula. In certain embodiments, the nutritional formula includes approximately 80 micrograms to approximately 100 micrograms of lutein per L of reconstituted, ready-to-use nutritional formula. In certain embodiments, the nutritional formula includes approximately 80 micrograms to approximately 90 micrograms of lutein per L of reconstituted, ready-to-use nutritional formula. In certain embodiments, the nutritional formula includes approximately 70 micrograms to approximately 90 micrograms of lutein per L of reconstituted, ready-to-use nutritional formula. In certain embodiments, the nutritional formula includes approximately 60 micrograms to approximately 90 micrograms of lutein per L of reconstituted, ready-to-use nutritional formula. In some embodiments, the nutritional formula includes approximately 86.4 micrograms of lutein per L of reconstituted, ready-to-use nutritional formula. In some embodiments, the nutritional formula includes approximately 0.015 grams to approximately 0.021 grams of lutein per L of reconstituted, ready-to-use nutritional formula.

In certain embodiments, the nutritional formula includes polyunsaturated fatty acids and salts thereof. In certain embodiments, the polyunsaturated fatty acids include docosahexanoic acid (DHA), arachidonic acid, linoleic acid, alpha-linolenic acid, or a combination thereof. In certain embodiments, the nutritional formula includes docosahexanoic acid, arachidonic acid, linoleic acid, and alpha-linolenic acid. The nutritional formula includes a specific ratio of a carotenoid antioxidant (e.g., lutein) to DHA for improvements including promoting postnatal development of the gastrointestinal tract, for example, promoting development of an infant's gastrointestinal tract, proper gastrointestinal function (e.g., intestinal microbiota), promoting nutrient (e.g., calcium) absorption, promoting immune system development; and/or improving bone strength, sleep (e.g., sleep patterns), decreased crying (duration, frequency), decreased fussiness, etc. In certain embodiments, the nutritional formula comprises a lutein to DHA ratio of approximately 0.5 to 1.0, approximately 0.75 to 1.0, approximately 0.8 to 1.0, approximately 1.0 to 1.0, approximately 1.0 to 1.1, approximately 1.0 to 0.9, or approximately 1.0 to 0.8. In certain embodiments, the nutritional formula comprises a lutein to DHA ratio of approximately 1.0 to 1.0. The rationale for the lutein to DHA ratio of approximately 1.0 to 1.0 includes, but is not limited to, provides protection during the uptake of DHA, as lutein is an antioxidant for DHA hydrolysis. In certain embodiments, the nutritional formula includes docosahexanoic acid and arachidonic acid.

In certain embodiments, the nutritional formula includes a combined fungal oil (e.g., *Mortierella alpina* oil) and microalgal oil (e.g., *Crypthecodinium cohnii* oil), which comprises arachidonic acid and docosahexanoic acid in a 2:1 ratio, that also includes the antioxidants of ascorbyl palmitate (approximately 250 ppm) and tocopherols (approximately 250-500 ppm). In certain embodiments, the nutritional formula includes *Crypthecodinium cohnii* oil, fish oil, or combinations, or powders thereof, which comprises the DHA. In certain embodiments, the nutritional formula includes *Crypthecodinium cohnii* oil in powdered form. In certain embodiments, the *Crypthecodinium cohnii* oil is between 15-20% docosahexanoic acid. In certain embodiments, the *Crypthecodinium cohnii* oil is between 15-18% docosahexanoic acid. In certain embodiments, the *Crypthecodinium cohnii* oil powder is approximately 19% docosahexanoic acid. In certain embodiments, the nutritional formula includes *Crypthecodinium cohnii* oil. In certain embodiments, the *Crypthecodinium cohnii* oil is between 5-20% docosahexanoic acid. In certain embodiments, the *Crypthecodinium cohnii* oil is between 10-15% docosahexanoic acid. In certain embodiments, the *Crypthecodinium cohnii* oil is between 8-14% docosahexanoic acid. In certain embodiments, the *Crypthecodinium cohnii* oil is approximately 12% docosahexanoic acid. In certain embodiments, the *Crypthecodinium cohnii* oil is between 15-18% docosahexanoic acid. In certain embodiments, the *Crypthecodinium cohnii* oil is approximately 19% docosahexanoic acid. In certain embodiments, the docosahexanoic acid is from *Crypthecodinium cohnii* oil, fish oil, and combinations, or a combination thereof. In certain embodiments, the docosahexanoic acid is from Driphorm® SCO DHA 50. In certain embodiments, the docosahexanoic acid is sourced from Martek Biosciences Corporation, NuMega Ingredients, DSM Nutritional Products, and/or Royal DSM. In certain embodiments, the docosahexanoic acid is sourced from Martek Biosciences Corporation, NuMega Ingredients, DSM Nutritional Products, Royal DSM, and/or the docosahexanoic acid is formulated as hexane-free Formulaid B. In certain embodiments, the docosahexanoic acid is from *Crypthecodinium cohnii* oil. In certain embodiments, the docosahexanoic acid is from *Schizochytrium* Sp. oil. In certain embodiments, the docosahexanoic acid is from microalgae *Schizochytrium* Sp. oil. In certain embodiments, the docosahexanoic acid is from fish oil. In certain embodiments, the docosahexanoic acid is from algal oil (e.g., microalgal oil, for example, freshwater microalgal oil). In certain embodiments, the docosahexanoic acid is from *Crypthecodinium cohnii* oil, *Schizochytrium* Sp. oil, or fish oil. In certain embodiments, the docosahexanoic acid is not microencapsulated. In certain embodiments, the arachidonic acid is not microencapsulated. In certain embodiments, the docosahexanoic acid and arachidonic acid are both not microencapsulated.

In certain embodiments, the nutritional formula includes the following weight range of docosahexanoic acid and arachidonic acid, in grams per liter (g/L) of reconstituted, ready-to-use nutritional formula: approximately 0.125 grams to approximately 1.5 grams of a combination of docosahexanoic acid and arachidonic acid per L of reconstituted, ready-to-use nutritional formula. In certain embodiments, the nutritional formula includes the following weight range of docosahexanoic acid and arachidonic acid, in grams per liter (g/L) of reconstituted, ready-to-use nutritional formula: approximately 0.05 grams to approximately 0.1 grams of a combination of docosahexanoic acid and arachidonic acid per L (g/L), approximately 0.1 grams to approximately 0.15 grams of a combination of docosahexanoic acid and arachidonic acid per L (g/L), approximately 0.15 grams to approximately 0.2 grams of a combination of docosahexanoic acid and arachidonic acid per L (g/L), approximately 0.2 grams to approximately 0.25 grams of a combination of docosahexanoic acid and arachidonic acid per L (g/L), approximately 0.25 grams to approximately 0.3 grams of a combination of docosahexanoic acid and arachidonic acid per L (g/L), approximately 0.3 grams to approximately 0.35 grams of a combination of docosahexanoic acid and arachidonic acid per L (g/L), approximately 0.35 grams to approximately 0.4 grams of a combination of docosahexanoic acid and arachidonic acid per L (g/L), approximately 0.4 grams to approximately 0.45 grams of a combination of docosahexanoic acid and arachidonic acid per L (g/L), approximately 0.45 grams to approximately 0.5 grams of a combination of docosahexanoic acid and arachidonic acid per L (g/L), approximately 0.1 grams to approximately 0.5 grams of a combination of docosahexanoic acid and arachidonic acid per L (g/L), approximately 0.5 grams to approximately 0.75 grams of a combination of docosahexanoic acid and arachidonic acid per L (g/L), approximately 0.75 grams to approximately 0.9 grams of a combination of docosahexanoic acid and arachidonic acid per L (g/L), approximately 0.9 grams to approximately 1.0 grams of a combination of docosahexanoic acid and arachidonic acid per L (g/L), approximately 1.0 grams to approximately 1.125 grams of a combination of docosahexanoic acid and arachidonic acid per L (g/L), approximately 1.125 grams to approximately 1.5 grams of a combination of docosahexanoic acid and arachidonic acid per L (g/L), approximately 1.5 grams to approximately 1.75 grams of a combination of docosahexanoic acid and arachidonic acid per L (g/L), approximately 1.75 grams to approximately 2.0 grams of a combination of docosahexanoic acid and arachidonic acid per L (g/L), of reconstituted, ready-to-use nutritional formula. In certain embodiments, the nutritional formula includes the following weight range of docosahexanoic acid and arachidonic acid, in grams per liter (g/L) of reconstituted, ready-to-use nutritional formula: approximately 0.075 grams to approximately 0.125 grams of a combination of docosahexanoic acid and arachidonic acid per L (g/L), approximately 0.125 grams to approximately 0.15 grams of a combination of docosahexanoic acid and arachidonic acid per L (g/L), approximately 0.15 grams to approximately 1.5 grams of a combination of docosahexanoic acid and arachidonic acid per L (g/L), approximately 0.15 grams to approximately 0.5 grams of a combination of docosahexanoic acid and arachidonic acid per L (g/L), or approximately 0.15 grams to approximately 0.45 grams of a combination of docosahexanoic acid and arachidonic acid per L (g/L), of reconstituted, ready-to-use nutritional formula. In certain embodiments, the nutritional formula includes approximately 0.15 grams to approximately 1.5 grams of a combination of docosahexanoic acid and arachidonic acid per L (g/L), of reconstituted, ready-to-use nutritional formula. In certain embodiments, the nutritional formula includes approximately 0.2 grams to approximately 1.5 grams of a combination of docosahexanoic acid and arachidonic acid per L of reconstituted, ready-to-use nutritional formula. In certain embodiments, the nutritional formula includes approximately 0.1 grams to approximately 0.5 grams of a combination of docosahexanoic acid and arachidonic acid per L of reconstituted, ready-to-use nutritional formula. In certain embodiments, the nutritional formula includes approximately 0.15 grams, approximately 0.2 grams, approximately 0.201 grams, approximately 0.202 grams, approximately 0.203 grams, approximately 0.204 grams, or approximately 0.205 grams, of a combination of docosahexanoic acid and arachidonic acid per L of reconstituted, ready-to-use nutritional formula. In certain embodiments, the nutritional formula includes approximately 0.205 grams of a combination of docosahexanoic acid and arachidonic acid per L of reconstituted, ready-to-use nutritional formula.

In certain embodiments, the nutritional formula includes docosahexanoic acid, and/or salt forms (e.g., salts, triturates) thereof. In certain embodiments, the nutritional formula includes approximately 0.001 grams to approximately 0.005 grams of docosahexanoic acid per L (g/L), approximately 0.005 grams to approximately 0.01 grams of docosahexanoic acid per L (g/L), approximately 0.01 grams to approximately 0.015 grams of docosahexanoic acid per L (g/L), approximately 0.01 grams to approximately 0.02 grams of docosahexanoic acid per L (g/L), approximately 0.02 grams to approximately 0.03 grams of docosahexanoic acid per L (g/L), approximately 0.03 grams to approximately 0.04 grams of docosahexanoic acid per L (g/L), approximately 0.04 grams to approximately 0.05 grams of docosahexanoic acid per L (g/L), approximately 0.05 grams to approximately 0.06 grams of docosahexanoic acid per L (g/L), approximately 0.06 grams to approximately 0.07 grams of docosahexanoic acid per L (g/L), approximately 0.07 grams to approximately 0.08 grams of docosahexanoic acid per L (g/L), approximately 0.08 grams to approximately 0.09 grams of docosahexanoic acid per L (g/L), approximately 0.09 grams to approximately 0.1 grams of docosahexanoic acid per L (g/L), approximately 0.1 grams to approximately 0.11 grams of docosahexanoic acid per L (g/L), or approximately 0.11 grams to approximately 0.12 grams of docosahexanoic acid per L (g/L), of reconstituted, ready-to-use nutritional formula. In certain embodiments, the nutritional formula includes approximately 0.01 grams to approximately 0.10 grams of docosahexanoic acid per L of reconstituted, ready-to-use nutritional formula. In certain embodiments, the nutritional formula includes approximately 0.03 grams to approximately 0.04 grams of docosahexanoic acid per L (g/L), approximately 0.04 grams to approximately 0.05 grams of docosahexanoic acid per L (g/L), approximately 0.05 grams to approximately 0.06 grams of docosahexanoic acid per L (g/L), approximately 0.06 grams to approximately 0.07 grams of docosahexanoic acid per L (g/L), approximately 0.07 grams to approximately 0.08 grams of docosahexanoic acid per L (g/L), approximately 0.08 grams to approximately 0.09 grams of docosahexanoic acid per L (g/L), approximately 0.09 grams to approximately 0.1 grams of docosahexanoic acid per L (g/L), or approximately 0.001 grams to approximately 0.01 grams of docosahexanoic acid per L (g/L), of reconstituted, ready-to-use nutritional formula. In certain embodiments, the nutritional formula includes approximately 0.05 grams to approximately 0.09 grams of docosahexanoic acid per L of reconstituted, ready-to-use nutritional formula. In certain embodiments, the nutritional formula includes approximately 0.05 grams to approximately 0.08 grams of docosahexanoic acid per L of reconstituted, ready-to-use nutritional formula. In certain embodiments, the nutritional formula includes approximately 0.06 grams to approximately 0.07 grams of docosahexanoic acid per L of reconstituted, ready-to-use nutritional formula. In certain embodiments, the nutritional formula includes approximately 0.01 grams to approximately 0.083 grams of docosahexanoic acid per L of reconstituted, ready-to-use nutritional formula. In certain embodiments, the nutritional formula includes approximately 0.06 grams to approximately 0.083 grams of docosahexanoic acid per L of reconstituted, ready-to-use nutritional formula. In certain embodiments, the nutritional formula includes approximately 0.06 grams of docosahexanoic acid per L (g/L), approximately 0.065 grams of docosahexanoic acid per L (g/L), approximately 0.07 grams of docosahexanoic acid per L (g/L), approximately 0.075 grams of docosahexanoic acid per L (g/L), or approximately 0.08 grams of docosahexanoic acid per L (g/L), of reconstituted, ready-to-use nutritional formula. In certain embodiments, the nutritional formula includes approximately 0.0675 grams of docosahexanoic acid per L of reconstituted, ready-to-use nutritional formula. In certain embodiments, the nutritional formula includes approximately 0.0681 grams of docosahexanoic acid per L of reconstituted, ready-to-use nutritional formula. In certain embodiments, the nutritional formula includes approximately 0.67 grams of docosahexanoic acid per L of reconstituted, ready-to-use nutritional formula. In certain embodiments, the nutritional formula includes approximately 0.060 grams of docosahexanoic acid per L of reconstituted, ready-to-use nutritional formula.

In certain embodiments, the nutritional formula includes the fungal oil, *Mortierella alpina* oil, which comprises arachidonic acid. In certain embodiments, the arachidonic acid is from *Mortierella alpina* oil. In certain embodiments, the nutritional formula includes arachidonic acid, and/or salt forms, or other forms (e.g., triturates) thereof. In certain embodiments, the arachidonic acid is sourced from Martek Biosciences Corporation (U.S.A.), NuMega Ingredients (Australia), DSM Nutritional Products (Netherlands), and/or Royal DSM (Netherlands). In certain embodiments, the nutritional formula includes approximately 0.1 grams to approximately 1.0 grams of arachidonic acid per L (g/L) of reconstituted, ready-to-use nutritional formula. In certain embodiments, the nutritional formula includes approximately 0.001 grams to approximately 0.005 grams of arachidonic acid per L (g/L), approximately 0.005 grams to approximately 0.01 grams of arachidonic acid per L (g/L), approximately 0.01 grams to approximately 0.015 grams of arachidonic acid per L (g/L), approximately 0.015 grams to approximately 0.02 grams of arachidonic acid per L (g/L), approximately 0.02 grams to approximately 0.05 grams of arachidonic acid per L (g/L), approximately 0.05 grams to approximately 0.1 grams of arachidonic acid, approximately 0.1 grams to approximately 0.2 grams of arachidonic acid per L (g/L), approximately 0.2 grams to approximately 0.3 grams of arachidonic acid per L (g/L), approximately 0.3 grams to approximately 0.4 grams of arachidonic acid per L (g/L), approximately 0.4 grams to approximately 0.5 grams of arachidonic acid per L (g/L), approximately 0.5 grams to approximately 0.6 grams of arachidonic acid per L (g/L), approximately 0.6 grams to approximately 0.7 grams of arachidonic acid per L (g/L), approximately 0.7 grams to approximately 0.8 grams of arachidonic acid per L (g/L), approximately 0.8 grams to approximately 0.9 grams of arachidonic acid per L (g/L), or approximately 0.9 grams to approximately 1.0 grams of arachidonic acid per L (g/L), of reconstituted, ready-to-use nutritional formula. In certain embodiments, the nutritional formula includes approximately 0.05 grams to approximately 0.075 grams of arachidonic acid per L (g/L), approximately 0.075 grams to approximately 0.1 grams of arachidonic acid per L (g/L), approximately 0.1 grams to approximately 0.2 grams of arachidonic acid per L (g/L), approximately 0.2 grams to approximately 0.3 grams of arachidonic acid per L (g/L), approximately 0.3 grams to approximately 0.4 grams of arachidonic acid per L (g/L), approximately 0.4 grams to approximately 0.5 grams of arachidonic acid per L (g/L), approximately 0.5 grams to approximately 0.6 grams of arachidonic acid per L (g/L), approximately 0.1 grams to approximately 0.5 grams of arachidonic acid per L (g/L), or approximately 0.001 grams to approximately 0.1 grams of arachidonic acid per L (g/L), of reconstituted, ready-to-use nutritional formula. In certain embodiments, the nutritional formula includes approximately 0.1 grams to approximately 0.5 grams of arachidonic acid per L of reconstituted, ready-to-use nutritional formula. In certain embodiments, the nutritional formula includes approximately 0.1 grams to approximately 0.2 grams of arachidonic acid per L of reconstituted, ready-to-use nutritional formula. In certain embodiments, the nutritional formula includes approximately 0.15 grams of arachidonic acid per L of reconstituted, ready-to-use nutritional formula. In certain embodiments, the nutritional formula includes approximately 0.14 grams of arachidonic acid per L of reconstituted, ready-to-use nutritional formula. In certain embodiments, the nutritional formula includes approximately 0.13 grams of arachidonic acid per L (g/L), approximately 0.135 grams of arachidonic acid per L (g/L), approximately 0.136 grams of arachidonic acid per L (g/L), approximately 0.137 grams of arachidonic acid per L (g/L), approximately 0.138 grams of arachidonic acid per L (g/L), approximately 0.139 grams of arachidonic acid per L (g/L), or approximately 0.14 grams of arachidonic acid per L (g/L), of reconstituted, ready-to-use nutritional formula. In certain embodiments, the nutritional formula includes approximately 0.135 grams of arachidonic acid per L of reconstituted, ready-to-use nutritional formula. In certain embodiments, the nutritional formula includes approximately 0.137 grams of arachidonic acid per L of reconstituted, ready-to-use nutritional formula. In certain embodiments, the nutritional formula includes approximately 0.2 grams of arachidonic acid per L of reconstituted, ready-to-use nutritional formula. In certain embodiments, the nutritional formula includes approximately 0.135 grams of arachidonic acid per L of reconstituted, ready-to-use nutritional formula. In certain embodiments, the nutritional formula includes approximately 0.1 grams of arachidonic acid per L of reconstituted, ready-to-use nutritional formula.

In certain embodiments, the nutritional formula includes linoleic acid and/or salt forms, or other forms (e.g., triturates) thereof. In certain embodiments, the nutritional formula includes approximately 0.25 grams to approximately 7.0 grams of linoleic acid per L of reconstituted, ready-to-use nutritional formula. In certain embodiments, the nutritional formula includes approximately 0.25 grams to approximately 6.0 grams of linoleic acid per L of reconstituted, ready-to-use nutritional formula. In certain embodiments, the nutritional formula includes approximately 5.0 grams to approximately 6.0 grams of linoleic acid per L of reconstituted, ready-to-use nutritional formula. In certain embodiments, the nutritional formula includes approximately 0.25 grams to approximately 5.0 grams of linoleic acid per L of reconstituted, ready-to-use nutritional formula. In certain embodiments, the nutritional formula includes approximately 0.25 grams to approximately 4.0 grams of linoleic acid per L of reconstituted, ready-to-use nutritional formula. In certain embodiments, the nutritional formula includes approximately 0.25 grams to approximately 3.0 grams of linoleic acid per L of reconstituted, ready-to-use nutritional formula. In certain embodiments, the nutritional formula includes approximately 0.25 grams to approximately 2.0 grams of linoleic acid per L of reconstituted, ready-to-use nutritional formula. In certain embodiments, the nutritional formula includes approximately 0.25 grams to approximately 1.0 grams of linoleic acid per L of reconstituted, ready-to-use nutritional formula. In certain embodiments, the nutritional formula includes approximately 0.25 grams to approximately 0.75 grams of linoleic acid per L of reconstituted, ready-to-use nutritional formula. In certain embodiments, the nutritional formula includes approximately 0.25 grams to approximately 0.5 grams of linoleic acid per L of reconstituted, ready-to-use nutritional formula. In certain embodiments, the nutritional formula includes approximately 0.45 grams to approximately 0.5 grams of linoleic acid per L of reconstituted, ready-to-use nutritional formula. In certain embodiments, the nutritional formula includes approximately 5.0 grams to approximately 6.0 grams of linoleic acid per L of reconstituted, ready-to-use nutritional formula. In certain embodiments, the nutritional formula includes approximately 6.0 grams of linoleic acid per L of reconstituted, ready-to-use nutritional formula. In certain embodiments, the nutritional formula includes approximately 5.0 grams to approximately 6.3 grams of linoleic acid, approximately 5.0 grams to approximately 6.2 grams of linoleic acid, approximately 5.3 grams to approximately 7.0 grams of linoleic acid, approximately 5.3 grams to approximately 6.0 grams of linoleic acid, or approximately 5.3 grams to approximately 6.2 grams of linoleic acid per L, approximately 5.3 grams to approximately 6.3 grams of linoleic acid, approximately 6.0 grams to approximately 6.1 grams of linoleic acid, approximately 6.1 grams to approximately 6.3 grams of linoleic acid, approximately 5.7 grams to approximately 6.3 grams of linoleic acid, approximately 5.8 grams to approximately 6.2 grams of linoleic acid of reconstituted, ready-to-use nutritional formula. In certain embodiments, the nutritional formula comprises approximately 5.3 grams to approximately 6.3 grams of linoleic acid per L of reconstituted, ready-to-use nutritional formula. In certain embodiments, the nutritional formula includes approximately 5.967 grams of linoleic acid per L of reconstituted, ready-to-use nutritional formula. In certain embodiments, the nutritional formula includes approximately 5.0 grams of linoleic acid per L of reconstituted, ready-to-use nutritional formula. In certain embodiments, the nutritional formula includes approximately 5.616 grams of linoleic acid per L of reconstituted, ready-to-use nutritional formula. In certain embodiments, the nutritional formula includes approximately 5.3 grams to approximately 6.2 grams of linoleic acid or approximately 5.9 grams or approximately 6.1 grams of linoleic acid per L of reconstituted, ready-to-use nutritional formula, (e.g., approximately 5.3 grams to approximately 6.2 grams of linoleic acid per L of reconstituted, ready-to-use nutritional formula). In certain embodiments, the nutritional formula includes approximately 5.0 grams to approximately 6.2 grams of linoleic acid per L of reconstituted, ready-to-use nutritional formula. In certain embodiments, the nutritional formula includes approximately 5.3 grams to approximately 6.2 grams of linoleic acid per L of reconstituted, ready-to-use nutritional formula. In certain embodiments, the nutritional formula includes approximately 0.45 grams of linoleic acid per L of reconstituted, ready-to-use nutritional formula.

In certain embodiments, the nutritional formula includes alpha-linolenic acid, and/or salt forms, or other forms (e.g., triturates) thereof. In certain embodiments, the nutritional formula includes approximately 0.020 grams to approximately 0.75 grams of alpha-linolenic acid per L of reconstituted, ready-to-use nutritional formula. In certain embodiments, the nutritional formula includes approximately 0.020 grams to approximately 0.6 grams of alpha-linolenic acid per L of reconstituted, ready-to-use nutritional formula. In certain embodiments, the nutritional formula includes approximately 0.050 grams to approximately 0.6 grams of alpha-linolenic acid per L of reconstituted, ready-to-use nutritional formula. In certain embodiments, the nutritional formula includes approximately 0.075 grams to approximately 0.6 grams of alpha-linolenic acid per L of reconstituted, ready-to-use nutritional formula. In certain embodiments, the nutritional formula includes approximately 0.1 grams to approximately 0.6 grams of alpha-linolenic acid per L of reconstituted, ready-to-use nutritional formula. In certain embodiments, the nutritional formula includes approximately 0.1 grams to approximately 0.6 grams, approximately 0.1 grams to approximately 0.25 grams, approximately 0.25 grams to approximately 0.4 grams, approximately 0.4 grams to approximately 0.55 grams, approximately 0.4 grams to approximately 0.5 grams, approximately 0.5 grams to approximately 0.6 grams, approximately 0.4 grams to approximately 0.6 grams, approximately 0.5 grams to approximately 0.65 grams, or approximately 0.25 grams to approximately 0.6 grams of alpha-linolenic acid per L of reconstituted, ready-to-use nutritional formula. In certain embodiments, the nutritional formula includes approximately 0.25 grams to approximately 0.6 grams of alpha-linolenic acid per L of reconstituted, ready-to-use nutritional formula. In certain embodiments, the nutritional formula includes approximately 0.2 grams to approximately 0.6 grams of alpha-linolenic acid per L of reconstituted, ready-to-use nutritional formula. In certain embodiments, the nutritional formula includes approximately 0.25 grams to approximately 0.6 grams of alpha-linolenic acid per L of reconstituted, ready-to-use nutritional formula. In certain embodiments, the nutritional formula includes approximately 0.4 grams to approximately 0.5 grams of alpha-linolenic acid per L of reconstituted, ready-to-use nutritional formula. In certain embodiments, the nutritional formula includes approximately 0.6 grams of alpha-linolenic acid per L of reconstituted, ready-to-use nutritional formula. In certain embodiments, the nutritional formula includes approximately 0.548 grams of alpha-linolenic acid per L of reconstituted, ready-to-use nutritional formula. In certain embodiments, the nutritional formula includes approximately 0.5 grams of alpha-linolenic acid per L of reconstituted, ready-to-use nutritional formula. In certain embodiments, the nutritional formula includes approximately 0.421 grams of alpha-linolenic acid per L of reconstituted, ready-to-use nutritional formula. In certain embodiments, the nutritional formula includes approximately 0.42 grams, approximately 0.53 grams, or approximately 0.54 grams of alpha-linolenic acid per L of reconstituted, ready-to-use nutritional formula. In certain embodiments, the nutritional formula includes approximately 0.4 grams of alpha-linolenic acid per L of reconstituted, ready-to-use nutritional formula.

In certain embodiments, the prebiotics include galactooligosaccharides and fructooligosaccharides. In certain embodiments, the nutritional formula includes approximately 1.75 grams to approximately 3.0 grams per L, approximately 1.75 grams to approximately 5.0 grams per L, approximately 2.0 grams to approximately 3.0 grams per L, approximately 2.5 grams to approximately 5.5 grams per L, approximately 3.0 grams to approximately 5.0 grams per L, or 0.1 grams to approximately 6.0 grams of prebiotics (e.g., galactooligosaccharides and fructooligosaccharides) per L of reconstituted, ready-to-use nutritional formula. In certain embodiments, the nutritional formula includes approximately 1.75 grams to approximately 3.0 grams per L, approximately 1.75 grams to approximately 5.0 grams per L, approximately 2.0 grams to approximately 2.2 grams per L, approximately 2.2 grams to approximately 2.5 grams per L, approximately 2.5 grams to approximately 3.0 grams per L, approximately 2.0 grams to approximately 3.0 grams per L, approximately 2.2 grams to approximately 4.0 grams per L, approximately 2.2 grams to approximately 2.8 grams per L, approximately 2.8 grams to approximately 3.0 grams per L, approximately 2.5 grams to approximately 5.5 grams per L, approximately 3.0 grams to approximately 5.0 grams per L, approximately 3.0 grams to approximately 3.5 grams per L, approximately 3.5 grams to approximately 4.0 grams per L, approximately 4.0 grams to approximately 4.15 grams per L, approximately 4.15 grams to approximately 4.25 grams per L, approximately 4.25 grams to approximately 4.5 grams per L, approximately 4.5 grams to approximately 5.0 grams per L, approximately 5.0 grams to approximately 5.25 grams per L, approximately 5.25 grams to approximately 5.5 grams per L, approximately 2.0 grams to approximately 5.0 grams per L, approximately 2.0 grams to approximately 4.5 grams per L, approximately 2.3 grams to approximately 4.45 grams per L, approximately 2.2 grams to approximately 5.5 grams, or 0.1 grams to approximately 6.0 grams of prebiotics (e.g., galactooligosaccharides, fructooligosaccharides, combinations thereof) per L of reconstituted, ready-to-use nutritional formula. In certain embodiments, the nutritional formula includes approximately 0.5 grams to approximately 5.0 grams of prebiotics (e.g., galactooligosaccharides and fructooligosaccharides) per L of reconstituted, ready-to-use nutritional formula. In certain embodiments, the nutritional formula includes approximately 0.5 grams to approximately 4.0 grams of prebiotics (e.g., galactooligosaccharides and fructooligosaccharides) per L of reconstituted, ready-to-use nutritional formula. In certain embodiments, the nutritional formula includes approximately 2.0 grams to approximately 3.0 grams of prebiotics (e.g., galactooligosaccharides and fructooligosaccharides) per L of reconstituted, ready-to-use nutritional formula. In certain embodiments, the nutritional formula includes approximately 2.2 grams to approximately 4.0 grams, of prebiotics (e.g., galactooligosaccharides, fructooligosaccharides, combinations thereof) per L of reconstituted, ready-to-use nutritional formula. In certain embodiments, the nutritional formula includes approximately 2.2 grams to approximately 4.5 grams, or approximately 2.2 grams to approximately 5.5 grams of prebiotics (e.g., galactooligosaccharides, fructooligosaccharides, combinations thereof) per L of reconstituted, ready-to-use nutritional formula. In certain embodiments, the nutritional formula includes approximately 2.2 grams to approximately 4.0 grams of prebiotics (e.g., galactooligosaccharides, fructooligosaccharides, combinations thereof) per L of reconstituted, ready-to-use nutritional formula. In certain embodiments, the nutritional formula includes approximately 2.2 grams to approximately 4.5 grams of prebiotics (e.g., galactooligosaccharides, fructooligosaccharides, combinations thereof) per L of reconstituted, ready-to-use nutritional formula. In certain embodiments, the nutritional formula includes approximately 2.2 grams to approximately 5.5 grams of prebiotics (e.g., galactooligosaccharides, fructooligosaccharides, combinations thereof) per L of reconstituted, ready-to-use nutritional formula. In certain embodiments, the nutritional formula includes approximately 3.0 grams to approximately 4.0 grams of prebiotics (e.g., galactooligosaccharides and fructooligosaccharides) per L of reconstituted, ready-to-use nutritional formula. In certain embodiments, the nutritional formula includes approximately 4.0 grams to approximately 5.0 grams of prebiotics (e.g., galactooligosaccharides and fructooligosaccharides) per L of reconstituted, ready-to-use nutritional formula. In certain embodiments, the nutritional formula includes approximately 4 grams of prebiotics (e.g., galactooligosaccharides and fructooligosaccharides) per L of reconstituted, ready-to-use nutritional formula. In certain embodiments, the nutritional formula includes approximately 4.185 grams of prebiotics (e.g., galactooligosaccharides and fructooligosaccharides) per L of reconstituted, ready-to-use nutritional formula. In certain embodiments, the nutritional formula includes approximately 2.5 grams of prebiotics (e.g., galactooligosaccharides and fructooligosaccharides) per L of reconstituted, ready-to-use nutritional formula. In certain embodiments, the nutritional formula includes approximately 2.591 grams of prebiotics (e.g., galactooligosaccharides and fructooligosaccharides) per L of reconstituted, ready-to-use nutritional formula.

In certain embodiments, the prebiotics include galactooligosaccharides, fructooligosaccharides, or a combination thereof. In certain embodiments, the prebiotics include galactooligosaccharides and fructooligosaccharides. In certain embodiments, the galactooligosaccharides are sourced from FrieslandCampina (Netherlands). In certain embodiments, the nutritional formula includes approximately 0.05 grams to approximately 0.056 grams of galactooligosaccharides per L (g/L), approximately 0.05 grams to approximately 0.6 grams of galactooligosaccharides per L (g/L), approximately 0.056 grams to approximately 0.6 grams of galactooligosaccharides per L (g/L), approximately 0.1 grams to approximately 0.5 grams of galactooligosaccharides per L (g/L), approximately 1.0 grams to approximately 2.0 grams of galactooligosaccharides per L (g/L), approximately 2.0 grams to approximately 3.0 grams of galactooligosaccharides per L (g/L), approximately 3.0 grams to approximately 4.0 grams of galactooligosaccharides per L (g/L), approximately 3.5 grams to approximately 4.5 grams of galactooligosaccharides per L (g/L), approximately 4.0 grams to approximately 4.5 grams of galactooligosaccharides per L (g/L), approximately 4.5 grams to approximately 5.0 grams of galactooligosaccharides per L (g/L), approximately 5.0 grams to approximately 5.4 grams of galactooligosaccharides per L (g/L), approximately 2.0 grams to approximately 4.0 grams of galactooligosaccharides per L (g/L), or approximately 0.5 grams to approximately 5.4 grams of galactooligosaccharides per L (g/L), of reconstituted, ready-to-use nutritional formula. In certain embodiments, the nutritional formula includes approximately 0.05 grams to approximately 0.056 grams of galactooligosaccharides per L (g/L), approximately 0.05 grams to approximately 0.6 grams of galactooligosaccharides per L (g/L), approximately 0.056 grams to approximately 0.6 grams of galactooligosaccharides per L (g/L), approximately 0.1 grams to approximately 0.5 grams of galactooligosaccharides per L (g/L), approximately 1.0 grams to approximately 2.0 grams of galactooligosaccharides per L (g/L), approximately 2.0 grams to approximately 2.1 grams of galactooligosaccharides per L (g/L), approximately 2.1 grams to approximately 2.5 grams of galactooligosaccharides per L (g/L), approximately 2.0 grams to approximately 2.5 grams of galactooligosaccharides per L (g/L), approximately 2.5 grams to approximately 3.0 grams of galactooligosaccharides per L (g/L), approximately 2.0 grams to approximately 3.0 grams of galactooligosaccharides per L (g/L), approximately 2.0 grams to approximately 3.5 grams of galactooligosaccharides per L (g/L), approximately 3.5 grams to approximately 4.0 grams of galactooligosaccharides per L (g/L), approximately 3.0 grams to approximately 4.0 grams of galactooligosaccharides per L (g/L), approximately 3.5 grams to approximately 4.5 grams of galactooligosaccharides per L (g/L), approximately 4.0 grams to approximately 4.5 grams of galactooligosaccharides per L (g/L), approximately 4.5 grams to approximately 5.0 grams of galactooligosaccharides per L (g/L), approximately 5.0 grams to approximately 5.4 grams of galactooligosaccharides per L (g/L), approximately 2.0 grams to approximately 4.0 grams of galactooligosaccharides per L (g/L), approximately 2.0 grams to approximately 4.2 grams of galactooligosaccharides per L (g/L), approximately 2.0 grams to approximately 4.1 grams of galactooligosaccharides per L (g/L), approximately 2.0 grams to approximately 5.0 grams of galactooligosaccharides per L (g/L), or approximately 0.5 grams to approximately 5.4 grams of galactooligosaccharides per L (g/L), of reconstituted, ready-to-use nutritional formula. In certain embodiments, the nutritional formula includes approximately 0.1 grams to approximately 10.0 grams of galactooligosaccharides per L of reconstituted, ready-to-use nutritional formula. In certain embodiments, the nutritional formula includes approximately 1.0 grams to approximately 8.0 grams of galactooligosaccharides per L of reconstituted, ready-to-use nutritional formula. In certain embodiments, the nutritional formula includes approximately 2.0 grams to approximately 3.5 grams of galactooligosaccharides per L of reconstituted, ready-to-use nutritional formula. In certain embodiments, the nutritional formula includes approximately 2.0 grams to approximately 4.2 grams of galactooligosaccharides per L of reconstituted, ready-to-use nutritional formula. In certain embodiments, the nutritional formula includes approximately 2.0 grams to approximately 5.0 grams of galactooligosaccharides per L of reconstituted, ready-to-use nutritional formula. In certain embodiments, the nutritional formula includes approximately 2.0 grams to approximately 8.0 grams of galactooligosaccharides per L of reconstituted, ready-to-use nutritional formula. In certain embodiments, the nutritional formula includes approximately 3.0 grams to approximately 8.0 grams of galactooligosaccharides per L of reconstituted, ready-to-use nutritional formula. In certain embodiments, the nutritional formula includes approximately 3.0 grams to approximately 7.0 grams of galactooligosaccharides per L of reconstituted, ready-to-use nutritional formula. In certain embodiments, the nutritional formula includes approximately 3.0 grams to approximately 6.0 grams of galactooligosaccharides per L of reconstituted, ready-to-use nutritional formula. In certain embodiments, the nutritional formula includes approximately 2.0 grams to approximately 5.0 grams of galactooligosaccharides per L of reconstituted, ready-to-use nutritional formula. In certain embodiments, the nutritional formula includes approximately 3.0 grams to approximately 5.0 grams of galactooligosaccharides per L of reconstituted, ready-to-use nutritional formula. In certain embodiments, the nutritional formula includes approximately 4 grams of galactooligosaccharides per L of reconstituted, ready-to-use nutritional formula. In certain embodiments, the nutritional formula includes approximately 3.915 grams of galactooligosaccharides per L of reconstituted, ready-to-use nutritional formula. In certain embodiments, the nutritional formula includes approximately 2.1 grams or approximately 2.3 grams of galactooligosaccharides per L of reconstituted, ready-to-use nutritional formula. In certain embodiments, the nutritional formula includes approximately 2 grams of galactooligosaccharides per L of reconstituted, ready-to-use nutritional formula. In certain embodiments, the nutritional formula includes approximately 2.331 grams of galactooligosaccharides per L of reconstituted, ready-to-use nutritional formula. In certain embodiments, the nutritional formula includes approximately 0.1 grams to approximately 1.0 grams of fructooligosaccharides per L of reconstituted, ready-to-use nutritional formula. In certain embodiments, the nutritional formula includes approximately 0.05 grams to approximately 0.6 grams of fructooligosaccharides per L (g/L), approximately 0.056 grams to approximately 0.6 grams of fructooligosaccharides per L (g/L), or approximately 1.0 grams to approximately 4.0 grams of fructooligosaccharides per L (g/L), of reconstituted, ready-to-use nutritional formula. In certain embodiments, the nutritional formula includes approximately 0.1 grams to approximately 1.0 grams of fructooligosaccharides per L of reconstituted, ready-to-use nutritional formula. In certain embodiments, the nutritional formula includes approximately 0.05 grams to approximately 0.6 grams of fructooligosaccharides per L (g/L), approximately 0.056 grams to approximately 0.6 grams of fructooligosaccharides per L (g/L), approximately 0.1 grams to approximately 0.3 grams of fructooligosaccharides per L (g/L), approximately 0.2 grams to approximately 0.25 grams of fructooligosaccharides per L (g/L), approximately 0.25 grams to approximately 0.3 grams of fructooligosaccharides per L (g/L), approximately 0.2 grams to approximately 0.27 grams of fructooligosaccharides per L (g/L), approximately 0.2 grams to approximately 0.3 grams of fructooligosaccharides per L (g/L), approximately 0.3 grams to approximately 0.4 grams of fructooligosaccharides per L (g/L), approximately 0.4 grams to approximately 0.5 grams of fructooligosaccharides per L (g/L), approximately 0.5 grams to approximately 0.75 grams of fructooligosaccharides per L (g/L), approximately 0.75 grams to approximately 1.0 grams of fructooligosaccharides per L (g/L), or approximately 1.0 grams to approximately 4.1 grams of fructooligosaccharides, approximately 1.0 grams to approximately 4.2 grams of fructooligosaccharides, per L (g/L), of reconstituted, ready-to-use nutritional formula. In certain embodiments, the nutritional formula includes approximately 1.0 grams to approximately 4.1 grams of fructooligosaccharides per L of reconstituted, ready-to-use nutritional formula. In certain embodiments, the nutritional formula includes approximately 0.5 grams to approximately 1.0 grams of fructooligosaccharides per L of reconstituted, ready-to-use nutritional formula. In certain embodiments, the nutritional formula includes approximately 0.2 grams to approximately 0.27 grams of fructooligosaccharides per L of reconstituted, ready-to-use nutritional formula. In certain embodiments, the nutritional formula includes approximately approximately 0.2 grams to approximately 0.42 grams of fructooligosaccharides per L of reconstituted, ready-to-use nutritional formula. In certain embodiments, the nutritional formula includes approximately 0.1 grams to approximately 0.5 grams of fructooligosaccharides per L of reconstituted, ready-to-use nutritional formula. In certain embodiments, the nutritional formula includes approximately 0.2 grams to approximately 0.4 grams of fructooligosaccharides per L of reconstituted, ready-to-use nutritional formula. In certain embodiments, the nutritional formula includes approximately 0.2 grams to approximately 0.3 grams of fructooligosaccharides per L of reconstituted, ready-to-use nutritional formula. In certain embodiments, the nutritional formula includes approximately 0.3 grams of fructooligosaccharides per L of reconstituted, ready-to-use nutritional formula. In certain embodiments, the nutritional formula includes approximately 0.260 grams of fructooligosaccharides per L of reconstituted, ready-to-use nutritional formula. In certain embodiments, the nutritional formula includes approximately 0.270 grams of fructooligosaccharides per L of reconstituted, ready-to-use nutritional formula. In certain embodiments, the nutritional formula includes approximately 0.21 grams or approximately 0.247 grams of fructooligosaccharides per L of reconstituted, ready-to-use nutritional formula. In certain embodiments, the nutritional formula includes approximately 0.21 grams of fructooligosaccharides per L of reconstituted, ready-to-use nutritional formula. In certain embodiments, the nutritional formula includes approximately 0.247 grams of fructooligosaccharides per L of reconstituted, ready-to-use nutritional formula. In certain embodiments, the nutritional formula includes approximately 0.4 grams of fructooligosaccharides per L of reconstituted, ready-to-use nutritional formula.

In certain embodiments, the nutritional formula further includes linoleic acid, alpha-linolenic acid, vitamins, minerals, nucleotides, and/or combinations thereof. In certain embodiments, the nutritional formula further includes linoleic acid, alpha-linolenic acid, vitamins, minerals, nucleosides, nucleotides, and/or combinations thereof. In certain embodiments, the nutritional formula further includes vitamins. In certain embodiments, the vitamins include Vitamin C, Vitamin E, inositol, Vitamin A, niacin, Vitamin D3, pantothenic acid, Vitamin K1, Vitamin B1, Vitamin B2, Vitamin B6, folic acid, biotin, Vitamin B12, or a combination thereof. In certain embodiments, the vitamins include vitamin C, Vitamin E, inositol, Vitamin A, niacin, Vitamin D3, pantothenic acid, Vitamin K1, Vitamin B1, Vitamin B2, Vitamin B6, folic acid, biotin, and Vitamin B12. In certain embodiments, the nutritional formula further includes minerals. In certain embodiments, the minerals include calcium, potassium, sodium, magnesium, iron, zinc, manganese, copper, iodine, selenium, chloride, and forms thereof (e.g., salts, triturates) and/or combinations thereof. In certain embodiments, the minerals include calcium, potassium, sodium, magnesium, iron, zinc, manganese, copper, iodine, selenium, chloride, and forms (e.g., salts, triturates) thereof. In certain embodiments, the minerals include calcium phosphate, calcium carbonate, potassium chloride, sodium citrate, magnesium phosphate, sodium selenite, iron (II) sulfate, zinc sulfate monohydrate, copper sulfate, manganese (II) sulfate monohydrate, or a combination thereof. In certain embodiments, the minerals include calcium phosphate, calcium carbonate, potassium chloride, sodium citrate, magnesium phosphate, sodium selenite, iron (II) sulfate, zinc sulfate monohydrate, copper sulfate, and manganese (II) sulfate monohydrate, or a combination thereof. In certain embodiments, the nutritional formula includes nucleotides. In certain embodiments, the nucleotides include adenosine 5'-monophosphate, cytidine 5'-monophosphate, guanosine 5'-monophosphate, uridine 5'-monophosphate, or a combination thereof. In certain embodiments, the nucleotides include adenosine 5'-monophosphate, cytidine 5'-monophosphate, guanosine 5'-monophosphate, and uridine 5'-monophosphate. In certain embodiments, the nutritional formula further includes nucleosides, diphosphate forms, and/or triphosphate forms thereof. In certain embodiments, the nutritional formula further includes nucleosides, diphosphate forms, and/or triphosphate forms (e.g., salts) thereof.

In certain embodiments, the nutritional formula further includes L-choline bitartrate, L-carnitine, beta-carotene, taurine, or a combination thereof. In certain embodiments, the nutritional formula includes L-choline bitartrate. In certain embodiments, the nutritional formula includes L-carnitine. In certain embodiments, the nutritional formula includes beta-carotene. In certain embodiments, the nutritional formula includes taurine. In certain embodiments, the nutritional formula further includes approximately 0.1 grams to approximately 0.5 grams of L-choline bitartrate, approximately 0.005 grams to approximately 0.03 grams of L-carnitine, approximately 0.0001 grams to approximately 0.0007 grams of beta-carotene, and approximately 0.03 grams to approximately 0.07 grams of taurine, all per L of reconstituted, ready-to-use nutritional formula.

In certain embodiments, the nutritional formula further includes

In certain embodiments, the nutritional formula does not include lycopene. In certain embodiments, the nutritional formula further includes optional ingredients, including, but not limited to, colorants, flavors, preservatives, further antioxidants, emulsifying agents, buffers, stabilizers, thickening agents, or a combination thereof.

In certain embodiments, the nutritional formula includes components in the following weight ranges, in grams per liter (g/L) of reconstituted, ready-to-use nutritional formula:

a) approximately 3 grams to approximately 10 grams whey protein concentrate that is not alpha-lactalbumin enriched, per L of reconstituted, ready-to-use nutritional formula;

b) approximately 2.5 grams to approximately 3.0 grams of alpha-lactalbumin enriched whey protein concentrate per L of reconstituted, ready-to-use nutritional formula;

c) approximately 20.0 grams to approximately 30.0 grams of demineralized whey per L of reconstituted, ready-to-use nutritional formula;

d) approximately 16.5 grams to approximately 18.5 grams of skimmed milk powder per L of reconstituted, ready-to-use nutritional formula;

e) approximately 0.02 grams to approximately 0.10 grams of lactoferrin per L of reconstituted, ready-to-use nutritional formula;

f) approximately 30.0 grams to approximately 42.0 grams of a vegetable oil blend comprising oleic acid-palmitic acid-oleic acid triglyceride; in which approximately 3.0 grams to approximately 7.0 grams of the vegetable oil blend is oleic acid-palmitic acid-oleic acid triglyceride per L of reconstituted, ready-to-use nutritional formula (e.g., wherein the triglyceride is vegetable-derived);

g) approximately 70 grams to approximately 80 grams of lactose per L of reconstituted, ready-to-use nutritional formula;

h) approximately 0.00006 grams to approximately 0.025 grams of lutein per L of reconstituted, ready-to-use nutritional formula;

i) approximately 0.05 grams to approximately 0.09 grams of docosahexanoic acid per L of reconstituted, ready-to-use nutritional formula;

j) approximately 0.1 grams to approximately 0.5 grams of arachidonic acid per L of reconstituted, ready-to-use nutritional formula;

k) approximately 5 grams to approximately 6 grams linoleic acid per L of reconstituted, ready-to-use nutritional formula;

l) approximately 0.25 grams to approximately 0.6 grams alpha-linolenic acid per L of reconstituted, ready-to-use nutritional formula;

m) approximately 3.0 grams to approximately 5.0 grams of galactooligosaccharides per L of reconstituted, ready-to-use nutritional formula;

n) approximately 0.10 grams to approximately 0.50 grams of fructooligosaccharides per L of reconstituted, ready-to-use nutritional formula;

o) approximately 0.05 grams to approximately 0.15 grams of Vitamin C, approximately 0.001 grams to approximately 0.05 grams of Vitamin E per L of reconstituted, ready-to-use nutritional formula; approximately 0.01 grams to approximately 0.05 grams of inositol per L of reconstituted, ready-to-use nutritional formula; approximately 0.0005 grams to approximately 0.02 grams of Vitamin A per L of reconstituted, ready-to-use nutritional formula, approximately 0.005 grams to approximately 0.009 grams of niacin per L of reconstituted, ready-to-use nutritional formula; approximately 0.00001 grams to approximately 0.006 grams of Vitamin D3 per L of reconstituted, ready-to-use nutritional formula; approximately 0.001 grams to approximately 0.005 grams of pantothenic acid per L of reconstituted, ready-to-use nutritional formula; approximately 0.0005 grams to approximately 0.0015 grams of Vitamin K1 per L of reconstituted, ready-to-use nutritional formula; approximately 0.0005 grams to approximately 0.0015 grams of Vitamin B1 per L of reconstituted, ready-to-use nutritional formula; approximately 0.00001 grams to approximately 0.001 grams of Vitamin B2 per L of reconstituted, ready-to-use nutritional formula; approximately 0.0001 grams to approximately 0.0008 grams of Vitamin B6 per L of reconstituted, ready-to-use nutritional formula; approximately 0.0001 grams to approximately 0.002 grams of folic acid per L of reconstituted, ready-to-use nutritional formula; approximately 0.00001 grams to approximately 0.004 grams of biotin per L of reconstituted, ready-to-use nutritional formula; and approximately 0.000001 grams to approximately 0.0005 grams of Vitamin B12 per L of reconstituted, ready-to-use nutritional formula;

p) approximately 0.5 grams to approximately 0.8 grams of dicalcium phosphate per L of reconstituted, ready-to-use nutritional formula; approximately 0.3 grams to approximately 0.8 grams of calcium carbonate per L of reconstituted, ready-to-use nutritional formula; approximately 0.3 grams to approximately 0.5 grams of potassium chloride per L of reconstituted, ready-to-use nutritional formula; approximately 0.4 grams to approximately 0.7 grams of tripotassium citrate monohydrate per L of reconstituted, ready-to-use nutritional formula; approximately 0.3 grams to approximately 0.5 grams of sodium citrate per L of reconstituted, ready-to-use nutritional formula; approximately 0.2 grams to approximately 0.5 grams of trisodium citrate dihydrate per L of reconstituted, ready-to-use nutritional formula; approximately 0.002 grams to approximately 0.006 grams of dimagnesium phosphate per L of reconstituted, ready-to-use nutritional formula; approximately 0.002 grams to approximately 0.005 grams of sodium selenite per L of reconstituted, ready-to-use nutritional formula; approximately 0.02 grams to approximately 0.06 grams of iron (II) sulfate per L of reconstituted, ready-to-use nutritional formula; approximately 0.01 grams to approximately 0.03 grams of zinc sulfate per L of reconstituted, ready-to-use nutritional formula; approximately 0.001 grams to approximately 0.004 grams of copper sulfate per L of reconstituted, ready-to-use nutritional formula; and approximately 0.001 grams to approximately 0.003 grams of manganese (II) sulfate per L of reconstituted, ready-to-use nutritional formula;

q) approximately 0.05 grams to approximately 0.1 grams of adenosine 5'-monophosphate per L of reconstituted, ready-to-use nutritional formula; approximately 0.01 grams to approximately 0.03 grams of cytidine 5'-monophosphate per L of reconstituted, ready-to-use nutritional formula; approximately 0.001 grams to approximately 0.006 grams of guanosine 5'-monophosphate per L of reconstituted, ready-to-use nutritional formula; and approximately 0.01 grams to approximately 0.03 grams of uridine 5'-monophosphate per L of reconstituted, ready-to-use nutritional formula;

r) approximately 0.1 grams to approximately 0.5 grams of L-choline bitartrate per L of reconstituted, ready-to-use nutritional formula; approximately 0.005 grams to approximately 0.03 grams of L-carnitine per L of reconstituted, ready-to-use nutritional formula;

s) approximately 0.0001 grams to approximately 0.0007 grams of beta-carotene per L of reconstituted, ready-to-use nutritional formula; approximately 0.03 grams to approximately 0.07 grams of taurine per L of reconstituted, ready-to-use nutritional formula;

t) approximately 0.3 grams to approximately 0.5 grams of soya lecithin per L of reconstituted, ready-to-use nutritional formula; and u) maltodextrin (e.g., at least approximately 0.00001 grams maltodextrin) per L of reconstituted, ready-to-use nutritional formula.

In certain embodiments, the nutritional formula includes components in the following weight ranges, in grams per liter (g/L) of reconstituted, ready-to-use nutritional formula:

a) approximately 3 grams to approximately 10 grams whey protein concentrate that is not alpha-lactalbumin enriched, per L of reconstituted, ready-to-use nutritional formula;

b) approximately 2.5 grams to approximately 3.0 grams of alpha-lactalbumin enriched whey protein concentrate per L of reconstituted, ready-to-use nutritional formula;

c) approximately 20.0 grams to approximately 30.0 grams of demineralized whey per L of reconstituted, ready-to-use nutritional formula;

d) approximately 16.5 grams to approximately 18.5 grams of skimmed milk powder per L of reconstituted, ready-to-use nutritional formula;

e) approximately 0.02 grams to approximately 0.10 grams of lactoferrin per L of reconstituted, ready-to-use nutritional formula;

f) approximately 30.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of reconstituted, ready-to-use nutritional formula (e.g., wherein the triglyceride is vegetable-derived);

g) approximately 70 grams to approximately 80 grams of lactose per L of reconstituted, ready-to-use nutritional formula;

h) approximately 0.00006 grams to approximately 0.025 grams of lutein per L of reconstituted, ready-to-use nutritional formula;

i) approximately 0.05 grams to approximately 0.09 grams of docosahexanoic acid per L of reconstituted, ready-to-use nutritional formula;

j) approximately 0.1 grams to approximately 0.5 grams of arachidonic acid per L of reconstituted, ready-to-use nutritional formula;

k) approximately 5 grams to approximately 6 grams linoleic acid per L of reconstituted, ready-to-use nutritional formula;

l) approximately 0.25 grams to approximately 0.6 grams alpha-linolenic acid per L of reconstituted, ready-to-use nutritional formula;

m) approximately 3.0 grams to approximately 5.0 grams of galactooligosaccharides per L of reconstituted, ready-to-use nutritional formula;

n) approximately 0.10 grams to approximately 0.50 grams of fructooligosaccharides per L of reconstituted, ready-to-use nutritional formula;

o) approximately 0.05 grams to approximately 0.15 grams of Vitamin C, approximately 0.001 grams to approximately 0.05 grams of Vitamin E per L of reconstituted, ready-to-use nutritional formula; approximately 0.01 grams to approximately 0.05 grams of inositol per L of reconstituted, ready-to-use nutritional formula; approximately 0.0005 grams to approximately 0.02 grams of Vitamin A per L of reconstituted, ready-to-use nutritional formula, approximately 0.005 grams to approximately 0.009 grams of niacin per L of reconstituted, ready-to-use nutritional formula; approximately 0.00001 grams to approximately 0.006 grams of Vitamin D3 per L of reconstituted, ready-to-use nutritional formula; approximately 0.001 grams to approximately 0.005 grams of pantothenic acid per L of reconstituted, ready-to-use nutritional formula; approximately 0.0005 grams to approximately 0.0015 grams of Vitamin K1 per L of reconstituted, ready-to-use nutritional formula; approximately 0.0005 grams to approximately 0.0015 grams of Vitamin B1 per L of reconstituted, ready-to-use nutritional formula; approximately 0.00001 grams to approximately 0.001 grams of Vitamin B2 per L of reconstituted, ready-to-use nutritional formula; approximately 0.0001 grams to approximately 0.0008 grams of Vitamin B6 per L of reconstituted, ready-to-use nutritional formula; approximately 0.0001 grams to approximately 0.002 grams of folic acid per L of reconstituted, ready-to-use nutritional formula; approximately 0.00001 grams to approximately 0.004 grams of biotin per L of reconstituted, ready-to-use nutritional formula; and approximately 0.000001 grams to approximately 0.0005 grams of Vitamin B12 per L of reconstituted, ready-to-use nutritional formula;

p) approximately 0.5 grams to approximately 0.8 grams of dicalcium phosphate per L of reconstituted, ready-to-use nutritional formula; approximately 0.3 grams to approximately 0.8 grams of calcium carbonate per L of reconstituted, ready-to-use nutritional formula; approximately 0.3 grams to approximately 0.5 grams of potassium chloride per L of reconstituted, ready-to-use nutritional formula; approximately 0.4 grams to approximately 0.7 grams of tripotassium citrate monohydrate per L of reconstituted, ready-to-use nutritional formula; approximately 0.3 grams to approximately 0.5 grams of sodium citrate per L of reconstituted, ready-to-use nutritional formula; approximately 0.2 grams to approximately 0.5 grams of trisodium citrate dihydrate per L of reconstituted, ready-to-use nutritional formula; approximately 0.002 grams to approximately 0.006 grams of dimagnesium phosphate per L of reconstituted, ready-to-use nutritional formula; approximately 0.00002 grams to approximately 0.00005 grams of sodium selenite per L of reconstituted, ready-to-use nutritional formula; approximately 0.02 grams to approximately 0.06 grams of iron (II) sulfate per L of reconstituted, ready-to-use nutritional formula; approximately 0.01 grams to approximately 0.03 grams of zinc sulfate per L of reconstituted, ready-to-use nutritional formula; approximately 0.001 grams to approximately 0.004 grams of copper sulfate per L of reconstituted, ready-to-use nutritional formula; and approximately 0.001 grams to approximately 0.003 grams of manganese (II) sulfate per L of reconstituted, ready-to-use nutritional formula;

q) approximately 0.05 grams to approximately 0.1 grams of adenosine 5'-monophosphate per L of reconstituted, ready-to-use nutritional formula; approximately 0.01 grams to approximately 0.03 grams of cytidine 5'-monophosphate per L of reconstituted, ready-to-use nutritional formula; approximately 0.001 grams to approximately 0.006 grams of guanosine 5'-monophosphate per L of reconstituted, ready-to-use nutritional formula; and approximately 0.01 grams to approximately 0.03 grams of uridine 5'-monophosphate per L of reconstituted, ready-to-use nutritional formula;

r) approximately 0.1 grams to approximately 0.5 grams of L-choline bitartrate per L of reconstituted, ready-to-use nutritional formula; approximately 0.005 grams to approximately 0.03 grams of L-carnitine per L of reconstituted, ready-to-use nutritional formula;

s) approximately 0.0001 grams to approximately 0.0007 grams of beta-carotene per L of reconstituted, ready-to-use nutritional formula; approximately 0.03 grams to approximately 0.07 grams of taurine per L of reconstituted, ready-to-use nutritional formula;

t) approximately 0.3 grams to approximately 0.5 grams of soya lecithin per L of reconstituted, ready-to-use nutritional formula; and u) approximately 0.00001 grams to approximately 0.00005 grams of maltodextrin per L of reconstituted, ready-to-use nutritional formula.

In certain embodiments, the nutritional formula includes components in the following weight ranges, in grams per liter (g/L) of reconstituted, ready-to-use nutritional formula:

a) approximately 3 grams to approximately 10 grams whey protein concentrate that is not alpha-lactalbumin enriched, per L of the reconstituted, ready-to-use nutritional formula;

b) approximately 2.5 grams to approximately 3.0 grams of alpha-lactalbumin enriched whey protein concentrate per L of the reconstituted, ready-to-use nutritional formula;

c) approximately 20.0 grams to approximately 30.0 grams of demineralized whey per L of the reconstituted, ready-to-use nutritional formula;

d) approximately 16.5 grams to approximately 18.5 grams of skimmed milk powder per L of the reconstituted, ready-to-use nutritional formula;

e) approximately 0.02 grams to approximately 0.17 grams of lactoferrin per L of the reconstituted, ready-to-use nutritional formula;

f) approximately 30.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;

g) approximately 65 grams to approximately 80 grams of lactose per L of the reconstituted, ready-to-use nutritional formula;

h) approximately 0.00006 grams to approximately 0.025 grams of lutein per L of the reconstituted, ready-to-use nutritional formula;

i) approximately 0.05 grams to approximately 0.09 grams of docosahexanoic acid per L of the reconstituted, ready-to-use nutritional formula;

j) approximately 0.1 grams to approximately 0.5 grams of arachidonic acid per L of the reconstituted, ready-to-use nutritional formula;

k) approximately 5 grams to approximately 6.2 grams linoleic acid per L of the reconstituted, ready-to-use nutritional formula;

l) approximately 0.25 grams to approximately 0.6 grams alpha-linolenic acid per L of the reconstituted, ready-to-use nutritional formula;

m) approximately 2.0 grams to approximately 5.0 grams of galactooligosaccharides per L of the reconstituted, ready-to-use nutritional formula;

n) approximately 0.10 grams to approximately 0.50 grams of fructooligosaccharides per L of the reconstituted, ready-to-use nutritional formula;

o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;

p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;

q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;

r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;

s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;

t) approximately 0.3 grams to approximately 0.5 grams of soya lecithin per L of the reconstituted, ready-to-use nutritional formula; and u) approximately 0.00001 grams to approximately 0.00005 grams of maltodextrin per L of the reconstituted, ready-to-use nutritional formula.

In certain embodiments, an exemplary nutritional formula described herein includes the following components. In certain embodiments, the nutritional formula includes a) approximately 3.0 grams to approximately 10.0 grams of whey protein concentrate per L of reconstituted, ready-to-use nutritional formula;

b) approximately 2.5 grams to approximately 3.0 grams of alpha-lactalbumin enriched whey protein concentrate per L of reconstituted, ready-to-use nutritional formula;

c) approximately 20.0 grams to approximately 30.0 grams of demineralized whey per L of reconstituted, ready-to-use nutritional formula;

d) approximately 16.5 grams to approximately 18.5 grams of skimmed milk powder per L of reconstituted, ready-to-use nutritional formula;

e) approximately 0.02 grams to approximately 0.17 grams of lactoferrin per L of reconstituted, ready-to-use nutritional formula;

f) approximately 30.0 grams to approximately 42.0 grams of a vegetable oil blend comprising oleic acid-palmitic acid-oleic acid triglyceride; in which approximately 3.0 grams to approximately 7.0 grams of the vegetable oil blend is oleic acid-palmitic acid-oleic acid triglyceride per L of reconstituted, ready-to-use nutritional formula (e.g., wherein the triglyceride is vegetable-derived);

g) approximately 70 grams to approximately 80 grams of lactose per L of reconstituted, ready-to-use nutritional formula;

h) approximately 0.00006 grams to approximately 0.025 grams of lutein per L of reconstituted, ready-to-use nutritional formula;

i) approximately 0.05 grams to approximately 0.1 grams of docosahexanoic acid per L of reconstituted, ready-to-use nutritional formula;

j) approximately 0.1 grams to approximately 0.2 grams of arachidonic acid per L of reconstituted, ready-to-use nutritional formula;

k) approximately 5.0 grams to approximately 7.0 grams linoleic acid per L of reconstituted, ready-to-use nutritional formula;

l) approximately 0.4 grams to approximately 0.6 grams alpha-linolenic acid per L of reconstituted, ready-to-use nutritional formula;

m) approximately 3.0 grams to approximately 5.0 grams of galactooligosaccharides per L of reconstituted, ready-to-use nutritional formula;

n) approximately 0.2 grams to approximately 0.3 grams of fructooligosaccharides per L of reconstituted, ready-to-use nutritional formula;

o) approximately 0.05 grams to approximately 0.15 grams of Vitamin C per L of reconstituted, ready-to-use nutritional formula; approximately 0.001 grams to approximately 0.05 grams of Vitamin E per L of reconstituted, ready-to-use nutritional formula; approximately 0.01 grams to approximately 0.05 grams of inositol per L of reconstituted, ready-to-use nutritional formula; approximately 0.0005 grams to approximately 0.02 grams of Vitamin A per L of reconstituted, ready-to-use nutritional formula, approximately 0.005 grams to approximately 0.009 grams of niacin per L of reconstituted, ready-to-use nutritional formula; approximately 0.00001 grams to approximately 0.006 grams (e.g., approximately 10 micrograms to approximately 20 micrograms, 0.005 grams to 0.006 grams, etc.) of Vitamin D3 per L of reconstituted, ready-to-use nutritional formula; approximately 0.001 grams to approximately 0.005 grams of pantothenic acid per L of reconstituted, ready-to-use nutritional formula; approximately 0.0005 grams to approximately 0.0015 grams of Vitamin K1 per L of reconstituted, ready-to-use nutritional formula; approximately 0.0005 grams to approximately 0.0015 grams (e.g., 0.0004 grams to 0.0006 grams, 0.0007 grams to 0.0013 grams, etc.) of Vitamin B1 per L of reconstituted, ready-to-use nutritional formula; approximately 0.00001 grams to approximately 0.001 grams (e.g., 0.0005 grams to 0.001 grams, 0.00003 to 0.00005 grams, etc.) of Vitamin B2 per L of reconstituted, ready-to-use nutritional formula; approximately 0.0001 grams to approximately 0.0008 grams of Vitamin B6 per L of reconstituted, ready-to-use nutritional formula; approximately 0.00001 grams to approximately 0.002 grams (e.g., 0.00001 grams to 0.00003 grams, 0.0005 to 0.0015 grams, etc.) of folic acid per L of reconstituted, ready-to-use nutritional formula; approximately 0.00001 grams to approximately 0.004 grams (e.g., 0.00001 grams to 0.00003 grams, 0.002 to 0.004 grams, etc.) of biotin per L of reconstituted, ready-to-use nutritional formula; and approximately 0.000001 grams to approximately 0.0005 grams (e.g., 0.000001 grams to 0.000003 grams, 0.0001 to 0.0005 grams, etc.) of Vitamin B12 per L of reconstituted, ready-to-use nutritional formula;
p) approximately 0.3 grams to approximately 0.7 grams of calcium phosphate per L of reconstituted, ready-to-use nutritional formula; approximately 0.25 grams to approximately 0.75 grams of calcium carbonate per L of reconstituted, ready-to-use nutritional formula; approximately 0.3 grams to approximately 0.5 grams of potassium chloride per L of reconstituted, ready-to-use nutritional formula; approximately 0.2 grams to approximately 0.5 grams of sodium citrate per L of reconstituted, ready-to-use nutritional formula; approximately 0.00003 grams to approximately 0.00005 grams of magnesium phosphate per L of reconstituted, ready-to-use nutritional formula; approximately 0.001 grams to approximately 0.005 grams of sodium selenite per L of reconstituted, ready-to-use nutritional formula; approximately 0.02 grams to approximately 0.06 grams of iron (II) sulfate per L of reconstituted, ready-to-use nutritional formula; approximately 0.01 grams to approximately 0.03 grams of zinc sulfate monohydrate per L of reconstituted, ready-to-use nutritional formula; approximately 0.002 grams to approximately 0.004 grams of copper sulfate per L of reconstituted, ready-to-use nutritional formula; and approximately 0.000001 grams to approximately 0.000003 grams of manganese (II) sulfate monohydrate per L of reconstituted, ready-to-use nutritional formula;
q) approximately 0.005 grams to approximately 0.01 grams of adenosine 5'-monophosphate per L of reconstituted, ready-to-use nutritional formula; approximately 0.01 grams to approximately 0.03 grams of cytidine 5'-monophosphate per L of reconstituted, ready-to-use nutritional formula; approximately 0.001 grams to approximately 0.005 grams of guanosine 5'-monophosphate per L of reconstituted, ready-to-use nutritional formula; and approximately 0.01 grams to approximately 0.03 grams of uridine 5'-monophosphate per L of reconstituted, ready-to-use nutritional formula;
r) approximately 0.1 grams to approximately 0.5 grams of L-choline bitartrate per L of reconstituted, ready-to-use nutritional formula; approximately 0.005 grams to approximately 0.03 grams of L-carnitine per L of reconstituted, ready-to-use nutritional formula;
s) approximately 0.0001 grams to approximately 0.0006 grams of beta-carotene per L of reconstituted, ready-to-use nutritional formula; approximately 0.03 grams to approximately 0.07 grams of taurine per L of reconstituted, ready-to-use nutritional formula;
t) approximately 0.3 grams to approximately 0.5 grams of soya lecithin per L of reconstituted, ready-to-use nutritional formula; and
u) approximately 0.00001 grams to approximately 0.00005 grams of maltodextrin per L of reconstituted, ready-to-use nutritional formula.

In certain embodiments, the nutritional formula includes the following components (e.g., alone, or in combination) in the following weight ranges, in grams per liter (g/L) of reconstituted, ready-to-use nutritional formula:
a) approximately 6 grams to approximately 10 grams whey protein concentrate that is not alpha-lactalbumin enriched, per L of reconstituted, ready-to-use nutritional formula;
b) approximately 2.5 grams to approximately 2.9 grams of alpha-lactalbumin enriched whey protein concentrate per L of the reconstituted, ready-to-use nutritional formula;
c) approximately 22.0 grams to approximately 26.0 grams of demineralized whey per L of the reconstituted, ready-to-use nutritional formula;
d) approximately 16.5 grams to approximately 18.0 grams of skimmed milk powder per L of the reconstituted, ready-to-use nutritional formula;
e) approximately 0.05 grams to approximately 0.17 grams of lactoferrin per L of the reconstituted, ready-to-use nutritional formula;
f) approximately 33.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;
g) approximately 65 grams to approximately 98.0 grams of lactose per L of the reconstituted, ready-to-use nutritional formula;
h) approximately 0.0005 grams to approximately 0.003 grams of lutein per L of the reconstituted, ready-to-use nutritional formula;
i) approximately 0.05 grams to approximately 0.09 grams of docosahexanoic acid per L of the reconstituted, ready-to-use nutritional formula;
j) approximately 0.1 grams to approximately 0.3 grams of arachidonic acid per L of the reconstituted, ready-to-use nutritional formula;
k) approximately 5 grams to approximately 6.2 grams linoleic acid per L of the reconstituted, ready-to-use nutritional formula;
l) approximately 0.25 grams to approximately 0.6 grams alpha-linolenic acid per L of the reconstituted, ready-to-use nutritional formula;
m) approximately 2.0 grams to approximately 5.0 grams of galactooligosaccharides per L of the reconstituted, ready-to-use nutritional formula;
n) approximately 0.10 grams to approximately 0.50 grams of fructooligosaccharides per L of the reconstituted, ready-to-use nutritional formula;
o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;

p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;

q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;

r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;

s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;

t) approximately 0.3 grams to approximately 0.5 grams of soya lecithin per L of the reconstituted, ready-to-use nutritional formula; and u) approximately 0.00001 grams to approximately 0.00005 grams of maltodextrin per L of the reconstituted, ready-to-use nutritional formula.

In certain embodiments, the nutritional formula includes the following components (e.g., alone, or in combination) in the following weight ranges, in grams per liter (g/L) of reconstituted, ready-to-use nutritional formula:

a) approximately 7 grams to approximately 10 grams whey protein concentrate that is not alpha-lactalbumin enriched, per L of the reconstituted, ready-to-use nutritional formula;

b) approximately 2.6 grams to approximately 2.9 grams of alpha-lactalbumin enriched whey protein concentrate per L of the reconstituted, ready-to-use nutritional formula;

c) approximately 23.0 grams to approximately 26.0 grams of demineralized whey per L of the reconstituted, ready-to-use nutritional formula;

d) approximately 16.75 grams to approximately 18.0 grams of skimmed milk powder per L of the reconstituted, ready-to-use nutritional formula;

e) approximately 0.06 grams to approximately 0.17 grams of lactoferrin per L of the reconstituted, ready-to-use nutritional formula;

f) approximately 34.0 grams to approximately 40.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;

g) approximately 65 grams to approximately 70.0 grams of lactose per L of the reconstituted, ready-to-use nutritional formula;

h) approximately 0.0006 grams to approximately 0.003 grams of lutein per L of the reconstituted, ready-to-use nutritional formula;

i) approximately 0.05 grams to approximately 0.09 grams of docosahexanoic acid per L of the reconstituted, ready-to-use nutritional formula;

j) approximately 0.1 grams to approximately 0.3 grams of arachidonic acid per L of the reconstituted, ready-to-use nutritional formula;

k) approximately 5 grams to approximately 6.2 grams linoleic acid per L of the reconstituted, ready-to-use nutritional formula;

l) approximately 0.25 grams to approximately 0.6 grams alpha-linolenic acid per L of the reconstituted, ready-to-use nutritional formula;

m) approximately 2.0 grams to approximately 5.0 grams of galactooligosaccharides per L of the reconstituted, ready-to-use nutritional formula;

n) approximately 0.10 grams to approximately 0.50 grams of fructooligosaccharides per L of the reconstituted, ready-to-use nutritional formula;

o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;

p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;

q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;

r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;

s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;

t) approximately 0.3 grams to approximately 0.5 grams of soya lecithin per L of the reconstituted, ready-to-use nutritional formula; and u) approximately 0.00001 grams to approximately 0.00005 grams of maltodextrin per L of the reconstituted, ready-to-use nutritional formula.

In certain embodiments, the nutritional formula includes the following components (e.g., alone, or in combination) in the following weight ranges, in grams per liter (g/L) of reconstituted, ready-to-use nutritional formula:

a) approximately 7 grams to approximately 9 grams whey protein concentrate that is not alpha-lactalbumin enriched, per L of the reconstituted, ready-to-use nutritional formula;

b) approximately 2.5 grams to approximately 2.8 grams of alpha-lactalbumin enriched whey protein concentrate per L of the reconstituted, ready-to-use nutritional formula;

c) approximately 22.0 grams to approximately 25.0 grams of demineralized whey per L of the reconstituted, ready-to-use nutritional formula;

d) approximately 16.75 grams to approximately 18.0 grams of skimmed milk powder per L of the reconstituted, ready-to-use nutritional formula;

e) approximately 0.06 grams to approximately 0.17 grams of lactoferrin per L of the reconstituted, ready-to-use nutritional formula;

f) approximately 34.0 grams to approximately 39.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;

g) approximately 65 grams to approximately 70.0 grams of lactose per L of the reconstituted, ready-to-use nutritional formula;

h) approximately 0.0006 grams to approximately 0.001 grams of lutein per L of the reconstituted, ready-to-use nutritional formula;

i) approximately 0.05 grams to approximately 0.09 grams of docosahexanoic acid per L of the reconstituted, ready-to-use nutritional formula;

j) approximately 0.1 grams to approximately 0.3 grams of arachidonic acid per L of the reconstituted, ready-to-use nutritional formula;

k) approximately 5 grams to approximately 6.2 grams linoleic acid per L of the reconstituted, ready-to-use nutritional formula;

l) approximately 0.25 grams to approximately 0.6 grams alpha-linolenic acid per L of the reconstituted, ready-to-use nutritional formula;

m) approximately 2.0 grams to approximately 5.0 grams of galactooligosaccharides per L of the reconstituted, ready-to-use nutritional formula;
n) approximately 0.10 grams to approximately 0.50 grams of fructooligosaccharides per L of the reconstituted, ready-to-use nutritional formula;
o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;
p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;
q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;
r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;
s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;
t) approximately 0.3 grams to approximately 0.5 grams of soya lecithin per L of the reconstituted, ready-to-use nutritional formula; and
u) approximately 0.00001 grams to approximately 0.00005 grams of maltodextrin per L of the reconstituted, ready-to-use nutritional formula.

In certain embodiments, the nutritional formula includes approximately 3.0 grams to approximately 10.0 grams of whey protein concentrate per L of reconstituted, ready-to-use nutritional formula; approximately 2.0 grams to approximately 3.0 grams of alpha-lactalbumin enriched whey protein concentrate per liter (L) of reconstituted, ready-to-use nutritional formula; demineralized whey; whey protein concentrate; skimmed milk powder; approximately 0.01 grams to approximately 0.2 grams of lactoferrin per L of reconstituted, ready-to-use nutritional formula; approximately 35 grams to approximately 38 grams of a vegetable oil blend comprising an oleic acid-palmitic acid-oleic acid triglyceride, in which the vegetable oil blend includes approximately 4.25 grams to approximately 5.25 grams of oleic acid-palmitic acid-oleic acid triglyceride per L of reconstituted, ready-to-use nutritional formula (e.g., wherein the triglyceride is vegetable-derived); approximately 70 grams to approximately 75 grams of lactose per L of reconstituted, ready-to-use nutritional formula; approximately 60 micrograms to approximately 0.025 grams of lutein per L of reconstituted, ready-to-use nutritional formula; approximately 0.05 grams to approximately 0.3 grams of docosahexanoic acid per L of reconstituted, ready-to-use nutritional formula; approximately 0.05 grams to approximately 0.3 grams of arachidonic acid per L of reconstituted, ready-to-use nutritional formula; approximately 5.0 grams to approximately 6.0 grams linoleic acid per L of reconstituted, ready-to-use nutritional formula; approximately 0.3 grams to approximately 0.6 grams alpha-linolenic acid per L of reconstituted, ready-to-use nutritional formula; approximately 2.5 grams to approximately 5.5 grams of galactooligosaccharides per L of reconstituted, ready-to-use nutritional formula; approximately 0.1 grams to approximately 0.5 grams of fructooligosaccharides per L of reconstituted, ready-to-use nutritional formula; approximately 0.05 grams to approximately 0.15 grams of Vitamin C per L of reconstituted, ready-to-use nutritional formula; approximately 0.001 grams to approximately 0.05 grams of Vitamin E per L of reconstituted, ready-to-use nutritional formula; approximately 0.01 grams to approximately 0.05 grams of inositol per L of reconstituted, ready-to-use nutritional formula; approximately 0.0005 grams to approximately 0.02 grams of Vitamin A (e.g., approximately 0.005 grams to 0.015 grams, 0.01 grams to 0.015 grams, 0.01 grams to 0.02 grams, etc.) per L of reconstituted, ready-to-use nutritional formula, approximately 0.005 grams to approximately 0.009 grams of niacin per L of reconstituted, ready-to-use nutritional formula; approximately 0.00001 grams to approximately 0.006 grams (e.g., approximately 10 micrograms to approximately 20 micrograms, 0.005 grams to 0.006 grams, etc.) of Vitamin D3 per L of reconstituted, ready-to-use nutritional formula; approximately 0.001 grams to approximately 0.005 grams of pantothenic acid per L of reconstituted, ready-to-use nutritional formula; approximately 0.0005 grams to approximately 0.0015 grams of Vitamin K1 per L of reconstituted, ready-to-use nutritional formula; approximately 0.0005 grams to approximately 0.0015 grams (e.g., 0.0004 grams to 0.0006 grams, 0.0007 grams to 0.0013 grams, etc.) of Vitamin B1 per L of reconstituted, ready-to-use nutritional formula; approximately 0.00001 grams to approximately 0.001 grams (e.g., 0.0005 grams to 0.001 grams, 0.00003 to 0.00005 grams, etc.) of Vitamin B2 per L of reconstituted, ready-to-use nutritional formula; approximately 0.0001 grams to approximately 0.0008 grams of Vitamin B6 per L of reconstituted, ready-to-use nutritional formula; approximately 0.00001 grams to approximately 0.002 grams (e.g., 0.00001 grams to 0.00003 grams, 0.0005 to 0.0015 grams, etc.) of folic acid per L of reconstituted, ready-to-use nutritional formula; approximately 0.00001 grams to approximately 0.004 grams (e.g., 0.00001 grams to 0.00003 grams, 0.002 to 0.004 grams, etc.) of biotin per L of reconstituted, ready-to-use nutritional formula; and approximately 0.000001 grams to approximately 0.0005 grams (e.g., 0.000001 grams to 0.000003 grams, 0.0001 to 0.0005 grams, etc.) of Vitamin B12 per L of reconstituted, ready-to-use nutritional formula; approximately 0.5 grams to approximately 0.8 grams of dicalcium phosphate per L of reconstituted, ready-to-use nutritional formula; approximately 0.3 grams to approximately 0.8 grams of calcium carbonate per L of reconstituted, ready-to-use nutritional formula; approximately 0.3 grams to approximately 0.5 grams of potassium chloride per L of reconstituted, ready-to-use nutritional formula; approximately 0.00004 grams to approximately 0.04 grams of potassium iodide per L of reconstituted, ready-to-use nutritional formula; approximately 0.4 grams to approximately 0.7 grams potassium citrate per L of reconstituted, ready-to-use nutritional formula; approximately 0.3 grams to approximately 0.5 grams of sodium citrate per L of reconstituted, ready-to-use nutritional formula; approximately 0.2 grams to approximately 0.5 grams of trisodium citrate dihydrate per L of reconstituted, ready-to-use nutritional formula; approximately 0.002 grams to approximately 0.006 grams of dimagnesium phosphate trihydrate per L of reconstituted, ready-to-use nutritional formula; approximately 0.2 grams to approximately 0.4 grams of magnesium chloride hexahydrate per L of reconstituted, ready-to-use nutritional formula; approximately 0.00002 grams to approximately 0.00005 grams of sodium selenite per L of reconstituted, ready-to-use nutritional formula; approximately 0.02 grams to approximately 0.06 grams of iron (II) sulfate per L of reconstituted, ready-to-use nutritional formula; approximately 0.01 grams to approximately 0.03 grams of zinc sulfate monohydrate per L of reconstituted, ready-to-use nutritional formula; approximately 0.001 grams to approximately 0.004 grams of copper sulfate per L of reconstituted, ready-to-use nutritional formula; and approximately 0.001 grams to approximately 0.003 grams of manganese (II) sulfate monohydrate per L of reconstituted, ready-to-use nutritional formula; and approximately 0.05 grams to approximately 0.1 grams of adenosine 5'-monophosphate per L of reconstituted, ready-to-use nutritional formula; approximately 0.01 grams to approximately 0.03 grams of cytidine 5'-monophosphate per L of reconstituted, ready-to-use nutritional formula; approximately 0.001 grams to approximately 0.006 grams of guanosine 5'-monophosphate per L of reconstituted, ready-to-use nutritional formula; and approximately 0.01 grams to approximately 0.03 grams of uridine 5'-monophosphate per L of reconstituted, ready-to-use nutritional formula; approximately 0.1 grams to approximately 0.5 grams of L-choline bitartrate per L of reconstituted, ready-to-use nutritional formula; approximately 0.01 grams to approximately 0.03 grams of L-carnitine per L of reconstituted, ready-to-use nutritional formula; approximately 0.0001 grams to approximately 0.0005 grams of beta-carotene per L of reconstituted, ready-to-use nutritional formula; approximately 0.03 grams to approximately 0.07 grams of taurine per L of reconstituted, ready-to-use nutritional formula; approximately 0.3 grams to approximately 0.5 grams of soya lecithin; and approximately 0.00001 grams to approximately 0.00005 grams of maltodextrin per L of reconstituted, ready-to-use nutritional formula per L of reconstituted, ready-to-use nutritional formula.

In certain embodiments, the nutritional formula includes approximately 3 grams to approximately 10 grams whey protein concentrate that is not alpha-lactalbumin enriched, per L of the reconstituted, ready-to-use nutritional formula; approximately 2.5 grams to approximately 3.0 grams of alpha-lactalbumin enriched whey protein concentrate per L of the reconstituted, ready-to-use nutritional formula; approximately 20.0 grams to approximately 30.0 grams of demineralized whey per L of the reconstituted, ready-to-use nutritional formula; approximately 16.5 grams to approximately 18.5 grams of skimmed milk powder per L of the reconstituted, ready-to-use nutritional formula; approximately 0.02 grams to approximately 0.17 grams of lactoferrin per L of the reconstituted, ready-to-use nutritional formula; approximately 30.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula; approximately 65 grams to approximately 80 grams of lactose per L of the reconstituted, ready-to-use nutritional formula; approximately 0.00006 grams to approximately 0.025 grams of lutein per L of the reconstituted, ready-to-use nutritional formula; approximately 0.05 grams to approximately 0.09 grams of docosahexanoic acid per L of the reconstituted, ready-to-use nutritional formula; approximately 0.1 grams to approximately 0.5 grams of arachidonic acid per L of the reconstituted, ready-to-use nutritional formula; approximately 5 grams to approximately 6.2 grams linoleic acid per L of the reconstituted, ready-to-use nutritional formula; approximately 0.25 grams to approximately 0.6 grams alpha-linolenic acid per L of the reconstituted, ready-to-use nutritional formula; approximately 2.0 grams to approximately 5.0 grams of galactooligosaccharides per L of the reconstituted, ready-to-use nutritional formula; approximately 0.10 grams to approximately 0.50 grams of fructooligosaccharides per L of the reconstituted, ready-to-use nutritional formula; approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula; approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula; approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula; approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula; approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula; approximately 0.3 grams to approximately 0.5 grams of soya lecithin per L of the reconstituted, ready-to-use nutritional formula; and approximately 0.00001 grams to approximately 0.00005 grams of maltodextrin per L of the reconstituted, ready-to-use nutritional formula.

In certain embodiments, the present disclosure provides a nutritional formula comprising:
a) alpha-lactalbumin enriched whey protein concentrate;
b) lactoferrin;
c) oleic acid-palmitic acid-oleic acid triglyceride, wherein palmitic acid is at the SN-2 position of the glycerol backbone of the triglyceride;
d) lactose;
e) lutein;
f) docosahexanoic acid;
g) arachidonic acid;
h) galactooligosaccharides; and
i) fructooligosaccharides.

In certain embodiments, the present disclosure provides a nutritional formula comprising:
a) alpha-lactalbumin enriched whey protein concentrate;
b) lactoferrin;
c) oleic acid-palmitic acid-oleic acid triglyceride, wherein palmitic acid is at the SN-2 position of the glycerol backbone of the triglyceride;
d) lactose;
e) lutein;
f) docosahexanoic acid;
g) arachidonic acid;
h) galactooligosaccharides;
i) fructooligosaccharides.
j) vitamins;
k) minerals;
l) nucleotides;
m) soya lecithin;
n) maltodextrin;
o) beta-carotene; and
p) taurine.

In certain embodiments, the present disclosure provides a nutritional formula comprising:
a) alpha-lactalbumin enriched whey protein concentrate;
b) lactoferrin;
c) oleic acid-palmitic acid-oleic acid triglyceride, wherein palmitic acid is at the SN-2 position of the glycerol backbone of the triglyceride;
d) lactose;
e) lutein;
f) docosahexanoic acid;
g) arachidonic acid;

h) galactooligosaccharides;
i) fructooligosaccharides.
j) vitamins;
k) minerals;
l) nucleotides;
m) soya lecithin;
n) beta-carotene; and
o) taurine.

In certain embodiments, the nutritional formula is provided in a powder form. In certain embodiments, the nutritional formula is provided in a liquid form.

The present disclosure also provides reconstituted formulations comprising a powder form of the nutritional formula described herein, reconstituted with water (e.g., approximately 450 mL to approximately 900 mL water) to yield a ready-to-feed liquid. In certain embodiments, the nutritional formulation is reconstituted with 450 mL or 500 mL water to form approximately 0.5 L of reconstituted nutritional formulation. In certain embodiments, the nutritional formulation is reconstituted with 900 mL water to form approximately 1 L of reconstituted nutritional formulation. In certain embodiments, the nutritional formulation is reconstituted with approximately 1 L water to form approximately 1.1 L of reconstituted nutritional formulation.

Also provided herein are liquid concentrates of a nutritional formula described herein, wherein the liquid concentrates can be diluted to form a ready-to-feed liquid formula.

Kits and Administration

Nutritional formulas described herein can be prepared by any method known in the art of nutritional formulations and manufacturing. In some embodiments, a preparatory method disclosed herein comprises combining ingredients of the nutritional formula into an aqueous slurry, including protein, carbohydrate, fat or lipid blends, prebiotics, minerals, lutein, beta-carotene, and/or combinations thereof, heating the aqueous slurry to approximately 140° F., and then homogenizing, pasteurizing, cooling, and spray drying the aqueous slurry. Other materials, including vitamins, minerals, nucleotides, polyunsaturated fatty acids (e.g., arachidonic acid and docosahexanoic acid), proteins (e.g., lactoferrin), and/or combinations thereof, may be added to the spray dried solution, followed by further processing and packaging.

In certain embodiments, such preparatory methods for preparing the nutritional formulas include a two-step process, as described above in the section titled "Methods of Preparing Nutritional Formulas." The first step involves the addition of macroingredients, including protein (e.g., alpha-lactalbumin enriched whey protein concentrate, whey protein concentrate, skimmed milk powder, demineralized whey), carbohydrate (e.g., maltodextrin, lactose), prebiotics (e.g., galactooligosaccharides, fructooligosaccharides), base mineral premix, fat or lipid (e.g., lecithin), lutein, beta-carotene, and/or combinations thereof, into a base mixing tank containing water (e.g., reverse osmosis processed water) and outfitted with a high speed mixer. In certain embodiments, the first step involves the addition of macroingredients, including protein (e.g., alpha-lactalbumin enriched whey protein concentrate, whey protein concentrate, skimmed milk powder, demineralized whey), carbohydrate (e.g., maltodextrin, lactose), prebiotics (e.g., galactooligosaccharides, fructooligosaccharides), base mineral premix, fat or lipid (e.g., lecithin), lutein, beta-carotene, and/or combinations thereof, into a base mixing tank containing water (e.g., reverse osmosis processed water) and outfitted with a high speed mixer. A vegetable oil blend (e.g., INFAT® fat blend, including OPO SN-2 oil) is then added into the base mixing tank and heated (e.g., heated to 140° F.). This forms an aqueous slurry. The aqueous slurry is then purified. In certain embodiments, the aqueous slurry is first transferred into a two-stage homogenizer, followed by transfer to a two-stage pasteurizer. Next, the slurry is dried. In certain embodiments, hot filtered air (e.g., with a temperature of approximately 350° F. to approximately 400° F.) is used to spray dry the mixture. Sifting is used to trap large particles, wherein these larger trapped particles are added back into the tall form spray drier to achieve complete drying. Once a low moisture level (e.g., a moisture level of approximately 2% or less) is achieved, the dried powder is transferred into a powder hopper for bagging into large nitrogen flushed bags (e.g., bags of 20-40 kg).

In some embodiments, the second stage of the process involves the addition of the vitamin premix, trace minerals premix, and nucleotides premix to one bag of 20-40 kg (e.g., a 25 kg bag), as a base. This mixture is placed in a small mixer with lactoferrin (e.g., freeze-dried lactoferrin), along with polyunsaturated fatty acids (e.g., arachidonic acid and docosahexanoic acid), and then gently blended. A total of approximately thirty to forty (e.g., thirty-five) of each bag (e.g., each 25 kg bag) that has undergone the above additions are combined in a large paddle blender. Next, the powdered forms of the nutritional formula are packaged and distributed. In certain embodiments, a screen magnet, vertical filler, and case sealer are used to fill and seal individual packets of the powder nutritional formula (e.g., powder packets), wherein approximately one hundred (e.g., 96) powder packets can be produced per minute. The completed product is placed into containers for distribution.

Also encompassed by the disclosure are kits (e.g., packages of powder nutritional formula). The kits provided may comprise a nutritional formulation described herein and a container (e.g., a suitable container), or reconstituted formulas described herein. Thus, in one aspect, provided are kits including a container comprising a nutritional formulation described herein. In certain embodiments, the kits are useful for providing methods, uses, and uses in the manufacture of a medicament for nutrition (e.g., promoting postnatal development of the gastrointestinal tract, promoting development of an infant's gastrointestinal tract, promoting proper gastrointestinal function (e.g., intestinal microbiota), promoting nutrient (e.g., calcium) absorption, promoting immune system development; and/or improving bone strength, sleep (e.g., sleep patterns), decreased crying (duration, frequency), and/or decreased fussiness, etc) to a subject (e.g., an infant). In certain embodiments, the kits are useful in a method described herein.

In certain embodiments, a kit described herein further includes instructions, for example, preparing (e.g., reconstituting) the powdered formula, administering the formula to a subject (e.g., infant) for using the powder nutritional formula included in the kit. The nutritional formula may be provided in convenient serving for administering (serving) to a subject. The kit may include a dehydrated nutritional formula and a diluting agent (e.g., water). In certain embodiments, the diluting agent is water. The kit may include multiple dosage units. For example, the kit may include 1-100 packages (e.g., servings). In certain embodiments, a kit includes multiple servings (e.g., one or more packages, wherein each package comprises approximately 1.0 g to 100 g, 1 g to 5 g, 5 g to 10 g, 10 g to 25 g, 25 g to 50 g, or 50 g to 100 g, of the powdered nutritional formula described herein. In certain embodiments, a serving is the amount of powdered nutritional formula described herein which produces the following amount of a reconstituted formula per administration (e.g., feeding): for example, approximately 0.1 L-0.25 L of the reconstituted formula, approximately 0.1 L-0.5 L of the reconstituted formula. In certain embodiments, a serving is the amount of powdered nutritional formula which produces the following amount of a reconstituted formula per administration (e.g., feeding): approximately 0.01 L-0.025 L, 0.025 L-0.05 L, 0.05 L-0.1 L, 0.25 L-0.5 L, 0.5 L-0.75 L, 0.6 L to 0.8 L, 0.6 L to 0.77 L, 0.5 L-1.0 L, 1.0 L-1.25 L, of the reconstituted formula. In certain embodiments, the kit comprises 1-100 servings, which comprises an administration of 0.5 L-1.0 L or 0.6 L-0.77 L of the reconstituted formula per day.

In some embodiments, the kits described herein also include information as required by a regulatory agency such as the U.S. Food and Drug Administration (FDA). In certain embodiments, the kits include instructions on calculating a serving and/or providing nutrition to a subject. Also encompassed by the disclosure are devices (e.g., bottles) for administering to (e.g., feeding) a subject the nutritional formula or reconstituted formula. The kits provided may comprise one or more packages of the nutritional formula described herein, in powder or liquid form, and instructions, for example, preparing (e.g., reconstituting with water) the powdered formula, or administering (e.g., feeding) the formula to a subject (e.g., infant).

Methods of Preparing Nutritional Formulas

Figure 1B:
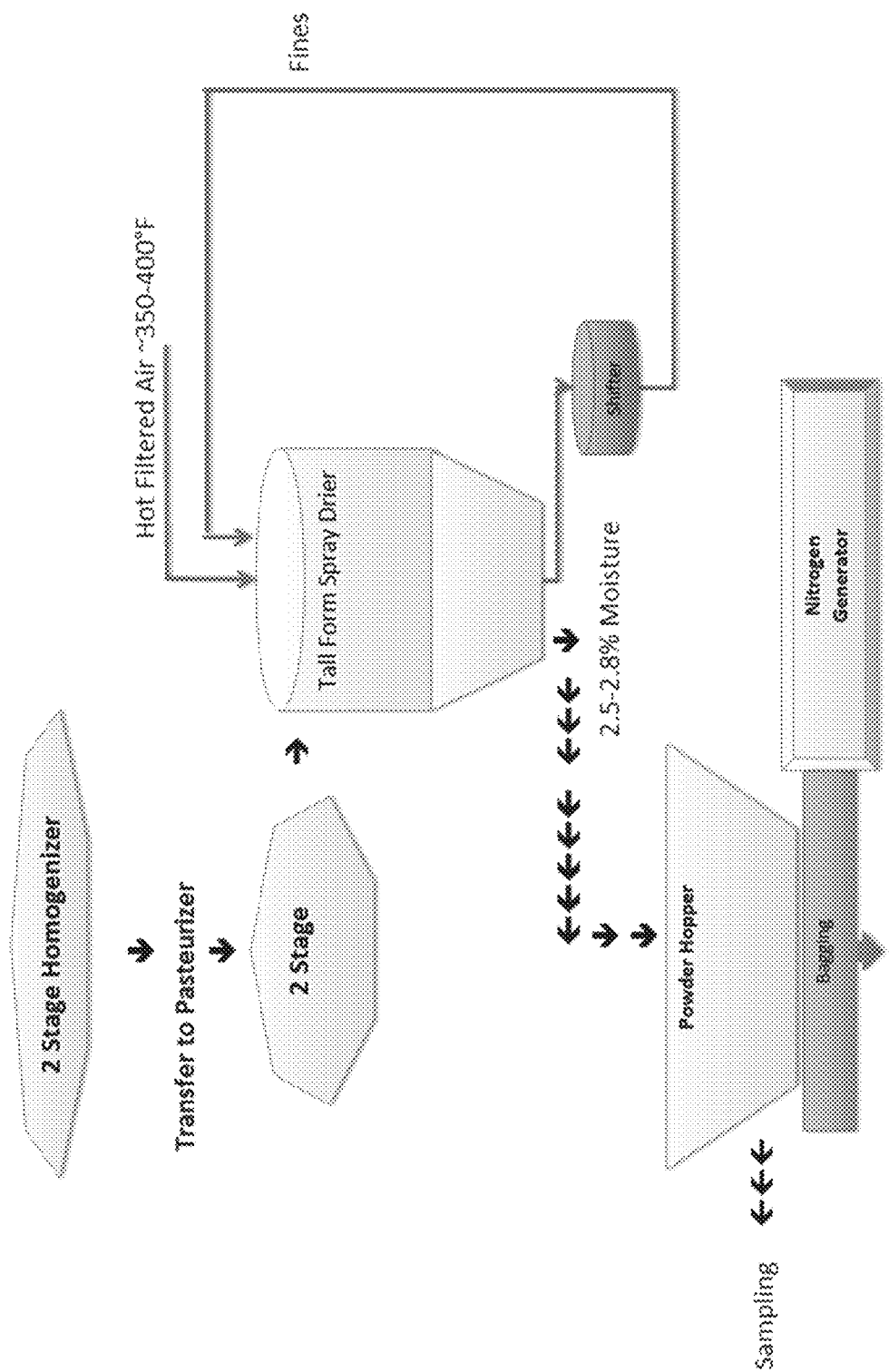
Figure 2:
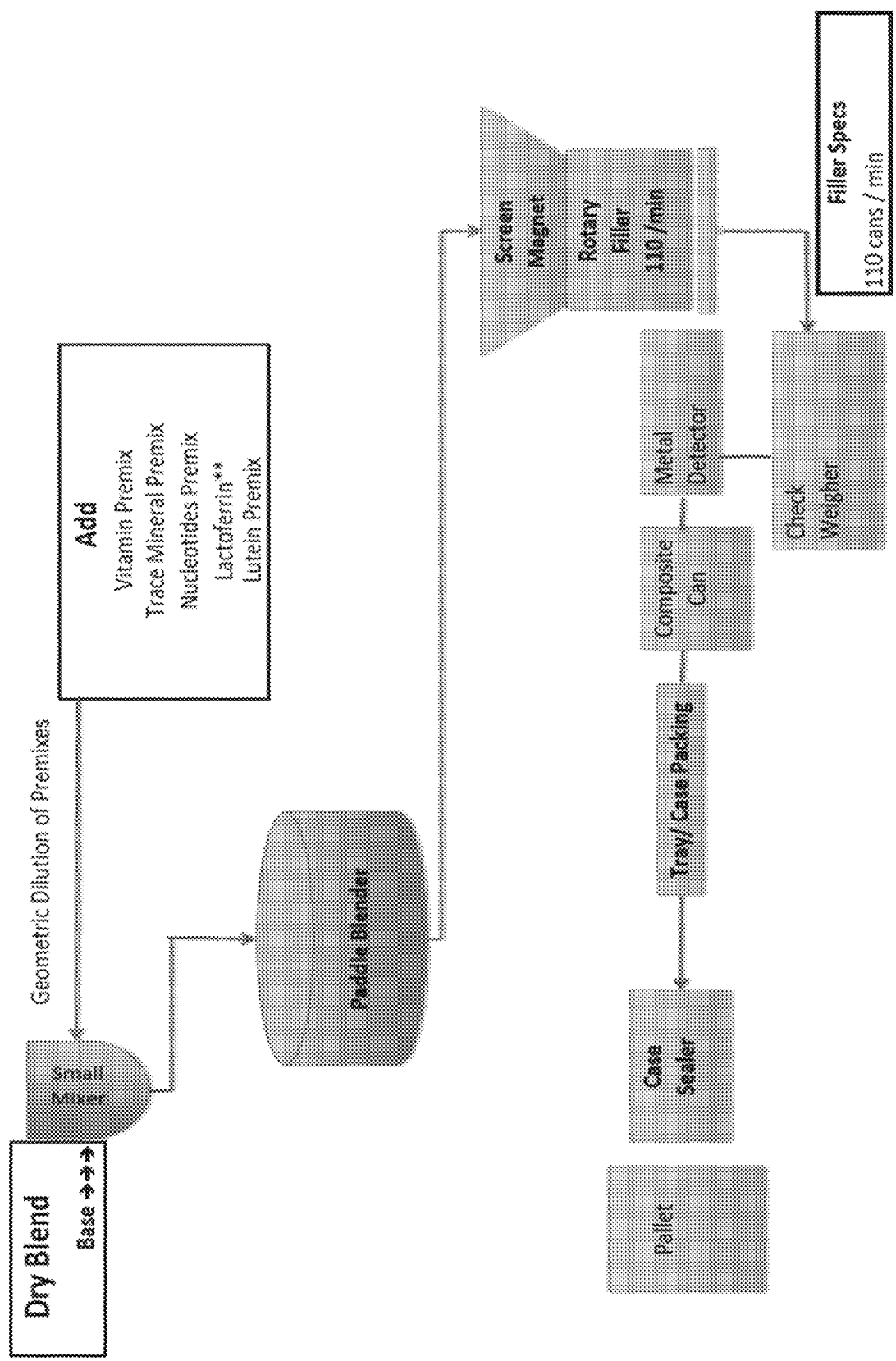
FIG. 2 shows the manufacturing process for the preparation of infant formula in which the formula is blended and packaged.

The present disclosure provides methods of preparing a nutritional formula described herein. In certain embodiments, the nutritional formula is prepared using a two-step process (e.g., as shown in FIGS. 1A, 1B, and 2). In certain embodiments, the nutritional formula is prepared with a first step that involves the addition of macroingredients (e.g., protein, milk powder, saccharide (e.g., lactose)), prebiotics, base mineral premix, and/or vitamins, into a base mixing tank containing processed water and outfitted with a high speed mixer. The vegetable oil blend (e.g., vegetable fat blend, including phospholipids, omega fatty acids) are then added into the base mixing tank and heated (e.g., to approximately 140° F.). In certain embodiments, the slurry is then transferred into a homogenizer (e.g., a two-stage homogenizer), followed by transfer to a pasteurizer (e.g., two-stage pasteurizer). In certain embodiments, next, hot filtered air (e.g., with a temperature of approximately 350° F. to approximately 400° F.) is used to spray dry the mixture; followed by sifting to trap larger particles, wherein these larger particles are added back into the spray drier to achieve complete drying. In certain embodiments, when an appropriate moisture level (e.g., of approximately 3% or less) is achieved, the nutritional formula powder is transferred into a powder hopper for bagging. In certain embodiments, the second stage of the process used to prepare the nutritional formula involves the addition of the vitamin premix (e.g., with lutein), trace minerals premix, nucleotides premix, and specific protein (e.g., lactoferrin), to the dry blend base; processed, blended, poached; and then the nutritional formula is stored. In certain embodiments, the nutritional formula is prepared as described in FIGS. 1A, 1B, and 2; and/or Example 1.

Methods of Administration and Feeding

The present disclosure provides methods of administering or providing nutrition to (e.g., feeding) a subject (e.g., newborn, infant) in need thereof. In certain embodiments, the method of providing nutrition to a subject comprises administering (e.g., feeding) a nutritional formula described herein to a subject. In certain embodiments, the administered nutritional formula is a previously reconstituted ready-to-feed liquid. In certain embodiments, the method of providing nutrition to a subject comprises preparing (e.g., reconstituting) the nutritional formula in powder form with water to form a ready-to-feed liquid. In certain embodiments, the methods of the disclosure include administering (e.g., feeding) the subject with the reconstituted formula. In certain embodiments, the methods of the disclosure include administering (e.g., feeding) the subject with approximately 0.1 L-0.25 L of the reconstituted formula per feeding, or approximately 0.1 L-0.5 L of the reconstituted formula per feeding. In certain embodiments, the methods of the disclosure include administering (e.g., feeding) the subject with 0.25 L-0.5 L, 0.5 L-0.75 L, 0.6 L to 0.8 L, 0.6 L to 0.77 L, 0.5 L-1.0 L, 1.0 L-1.25 L, of the reconstituted formula per day. In certain embodiments, the methods of the disclosure include administering (e.g., feeding) the subject with 0.5 L-1.0 L of the reconstituted formula per day. In certain embodiments, the methods of the disclosure include administering (e.g., feeding) the subject with 0.6 L-0.77 L of the reconstituted formula per day. In certain embodiments, the method comprises administering (e.g., feeding) the subject one to six servings (e.g., feedings) per day, or administering (e.g., feeding) the subject four to six servings (e.g., feedings) per day. In certain embodiments, the subject is a human (e.g., an infant). In certain embodiments, the subject is not more than about two years of age. In certain embodiments, the subject is a newborn that is not more than about 4 weeks of age. In certain embodiments, the subject is an infant from about 0 to about 4 months of age, from about 4 to about 8 months of age, from about 8 to about 12 months of age, from about 12 to about 16 months of age, from about 16 to about 18 months of age, from about 18 to about 24 months of age, and from about 24 to about 30 months of age, from about 30 to about 36 months of age, and preterm infants that are less than about 37 weeks gestational age. In certain embodiments, the subject is an infant not more than about thirty-six (36) months of age, an infant not more than about thirty months of age, an infant not more than about two years of age, an infant not more than about eighteen months of age, an infant not more than about one year of age, an infant not more than about six months of age, or a newborn. In certain embodiments, the subject is a newborn infant that is not more than about 4 weeks of age, an infant from about 0 to about 1 week of age, from about 1 to about 2 weeks of age, from about 2 to about 3 weeks of age, and from about 3 to about 4 weeks of age. In certain embodiments, the subject is a newborn infant that is not more than about 10 days of age, not more than about 11 days of age, not more than about 12 days of age, not more than about 13 days of age, not more than about 14 days of age, not more than about 4 weeks of age, an infant from about 0 to about 1 week of age, from about 1 to about 2 weeks of age, from about 2 to about 3 weeks of age, and from about 3 to about 4 weeks of age. In certain embodiments, the subject is a newborn infant that is an early-term infant of less than 37 weeks; a full-term infant of no less than 37 weeks; a late term infant of no greater than 41 weeks; or a late term infant of no greater than 41 weeks, 6 days. In certain embodiments, the subject is a newborn infant that is a full-term infant of no less than 37 weeks; a late term infant of no greater than 41 weeks; or a late term infant of no greater than 41 weeks, 6 days.

In certain embodiments, the method of providing nutrition or administering (e.g., feeding) may be useful for providing nutrition as well as methods, uses, and uses in the manufacture of a medicament for promoting postnatal development of the gastrointestinal tract, for example, promoting development of an infant's gastrointestinal tract, proper gastrointestinal function (e.g., intestinal microbiota), promoting nutrient (e.g., calcium) absorption, promoting immune system development; and/or improving bone strength, sleep (e.g., sleep patterns), decreased crying (duration, frequency), and/or decreased fussiness, etc. In certain embodiments, the methods, uses, and uses in the manufacture of a medicament for of providing nutrition may be useful for postnatal development of the gastrointestinal tract. In certain embodiments, the methods of providing nutrition may be useful for promoting nutrient absorption. In certain embodiments, the methods of providing nutrition may be useful for immune system development.

In certain embodiments, the methods of the disclosure include administering to a subject an effective amount of a nutritional formula described herein. In certain embodiments, the subject is a human. In certain embodiments, the subject is a child. In certain embodiments, the subject is an infant. In certain embodiments, the subject is an infant not more than about thirty-six (36) months of age, an infant not more than about thirty months of age, an infant not more than about two years of age, an infant not more than about eighteen months of age, an infant not more than about one year of age, an infant not more than about six months of age, or a newborn. In certain embodiments, the subject is a newborn. In certain embodiments, the subject is a toddler. In certain embodiments, the subject is an adult. In certain embodiments, the subject is an adolescent.

In certain embodiments, provided are uses of the nutritional composition described herein, or a reconstituted form thereof, for providing nutrition as well as promoting postnatal development of the gastrointestinal tract, for example, promoting development of an infant's gastrointestinal tract, proper gastrointestinal function (e.g., intestinal microbiota), promoting nutrient (e.g., calcium) absorption, promoting immune system development; and/or improving bone strength, sleep (e.g., sleep patterns), decreased crying (duration, frequency), and/or decreased fussiness, in a subject. In certain embodiments, provided are the nutritional composition described herein, or a reconstituted form thereof, for use in providing nutrition as well as promoting postnatal development of the gastrointestinal tract, for example, promoting development of an infant's gastrointestinal tract, proper gastrointestinal function (e.g., intestinal microbiota), promoting nutrient (e.g., calcium) absorption, promoting immune system development; and/or improving bone strength, sleep (e.g., sleep patterns), decreased crying (duration, frequency), and/or decreased fussiness, in a subject.

EXEMPLARY EMBODIMENTS

First Exemplary Set of Embodiments

Embodiment 1. A nutritional formula comprising:
a) alpha-lactalbumin enriched whey protein concentrate;
b) lactoferrin;
c) oleic acid-palmitic acid-oleic acid triglyceride, wherein palmitic acid is at the SN-2 position of the glycerol backbone of the triglyceride;
d) lactose;
e) lutein;
f) docosahexanoic acid;
g) arachidonic acid;
h) galactooligosaccharides; and
i) fructooligosaccharides.

Embodiment 2. The nutritional formula of embodiment 1 further comprising linoleic acid.

Embodiment 3. The nutritional formula of any one of embodiments 1-2 further comprising alpha-linolenic acid.

Embodiment 4. The nutritional formula of any one of embodiments 1-3 further comprising vitamins, minerals, nucleotides, or a combination thereof.

Embodiment 5. The nutritional formula of any one of embodiments 1-4 further comprising L-choline bitartrate, L-carnitine, or a combination thereof.

Embodiment 6. The nutritional formula of any one of embodiments 1-5 further comprising soya lecithin.

Embodiment 7. The nutritional formula of any one of embodiments 1-6 further comprising beta-carotene, taurine, or a combination thereof.

Embodiment 8. The nutritional formula of any one of embodiments 4-7, wherein the vitamins comprise Vitamin C, Vitamin E, inositol, Vitamin A, niacin, Vitamin D3, pantothenic acid, Vitamin K1, Vitamin B1, Vitamin B2, Vitamin B6, folic acid, biotin, Vitamin B12, or a combination thereof.

Embodiment 9. The nutritional formula of any one of embodiments 4-8, wherein the minerals comprise calcium, potassium, sodium, magnesium, iron, zinc, manganese, copper, iodine, selenium, chloride, and forms thereof.

Embodiment 10. The nutritional formula of any one of embodiments 4-9, wherein the minerals comprise calcium phosphate, calcium carbonate, potassium chloride, potassium citrate, potassium iodide, sodium citrate, sodium selenite, magnesium phosphate, magnesium chloride, iron (II) sulfate, zinc sulfate monohydrate, copper sulfate, manganese (II) sulfate monohydrate, or a combination thereof.

Embodiment 11. The nutritional formula of any one of embodiments 4-10, wherein the nucleotides comprise adenosine 5'-monophosphate, cytidine 5'-monophosphate, guanosine 5'-monophosphate, uridine 5'-monophosphate, or a combination thereof.

Embodiment 12. The nutritional formula of any one of embodiments 4-11, wherein the nucleotides comprise adenosine 5'-monophosphate, cytidine 5'-monophosphate, guanosine 5'-monophosphate, and uridine 5'-monophosphate.

Embodiment 13. The nutritional formula of any one of embodiments 1-12, wherein the nutritional formula comprises approximately 0.5 grams to approximately 4.2 grams of alpha-lactalbumin enriched whey protein concentrate per L of reconstituted, ready-to-use nutritional formula.

Embodiment 14. The nutritional formula of any one of embodiments 1-13, wherein the nutritional formula comprises approximately 0.02 grams to approximately 1.0 grams of lactoferrin per L of reconstituted, ready-to-use nutritional formula.

Embodiment 15. The nutritional formula of embodiment 14, wherein the nutritional formula comprises approximately 0.02 grams to approximately 0.135 grams of lactoferrin per L of reconstituted, ready-to-use nutritional formula.

Embodiment 16. The nutritional formula of any one of embodiments 1-15, wherein the nutritional formula comprises approximately 1.0 grams to approximately 14.0 grams of the oleic acid-palmitic acid-oleic acid triglyceride per L of reconstituted, ready-to-use nutritional formula, wherein the palmitic acid is at the SN-2 position of a glycerol backbone of the triglyceride.

Embodiment 17. The nutritional formula of embodiment 16, wherein the nutritional formula comprises approximately 2.0 grams to approximately 5.0 grams of the oleic acid-palmitic acid-oleic acid triglyceride per L of reconstituted, ready-to-use nutritional formula.

Embodiment 18. The nutritional formula of any one of embodiments 1-17, wherein the nutritional formula comprises approximately 60 micrograms to approximately 0.05 grams of lutein per L of reconstituted, ready-to-use nutritional formula.

Embodiment 19. The nutritional formula of embodiment 18, wherein the nutritional formula comprises approximately 0.015 grams to approximately 0.025 grams of lutein per L of reconstituted, ready-to-use nutritional formula.

Embodiment 20. The nutritional formula of embodiment 18, wherein the nutritional formula comprises approximately 60 micrograms to approximately 100 micrograms of lutein per L of reconstituted, ready-to-use nutritional formula.

Embodiment 21. The nutritional formula of embodiment 18, wherein the nutritional formula comprises a lutein to DHA ratio of approximately 1.0 to 1.0.

Embodiment 22. The nutritional formula of any one of embodiments 1-21, wherein the nutritional formula comprises approximately 0.001 grams to approximately 0.1 grams of docosahexanoic acid per L of reconstituted, ready-to-use nutritional formula.

Embodiment 23. The nutritional formula of embodiment 22, wherein the nutritional formula comprises approximately 0.1 grams to approximately 1.0 grams of arachidonic acid per L of reconstituted, ready-to-use nutritional formula.

Embodiment 24. The nutritional formula of embodiment 22 or 23, wherein the nutritional formula comprises approximately 0.05 grams to approximately 0.09 grams of docosahexanoic acid per L of reconstituted, ready-to-use nutritional formula.

Embodiment 25. The nutritional formula of any one of embodiments 1-24, wherein the docosahexanoic acid is from *Crypthecodinium cohnii* oil, *Schizochytrium* Sp. oil, or fish oil.

Embodiment 26. The nutritional formula of any one of embodiments 1-25, wherein the arachidonic acid is from *Mortierella alpina* oil.

Embodiment 27. The nutritional formula of any one of embodiments 1-26, wherein the oleic acid-palmitic acid-oleic acid triglyceride is approximately 30% to 50% of a vegetable oil blend.

Embodiment 28. The nutritional formula of any one of embodiments 1-27, wherein the nutritional formula comprises approximately 1.0 grams to approximately 4.1 grams of galactooligosaccharides per L of reconstituted, ready-to-use nutritional formula.

Embodiment 29. The nutritional formula of any one of embodiments 1-28, wherein the nutritional formula comprises approximately 0.1 grams to approximately 0.5 grams of fructooligosaccharides per L of reconstituted, ready-to-use nutritional formula.

Embodiment 30. The nutritional formula of any one of embodiments 1-29, wherein the nutritional formula comprises approximately 2.5 grams to approximately 3.0 grams of alpha-lactalbumin enriched whey protein concentrate per L of reconstituted, ready-to-use nutritional formula.

Embodiment 31. The nutritional formula of any one of embodiments 1-30, wherein the nutritional formula comprises approximately 2.6 grams to approximately 2.9 grams of alpha-lactalbumin enriched whey protein concentrate per L of reconstituted, ready-to-use nutritional formula.

Embodiment 32. The nutritional formula of any one of embodiments 1-31, wherein the nutritional formula comprises approximately 0.5 grams to approximately 1.2 grams of alpha-lactalbumin per 100 grams of nutritional formula in powder form.

Embodiment 33. The nutritional formula of any one of embodiments 1-32, wherein the nutritional formula comprises approximately 35 grams to approximately 80 grams of lactose per L of reconstituted, ready-to-use nutritional formula.

Embodiment 34. The nutritional formula of any one of embodiments 1-33, wherein the nutritional formula comprises at most 85 grams of lactose per L of reconstituted, ready-to-use nutritional formula.

Embodiment 35. The nutritional formula of any one of embodiments 1-34, wherein the nutritional formula comprises approximately 5.3 grams to approximately 6.3 grams of linoleic acid per L of reconstituted, ready-to-use nutritional formula.

Embodiment 36. The nutritional formula of any one of embodiments 1-35, wherein the nutritional formula comprises approximately 5.3 grams to approximately 6.0 grams of linoleic acid per L of reconstituted, ready-to-use nutritional formula.

Embodiment 37. The nutritional formula of any one of embodiments 1-36, wherein the nutritional formula comprises approximately 0.25 grams to approximately 0.75 grams of alpha-linolenic acid per L of reconstituted, ready-to-use nutritional formula.

Embodiment 38. The nutritional formula of any one of embodiments 1-37, wherein the nutritional formula comprises approximately 2.2 grams to approximately 5.5 grams of prebiotics per L of reconstituted, ready-to-use nutritional formula, wherein the prebiotics comprise galactooligosaccharides, fructooligosaccharides, or a combination thereof.

Embodiment 39. The nutritional formula of any one of embodiments 1-37, wherein the nutritional formula comprises approximately 2.5 grams to approximately 5.5 grams of prebiotics per L of reconstituted, ready-to-use nutritional formula, wherein the prebiotics comprise galactooligosaccharides, fructooligosaccharides, or a combination thereof.

Embodiment 40. The nutritional formula of any one of embodiments 1-39, wherein the nutritional formula comprises approximately 3.0 grams to approximately 5.0 grams of prebiotics per L of reconstituted, ready-to-use nutritional formula, wherein the prebiotics comprise galactooligosaccharides, fructooligosaccharides, or a combination thereof.

Embodiment 41. The nutritional formula of any one of embodiments 1-38, wherein the nutritional formula comprises approximately 2.2 grams to approximately 4.5 grams of prebiotics per L of reconstituted, ready-to-use nutritional formula, wherein the prebiotics comprise galactooligosaccharides, fructooligosaccharides, or a combination thereof.

Embodiment 42. The nutritional formula of any one of embodiments 1-41, wherein the nutritional formula comprises approximately 3.5 grams to approximately 4.5 grams of galactooligosaccharides per L of reconstituted, ready-to-use nutritional formula.

Embodiment 43. The nutritional formula of any one of embodiments 1-41, wherein the nutritional formula comprises approximately 2.0 grams to approximately 4.2 grams of galactooligosaccharides per L of reconstituted, ready-to-use nutritional formula.

Embodiment 44. The nutritional formula of any one of embodiments 1-43, wherein the nutritional formula comprises approximately 0.1 grams to approximately 0.3 grams of fructooligosaccharides per L of reconstituted, ready-to-use nutritional formula.

Embodiment 45. The nutritional formula of any one of embodiments 1-43, wherein the nutritional formula comprises approximately 0.2 grams to approximately 0.42 grams of fructooligosaccharides per L of reconstituted, ready-to-use nutritional formula.

Embodiment 46. The nutritional formula of any one of embodiments 1-45 further comprising at least approximately 0.00001 grams of maltodextrin.

Embodiment 47. A nutritional formula comprising:
  a) alpha-lactalbumin enriched whey protein concentrate;
  b) lactoferrin;
  c) oleic acid-palmitic acid-oleic acid triglyceride, wherein palmitic acid is at the SN-2 position of the glycerol backbone of the triglyceride;
  d) lactose;
  e) lutein;
  f) docosahexanoic acid;
  g) arachidonic acid;
  h) galactooligosaccharides; and
  i) fructooligosaccharides; and a powder form thereof.

Embodiment 48. The nutritional formula of any one of embodiments 1-47 further comprising demineralized whey.

Embodiment 49. The nutritional formula of any one of embodiments 1-48, wherein the oleic acid-palmitic acid-oleic acid triglyceride is vegetable-derived.

Embodiment 50. The nutritional formula of any one of embodiments 1-49, further comprising whey protein concentrate that is not alpha-lactalbumin enriched.

Embodiment 51. The nutritional formula of any one of embodiments 1-50 further comprising skimmed milk powder.

Embodiment 52. The nutritional formula of any one of embodiments 1-51 comprising the following weight ranges, in grams per liter (g/L) of reconstituted, ready-to-use nutritional formula:
  a) approximately 3 grams to approximately 10 grams whey protein concentrate that is not alpha-lactalbumin enriched, per L of reconstituted, ready-to-use nutritional formula;
  b) approximately 2.5 grams to approximately 3.0 grams of alpha-lactalbumin enriched whey protein concentrate per L of reconstituted, ready-to-use nutritional formula;
  c) approximately 20.0 grams to approximately 30.0 grams of demineralized whey per L of reconstituted, ready-to-use nutritional formula;
  d) approximately 16.5 grams to approximately 18.5 grams of skimmed milk powder per L of reconstituted, ready-to-use nutritional formula;
  e) approximately 0.02 grams to approximately 0.10 grams of lactoferrin per L of reconstituted, ready-to-use nutritional formula;
  f) approximately 30.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of reconstituted, ready-to-use nutritional formula;
  g) approximately 70 grams to approximately 80 grams of lactose per L of reconstituted, ready-to-use nutritional formula;
  h) approximately 0.00006 grams to approximately 0.025 grams of lutein per L of reconstituted, ready-to-use nutritional formula;
  i) approximately 0.05 grams to approximately 0.09 grams of docosahexanoic acid per L of reconstituted, ready-to-use nutritional formula;
  j) approximately 0.1 grams to approximately 0.5 grams of arachidonic acid per L of reconstituted, ready-to-use nutritional formula;
  k) approximately 5 grams to approximately 6 grams linoleic acid per L of reconstituted, ready-to-use nutritional formula;
  l) approximately 0.25 grams to approximately 0.6 grams alpha-linolenic acid per L of reconstituted, ready-to-use nutritional formula;
  m) approximately 3.0 grams to approximately 5.0 grams of galactooligosaccharides per L of reconstituted, ready-to-use nutritional formula;
  n) approximately 0.10 grams to approximately 0.50 grams of fructooligosaccharides per L of reconstituted, ready-to-use nutritional formula;
  o) approximately 0.05 grams to approximately 0.15 grams of Vitamin C, approximately 0.001 grams to approximately 0.05 grams of Vitamin E per L of reconstituted, ready-to-use nutritional formula; approximately 0.01 grams to approximately 0.05 grams of inositol per L of reconstituted, ready-to-use nutritional formula; approximately 0.0005 grams to approximately 0.02 grams of Vitamin A per L of reconstituted, ready-to-use nutritional formula, approximately 0.005 grams to approximately 0.009 grams of niacin per L of reconstituted, ready-to-use nutritional formula; approximately 0.00001 grams to approximately 0.006 grams of Vitamin D3 per L of reconstituted, ready-to-use nutritional formula; approximately 0.001 grams to approximately 0.005 grams of pantothenic acid per L of reconstituted, ready-to-use nutritional formula; approximately 0.0005 grams to approximately 0.0015 grams of Vitamin K1 per L of reconstituted, ready-to-use nutritional formula; approximately 0.0005 grams to approximately 0.0015 grams of Vitamin B1 per L of reconstituted, ready-to-use nutritional formula; approximately 0.00001 grams to approximately 0.001 grams of Vitamin B2 per L of reconstituted, ready-to-use nutritional formula; approximately 0.0001 grams to approximately 0.0008 grams of Vitamin B6 per L of reconstituted, ready-to-use nutritional formula; approximately 0.0001 grams to approximately 0.002 grams of folic acid per L of reconstituted, ready-to-use nutritional formula; approximately 0.00001 grams to approximately 0.004 grams of biotin per L of reconstituted, ready-to-use nutritional formula; and approximately 0.000001 grams to approximately 0.0005 grams of Vitamin B12 per L of reconstituted, ready-to-use nutritional formula;
  p) approximately 0.5 grams to approximately 0.8 grams of dicalcium phosphate per L of reconstituted, ready-to-use nutritional formula; approximately 0.3 grams to approximately 0.8 grams of calcium carbonate per L of reconstituted, ready-to-use nutritional formula; approximately 0.3 grams to approximately 0.5 grams of potassium chloride per L of reconstituted, ready-to-use nutritional formula; approximately 0.4 grams to approximately 0.7 grams of tripotassium citrate monohydrate per L of reconstituted, ready-to-use nutritional formula; approximately 0.3 grams to approximately 0.5 grams of sodium citrate per L of reconstituted, ready-to-use nutritional formula; approximately 0.2 grams to approximately 0.5 grams of trisodium citrate dihydrate per L of reconstituted, ready-to-use nutritional formula; approximately 0.002 grams to approximately 0.006 grams of dimagnesium phosphate per L of reconstituted, ready-to-use nutritional formula; approximately 0.00002 grams to approximately 0.00005 grams of sodium selenite per L of reconstituted, ready-to-use nutritional formula; approximately 0.02 grams to approximately 0.06 grams of iron (II) sulfate per L of reconstituted, ready-to-use nutritional formula; approximately 0.01 grams to approximately 0.03 grams of zinc sulfate per L of reconstituted, ready-to-use nutritional formula; approximately 0.001 grams to approximately 0.004 grams of copper sulfate per L of reconstituted, ready-to-use nutritional formula; and approximately 0.001 grams to approximately 0.003 grams of manganese (II) sulfate per L of reconstituted, ready-to-use nutritional formula;

q) approximately 0.05 grams to approximately 0.1 grams of adenosine 5'-monophosphate per L of reconstituted, ready-to-use nutritional formula; approximately 0.01 grams to approximately 0.03 grams of cytidine 5'-monophosphate per L of reconstituted, ready-to-use nutritional formula; approximately 0.001 grams to approximately 0.006 grams of guanosine 5'-monophosphate per L of reconstituted, ready-to-use nutritional formula; and approximately 0.01 grams to approximately 0.03 grams of uridine 5'-monophosphate per L of reconstituted, ready-to-use nutritional formula;

r) approximately 0.1 grams to approximately 0.5 grams of L-choline bitartrate per L of reconstituted, ready-to-use nutritional formula; approximately 0.005 grams to approximately 0.03 grams of L-carnitine per L of reconstituted, ready-to-use nutritional formula;

s) approximately 0.0001 grams to approximately 0.0007 grams of beta-carotene per L of reconstituted, ready-to-use nutritional formula; approximately 0.03 grams to approximately 0.07 grams of taurine per L of reconstituted, ready-to-use nutritional formula;

t) approximately 0.3 grams to approximately 0.5 grams of soya lecithin per L of reconstituted, ready-to-use nutritional formula; and u) approximately 0.00001 grams to approximately 0.00005 grams of maltodextrin per L of reconstituted, ready-to-use nutritional formula.

Embodiment 53. The nutritional formula of any one of embodiments 1-51 comprising the following weight ranges, in grams per liter (g/L) of reconstituted, ready-to-use nutritional formula:

a) approximately 3 grams to approximately 10 grams whey protein concentrate that is not alpha-lactalbumin enriched, per L of the reconstituted, ready-to-use nutritional formula;

b) approximately 2.5 grams to approximately 3.0 grams of alpha-lactalbumin enriched whey protein concentrate per L of the reconstituted, ready-to-use nutritional formula;

c) approximately 20.0 grams to approximately 30.0 grams of demineralized whey per L of the reconstituted, ready-to-use nutritional formula;

d) approximately 16.5 grams to approximately 18.5 grams of skimmed milk powder per L of the reconstituted, ready-to-use nutritional formula;

e) approximately 0.02 grams to approximately 0.17 grams of lactoferrin per L of the reconstituted, ready-to-use nutritional formula;

f) approximately 30.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;

g) approximately 65 grams to approximately 80 grams of lactose per L of the reconstituted, ready-to-use nutritional formula;

h) approximately 0.00006 grams to approximately 0.025 grams of lutein per L of the reconstituted, ready-to-use nutritional formula;

i) approximately 0.05 grams to approximately 0.09 grams of docosahexanoic acid per L of the reconstituted, ready-to-use nutritional formula;

j) approximately 0.1 grams to approximately 0.5 grams of arachidonic acid per L of the reconstituted, ready-to-use nutritional formula;

k) approximately 5 grams to approximately 6.2 grams linoleic acid per L of the reconstituted, ready-to-use nutritional formula;

l) approximately 0.25 grams to approximately 0.6 grams alpha-linolenic acid per L of the reconstituted, ready-to-use nutritional formula;

m) approximately 2.0 grams to approximately 5.0 grams of galactooligosaccharides per L of the reconstituted, ready-to-use nutritional formula;

n) approximately 0.10 grams to approximately 0.50 grams of fructooligosaccharides per L of the reconstituted, ready-to-use nutritional formula;

o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;

p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;

q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;

r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;

s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;

t) approximately 0.3 grams to approximately 0.5 grams of soya lecithin per L of the reconstituted, ready-to-use nutritional formula; and u) approximately 0.00001 grams to approximately 0.00005 grams of maltodextrin per L of the reconstituted, ready-to-use nutritional formula.

Embodiment 54. The nutritional formula of any one of embodiments 1-51 comprising the following weight ranges, in grams per liter (g/L) of reconstituted, ready-to-use nutritional formula:

a) approximately 6 grams to approximately 10 grams whey protein concentrate that is not alpha-lactalbumin enriched, per L of the reconstituted, ready-to-use nutritional formula;

b) approximately 2.5 grams to approximately 2.9 grams of alpha-lactalbumin enriched whey protein concentrate per L of the reconstituted, ready-to-use nutritional formula;

c) approximately 22.0 grams to approximately 26.0 grams of demineralized whey per L of the reconstituted, ready-to-use nutritional formula;

d) approximately 16.5 grams to approximately 18.0 grams of skimmed milk powder per L of the reconstituted, ready-to-use nutritional formula;

e) approximately 0.05 grams to approximately 0.17 grams of lactoferrin per L of the reconstituted, ready-to-use nutritional formula;

f) approximately 33.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;

g) approximately 65 grams to approximately 98.0 grams of lactose per L of the reconstituted, ready-to-use nutritional formula;

h) approximately 0.0005 grams to approximately 0.003 grams of lutein per L of the reconstituted, ready-to-use nutritional formula;

i) approximately 0.05 grams to approximately 0.09 grams of docosahexanoic acid per L of the reconstituted, ready-to-use nutritional formula;

j) approximately 0.1 grams to approximately 0.3 grams of arachidonic acid per L of the reconstituted, ready-to-use nutritional formula;

k) approximately 5 grams to approximately 6.2 grams linoleic acid per L of the reconstituted, ready-to-use nutritional formula;

l) approximately 0.25 grams to approximately 0.6 grams alpha-linolenic acid per L of the reconstituted, ready-to-use nutritional formula;

m) approximately 2.0 grams to approximately 5.0 grams of galactooligosaccharides per L of the reconstituted, ready-to-use nutritional formula;

n) approximately 0.10 grams to approximately 0.50 grams of fructooligosaccharides per L of the reconstituted, ready-to-use nutritional formula;

o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;
p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;
q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;
r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;
s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;
t) approximately 0.3 grams to approximately 0.5 grams of soya lecithin per L of the reconstituted, ready-to-use nutritional formula; and
u) approximately 0.00001 grams to approximately 0.00005 grams of maltodextrin per L of the reconstituted, ready-to-use nutritional formula.

Embodiment 55. The nutritional formula of any one of embodiments 1-51 comprising the following weight ranges, in grams per liter (g/L) of reconstituted, ready-to-use nutritional formula:
a) approximately 7 grams to approximately 10 grams whey protein concentrate that is not alpha-lactalbumin enriched, per L of the reconstituted, ready-to-use nutritional formula;
b) approximately 2.6 grams to approximately 2.9 grams of alpha-lactalbumin enriched whey protein concentrate per L of the reconstituted, ready-to-use nutritional formula;
c) approximately 23.0 grams to approximately 26.0 grams of demineralized whey per L of the reconstituted, ready-to-use nutritional formula;
d) approximately 16.75 grams to approximately 18.0 grams of skimmed milk powder per L of the reconstituted, ready-to-use nutritional formula;
e) approximately 0.06 grams to approximately 0.17 grams of lactoferrin per L of the reconstituted, ready-to-use nutritional formula;
f) approximately 34.0 grams to approximately 40.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;
g) approximately 65 grams to approximately 70.0 grams of lactose per L of the reconstituted, ready-to-use nutritional formula;
h) approximately 0.0006 grams to approximately 0.003 grams of lutein per L of the reconstituted, ready-to-use nutritional formula;
i) approximately 0.05 grams to approximately 0.09 grams of docosahexanoic acid per L of the reconstituted, ready-to-use nutritional formula;
j) approximately 0.1 grams to approximately 0.3 grams of arachidonic acid per L of the reconstituted, ready-to-use nutritional formula;
k) approximately 5 grams to approximately 6.2 grams linoleic acid per L of the reconstituted, ready-to-use nutritional formula;
l) approximately 0.25 grams to approximately 0.6 grams alpha-linolenic acid per L of the reconstituted, ready-to-use nutritional formula;
m) approximately 2.0 grams to approximately 5.0 grams of galactooligosaccharides per L of the reconstituted, ready-to-use nutritional formula;
n) approximately 0.10 grams to approximately 0.50 grams of fructooligosaccharides per L of the reconstituted, ready-to-use nutritional formula;
o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;

p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;

q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;

r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;

s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;

t) approximately 0.3 grams to approximately 0.5 grams of soya lecithin per L of the reconstituted, ready-to-use nutritional formula; and u) approximately 0.00001 grams to approximately 0.00005 grams of maltodextrin per L of the reconstituted, ready-to-use nutritional formula.

Embodiment 56. The nutritional formula of any one of embodiments 1-51 comprising the following weight ranges, in grams per liter (g/L) of reconstituted, ready-to-use nutritional formula:

a) approximately 7 grams to approximately 9 grams whey protein concentrate that is not alpha-lactalbumin enriched, per L of the reconstituted, ready-to-use nutritional formula;

b) approximately 2.5 grams to approximately 2.8 grams of alpha-lactalbumin enriched whey protein concentrate per L of the reconstituted, ready-to-use nutritional formula;

c) approximately 22.0 grams to approximately 25.0 grams of demineralized whey per L of the reconstituted, ready-to-use nutritional formula;

d) approximately 16.75 grams to approximately 18.0 grams of skimmed milk powder per L of the reconstituted, ready-to-use nutritional formula;

e) approximately 0.06 grams to approximately 0.17 grams of lactoferrin per L of the reconstituted, ready-to-use nutritional formula;

f) approximately 34.0 grams to approximately 39.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;

g) approximately 65 grams to approximately 70.0 grams of lactose per L of the reconstituted, ready-to-use nutritional formula;

h) approximately 0.0006 grams to approximately 0.001 grams of lutein per L of the reconstituted, ready-to-use nutritional formula;

i) approximately 0.05 grams to approximately 0.09 grams of docosahexanoic acid per L of the reconstituted, ready-to-use nutritional formula;

j) approximately 0.1 grams to approximately 0.3 grams of arachidonic acid per L of the reconstituted, ready-to-use nutritional formula;

k) approximately 5 grams to approximately 6.2 grams linoleic acid per L of the reconstituted, ready-to-use nutritional formula;

l) approximately 0.25 grams to approximately 0.6 grams alpha-linolenic acid per L of the reconstituted, ready-to-use nutritional formula;

m) approximately 2.0 grams to approximately 5.0 grams of galactooligosaccharides per L of the reconstituted, ready-to-use nutritional formula;

n) approximately 0.10 grams to approximately 0.50 grams of fructooligosaccharides per L of the reconstituted, ready-to-use nutritional formula;

o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;

p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;

q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;

r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;

s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;

t) approximately 0.3 grams to approximately 0.5 grams of soya lecithin per L of the reconstituted, ready-to-use nutritional formula; and u) approximately 0.00001 grams to approximately 0.00005 grams of maltodextrin per L of the reconstituted, ready-to-use nutritional formula.

Embodiment 57. The nutritional formula of any one of embodiments 1-56, further comprising water to form a reconstituted, ready-to-use nutritional formula.

Embodiment 58. The nutritional formula of embodiment 57, wherein the water comprises approximately 450 mL to approximately 900 mL water.

Embodiment 59. A method of providing nutrition to a subject, wherein the method comprises: administering the nutritional formula of any one of embodiments 1-56 or administering the reconstituted formula of embodiment 57 or 58 to the subject.

Embodiment 60. A method of providing nutrition to a subject, wherein the method comprises feeding the subject with the nutritional formula of any one of embodiments 1-56 or feeding the subject with the reconstituted formula of embodiment 57 or 58.

Embodiment 61. A method of providing nutrition to a subject, wherein the method comprises reconstituting the formula of any one of embodiments 1-56 with water to form a ready-to-feed liquid.

Embodiment 62. The method of any one of embodiments 59-61 wherein the administering comprises administering to the subject approximately 0.1 L-0.25 L of the reconstituted formula per feeding.

Embodiment 63. The method of any one of embodiments 59-61 wherein the administering comprises administering to the subject 0.5 L-1.0 L of the reconstituted formula per day.

Embodiment 64. The method of any one of embodiments 59-61 or 63 wherein the administering comprises administering to the subject 0.6 L-0.77 L of the reconstituted formula per day.

Embodiment 65. The method of any one of embodiments 59-64 wherein the administering comprises administering to the subject one to six feedings per day.

Embodiment 66. The method of any one of embodiments 59-65 wherein the administering comprises administering to the subject four to six feedings per day.

Embodiment 67. The method of any one of embodiments 59-66, wherein the subject is human.

Embodiment 68. The method of any one of embodiments 59-67, wherein the subject is not more than about two years of age.

Embodiment 69. The method of any one of embodiments 59-68, wherein the subject is a newborn that is not more than about 4 weeks of age.

Embodiment 70. The method of any one of embodiments 59-69, wherein the subject is a newborn that is not more than about 14 days of age.

Embodiment 71. The method of any one of embodiments 59-70, wherein the method promotes postnatal development of the gastrointestinal tract, promotes proper gastrointestinal function, promotes nutrient absorption, and/or promotes proper immune system development.

Embodiment 72. Use of a nutritional formula of any one of embodiments 1-56, or a reconstituted form thereof, for providing nutrition, promoting postnatal development of the gastrointestinal tract, promoting proper gastrointestinal function, promoting nutrient absorption, and/or promoting proper immune system development to a subject.

Embodiment 73. Use of a nutritional formula of any one of embodiments 1-56, or a reconstituted form thereof, the manufacture of a medicament for providing nutrition, promoting postnatal development of the gastrointestinal tract, promoting proper gastrointestinal function, promoting nutrient absorption, and/or promoting proper immune system development.

Embodiment 74. A kit comprising:
  i. one or more packages of the nutritional formula of any one of embodiments 1-56, in powder form;
  ii. reconstituting the nutritional formula by adding water; and
  iii. instructions for administering the nutritional formula to a subject.

Embodiment 75. The kit of embodiment 74, comprising the nutritional formula of any one of embodiments 1-56 and a diluting agent.

Second Exemplary Set of Embodiments

Embodiment 1. A nutritional formula comprising:
  a) alpha-lactalbumin enriched whey protein concentrate;
  b) lactoferrin;
  c) oleic acid-palmitic acid-oleic acid triglyceride, wherein palmitic acid is at the SN-2 position of the glycerol backbone of the triglyceride;
  d) lactose;
  e) lutein;
  f) docosahexanoic acid;
  g) arachidonic acid;
  h) galactooligosaccharides; and
  i) fructooligosaccharides.

Embodiment 2. The nutritional formula of embodiment 1 further comprising linoleic acid.

Embodiment 3. The nutritional formula of embodiment 1 further comprising alpha-linolenic acid.

Embodiment 4. The nutritional formula of embodiment 1 further comprising vitamins, minerals, nucleotides, or a combination thereof.

Embodiment 5. The nutritional formula of embodiment 1 further comprising L-choline bitartrate, L-carnitine, or a combination thereof.

Embodiment 6. The nutritional formula of embodiment 1 further comprising soya lecithin.

Embodiment 7. The nutritional formula of embodiment 1 further comprising beta-carotene, taurine, or a combination thereof.

Embodiment 8. The nutritional formula of embodiment 4, wherein the nucleotides comprise adenosine 5'-monophosphate, cytidine 5'-monophosphate, guanosine 5'-monophosphate, uridine 5'-monophosphate, or a combination thereof.

Embodiment 9. The nutritional formula of embodiment 1, wherein the nutritional formula comprises approximately 0.5 grams to approximately 4.2 grams of alpha-lactalbumin enriched whey protein concentrate per L of reconstituted, ready-to-use nutritional formula.

Embodiment 10. The nutritional formula of embodiment 1, wherein the nutritional formula comprises approximately 0.02 grams to approximately 1.0 grams of lactoferrin per L of reconstituted, ready-to-use nutritional formula.

Embodiment 11. The nutritional formula of embodiment 1, wherein the nutritional formula comprises approximately 1.0 grams to approximately 14.0 grams of the oleic acid-palmitic acid-oleic acid triglyceride per L of reconstituted, ready-to-use nutritional formula.

Embodiment 12. The nutritional formula of embodiment 1, wherein the nutritional formula comprises approximately 60 micrograms to approximately 0.05 grams of lutein per L of reconstituted, ready-to-use nutritional formula.

Embodiment 13. The nutritional formula of embodiment 1, wherein the nutritional formula comprises approximately 0.001 grams to approximately 0.1 grams of docosahexanoic acid per L of reconstituted, ready-to-use nutritional formula.

Embodiment 14. The nutritional formula of embodiment 1, wherein the nutritional formula comprises approximately 0.1 grams to approximately 1.0 grams of arachidonic acid per L of reconstituted, ready-to-use nutritional formula.

Embodiment 15. The nutritional formula of embodiment 1, wherein the nutritional formula comprises approximately 1.0 grams to approximately 4.1 grams of galactooligosaccharides per L of reconstituted, ready-to-use nutritional formula.

Embodiment 16. The nutritional formula of embodiment 1, wherein the nutritional formula comprises approximately 0.1 grams to approximately 0.5 grams of fructooligosaccharides per L of reconstituted, ready-to-use nutritional formula.

Embodiment 17. The nutritional formula of embodiment 1, wherein the nutritional formula comprises approximately 2.5 grams to approximately 5.5 grams of prebiotics per L of reconstituted, ready-to-use nutritional formula, wherein the prebiotics comprise galactooligosaccharides, fructooligosaccharides, or a combination thereof.

Embodiment 18. The nutritional formula of embodiment 1 wherein the nutritional formula comprises approximately 35 grams to approximately 80 grams of lactose per L of reconstituted, ready-to-use nutritional formula.

Embodiment 19. The nutritional formula of embodiment 1, wherein the nutritional formula comprises approximately 5.3 grams to approximately 6.3 grams of linoleic acid per L of reconstituted, ready-to-use nutritional formula.

Embodiment 20. The nutritional formula of embodiment 1, in a powder form.

Embodiment 21. The nutritional formula of embodiment 1 comprising the following weight ranges, in grams per liter (g/L) of reconstituted, ready-to-use nutritional formula:
  a) approximately 3 grams to approximately 10 grams whey protein concentrate that is not alpha-lactalbumin enriched, per L of the reconstituted, ready-to-use nutritional formula;
  b) approximately 2.5 grams to approximately 3.0 grams of alpha-lactalbumin enriched whey protein concentrate per L of the reconstituted, ready-to-use nutritional formula;

c) approximately 20.0 grams to approximately 30.0 grams of demineralized whey per L of the reconstituted, ready-to-use nutritional formula;

d) approximately 16.5 grams to approximately 18.5 grams of skimmed milk powder per L of the reconstituted, ready-to-use nutritional formula;

e) approximately 0.02 grams to approximately 0.17 grams of lactoferrin per L of the reconstituted, ready-to-use nutritional formula;

f) approximately 30.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;

g) approximately 65 grams to approximately 80 grams of lactose per L of the reconstituted, ready-to-use nutritional formula;

h) approximately 0.00006 grams to approximately 0.025 grams of lutein per L of the reconstituted, ready-to-use nutritional formula;

i) approximately 0.05 grams to approximately 0.09 grams of docosahexanoic acid per L of the reconstituted, ready-to-use nutritional formula;

j) approximately 0.1 grams to approximately 0.5 grams of arachidonic acid per L of the reconstituted, ready-to-use nutritional formula;

k) approximately 5 grams to approximately 6.2 grams linoleic acid per L of the reconstituted, ready-to-use nutritional formula;

l) approximately 0.25 grams to approximately 0.6 grams alpha-linolenic acid per L of the reconstituted, ready-to-use nutritional formula;

m) approximately 2.0 grams to approximately 5.0 grams of galactooligosaccharides per L of the reconstituted, ready-to-use nutritional formula;

n) approximately 0.10 grams to approximately 0.50 grams of fructooligosaccharides per L of the reconstituted, ready-to-use nutritional formula;

o) approximately 0.05 grams to approximately 0.15 grams of Vitamin C, approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula, approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;

p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;

q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;

r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;

s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula;

t) approximately 0.3 grams to approximately 0.5 grams of soya lecithin per L of the reconstituted, ready-to-use nutritional formula; and u) approximately 0.00001 grams to approximately 0.00005 grams of maltodextrin per L of the reconstituted, ready-to-use nutritional formula.

Embodiment 22. A method of providing nutrition to a subject, wherein the method comprises: administering the nutritional formula of embodiment 1 to the subject.

Embodiment 23. The method of embodiment 18, wherein the method comprises reconstituting the nutritional formula with water to form a ready-to-feed liquid.

Embodiment 24. A kit comprising:
   i. one or more packages of the nutritional formula of embodiment 1, in powder form,
   ii. reconstituting the nutritional formula by adding water; and
   iii. instructions for administering the nutritional formula to a subject.

EXAMPLES

In order that the present disclosure may be more fully understood, the following examples are set forth. The examples described in this application are offered to illustrate the nutritional formulas, reconstituted formulas, and methods provided herein and are not to be construed in any way as limiting their scope.

Preparation of the Formulations Described Herein

The nutritional formulas provided herein can be prepared from readily available starting materials using the following exemplary methods and procedures. For example, nutritional formulas can be prepared according to Example 1.

Example 1. Exemplary Preparation of Nutritional Formulas

Example 1A. First Exemplary Nutritional Formula

This example illustrates a nutritional formula disclosed herein, including a method for making the formula. The formula ingredients are listed in the following table.

| Ingredient | Quantity g/L reconstituted formula** |
|---|---|
| Kerry Base: | |
| Demineralized whey | 24.436 |
| Vegetable blend (contains OPO) | 36.519 |
| Whey protein concentrate | 6.750 |
| Skimmed milk powder | 17.550 |
| Mineral Premix | |
| Carrier (lactose) | 1.059 |
| Dicalcium phosphate (anhydrous) | 0.603 |
| Calcium carbonate (precipitated) | 0.497 |
| L-Choline bitartrate (conditioned) | 0.459 |
| Potassium chloride | 0.442 |
| Magnesium chloride 6 $H_2O$ | 0.282 |
| Sodium citrate | 0.396 |
| L-carnitine | 0.010968 |
| Potassium Iodide | 0.000115 |
| Potassium citrate | 0.540 |
| Dimagnesium phosphate 3 $H_2O$ | 0.000034 |
| Sodium selenite | 0.002554 |
| Maltodextrin | 0.011380 |
| Lactose | 39.621 |
| α-lactalbumin enriched Whey Protein Concentrate | 2.715 |
| Galactoligosaccharides | 2.310 |
| Fructooligosaccharides | 0.257 |
| Soya lecithin | 0.414 |

-continued

| Ingredient | Quantity g/L reconstituted formula** |
|---|---|
| Lutein | 0.021 |
| β-carotene | 0.000540 |
| Fungal/Algal Oil Blend (2:1 ARA:DHA) | 0.562 |
| Vitamin premix: | |
| Vitamin C (ascorbic acid) | 0.1096875 |
| Carrier (lactose) | 0.06934 |
| Taurine | 0.067511 |
| Vitamin E 50% (dl-α-tocopheryl acetate, 500 IU) | 0.0324 |
| Inositol | 0.02565 |
| Vitamin A (retinol palmitate), 250000 IU | 0.011275 |
| Niacin (Niacinamide) | 0.0081 |
| Vitamin D3 (cholecalciferol), 100000 IU | 0.0054 |
| Pantothenic acid (calcium-D-pantothenate) | 0.003915 |
| Vitamin K1, 5% | 0.00135 |
| Vitamin B1 (thiamine hydrochloride) | 0.00105975 |
| Vitamin B2 (riboflavin) | 0.000837 |
| Vitamin B6 (pyridoxine hydrochloride) | 0.000594 |
| Folic acid | 0.00013851 |
| Biotin | 0.00003915 |
| Vitamin B12 (cyanocobalamin) | 0.000003564 |
| Trace mineral premix: | |
| Carrier (lactose) | 0.07353 |
| Iron (II) sulfate (dried) | 0.046845 |
| Zinc sulfate 1$H_2O$ | 0.016605 |
| Copper sulfate | 0.002646 |
| Manganese (II) sulfate 1$H_2O$ | 0.0000018 |
| Nucleotides premix | |
| Cytidine 5'-Monophosphate free acid | 0.016416 |
| Uridine 5'-Monophosphate Disodium Salt | 0.012798 |
| Guanosine 5'-Monophosphate Disodium Salt | 0.003672 |
| Adenosine 5'-Monophosphate free acid | 0.00864 |
| Carrier | 0.084024 |
| Lactoferrin | 0.064 |

**900 mL of water added to ingredients to give 1 Liter (L) reconstituted formula The nutritional formula is typically prepared using a two-step process (e.g., as shown in FIGS. 1A, 1B, and 2). The nutritional formula of Example 1A was prepared using a two-step process outlined below (e.g., as shown in FIGS. 1A, 1B, and 2). The first step involves the addition of macroingredients (e.g., alpha-lactalbumin enriched whey protein concentrate, demineralized whey, whey protein concentrate, skimmed milk powder, and lactose), prebiotics (e.g., galactooligosaccharides and fructooligosaccharides), base mineral premix, lutein, trisodium and tripotassium citrates, and beta-carotene into a base mixing tank containing reverse osmosis processed water and outfitted with a high speed mixer. The vegetable oil blend (e.g., INFAT® fat blend, including OPO SN-2 oil), DHA/ARA blend and lecithin are then added into the base mixing tank and heated to 140° F. (FIG. 1A).

The slurry is then transferred into a two-stage homogenizer, followed by transfer to a two-stage pasteurizer. Hot filtered air with a temperature of approximately 350° F. to approximately 400° F. is used to spray dry the mixture. Sifting is used to trap large particles, wherein these larger particles are added back into the tall form spray drier to achieve complete drying. When a moisture level of approximately 2.5% to approximately 2.8% or less is achieved, powder is transferred into a powder hopper for bagging into 25 kg nitrogen flushed bags. Samples are taken from the powder hopper (FIG. 1B).

The second stage of the process used to prepare nutritional formula involves the addition of the vitamin premix, trace minerals premix, nucleotides premix, lactoferrin, and lutein premix to the dry blend base. This mixture is placed in a small mixer. The addition of lactoferrin at this stage in the process aids in the preservation of intact ingredients and prevents oxidative degradation during processing, blending, poaching, and storage. The mixture is then transferred into a large paddle blender. A screen magnet, rotary filler, and composite can crimper, are used to fill and seal individual containers of the powder nutritional formula, wherein approximately 110 cans of powder can be produced per minute. The cans are then transferred to a case sealer, and the completed product is placed into suitable containers for distribution (FIG. 2).

The prepared nutritional formulation of Example 1A is analyzed to obtain the following nutritional information.

| Items | /per 100 g powder | /per 100 ml prepared formula | /per 100 kcal |
|---|---|---|---|
| MACRO NUTRIENTS | | | |
| Energy, kcal | 520 | 70 | 100 |
| Protein, g | 12.5 | 1.7 | 2.4 |
| Fat, g | 28.1 | 3.8 | 5.4 |
| OPO, g | 3.6 | 0.5 | 0.7 |
| Carbohydrate, g | 54.6 | 7.4 | 10.5 |
| Lactose, g | 54.6 | 7.4 | 10.5 |
| Dietary fiber, mg | 1920 | 260 | 369 |
| Galactoligosaccharides, mg | 1730 | 233 | 332 |
| Fructooligosaccharides, mg | 192 | 26.0 | 37 |
| Linoleic acid, mg | 4420 | 597 | 850 |
| α-Linolenic acid, mg | 406 | 54.8 | 78 |
| DHA, mg | 50.4 | 6.8 | 9.7 |
| ARA, mg | 101 | 13.7 | 19.5 |
| VITAMINS | | | |
| Vitamin A, IU | 1560 | 211 | 300 |
| Vitamin A re (mcg) | 468 | 63.2 | 90 |
| Vitamin D, IU | 312 | 42.1 | 60 |
| Vitamin D (mcg) | 7.59 | 1.02 | 1.46 |
| Vitamin E, IU | 10.4 | 1.4 | 2.0 |
| Vitamin E (mg) a-te | 9.36 | 1.26 | 1.80 |
| Vitamin K, mcg | 46.8 | 6.32 | 9 |
| Thiamine (Vitamin B1), mcg | 416 | 56.2 | 80 |
| Riboflavin (Vitamin B2), mcg | 728 | 98.3 | 140 |
| Vitamin B6, mcg | 312 | 42.1 | 60 |
| Vitamin B12, mcg | 1.56 | 0.21 | 0.3 |
| Niacin, mcg | 5200 | 702 | 1000 |
| Folic acid (Folacin), mcg | 83.2 | 11.2 | 16 |
| Pantothenic acid, mcg | 3120 | 421 | 600 |
| Biotin, mcg | 15.6 | 2.1 | 3 |
| Vitamin C (Ascorbic acid), mg | 62.4 | 8.42 | 12 |
| OTHER | | | |
| Choline, mg | 125 | 16.8 | 24 |
| Inositol, mg | 31.2 | 4.21 | 6 |
| Nucleotides, mg | 20.8 | 2.81 | 4 |
| L-Carnitine, mg | 6.97 | 0.94 | 1.34 |
| Lutein, mcg | 1780 | 240 | 342 |
| β-carotene, mcg | 98.8 | 13.3 | 19 |
| Taurine, mg | 30.16 | 4.07 | 5.8 |
| Lactoferrin, mg | 47.3 | 6.39 | 9.1 |
| MINERALS | | | |
| Calcium, mg | 406 | 54.8 | 78 |
| Phosphorus, mg | 224 | 30.2 | 43 |
| Magnesium, mg | 41.6 | 5.6 | 8 |
| Iron, mg | 9.36 | 1.26 | 1.8 |
| Zinc, mg | 5.2 | 0.7 | 1 |
| Manganese, mcg | 78 | 10.5 | 15 |
| Copper, mcg | 390 | 52.7 | 75 |
| Iodine, mcg | 78 | 10.5 | 15 |
| Selenium, mcg | 14.6 | 1.97 | 2.8 |
| Sodium, mg | 140 | 19.0 | 27 |
| Potassium, mg | 562 | 75.8 | 108 |
| Chloride, mg | 327 | 44.2 | 62.9 |

Example 1B. Second Exemplary Nutritional Formula

This example illustrates a second nutritional formula disclosed herein, including a method for making the formula. The formula ingredients are listed in the following table.

| Ingredient | Quantity g/L reconstituted formula** |
|---|---|
| Kerry Base: | |
| Demineralized whey | 24.3 |
| Whey protein concentrate | 8.1 |
| Vegetable oil blend (contains OPO) | 36.315 |
| Skimmed milk powder | 17.550 |
| Mineral Premix: | |
| Carrier (lactose) | 0.737 |
| Dicalcium phosphate (anhydrous) | 0.907 |
| Calcium carbonate (precipitated) | 0.450 |
| L-Choline bitartrate (conditioned) | 0.461 |
| Potassium chloride | 0.575 |
| Magnesium chloride•6H$_2$O | 0.341 |
| Sodium citrate•2H$_2$O | 0.254 |
| L-carnitine | 0.011 |
| Potassium iodide (1% on maltodextrin) | 0.0201 |
| Potassium citrate | 0.0000344 |
| Magnesium phosphate | 0.0000344 |
| Sodium selenite (1% on maltodextrin) | 0.004914 |
| Sodium chloride | 0.0233 |
| Lactose | 35.527 |
| α-lactalbumin enriched Whey Protein Concentrate | 2.700 |
| Galactoligosaccharides | 3.915 |
| Fructooligosaccharides | 0.270 |
| Soya lecithin | 0.412 |
| Lutein | 0.016875 |
| β-carotene | 0.00054 |
| Trisodium citrate dihydrate | 0.3375 |
| Tripotassium citrate monohydrate | 0.54 |
| Fungal/Algal Oil Blend (2:1 ARA:DHA) | 0.5616 |
| Vitamin premix: | |
| Vitamin C (ascorbic acid) | 0.1109 |
| Carrier (lactose) | 0.0640 |
| Taurine | 0.0694 |
| Vitamin E acetate | 0.0347 |
| Inositol | 0.0262 |
| Vitamin A (retinol palmitate) | 0.0114 |
| Niacin (Niacinamide) | 0.0082 |
| Vitamin D3 (cholecalciferol) | 0.0055 |
| Pantothenic acid (calcium-D-pantothenate) | 0.003896 |
| Vitamin K1 (as Phylloquimone) | 0.001364 |
| Vitamin B1 (thiamine hydrochloride) | 0.001094 |
| Vitamin B2 (riboflavin) | 0.00003753 |
| Vitamin B6 (pyridoxine hydrochloride) | 0.0005965 |
| Folic acid (Trit on maltodextrin) | 0.001398 |
| Biotin (as D-biotin on maltodextrin) | 0.003954 |
| Vitamin B12 (as cyanocobalamin Trit on maltodextrin) | 0.0003614 |

-continued

| Ingredient | Quantity g/L reconstituted formula** |
|---|---|
| Trace mineral premix: | |
| Carrier (lactose) | 0.635 |
| Iron (II) sulfate (dried) | 0.04277 |
| Zinc sulfate•1H$_2$O | 0.02121 |
| Copper sulfate | 0.001733 |
| Manganese (II) sulfate•1H$_2$O | 0.001214 |
| Nucleotides premix | |
| Cytidine 5'-Monophosphate free acid | 0.02136 |
| Uridine 5'-Monophosphate Disodium Salt | 0.02117 |
| Guanosine 5'-Monophosphate Disodium Salt | 0.00596 |
| Adenosine 5'-Monophosphate free acid | 0.01136 |
| Carrier | 0.07651 |
| Lactoferrin | 0.0653 |

900 mL of water added to ingredients to give 1 Liter (L) reconstituted formula The nutritional formula is typically prepared using a two-step process (e.g., as shown in FIGS. 1A, 1B, and 2). The nutritional formula of Example 1B was prepared using a two-step process outlined below (e.g., as shown in FIGS. 1A, 1B, and 2). The first step involves the addition of macroingredients (e.g., alpha-lactalbumin enriched whey protein concentrate, demineralized whey, whey protein concentrate, skimmed milk powder, and lactose), prebiotics (e.g., galactooligosaccharides and fructooligosaccharides), base mineral premix, lutein, trisodium and tripotassium citrates, and beta-carotene into a base mixing tank containing reverse osmosis processed water and outfitted with a high speed mixer. The vegetable oil blend (e.g., INFAT® fat blend, including OPO SN-2 oil), DHA/ARA blend and lecithin are then added into the base mixing tank and heated to 140° F. (FIG. 1A**).

The slurry is then transferred into a two-stage homogenizer, followed by transfer to a two-stage pasteurizer. Hot filtered air with a temperature of approximately 350° F. to approximately 400° F. is used to spray dry the mixture. Sifting is used to trap large particles, wherein these larger particles are added back into the tall form spray drier to achieve complete drying. When a moisture level of approximately 2.5% to approximately 2.8% or less is achieved, powder is transferred into a powder hopper for bagging into 25 kg nitrogen flushed bags. Samples are taken from the powder hopper (FIG. 1B).

The second stage of the process used to prepare nutritional formula involves the addition of the vitamin premix, trace minerals premix, nucleotides premix, lactoferrin, and lutein premix to the dry blend base. This mixture is placed in a small mixer. The addition of lactoferrin at this stage in the process aids in the preservation of intact ingredients and prevents oxidative degradation during processing, blending, poaching, and storage. The mixture is then transferred into a large paddle blender. A screen magnet, rotary filler, and composite can crimper, are used to fill and seal individual containers of the powder nutritional formula, wherein approximately 110 cans of powder can be produced per minute. The cans are then transferred to a case sealer, and the completed product is placed into suitable containers for distribution (FIG. 2).

The Example 1B prepared nutritional formulation is analyzed to obtain the following nutritional information.

| Items | /per 100 g powder | /per 100 ml prepared formula | /per 100 kcal |
|---|---|---|---|
| MACRO NUTRIENTS | | | |
| Energy, kcal | 520 | 70.2 | 100 |
| Protein, g | 12.3 | 1.7 | 2.4 |
| Alpha-lactalbumin | 863 | 117 | 166 |
| Fat, g | 27 | 3.6 | 5.2 |
| OPO, g | 3.6 | 0.5 | 0.7 |
| Linoleic acid, mg | 4160 | 562 | 800 |
| α-Linolenic acid, mg | 312 | 42.1 | 60 |
| Carbohydrate, g | 55 | 7.4 | 10.6 |
| Lactose, g | 54 | 7.3 | 10 |
| Dietary fiber, mg | 3100 | 419 | 596 |
| Galactooligosaccharides, mg | 2900 | 392 | 558 |
| Fructooligosaccharides, mg | 200 | 27.0 | 38 |
| DHA, mg | 50 | 6.8 | 10 |
| ARA, mg | 100 | 13.5 | 19 |
| VITAMINS | | | |
| Vitamin A, IU | 1545 | 211 | 300 |
| Vitamin D, IU | 309 | 42 | 60 |
| Vitamin E, IU | 10.3 | 1.4 | 2 |
| Vitamin K, mcg | 46.4 | 6.3 | 9 |
| Thiamine (Vitamin B1), mcg | 412 | 56 | 80 |
| Riboflavin (Vitamin B2), mcg | 721 | 98.3 | 140 |
| Vitamin B6, mcg | 309 | 42 | 60 |
| Vitamin B12, mcg | 1.5 | 0.2 | 0.3 |
| Niacin, mcg | 5150 | 702 | 1000 |
| Folic acid (Folacin), mcg | 82 | 11 | 16 |
| Pantothenic acid, mcg | 2600 | 355 | 505 |
| Biotin, mcg | 15.5 | 2.1 | 3 |
| Vitamin C (Ascorbic acid), mg | 62 | 8.5 | 12 |
| OTHER | | | |
| Choline, mg | 124 | 17 | 24 |
| Inositol, mg | 31 | 4.2 | 6 |
| Nucleotides, mg | 20 | 2.7 | 4 |
| L-Carnitine, mg | 6.9 | 0.9 | 1.34 |
| Lutein, mcg | 64 | 8.7 | 12 |
| β-carotene, mcg | 100 | 14 | 19 |
| Taurine, mg | 30 | 4.1 | 5.8 |
| Lactoferrin, mg | 47 | 6.4 | 9.1 |
| MINERALS | | | |
| Calcium, mg | 402 | 54.8 | 78 |
| Phosphorus, mg | 221 | 30 | 43 |
| Magnesium, mg | 41 | 6 | 8 |
| Iron, mg | 9.3 | 1.3 | 1.8 |
| Zinc, mg | 5.2 | 0.7 | 1 |
| Manganese, mcg | 77 | 10.5 | 15 |
| Copper, mcg | 386 | 52.6 | 75 |
| Iodine, mcg | 77 | 10.5 | 15 |
| Selenium, mcg | 14.4 | 2.0 | 2.8 |
| Sodium, mg | 139 | 19 | 27 |
| Potassium, mg | 556 | 75.8 | 108 |
| Chloride, mg | 324 | 44 | 62.9 |

Example 2-1 illustrates a nutritional formula disclosed herein, including a method for making the formula. The formula ingredients are listed in the following Table 1B.

TABLE 1B

| | | g/L |
|---|---|---|
| Kerry Base | Demineralized whey | 24.3000 |
| | Whey protein concentrate | 8.100 |
| | Vegetable oil blend (contains OPO) | 36.315 |
| | Skimmed milk powder | 17.550 |

TABLE 1B-continued

| | | g/L |
|---|---|---|
| Mineral Premix | Dicalcium phosphate anhydrous | 0.907200 |
| | Carrier (lactose) | 0.737100 |
| | Potassium chloride | 0.574560 |
| | L-Choline bitartrate (conditioned) | 0.461160 |
| | Calcium carbonate (precipitated) | 0.449820 |
| | Magnesium chloride 6H2O | 0.340956 |
| | Sodium citrate 2H2O | 0.254016 |
| | Sodium Chloride | 0.023323 |
| | Potassium Iodide (1% on Maltodextrin) | 0.020072 |
| | L-carnitine | 0.011000 |
| | Sodium selenite (1% on Maltodextrin) | 0.004914 |
| | Potassium citrate | 0.000034 |
| | Magnesium phosphate | 0.000034 |
| | Lactose | 29.276 |
| | α-lactalbumin enriched WPC | 2.700 |
| | Fructooligosaccharides | 0.270 |
| | Galactoligosaccharides (Vivinal GOS Syrup 59%) | 3.915 |
| | Soya lecithin | 0.412 |
| | Lutein | 0.017 |
| | β-carotene | 0.001 |
| | Trisodium Citrate Dihydrate | 0.338 |
| | Tripotassium Citriate Monohydrate | 0.540 |
| | Fungal /Algal Oil Blend (2:1 ARA/DHA) | 0.562 |
| DSM Vitamin Premix | Vitamin C (ascorbic acid) | 0.111 |
| | Carrier (lactose) | 0.064 |
| | Taurine | 0.069 |
| | Vitamin E Acetate | 0.033 |
| | Inositol | 0.026 |
| | Vitamin A (retinol palmitate) | 0.011 |
| | Niacin (Niacinamide) | 0.008 |
| | Vitamin D3 (cholecalciferol) | 0.005 |
| | Pantothenic acid (calcium-D-pantothenate) | 0.004 |
| | )Vitamin K1 (as Phylloquimone) | 0.001 |
| | Vitamin B1 (thiamine hydrochloride) | 0.001 |
| | Vitamin B2 (riboflavin) | 0.000 |
| | Vitamin B6 (pyridoxine hydrochloride) | 0.001 |
| | Folic acid (Trit on MD) | 0.001 |
| | Biotin (asD-Biotin on MD) | 0.004 |
| | Vitamin B12 (as cyanocobalamin Trit n MD) | 0.000 |
| DSM Mineral premix | Carrier (lactose) | 0.635 |
| | Iron (II) sulphate (dried) | 0.043 |
| | Zinc sulphate 1H2O | 0.021 |
| | Copper sulphate | 0.002 |
| | Manganese (II) sulphate 1H2O Trit MD | 0.001 |
| DSM Nucleotides premix | Cytidine 5'-Monophsphate free acid | 0.021 |
| | Uridine 5'-Monophosphate Disodium Salt | 0.021 |
| | Guanosine 5'-Monophosphate Disodium Salt | 0.006 |
| | Adenosine 5'-Monophosphate free acid | 0.011 |
| | Carrier (lactose) | 0.077 |
| DSM Lutein Premix FN-200408 | Lutein 5% SD/S (DSM | 0.007 |
| | Lactose | 5.670 |
| Lactoferrin (Milei MLF - 2M) | | 0.065 |

** 900 mL of water added to ingredients to give 1 Liter (L) reconstituted formula Example 2-2 illustrates a nutritional formula disclosed herein, including a method for making the formula. The formula ingredients are listed in the following Table 1C.

TABLE 1C

| | | g/L | g/100 g |
|---|---|---|---|
| Kerry Base 9265 20492074 | Demineralized whey | 24.300 | 18.0000 |
| | Whey protein concentrate | 8.100 | 6.0000 |
| | Vegetable oil blend (contains OPO) | 36.315 | 26.9000 |
| | Skimmed milk powder | 17.550 | 13.0000 |
| Mineral Premix RE29249/A | Dicalcium phosphate anhydrous | 0.907200 | 0.6720000 |
| | Carrier (lactose) | 0.737100 | 0.5460000 |
| | Potassium chloride | 0.574560 | 0.4256000 |
| | L-Choline bitartrate (conditioned) | 0.461160 | 0.3416000 |
| | Calcium carbonate (precipitated) | 0.449820 | 0.3332000 |
| | Magnesium chloride 6H2O | 0.340956 | 0.2525600 |
| | Sodium citrate 2H2O | 0.254016 | 0.1881600 |
| | Sodium Chloride | 0.023323 | 0.0172760 |
| | Potassium Iodide (1% on Maltodextrin) | 0.020072 | 0.0148680 |
| | L-carnitine | 0.011000 | 0.0081480 |
| | Sodium selenite (1% on Maltodextrin) | 0.004914 | 0.0036400 |
| | Potassium citrate | 0.000034 | 0.0000255 |
| | Magnesium phosphate | 0.000034 | 0.0000255 |
| | Lactose | 29.276 | 21.685556 |
| | α-lactalbumin enriched WPC | 2.700000 | 2.000000 |
| | Fructooligosaccharides | 0.270000 | 0.200000 |
| | Galactoligosaccharides (Vivinal GOS Syrup 59%) | 3.915000 | 2.900000 |
| | Soya lecithin | 0.411750 | 0.305000 |
| | Lutein | 0.016875 | 0.012500 |
| | β-carotene | 0.000540 | 0.000400 |
| | Trisodium Citrate Dihydrate | 0.337500 | 0.250000 |
| | Tripotassium Citriate Monohydrate | 0.540000 | 0.400000 |
| | Fungal/Algal Oil Blend (Formulaid 2:1 ARA/DHA) | 0.561600 | 0.416000 |
| DSM Vitamin Premix XR71008 | Vitamin C (ascorbic acid) | 0.110893 | 0.0821433 |
| | Carrier (lactose) | 0.063952 | 0.0473715 |
| | Taurine | 0.069351 | 0.0513711 |
| | Vitamin E Acetate | 0.032724 | 0.0242400 |
| | Inositol | 0.026166 | 0.0193819 |
| | Vitamin A (retinol palmitate) | 0.011389 | 0.0084360 |
| | Niacin (Niacinamide) | 0.008246 | 0.0061080 |
| | Vitamin D3 (cholecalciferol) | 0.005454 | 0.0040400 |
| | Pantothenic acid (calcium-D-pantothenate) | 0.003896 | 0.0028861 |
| | (Vitamin K1 (as Phylloquimone) | 0.001364 | 0.0010100 |
| | Vitamin B1 (thiamine hydrochloride) | 0.001094 | 0.0008105 |

TABLE 1C-continued

|  |  | g/L | g/100 g |
|---|---|---|---|
|  | Vitamin B2 (riboflavin) | 0.000038 | 0.0000278 |
|  | Vitamin B6 (pyridoxine hydrochloride) | 0.000597 | 0.0004419 |
|  | Folic acid (Trit on MD) | 0.001398 | 0.0010353 |
|  | Biotin (asD-Biotin on MD) | 0.003954 | 0.0029290 |
|  | Vitamin B12 (as cyanocobalamin Trit n MD) | 0.000361 | 0.0002677 |
| DSM Mineral premix XR71284 Dosage 100 mg/100 kcal | Carrier (lactose) | 0.635282 | 0.4705792 |
|  | Iron (II) sulphate (dried) | 0.042766 | 0.0316784 |
|  | Zinc sulphate 1H2O | 0.021214 | 0.0157144 |
|  | Copper sulphate | 0.001733 | 0.0012840 |
|  | Manganese (II) sulphate 1H2O Trit MD | 0.001214 | 0.0008996 |
| DSM Nucleotides premix XR71224 | Cytidine 5'-Monophsphate free acid | 0.021357 | 0.0158198 |
|  | Uridine 5'-Monophosphate Disodium Salt | 0.021171 | 0.0156823 |
|  | Guanosine 5'-Monophosphate Disodium Salt | 0.005956 | 0.0044117 |
|  | Adenosine 5'-Monophosphate free acid | 0.011359 | 0.0084143 |
|  | Carrier (lactose) | 0.076507 | 0.0566721 |
| DSM Lutein Premix XR | Lutein 1% SD/S (DSM | 0.007324 | 0.0054250 |
|  | Lactose | 5.670000 | 4.2000000 |
| Lactoferrin (Milei MLF - 2M) |  | 0.065286 | 0.048 |
|  |  |  | 100.000000 |

Example 2-3 illustrates a nutritional formula disclosed herein, including a method for making the formula. The formula ingredients are listed in the following Table 1D.

TABLE 1D

|  |  | g/L | g/100 g |
|---|---|---|---|
| Kerry Base | Demineralized whey | 24.300 | 18.0000 |
|  | Whey protein concentrate | 8.100 | 6.0000 |
|  | Vegetable oil blend (contains OPO) | 36.315 | 26.9000 |
|  | Skimmed milk powder | 17.550 | 13.0000 |
| Mineral Premix | Dicalcium phosphate anhydrous | 0.907200 | 0.6720000 |
|  | Canier (lactose) | 0.737100 | 0.5460000 |
|  | Potassium chloride | 0.574560 | 0.4256000 |
|  | L-Choline bitartrate (conditioned) | 0.461160 | 0.3416000 |
|  | Calcium carbonate (precipitated) | 0.449820 | 0.3332000 |
|  | Magnesium chloride 6H2O | 0.340956 | 0.2525600 |
|  | Sodium citrate 2H2O | 0.254016 | 0.1881600 |
|  | Sodium Chloride | 0.023323 | 0.0172760 |
|  | Potassium Iodide (1% on Maltodextrin) | 0.020072 | 0.0148680 |
|  | L-carnitine | 0.011000 | 0.0081480 |
|  | Sodium selenite (1% on Maltodextrin) | 0.004914 | 0.0036400 |
|  | Potassium citrate | 0.000034 | 0.0000255 |
|  | Magnesium phosphate | 0.000034 | 0.0000255 |
|  | Lactose | 34.949741 | 25.888697 |
|  | α-lactalbumin enriched WPC | 2.700000 | 2.000000 |
|  | Fructooligosaccharides | 0.270000 | 0.200000 |
|  | Galactoligosaccharides (Vivinal GOS Syrup 59%) | 3.915000 | 2.900000 |
|  | Soya lecithin | 0.411750 | 0.305000 |
|  | Lutein | 0.020655 | 0.015300 |
|  | β-carotene | 0.000540 | 0.000400 |
|  | Trisodium Citrate Dihydrate | 0.337500 | 0.250000 |
|  | Tripotassium Citrate Monohydrate | 0.540000 | 0.400000 |
|  | Fungal/Algal Oil Blend (Formulaid B 2:1 ARA/DHA) | 0.561600 | 0.416000 |
| DSM Vitamin Premix XR72986 | Vitamin C (ascorbic acid) | 0.110893 | 0.0821433 |
|  | Carrier (lactose DC) | 0.063952 | 0.0473715 |
|  | Taurine | 0.069351 | 0.0513711 |
|  | Vitamin E Acetate | 0.032724 | 0.0242400 |
|  | Inositol | 0.026166 | 0.0193819 |
|  | Vitamin A (retinol palmitate) | 0.011389 | 0.0084360 |
|  | Niacin (Niacinamide) | 0.008246 | 0.0061080 |
|  | Vitamin D3 (cholecalciferol) | 0.005454 | 0.0040400 |
|  | Pantothenic acid (calcium-D-pantothenate) | 0.003896 | 0.0028861 |
|  | )Vitamin K1 (Phylloquimone SD Gran) | 0.001364 | 0.0010100 |
|  | Vitamin B1 (thiamine hydrochloride) | 0.001094 | 0.0008105 |
|  | Vitamin B2 (riboflavin) | 0.000038 | 0.0000278 |
|  | Vitamin B6 (pyridoxine hydrochloride) | 0.000597 | 0.0004419 |
|  | Folic acid (Trit on DCP) | 0.001398 | 0.0010353 |
|  | Biotin (asD-Biotin on DCP) | 0.003954 | 0.0029290 |
|  | Vitamin B12 (as cyanocobalamin Trit DCP) | 0.000361 | 0.0002677 |

TABLE 1D-continued

|  |  | g/L | g/100 g |
|---|---|---|---|
| DSM Mineral premix XR72987 | Carrier (lactose) | 0.629673 | 0.4664244 |
|  | Iron (II) sulphate (dried) | 0.049182 | 0.0364312 |
|  | Zinc sulphate 1H2O | 0.021214 | 0.0157144 |
|  | Copper sulphate | 0.001523 | 0.0011284 |
|  | Manganese (II) sulphate 1H2O | 0.000407 | 0.0003016 |
| DSM Nucleotides premix XR71224 | Cytidine 5'-Monophsphate free acid | 0.021356 | 0.0158196 |
|  | Uridine 5'-Monophsphate Disodium Salt | 0.021171 | 0.0156823 |
|  | Guanosine 5'-Monophosphate Disodium Salt | 0.005956 | 0.0044117 |
|  | Adenosine 5'-Monophosphate free acid | 0.011359 | 0.0084143 |
|  | Carrier (lactose) | 0.076507 | 0.0566721 |
| Lactoferrin (Milei MLF - 2M) |  | 0.064800 | 0.0480000 |
|  |  |  | 100.00000 |

The nutritional formula is typically prepared using a two-step process (e.g., as shown in FIGS. 1A, 1B, and 2). The nutritional formula of Examples 2-1, 2-2, and 2-3 were prepared using a two-step process outlined below (e.g., as shown in FIGS. 1A, 1B, and 2). The first step involves the addition of macroingredients (e.g., alpha-lactalbumin enriched whey protein concentrate, demineralized whey, whey protein concentrate, skimmed milk powder, and lactose), prebiotics (e.g., galactooligosaccharides and fructooligosaccharides), base mineral premix, lutein, trisodium and tripotassium citrates, and beta-carotene into a base mixing tank containing reverse osmosis processed water and outfitted with a high speed mixer. The vegetable oil blend (e.g., INFAT® fat blend, including OPO SN-2 oil), DHA/ARA blend and lecithin are then added into the base mixing tank and heated to 140° F. (FIG. 1A).

The slurry is then transferred into a two-stage homogenizer, followed by transfer to a two-stage pasteurizer. Hot filtered air with a temperature of approximately 350° F. to approximately 400° F. is used to spray dry the mixture. Sifting is used to trap large particles, wherein these larger particles are added back into the tall form spray drier to achieve complete drying. When a moisture level of approximately 2.5% to approximately 2.8% or less is achieved, powder is transferred into a powder hopper for bagging into 25 kg nitrogen flushed bags. Samples are taken from the powder hopper (FIG. 1B).

The second stage of the process used to prepare nutritional formula involves the addition of the vitamin premix, trace minerals premix, nucleotides premix, lactoferrin, and lutein premix to the dry blend base. This mixture is placed in a small mixer. The addition of lactoferrin at this stage in the process aids in the preservation of intact ingredients and prevents oxidative degradation during processing, blending, poaching, and storage. The mixture is then transferred into a large paddle blender. A screen magnet, rotary filler, and composite can crimper, are used to fill and seal individual containers of the powder nutritional formula, wherein approximately 110 cans of powder can be produced per minute. The cans are then transferred to a case sealer, and the completed product is placed into suitable containers for distribution (FIG. 2).

The Examples 2-1, 2-2, and/or 2-3 prepared nutritional formulations are and/or were analyzed using standard analytical techniques in the field for the clinical and Protein Efficiency Ratio (PER) study in rats, to obtain the following nutritional information and microbiology information for lots #1 and #2 shown in Table 1A.

TABLE 1A

Nutritional information and microbiology information for Example 2-1, Example 2-2, Example 2-3, Tables 1B, 1C, and/or 1D.

|  | per 100 g of Powder | | | | | | per 100 kcal | |
|---|---|---|---|---|---|---|---|---|
| Analytical | Lot #1 | Lot #2 | Average Results | Label Claim | Lower Limit | Upper Limit | Average Results | Label Claim |
| Protein, g | 13.6 | 13.6 | 13.6 | 13.0 | 13.0 | 14.0 | 2.7 | 2.5 |
| Fat, g | 26.3 | 26.3 | 26.3 | 26.0 | 26.0 | 28.8 | 5.2 | 5.1 |
| OPO, g | 3.7 | 3.7 | 3.7 | 3.6 | 3 | 8 | 0.7 | 0.7 |
| Linoleic acid, mg | 4550 | 4520 | 4535 | 4420 | 4420 | 4600 | 896 | 850 |
| α-Linolenic acid, mg | 393 | 390 | 392 | 312 | 312 | 400 | 77 | 60 |
| Carbohydrate, g* | 54.6 | 54.6 | 54.6 | 54 | 54 | 65 | 10.8 | 10.5 |
| Lactose, g** | 50.3 | 49.6 | 50 | 49 | 49 | 72 | 9.9 | 9.5 |
| Dietary Fiber, mg | 1737 | 1759 | 1748 | 1716 | 1100 | 3300 | 345 | 330 |
| Galactooligosaccharides mg | 1560 | 1570 | 1565 | 1560 | 1000 | 3000 | 309 | 300 |
| Fructooligosaccharide mg | 177 | 189 | 183 | 156 | 100 | 300 | 36 | 30 |
| DHA, mg | 51 | 52 | 52 | 50 | 50 | 60 | 10.2 | 9.6 |
| ARA, mg | 105 | 105 | 105 | 100 | 100 | 120 | 21 | 19 |
| Vitamins |  |  |  |  |  |  | 0.0 |  |
| Vitamin A, IU | 3180 | 2337 | 2759 | 1560 | 1560 | 3700 | 545 | 300 |
| Vitamin D, IU | 442 | 416 | 429 | 312 | 312 | 520 | 85 | 60 |
| Vitamin E, IU | 14.5 | 13.5 | 14.0 | 10.4 | 10.4 | 15 | 3 | 2 |
| Vitamin K, mcg | 73.6 | 75.1 | 74.4 | 46.8 | 46.8 | 80.0 | 15 | 9 |
| Thiamine (Vitmain B1), mcg | 803 | 821 | 812 | 416 | 416 | 850 | 160 | 80 |
| Riboflavin (Vitamin B2), mcg | 1400 | 1380 | 1390 | 728 | 728 | 1500 | 275 | 140 |
| Vitamin B6, mcg | 432 | 430 | 431 | 312 | 312 | 450 | 85 | 60 |

TABLE 1A-continued

Nutritional information and microbiology information for Example
2-1, Example 2-2, Example 2-3, Tables 1B, 1C, and/or 1D.

| | | | | | | | | |
|---|---|---|---|---|---|---|---|---|
| Vitmain B12, mcg | 5.76 | 5.36 | 5.6 | 1.5 | 1.6 | 9.6 | 1 | 0.3 |
| Niacin, mcg | 6560 | 5850 | 6205 | 5200 | 5200 | 6600 | 1226 | 1000 |
| Folic acid (Folacin), mcg | 101 | 106 | 104 | 83 | 83 | 110 | 20 | 16 |
| Pantothenic acid, mcg | 4280 | 4060 | 4170 | 3120 | 3120 | 4300 | 824 | 600 |
| Biotin, mcg | 37.4 | 31.8 | 34.6 | 15.6 | 15.6 | 40.0 | 7 | 3 |
| Vitamin C (Ascorbic acid), mg | 80.2 | 98.5 | 89 | 62 | 62 | 120 | 18 | 12 |
| Other | | | | | | | 0.0 | |
| Choline, mg | 195 | 189 | 192 | 125 | 125 | 250 | 38 | 24 |
| Inositol, mg | 37.9 | 37.4 | 38 | 31 | 31 | 40 | 7 | 6 |
| Nucleotides, mg | 36.8 | 38.3 | 38 | 20 | 20 | 40 | 7 | 4 |
| L-Carnitine, mg | 18.5 | 18.3 | 18 | 6.8 | 6.8 | 50 | 3.6 | 1.3 |
| Lutein, mcg | 63.5 | 75.6 | 70 | 52 | 30 | 200 | 14 | 10 |
| β-carotene, mcg | 128 | 130 | 129 | 98 | 98 | 240 | 25 | 19 |
| Taurine, mg | 58.7 | 55.3 | 57 | 31 | 31 | 60 | 11 | 6 |
| Lactoferrin | 98.7 | 98.5 | 99 | 47 | 47 | 120 | 19 | 9 |
| Moisture | 2.30 | 2.23 | 2.27 | — | — | <3 | 0.45 | <3 |
| Minerals | | | | | | | 0.0 | |
| Calcium, mg | 553 | 563 | 558 | 402 | 402 | 700 | 110 | 78 |
| Phosphorus, mg | 364 | 363 | 364 | 221 | 221 | 450 | 72 | 43 |
| Magnesium, mg | 59.7 | 59.4 | 60 | 41 | 41 | 75 | 12 | 8 |
| Iron, mg | 9.8 | 10.1 | 10.0 | 9.3 | 9.3 | 15.0 | 2.0 | 1.8 |
| Zinc, mg | 6.33 | 6.53 | 6.4 | 5.2 | 5.2 | 7.0 | 1 | 1 |
| Manganese, mcg | 152 | 152 | 152 | 77 | 77 | 160 | 30 | 8 |
| Copper, mcg | 432 | 471 | 452 | 386 | 386 | 463 | 89 | 75 |
| Iodine, mcg | 174 | 176 | 175 | 77 | 77 | 375 | 35 | 15 |
| Selenium, mcg | 24.7 | 24.7 | 24.7 | 14.4 | 14.4 | 35.0 | 4.9 | 2.8 |
| Sodium, mg | 230 | 236 | 233 | 139 | 139 | 300 | 46 | 27 |
| Potassium, mg | 679 | 685 | 682 | 556 | 556 | 1000 | 135 | 108 |
| Chloride, mg | 432 | 432 | 432 | 324 | 324 | 750 | 85.4 | 63.0 |

| Microbiology | Lot #1 | Lot #2 | |
|---|---|---|---|
| *Salmonella* | Pass | Pass | Neg/25 g |
| Enterobacter Sakazakii #1 | Pass | Pass | Absent/100 g |
| Enterobacter Sakazakii #2 | Pass | Pass | Absent/100 g |
| Enterobacter Sakazakii #3 | Pass | Pass | Absent/100 g |
| Enterobacteriaceae Count | Pass | Pass | <10 CFU[1]/g |
| Listeria | Pass | Pass | Neg/25 g |
| *Staphylococcus* | Pass | Pass | <10 CFU/g |
| Yeast Count | Pass | Pass | <10 CFU/g |
| Mold Count | Pass | Pass | <10 CFU/g |
| Aerobic Plate Count | Pass | Pass | <1,000 CFU/g |
| Bacillus Cereus Plate Count | Pass | Pass | <100 CFU/g |
| Clostridium Perfringens | Pass | Pass | <10 CFU/g |
| Total Coliforms | Pass | Pass | <10 CFU/g |
| *Escherichia Coli* | Pass | Pass | <10 CFU/g |

[1] CFU refers to colony forming units.

Example 2A

The standard analytical techniques in the field were used for the clinical and Protein Efficiency Ratio (PER) study in rats, to obtain the following nutritional information and microbiology information for lots #1 and #2 shown in Table 1A are as described below. The testing followed the guidelines in *Protein Efficiency Ratio*. AOAC Official Method 960.48, Paragraph 45.3.04. AOAC International (18th Edition, 2005) *FO-1, Determination of Protein Rating*. Official Method, Health Protection Branch, Ottawa. Oct. 15, 1981, and was as described below.

Purpose

The Protein Efficiency Ratio (PER) study was conducted to demonstrate that the protein in the Test Article meets the quality factor of sufficient biological quality of protein by establishing the biological quality of the protein in the finished product when fed as a sole source of nutrition using an appropriate modification of the Protein Efficiency Ratio (PER) rat bioassay described in the "Official Methods of Analysis of AOAC International", 18th ed., sections 45.3.04 and 453.05, "AOAC Official Method 960.48 Protein Efficiency Ratio Rat Bioassay," which is incorporated by reference at 106.160.

Background

Whether the protein ingredients of infant formula (typically bovine milk, whey concentrates and/or protein hydrolysates) retain their full complement of bioavailable amino acids through the infant formula manufacturing process is tested experimentally. Formation of Maillard reaction products, generated during the thermal processes of formula production, may negatively impact the protein quality of the formula (Boye, Wijesinha-Bettoni, & Burlingame, 2012). This reaction has the potential to dramatically reduce the lysine content of thermally processed foods. For example, Mitchel et al. reported that the Protein Efficiency Ratio (PER) of non-fat dried skim milk was 3.2 g weight gain per g of protein consumed, whereas that of the same protein which had been heated was only 1.7 g/g (Mitchell, Jenkins, & Grundel, 1989). In addition to loss of protein quality through the Maillard reaction, protein quality may be negatively affected by other factors, as outlined by Boye et al. (2012).

Dietary Protein Concentration

The growth rate of rats depends on the amount of protein present in their diet, a fact that has been recognized for 100 years (Osborne, T., Mendel, L., Perry, 1919). Rats consuming diets with increasing concentrations of casein reach a weight plateau when the protein concentration constitutes approximately 16% of total diet (Mercer, May, & Dodds, 1989). Below that level a dose-response relationship exists between protein concentration and growth (Finke, DeFoliart, & Benevenga, 1987, Mercer et al., 1989). Therefore, at a dietary protein concentration of 10%, the concentration typically used in PER studies, feeding diets containing low quality protein (diets with low levels of even one essential amino) will result in a relatively low level of weight gain per gram of diet consumed. With ANCR casein as a control, all diets should be formulated to contain as close to 10% protein as possible.

B. Sulfur Containing Amino Acids

Methionine and cystine are both sulfur containing amino acids, while only methionine is considered an essential amino acid. This is because methionine is endogenously converted to cystine; if cystine is present in the diet it can reduce the dietary methionine requirement by up to 50% (NRC, 1995; Shannon, Howe, & Clark, 1972). The AOAC PER method requires a casein control group with no added sulfur containing amino acids. The amount of sulfur containing amino acids present in a 10% casein control diet places rats on a sensitive part of the weight gain dose-response curve (Gahl, Finke, Crenshaw, & Benevenga, 1991; Benevenga, Gahl, Crenshaw, & Finke, 1994). Supplementation with additional sulfur containing amino acids is not required.

C. Lactose Intolerance

All mammalian milk contains lactose (a glucose-galactose dimer) as the principle carbohydrate. The hydrolytic action of intestinal lactase produces the individual monomers, which are absorbed. Intestinal lactase activity is high in the rat small intestine until weaning, at which point a dramatic decrease occurs (Tadesse, 1990). Lactose fed to adult rats is poorly absorbed in the small intestine. It is treated as a dietary fiber and is fermented in the cecum resulting in a threefold increase in cecal weight compared to animals receiving a comparable amount of the maltodextrin, the primary carbohydrate found in AIN 93G (van de Heijning et al., 2015).

Exemplary infant formulas contain lactose as the primary carbohydrate. It is essential that control diets and formula-containing diets are balanced for lactose levels. In addition, animals must be as close as possible to the same age and weight in all study groups at study initiation, thus minimizing differences in the loss of intestinal lactase during the study. In studies requiring high lactose diets, exposing all animals to a modest length acclimation period (5-7 days) is recommended. Experimental work from the FDA demonstrated that the weekly PER (over a four week test period) of infant formulas devoid of lactose (soy-based formulas) ranged from 2.9-3.7 g/g, while lactose containing formulas (milk-based) had much lower PERs, ranging from 1.0-2.3 g/g (G. V. Mitchell & Jenkins, 1985). Experimental and control PER diets should contain the same amount of lactose.

Summary of PER Study

All diets were prepared by Dyets Inc. to target the AOAC test method nutrient content, and to meet the minimum nutritional requirements of the rats (see Appendices A and B). Prior to study initiation the test diet and control diets were subjected to analysis to assess suitability as comparators. The diets were analyzed for protein which was used to calculate the protein consumption by the rats. The PER (body weight gain divided by protein consumption) was calculated for each animal.

In preparation for the test, a group of Sprague-Dawley derived, albino rats were received from Envigo, RMS Inc. The animals were singly housed in suspended stainless steel caging.

Litter paper was placed beneath the cages and was changed at least three times per week. The animal room was temperature controlled and had a 12-hour light/dark cycle. The animals were fed an acclimation diet (Modified casein control Diet) and filtered tap water was supplied ad libitum. The animals were observed daily and body weights and diet consumption were also measured and recorded daily. Following a 6-day acclimation period, the animals were weighed and examined for health. Forty (40) healthy naive male rats (not previously tested) were selected and randomly distributed (10/group) into each of the test or control groups.

The test and control diets were presented ad libitum to the animals from each group for 28 consecutive days. Body weights were recorded prior to initiation (Day 0) and at least twice each week thereafter. Individual diet consumption was measured and recorded weekly. At study termination, all animals were euthanized by $CO_2$ inhalation.

Total individual body weight gain and diet consumption were calculated for each animal over the 4-week test period. Protein consumption was calculated by multiplying total diet consumption by the percent of protein contained in the prepared diet. The PER (body weight gain divided by protein consumption) was calculated for each animal using these values. An adjusted PER was calculated by "normalizing" the test group to Casein at a PER of 2.5.

Storage

The test and control diets were stored refrigerated under a nitrogen blanket except when presented to the rats.

General Test System Parameters

Animal Requirements

Number of Animals: 40

Number of Groups: 4

Number of Animals per Group: 10

Sex: Male

Species/Strain: Rat/Sprague-Dawley derived, albino

Age/Weight: Arrival: 21-23 days/38.4-48.1 grams

Study Start: 27-29 days/46.1-57.8 grams

Test System Justification

The rat is the system of choice because, historically, it has been the preferred and most commonly used species for protein efficiency testing.

Husbandry

Housing: Animals were housed individually in suspended stainless steel cages which conform to the size recommendations in the most recent Guide for the Care and Use of Laboratory Animals (Natl. Res. Council, 2011). Litter paper placed beneath the cage and was changed at least three times/week. The animal room had a 12-hour light/dark cycle and was kept clean and vermin free. Environmental controls were set to maintain temperature and relative humidity ranges of 21±2° C. and 30-70%, respectively. The observed values/ranges are documented in the raw data. In addition, airflow in the animal room was maintained at or above 10 air changes per hour.

Animal Room Temperature and Relative Humidity Ranges: 19-22° C. and 29-68%, respectively.

Animal Room Air Changes/Hour: 21 or 22. Airflow measurements are evaluated regularly and the records are kept on file at Product Safety Labs.

Photoperiod: 12-hour light/dark cycle

Acclimation: The animals were conditioned to the housing facilities for six days prior to testing.

Food: During the acclimation period, animals were fed Modified casein control Diet, ad libitum. During the study, animals were offered their respective test or control diets ad libitum according to their assigned group.

Water: Filtered tap water was available ad libitum.

Contaminants: There are no known contaminants reasonably expected to be found in the food or water at levels which would interfere with the results of this study. Analysis of the water is conducted regularly and the results are kept on file at PSL.

Identification

Cage: Each cage was identified by a cage card indicating the study number, dose group, identification, and sex of the animal.

Animal: Each animal was uniquely identified with a stainless steel ear tag or color marking. Animals assigned to test were also assigned a sequential animal number. Except for acclimation data, only the sequential animal number is presented in this report.

Experimental Design

Route of Administration

The test and control articles were administered in the diet.

Justification of Route of Administration

The dietary route of administration was used because it is recommended in the referenced guidelines, and because it is the intended route of human exposure.

Control of Bias

Animals were randomly assigned to test groups, stratified by body weight.

Dose Groups

Ten male animals were assigned to each of the following test groups:

| Group No. | No. Animals/Group | Protein Source | Product Description |
| --- | --- | --- | --- |
| 1 | 10 | Test Article Diet | Solid |
| 2 | 10 | Modified Casein Control Diet | Solid |
| 3 | 10 | Standard Casein Control Diet | Solid |
| 4 | 10 | Enfamil ® Comparison Diet | Solid |

Procedure

Analysis

Prior to diet formulation, a Certificate of Analysis was obtained for the batch of test article to be used in the study. This Certificate of Analysis includes the results of a proximate analysis, a carbohydrate profile and analysis of the vitamins and minerals contained in the test article.

Prior to preparation of the diets, the test article was analyzed for the below listed parameters.

| | |
| --- | --- |
| Moisture | Lactose |
| Ash | Total fat |
| Protein | Total Carbohydrates |
| Crude Fiber | Vitamin content |
| | Mineral content |

A proximate analysis was completed for the batch of casein to be used on the study along with select minerals commonly found in casein. Casein is not known to contain any vitamins at a level that would have any impact on the outcome of the study.

Following diet formulation, all diets were subjected to a proximate analysis. Since the objective of this study was to evaluate the biological quality of the protein, the protein content of each diet was confirmed from 3 representative samples, generally the top, middle and bottom of the bulk diet, to demonstrate homogeneity of the diet mix. The mean of these values was considered the protein content for each diet. A diet was deemed homogeneous if the % RSD was within 5%. The mean protein value should be between 9.5% and 11% (target protein concentration is 10%) of the respective diet. A sample of each diet was collected and stored frozen for analysis.

In addition, the concentration of Lactose (where applicable) in the final diets was confirmed. The remaining carbohydrates were not analyzed.

Finally, one representative vitamin (Riboflavin) and mineral (zinc) for the purpose of demonstrating proper addition of the vitamin and mineral pre-mixes was confirmed by analysis.

Diet Formulations

The formulation of all diets were guided by the AOAC published method for the PER test. The test diet was formulated with appropriate modifications of the AOAC method to minimize the addition of nutrients[2] other than those necessary to ensure the diet meets the minimum nutritional requirements of the rat (with the exception of protein).

[2] As clarified by the FDA, this is to comply with the final rule which states the protein quality must be demonstrated in the infant formula.

Once the final test diet was formulated, a modified control diet was formulated to be comparable in all of its ingredients (to the extent possible) to the final test diet. After assuring 10% protein (by wt.), adjustments were made to carbohydrate sources, total fat (and potentially fat sources) and total crude fiber along with all vitamins and minerals.

The Standard Casein Control Diet (Group 3) was formulated to be consistent with the AOAC prescribed method. The sole source of protein was casein and the fat source was soybean oil. Carbohydrate sources were limited to sucrose and corn starch. Vitamin and mineral content in the standard casein control diet were provided via standard premixes designed to meet all of the NRC recommended minimum requirements for the growing rat.

The addition of the infant formula product satisfies or exceeds many of the vitamin and mineral requirements of the rats. Therefore, the test diet was supplemented only with those individual vitamin and minerals needed to bring all necessary micronutrients up to required levels for the rat.

The modified control diet was then supplemented with sufficient vitamin and mineral premixes to bring all micronutrients to the minimum required levels and then individually supplemented as necessary to be more closely aligned with the final levels achieved in the test diet.

Adjustments to the Test Diet (Group 1) and Enfamil® Comparison Diet (Group 4) was determined from the analysis of the respective test article (BBN Formula or Enfamil® Formula). The Modified Casein Control Diet (Group 2) was formulated to match the macronutrient and micronutrient contents of their respective Test Diet (Group 1)[3]. The Modified casein control and Test diets contained 10% protein (wt/wt) to be in line with typical diets used for PER and the carbohydrate content were adjusted with the focus on matching the lactose of the modified casein control diet to the test diet followed by consideration of the remaining carbohydrates to the extent possible. Due to the high volume of oil and potentially additional moisture to be added to the modified casein control, further addition of sugars to the modified casein control may result in diets that are unappealing or physically not editable to the rats. The use of corn starch, as prescribed by the AOAC method, to fill out the balance of the modified casein control diet was used as needed to ensure better absorption and distribution of the fat source in the diet. The ability of the rats to routinely consume the diets was paramount relative to any other considerations that may have been given to the matching of the carbohydrate sources beyond the lactose.

[3] The Enfamil® diet is for commercial comparison to the test diet, therefore it does not have a corresponding modified control diet.

Casein was used as the sole protein source for the Modified casein control Diet. Carbohydrate sources used in the Test Article were used in the Modified casein control Diet to achieve similar carbohydrate content if possible (as previously described), with specific attention on the lactose content. The oil blend used in the Test Article was used in the Modified casein control Diet to achieve the same fatty acid content. A full list of ingredients for both the Standard casein control and Modified casein control Diets and the Test Diet formulations, and their analyses are presented in Appendices A-D.

Test Diet Preparation

All diets were prepared by Dyets Inc. Sufficient quantity of the Modified casein control Diet was prepared so that all animals were fed this diet during the acclimation period.

Animal Selection

Ten healthy rats within the designated age range were selected for each test/control group. Animals were selected for test on the basis of adequate body weight gain and freedom from clinical signs of disease or injury. Selected rats were randomly assigned to groups, stratified by body weight.

Diet Consumption

The rats were fed their respective diets ad libitum for 28 consecutive days. Individual diet consumption was measured and recorded daily during acclimation and twice weekly during the test after taking into account any measured spillage.

Body Weight

Individual body weights were recorded daily during acclimation, on the first day of diet presentation, and twice weekly thereafter.

Clinical Observations

All animals were observed twice daily for viability. Clinical observations were performed and recorded daily, and included, but was not limited to, gross evaluation of skin and fur, eyes and mucous membranes, respiratory, circulatory, autonomic and central nervous systems, somatomotor activity and behavior pattern. Particular attention was directed to symptoms associated with a high-lactose diet (diarrhea, soft stools, red discoloration on fur, oily coat, etc.).

Calculation of Per

Individual body weight gain, diet consumption and protein consumption for the entire 28-day test period were tabulated and individual, experimental PERs were calculated as follows:

$$\text{Experimental PER} = \frac{\text{bodyweight gain (g)}}{\text{protein consumed (g)}}$$

The experimental PERs of the test groups were also adjusted relative to the casein control to calculate an adjusted PER:

$$\text{Adjusted PER} = \frac{\text{experimental PER (test group)} \times 2.5}{\text{experimental PER (casein)}}$$

The mean experimental and adjusted PER values are reported for each group.

Statistical Analysis

Statistical analysis was the calculation of mean and standard deviations. In addition, a one-way ANOVA was conducted on experimental PER values comparing all test groups to the casein control group.

Study Conduct

Test Procedure Guidelines

The procedures described in this test method were based on one or more of the following testing guidelines:

*Protein Efficiency Ratio.* AOAC Official Method 960.48, Paragraph 45.3.04. AOAC International ($18^{th}$ Edition, 2005)

*FO-1, Determination of Protein Rating.* Official Method, Health Protection Branch, Ottawa. Oct. 15, 1981

Results and Conclusion

Figure 3:
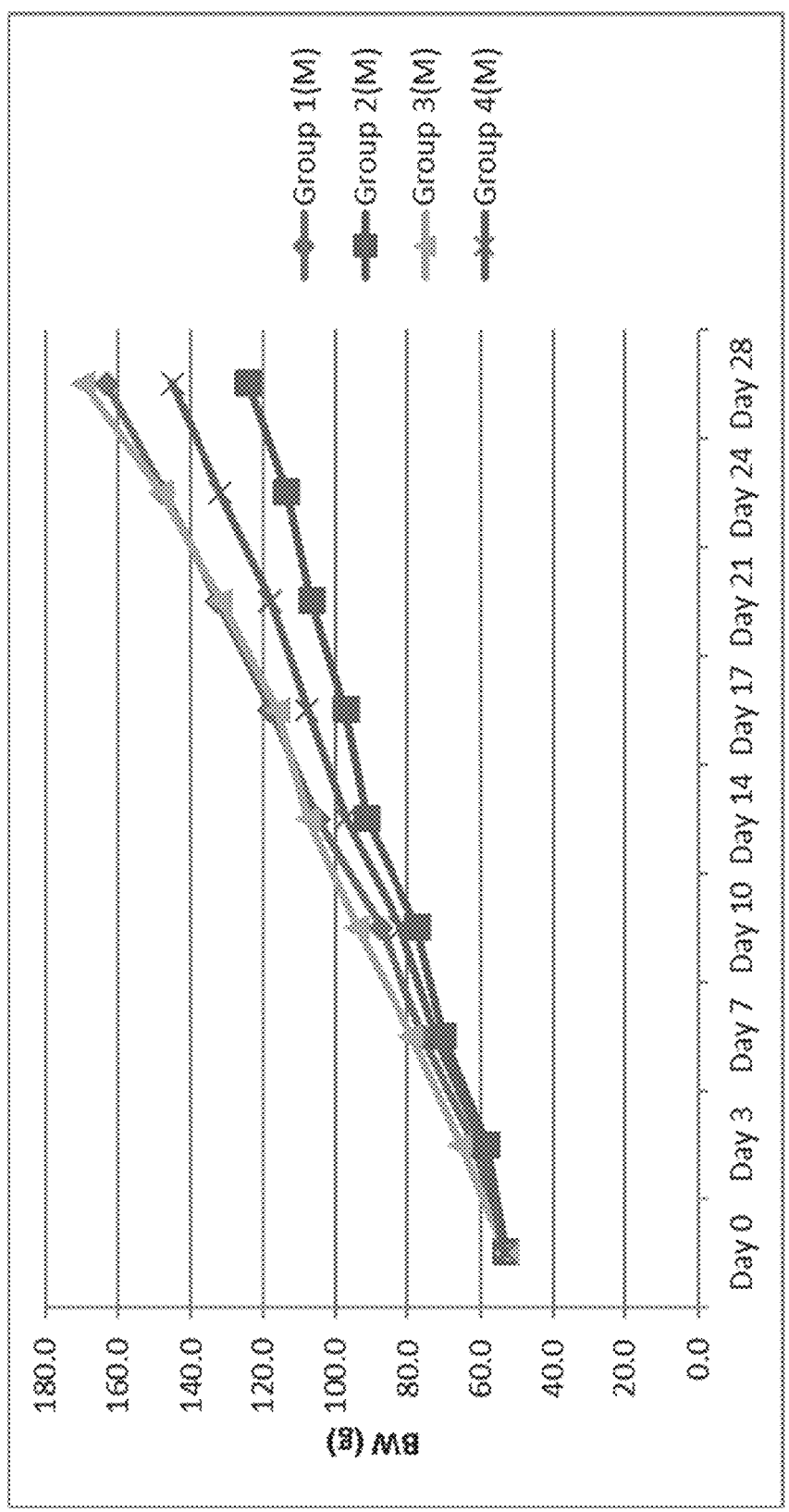
FIG. 3 shows the growth chart of animals (body weight by group) in the Protein Efficiency Ratio (PER) study in rats of Example 2 over time.
Figure 4:
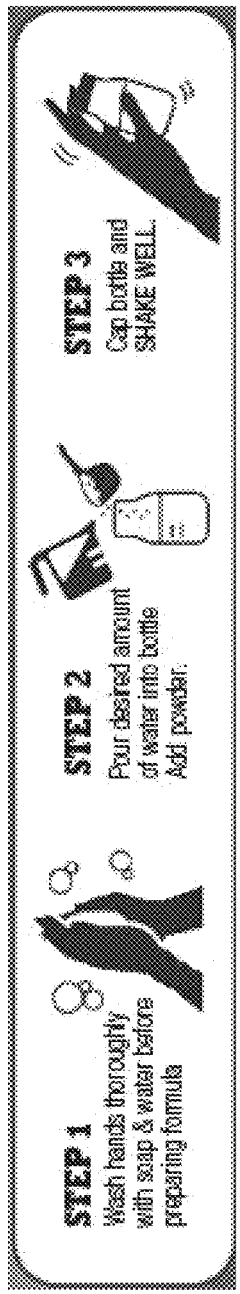
FIG. 4 is a schematic showing instructions for preparing an exemplary infant formula, in which the formula powder is mixed with water.

Total weight gain for each group over time is presented in FIG. 3. Individual total diet consumption for each group is presented in Tables 2A-F. Experimental PER is presented in Tables 3A-D. Individual daily in-life observations for each group are presented in Table 4. The Test Method and the results of diet analyses are presented in Appendices A, B, B1, C, and D.

Analytical confirmation results of both the test and control finished diets demonstrated that the diets were nutritionally comparable, with the only notable difference being the source of protein. Differences observed in the growth of the rats per gram of protein consumed are attributed to the protein source within each diet.

One Group 3 animal (1028) was found dead on Day 12. Apart from a reduced fecal volume on Days 10-11, the animal appeared active and healthy and was gaining body weight. Gross necropsy observations of the decedent revealed slight dilation of the kidneys, slight discoloration of the lungs, and white frothy liquid in the trachea. Although the cause of death was not determined, this animal's death is not considered to be related to the casein diet. Further, this animal's death has no impact on the outcome of the study. The animal was removed from the Group 3 averages in the below Table A2.

TABLE A2

| Group No. | Mean Bodyweight (g) | | | Diet Consumption (g) | Protein in Diet (%) | Mean Protein Consumption (g) | Mean Exp. PER | Adjusted PER |
|---|---|---|---|---|---|---|---|---|
| | Initial | Final | Gain | | | | | |
| 1 | 53.2 | 163.3 | 110.1 | 307.8 | 9.92 | 30.5 | 3.62** | 3.28 |
| 2 | 53.1 | 124.3 | 71.2 | 259.8 | 9.9 | 25.7 | 2.76 | 2.50 |
| 3 | 53.0 | 169.8 | 117.09 | 369.79 | 10.04 | 37.13 | 3.15** | 2.86 |
| 4 | 53.3 | 145.2 | 91.9 | 276.7 | 9.88 | 27.3 | 3.37** | 3.05 |

**$p < 0.01$ in comparison to Group 2 by Dunnett's Multiple Comparisons Test.

According to AOAC Method 960.48, the protein quality of the Test Article Diet was 131.2%[4] of the adjusted PER for the Modified Casein Control Diet, respectively. The Test Article Diet was also found to have a protein quality that was 107.5% of the adjusted PER for the Enfamil® Comparison Diet.

[4](Adj. PER of Test Diet/Adj. PER of Control Diet)*100

According to AOAC Method 960.48, the protein quality of the Standard Casein Control Diet was 114.4% of the adjusted PER for the Modified Casein Control Diet, respectively.

According to AOAC Method 960.48, the protein quality of the Enfamil® Comparison Diet was 122% of the adjusted PER for the Modified Casein Control Diet, respectively.

APPENDIX A

Diet Formulation for Production (Recipe)

| Nutrient | Individual Ingredient to add | Test Diet g/kg | Modified Casein Control g/kg | Standard Casein Control g/kg | Enfamil® Comparison Diet g/kg |
|---|---|---|---|---|---|
| Formulation A | Test Article | 735.30 | | | |
| Casein, 80 Mesh, DYETS #400601, Lot # 20017 | Casein | | 115.50 | 115.50 | |
| Enfamil® Infant Formula | Comparison Test Article | | | | 976.6 |
| Fat (Soybean Oil) | Soybean Oil | | | 78.60 | |
| Fat: | Sponsor Fat Blend | | 192.00 | | |
| Moisture: | | 13.30 | 5.30 | 0.00 | 21.3 |
| Ash: | Mineral Mix | 0.00 | 31.01 | 41.89 | 0 |
| Sodium (Na) | Sodium Chloride (39.3% Na) (60.7% Cl) | 0.0000 | 2.090842 | | 0 |
| Chloride (Cl) | | | | | |
| Calcium (Ca) | Calcium Carbonate (40.0% Ca) | 2.2426 | 0.726817 | | 0.32912 |
| Phosphorous (P) | Potassium Phosphate, Monobasic (28.7% K, 22.8% P) | 1.4350 | 2.835375 | | 1.76423 |
| Potassium (K) | Potassium Citrate - 1 H2O (36.2% K) | 0.0000 | 4.520292 | | 0 |
| Magnesium (Mg) | Magnesium Sulfate, Anhydrous (9.9% Mg, 13% S) | 0.1030 | 0.759867 | | 0 |
| Sulfur (S) | Potassium Sulfate (44.9% K, 18.4% S) | 0.0000 | 0 | | 0 |
| Chromium (Cr) | Chromium K Sulfate - 12 H2O (10.4% Cr, 7.8% K, 12.8% S) | 0.0000 | 0 | | 0 |
| Copper (Cu) | Cupric Carbonate (57.5% Cu) | 0.0029 | 0.000175 | | 0.00012 |
| Fluoride (F) | Sodium Fluoride (45.2% F, 54.8% Na) | 0.0000 | 0 | | 0 |
| Iodine (I) | Potassium Iodate (59.3% I, 18.2% K) | 0.0000 | 0.001992 | | 0 |
| Iron (Fe) | Ferric Citrate (17.4% Fe) | 0.0000 | 0.219117 | | 0 |
| Manganese (Mn) | Manganese Carbonate (47.8% Mn) | 0.0186 | 0.002367 | | 0.01874 |
| Molybdenum (Mo) | Ammonium Molybdate - 4 H2O (54.3% Mo) | 0.0003 | 0.000167 | | 0.000276 |
| Selenium (Se) | Sodium Selenate (41.8% Se) | 0.0000 | 0.000142 | | 0 |
| Zinc (Zn) | Zinc Carbonate (52.1% Zn) | 0.0000 | 0.038442 | | 0 |

TABLE A1

List of ingredients and nutrients in Test Diets of Modified Casein Control Diet, Standard Casein Control, and Enfamil® Comparison Diet

| Nutrient | Individual Ingredient to add | Test Diet g/kg | Modified Casein Control g/kg | Standard Casein Control g/kg | Enfamil® Comparison Diet g/kg |
|---|---|---|---|---|---|
| Fiber: | Cellulose | 0.00 | 8.87 | 8.87 | 0 |
| Vitamin Pre-Mix | Vitamin Pre-Mix | 0 | 5.50 | 10.00 | 0 |
| Vitamin A (IU/kg) | Vitamin A (IU/kg) | | 18259.25 | | |
| Vitamin E (IU/kg) | Vitamin E (IU/kg) | | 0.00 | | |
| Vitamin D (IU/kg) | Vitamin D (IU/kg) | | 2724.89 | | |
| Nicotinic Acid | Niacin | | 0.0281 | | |
| Pantothenic Acid | Ca-D-pantothenate | | 0.0225 | | |
| B2 | Riboflavin | | 0.0074 | | |
| B1 | Thiamine-HCL | | 0.0030 | | |
| B6 | Pyridoxince-HCL | | 0.0017 | | |
| Folic Acid | Folic Acid | | 0.0000 | | |
| Biotin | Biotin | | 0.0001 | | |
| B12; Cyanocobalamin | Vitamin B12 | | 0.0000 | | |
| K1 | Pylloquinone | | 0.0005 | | |
| Vitamin C | Ascorbic Acid | | 0.6570 | | |
| Choline | Choline Bitartrate | 0.0 | 3.4307 | 2.00 | 0 |
| L-Carnitine | L-Carnitine | | 0.1353 | | |
| Taurine | Taurine | | 0.4191 | | |

TABLE A1-continued

List of ingredients and nutrients in Test Diets of Modified Casein Control Diet, Standard Casein Control, and Enfamil ® Comparison Diet

| Nutrient | Individual Ingredient to add | Test Diet g/kg | Modified Casein Control g/kg | Standard Casein Control g/kg | Enfamil ® Comparison Diet g/kg |
|---|---|---|---|---|---|
| Inositol | M-Inositol | | 0.2768 | | |
| Nucleotides | Nucleotide Pre-mix (Sponsor Supplied) | | 0.2761 | | |
| Lutein | Lactose-Lutein Pre-mix (Sponsor Supplied) | | 32.8057 | | |
| Beta Carotene | Beta Carotene | | 0.0009 | | |
| Lactose | Lactose, alpha Monohydrate, Plant EU # 2118720 (DYETS supplied) | | 369.856 | | |
| Glucose | Glucose | | 14.7060 | | |
| Corn Starch: | Corn Starch | 247.59 | 211.2020 | 694.14 | 0 |
| Sucrose | Sucrose | | | 50.00 | |
| Total Target: | | 1000 | 1000 | 1000 | 1000 |

APPENDIX B

| per kg diet | Rat growth requirements (1995 NRC, table 2-2) | Infant Formula Test Diet 1 Test Diet | Modified Casein Control Diet 2 Modified Casein Control | Standard Casein Control Diet 3 Standard Casein Control | Enfamil ® Comparison Diet 4 Enfamil ® Comparison Diet |
|---|---|---|---|---|---|
| g | | | | | |
| Protein | 150 | 100.0 | 100.0 | 100.0 | 100.0 |
| N | | 16.00 | 16.0 | 16.0 | 16.0 |
| Lactose | | 367.28 | 367.25 | 0.00 | 507.83 |
| CHO, total | | 625.79 | 567.62 | 646.68 | 561.53 |
| Fat, total | | 193.38 | 193.39 | 79.99 | 267.59 |
| Fiber | | 12.85 | 10.00 | 10.00 | 46.44 |
| Moisture | | 51.00 | 50.93 | 69.00 | 46.98 |
| Ash | | 27.18 | 37.40 | 34.96 | 29.41 |
| g % | | | | | |
| Protein | | 10.00% | 10.00% | 10.00% | 10.00% |
| Lactose | | 36.73% | 36.72% | 0.00% | 50.78% |
| Fat | | 19.34% | 19.34% | 8.00% | 26.76% |
| Fiber | | 1.29% | 1.00% | 1.00% | 4.64% |
| Moisture | | 5.10% | 5.09% | 6.90% | 4.70% |
| Ash | | 2.72% | 3.74% | 3.50% | 2.94% |
| IU/kg | | | | | |
| Vitamin A (IU) | 2,300 | 20283 | 20283 | 3680 | 62502 |
| Vitamin E (IU) | 27 | 103 | 144.3 | 85.2 | 154.3 |
| Vitamin D (IU) | 1000 | 3154 | 3154 | 781 | 3281 |
| mg/kg | | | | | |
| Niacin | 15.00 | 45.63 | 45.63 | 31.80 | 61.53 |
| Pantothenate | 10.00 | 30.66 | 30.66 | 14.80 | 36.87 |
| Riboflavin | 3.00 | 10.22 | 10.22 | 5.04 | 12.31 |
| Thiamin | 4.00 | 5.97 | 5.97 | 5.39 | 4.98 |
| B6 (Pyridoxine) | 6.00 | 6.00 | 6.00 | 7.76 | 6.00 |
| g | | | | | |
| Folic Acid | 1.00 | 1.00 | 1.00 | 1.82 | 1.00 |
| Biotin | 0.20 | 0.25 | 0.25 | 0.32 | 0.28 |
| B12 | 0.05 | 0.05 | 0.05 | 0.03 | 0.05 |
| Vitamin K | 1.00 | 1.00 | 1.00 | 0.94 | 1.00 |
| Vitamin C | 0.00 | 656.99 | 656.99 | 0.00 | 874.06 |

Finished Rodent Diets (Nutrient Composition)

Finished Rodent Diets
(Nutrient Composition)

| per kg diet | Rat growth requirements (1995 NRC, table 2-2) | Infant Formula Test Diet 1 Test Diet | Modified Casein Control Diet 2 Modified Casein Control | Standard Casein Control Diet 3 Standard Casein Control | Enfamil ® Comparison Diet 4 Enfamil ® Comparison Diet |
|---|---|---|---|---|---|
| mg/kg | | | | | |
| Choline | 750 (or 2000 of Choline Bitartrate) | 1411.8 | 1410.0 | 822 | 1635.805 |
| gm/kg | | | | | |
| Sodium | 0.5 | 1.713 | 1.713 | 1.213 | 1.489 |
| Chloride | 0.5 | 3.176 | 2.653 | 1.867 | 3.721 |
| Calcium | 5 | 5.000 | 5.000 | 6.387 | 5.000 |
| Phosphorus | 3 | 3.000 | 3.000 | 3.010 | 3.000 |
| Potassium | 3.6 | 5.427 | 5.427 | 4.042 | 7.098 |
| Magnesium | 0.5 | 0.500 | 0.500 | 0.595 | 0.537 |
| Sulfur[5] | | 0.013 | 0.446 | 0.469 | 0.000 |
| mg/kg | | | | | |
| Chromium[1] | | 0.000 | 0.887 | 1.198 | 0.000 |
| Copper | 5 | 4.999 | 5.207 | 7.312 | 5.001 |
| Fluoride[1] | | 0.000 | 0.567 | 0.767 | 0.000 |
| Iodine | 0.15 | 1.287 | 1.285 | 0.140 | 1.436 |
| Iron | 35 | 73.162 | 73.162 | 48.720 | 104.008 |
| Manganese | 10 | 9.999 | 9.999 | 11.980 | 9.998 |
| Molybdenum | 0.15 | 0.150 | 0.149 | 0.079 | 0.150 |
| Selenium | 0.15 | 0.182 | 0.182 | 0.166 | 0.251 |
| Zinc | 12 | 47.280 | 47.282 | 37.097 | 61.526 |
| mg/kg | | | | | |
| L-Carnitine | Not established | 135.3 | 135.3 | | 172.37 |
| Taurine | Not established | 419.12 | 419.12 | | 392.10 |
| M-Inositol | Not established | 276.8 | 276.8 | | 433.12 |
| Nucleotides | Not established | 276.1 | 276.1 | | 0 |
| Lutein | Not established | 0.5 | 0.5 | | 0 |
| Beta Carotene | Not established | 0.9 | 0.9 | | 0 |

[5]Sulfur, Chromium and Fluoride are not required under NRC but are present in the certified mineral mix added to the control diets.

APPENDIX C

Selected Ingredient Specifications

| Vitamin | Spec Vitamin Premix (mg/10 g) | DYETS 310113: Vitamin Premix Lot # 0112-A mg/g of mix |
|---|---|---|
| Vitamin A(IU) | 4000 | 368 |
| Vitamin E (IU) | 75 | 8.52 |
| Vitamin D (IU) | 1000 | 78.1 |
| Menadione | 0 | 0.0000 |
| Choline | 0 | 0.0000 |
| p-Aminobenzoic | 0 | 0.0000 |
| Inositol | 0 | 0.0000 |
| Niacin | 30 | 3.1800 |
| Ca-D-pantothenate | 16 | 1.4800 |
| Riboflavin | 6 | 0.5040 |
| Thiamine-HCL | 6 | 0.5390 |
| Pyridoxine-HCL | 7 | 0.7760 |
| Folic Acid | 2 | 0.1820 |
| Biotin | 0.3 | 0.0318 |
| Vitamin B12 | 0.05 | 0.0025 |
| Pylloquinone | 1.25 | 0.0944 |
| Sucrose: qs to (mg) | 1000 | 1000 |

Selected Ingredient Specifications

| | | Mineral Mix | |
|---|---|---|---|
| Ingredient | Mineral | Spec Mineral Mix (mg/35 g) | DYET #210050 Mineral Mix, Lot # 0112-B mg/g of mix |
| Calcium Carbonate (40.0% Ca) | Calcium (Ca) | 5000.0 | 151.0000 |
| Potassium Phosphate, Monobasic (28.7% K, 22.8% P) | Phosphorous (P) | 1995.0 | 50.8000 |
| Potassium Citrate - 1 H2O (36.2% K) | Potassium (K) | 354.8 | 96.00 |
| Potassium Sulfate (44.9% K, 18.4% S) | Sulfur (S) | 300.0 | 11.20 |
| Magnesium Oxide (60.3% Mg) | Magnesium (Mg) | 500.0 | 13.70 |
| Sodium Chloride | Sodium (Na) | 1000.0 | 27.60 |
| (39.3% Na, 60.7% Cl) | Chloride (Cl) | 1600.0 | 40.60 |
| Cupric Carbonate (57.5% Cu) | Copper (Cu) | 6.00 | 0.1580 |
| Potassium Iodate (59.3% I) | Iodine (I) | 0.20 | 0.00334 |
| Ferric Citrate (17.4% Fe) | Iron (Fe) | 37.00 | 1.130 |
| Manganese Carbonate (47.8% Mn) | Manganese (Mn) | 10.50 | 0.2860 |
| Sodium Selenate (41.8% Se) | Selenium (Se) | 0.20 | 0.0040 |
| Zinc Carbonate (52.1% Zn) | Zinc (Zn) | 30.00 | 0.8790 |
| Chromium K Sulfate - 12 H2O (10.4% Cr) | Chromium (Cr) | 0.9625 | 0.0286 |
| Ammonium Molybdate - 4 H2O (54.3% Mo) | Molybdenum (Mo) | 0.1511 | 0.00189 |
| Sodium Silicate (9.89% Si) | | 0.0414 | 0.0183 |
| Lithium Chloride | | 0.0005 | 0.0012 |
| Boric Acid | | 0.0023 | 0.000014 |
| Sodium Fluoride (45.2% F) | Fluoride (F) | 1.0000 | 0.000066 |
| Nickel Carbonate | | 0.0009 | 0.000026 |
| Ammonium Vanadate | | 0.0002 | 0.000006 |
| Sucrose | | 7.34 g | 209.81 mg |

| Product: Lactose Monohydrate | | |
|---|---|---|
| Nutrient | g/kg of product | % of product |
| Protein: | 0.00 | 0.00% |
| Fat: | 0.00 | 0.00% |
| Moisture: | 48.3 | 4.83% |
| Ash: | 0.9 | 0.09% |
| Lactose: | 950.1 | 95.01% |
| Fiber: | 0.00 | 0.00% |

| Product ID (name and Lot #): Casein, 80 Mesh, DYETS #400601, Lot # 20017 | | |
|---|---|---|
| Nutrient | g/kg of product | % of product |
| Protein: | 866 | 86.60% |
| Fat: | 12 | 1.20% |
| Moisture: | 87.3 | 8.73% |
| Ash: | 10.1 | 1.01% |
| Lactose: | 0 | 0.00% |
| Fiber: | 9.77 | 0.98% |
| Minerals | | unit |
| Sodium | 31 | mg/100 g |
| Chloride | 108 | mg/100 g |
| Calcium | 23.8 | mg/100 g |
| Phosphorus | 674 | mg/100 g |
| Magnesium | 0 | mg/100 g |

APPENDIX D

Analysis - Formulation A

Sponsor:
Building Block Nutritionals
Product ID (name and Lot #):
Formulation A

| Nutrient | g/100 g of product | % of product |
|---|---|---|
| Protein: | 13.60 | 13.60% |
| Fat: | 26.30 | 26.30% |
| Moisture: | 2.265 | 2.27% |
| Ash: | 3.180 | 3.18% |
| Fiber: | 1.748 | 1.748% |
| Lactose: | 49.950 | 49.95% |
| Total Carbohydrates | 54.600 | 54.60% |

| Fat Breakdown | | % of Total Fat |
|---|---|---|
| Fat Blend | 26.3000 | 100.00% |

| Carbohydrate Breakdown | | |
|---|---|---|
| Lactose: | 49.95 | 49.95% |
| Glucose | 2.00 | 2.00% |
| Balance of Carbs | 2.65 | 2.65% |

| Vitamins | | unit |
|---|---|---|
| Vitamin A (Retinol) | 2758.5000 | IU/100 g |
| Vitamin E (DL-I-tocopherol) | 14.00 | IU/100 g |
| Vitamin D3 | 429.00 | IU/100 g |
| Niacin | 6.2050 | mg/100 g |
| Pantothenate | 4.1700 | mg/100 g |
| Riboflavin (B2) | 1.3900 | mg/100 g |
| Thiamin (B1) | 0.8120 | mg/100 g |
| B6 (Pyridoxine) | 0.4310 | mg/100 g |
| Folic Acid | 0.1035 | mg/100 g |
| Biotin | 0.0346 | mg/100 g |
| B12 | 0.0056 | mg/100 g |
| Vitamin K1 | 0.0744 | mg/100 g |
| Vitamin C | 89.35 | mg/100 g |
| Choline (Choline Bitartrate) | 0.1920 | g/100 g |

| Minerals | | unit |
|---|---|---|
| Sodium | 233 | mg/100 g |
| Chloride | 432 | mg/100 g |
| Calcium | 558 | mg/100 g |
| Phosphorus | 363.5 | mg/100 g |
| Potassium | 682 | mg/100 g |
| Magnesium | 59.55 | mg/100 g |
| Sulfur | | mg/100 g |
| Chromium | | mg/100 g |
| Copper | 0.4515 | mg/100 g |
| Fluoride | | mg/100 g |
| Iodine | 0.1750 | mg/100 g |
| Iron | 9.9500 | mg/100 g |
| Manganese | 0.1520 | mg/100 g |
| Molybdenum | | mg/100 g |
| Selenium | 0.0247 | mg/100 g |
| Zinc | 6.4300 | mg/100 g |

| Additional Ingredients | | unit |
|---|---|---|
| L-Carnitine | 18.4 | mg/100 g |
| Taurine | 57 | mg/100 g |
| M-Inositol | 37.65 | mg/100 g |
| Nucleotides | 37.55 | mg/100 g |
| Lutein | 0.0696 | mg/100 g |
| Beta Carotene | 0.129 | mg/100 g |

TABLE 2A

INDIVIDUAL TOTAL DIET CONSUMPTION
Acclimation Period Diet Consumption

| Day −6 | Day −5 | Day −4 | Day −3 | Day −2 | Day −1 |
|---|---|---|---|---|---|

TABLE 2B

INDIVIDUAL TOTAL DIET CONSUMPTION
Acclimation Period Diet Consumption

| | Day −6 | Day −5 | Day −4 | Day −3 | Day −2 | Day −1 |
|---|---|---|---|---|---|---|
| Average | 4.5 | 5.2 | 6.3 | 6.1 | 5.6 | 6.1 |
| SD | 0.7 | 0.8 | 1.2 | 0.9 | 0.7 | 0.7 |

TABLE 2C

INDIVIDUAL TOTAL DIET CONSUMPTION

| Group 1(M); Week #s 1-4 | Week #1 | Week #2 | Week #3 | Week #4 | Total Food Consumption |
|---|---|---|---|---|---|
| Average | 51.7 | 72.8 | 90.5 | 92.8 | 307.8 |
| SD | 5.55 | 6.67 | 5.73 | 8.77 | 21.44 |

TABLE 2D

INDIVIDUAL TOTAL DIET CONSUMPTION

| Group 2(M); Week #s 1-4 | Animal # | Week #1 | Week #2 | Week #3 | Week #4 | Total Food Consumption |
|---|---|---|---|---|---|---|
| Average | | 50.3 | 65.9 | 71.7 | 71.9 | 259.8 |
| SD | | 3.30 | 5.58 | 6.69 | 10.18 | 24.72 |

TABLE 2E

INDIVIDUAL TOTAL DIET CONSUMPTION

| Group 3(M); Week #s 1-4 | Week #1 | Week #2 | Week #3 | Week #4 | Total Food Consumption |
|---|---|---|---|---|---|
| Average[6] | 72.01 | 91.68 | 99.36 | 109.74 | 372.79 |
| SD[1] | 3.70 | 8.83 | 6.48 | 7.80 | 21.31 |

[6]The average and standard deviation do not include Animal #1028.

TABLE 2F

INDIVIDUAL TOTAL DIET CONSUMPTION

| Group 4(M); Week #s 1-4 | Week #1 | Week #2 | Week #3 | Week #4 | Total Food Consumption |
|---|---|---|---|---|---|
| Average | 43.8 | 66.2 | 80.9 | 85.8 | 276.7 |
| SD | 4.59 | 4.74 | 3.54 | 6.08 | 14.18 |

TABLE 3A

EXPERIMENTAL PER

| Group 1(M); Week #s 1-4 | Protein Efficiency Ratio |
|---|---|
| Average | 3.62 |
| SD | 0.28 |

TABLE 3B

| EXPERIMENTAL PER | |
|---|---|
| Group 2(M); Week #s 1-4 | Protein Efficiency Ratio |
| Average | 2.76 |
| SD | 0.11 |

TABLE 3C

| EXPERIMENTAL PER | |
|---|---|
| Group 3(M); Week #s 1-4 | Protein Efficiency Ratio |
| Average | 3.15[7] |
| SD | 0.22 |

TABLE 3C-continued

| EXPERIMENTAL PER | |
|---|---|
| Group 3(M); Week #s 1-4 | Protein Efficiency Ratio |

[7]The average and standard deviation do not include Animal #1028.28one animal; which was found dead on Day 12

TABLE 3D

| EXPERIMENTAL PER | |
|---|---|
| Group 4(M); Week #s 1-4 | Protein Efficiency Ratio |
| Average | 3.37 |
| SD | 0.23 |

TABLE 4

INDIVIDUAL IN-LIFE OBSERVATIONS

Acclimation Period

| Animal #[8] | Ear Tag | Observation | Grade | -6 | -5 | -4 | -3 | -2 | -1 | 0 |
|---|---|---|---|---|---|---|---|---|---|---|
| 1001 | 593 | Active and healthy | | x | x | x | | | | |
| | | Coat soiled, body, oily | Slight | | | | x | x | | |
| | | Reduced fecal volume | | | | | | | x | x |
| | | Coat soiled, body, oily | Moderate | | | | | | x | x |
| 1011 | 594 | Active and healthy | | x | x | | | | | |
| | | Soft feces | | | | | x | x | | |
| | | Ano-genital staining | | | | | x | | | |
| | | Coat soiled, body, oily | Slight | | | | x | x | x | x |
| | | Reduced fecal volume | | | | | | | x | |
| 1034 | 595 | Active and healthy | | x | | | | | | |
| | | Soft feces | | | x | | | | | |
| | | Ano-genital staining | | | x | x | | | | |
| | | Reduced fecal volume | | | | | x | x | x | |
| | | Coat soiled, body, oily | Slight | | | | x | x | x | x |
| | | Coat soiled, body, oily | Moderate | | | | | | | x |
| 1012 | 596 | Active and healthy | | x | | | | | | |
| | | Ano-genital staining | | | x | | | | | |
| | | Coat soiled, body, oily | Slight | | | | x | x | x | |
| | | Coat soiled, body, oily | Moderate | | | | | | x | x |
| — | 597 | Active and healthy | | x | x | x | | | | |
| | | Coat soiled, body, oily | Slight | | | | x | x | x | x |
| | | Reduced fecal volume | | | | | | | x | x |

Acclimation Period

| Animal #[9] | Ear Tag | Observation | Grade | -6 | -5 | -4 | -3 | -2 | -1 | 0 |
|---|---|---|---|---|---|---|---|---|---|---|
| — | 598 | Active and healthy | | x | x | | | | | |
| | | Reduced fecal volume | | | | x | x | x | x | x |
| | | Coat soiled, body, oily | Slight | | | | x | x | x | x |
| — | 599 | Active and healthy | | x | | | | | | |
| | | Soft feces | | | x | x | x | | | |
| | | Coat soiled, body, oily | Slight | | | | x | x | x | x |
| | | Reduced fecal volume | | | | | | | x | |
| 1039 | 600 | Active and healthy | | x | x | | | | | |
| | | Reduced fecal volume | | | | x | x | x | x | x |
| | | Coat soiled, body, oily | Slight | | | | x | x | x | x |
| | | Soft feces | | | | | | x | x | |
| 1010 | 601 | Active and healthy | | x | | | | | | |
| | | Soft feces | | | x | x | x | x | | |
| | | Coat soiled, body, oily | Slight | | | | x | x | x | x |
| | | Reduced fecal volume | | | | | | x | x | x |
| 1038 | 602 | Active and healthy | | x | x | x | x | | | |
| | | Coat soiled, body, oily | Slight | | | | | x | x | x |
| | | Reduced fecal volume | | | | | | | x | x |

TABLE 4-continued

INDIVIDUAL IN-LIFE OBSERVATIONS

| 1004 | 603 | Active and healthy | | x | x | x | | | | |
| | | Coat soiled, body, oily | Slight | | | | x | x | x | x |
| | | Reduced fecal volume | | | | | | | | x |

Acclimation Period

| Animal #[10] | Ear Tag | Observation | Grade | Day of Occurrence | | | | | | |
| --- | --- | --- | --- | --- | --- | --- | --- | --- | --- | --- |
| | | | | −6 | −5 | −4 | −3 | −2 | −1 | 0 |
| 1016 | 604 | Active and healthy | | x | | | x | x | | |
| | | Soft feces | | | x | | | | | |
| | | Diarrhea | | | | x | | | | |
| | | Reduced fecal volume | | | | | | | x | x |
| 1036 | 605 | Active and healthy | | x | x | x | | | | |
| | | Coat soiled, body, oily | Slight | | | | x | x | x | x |
| | | Reduced fecal volume | | | | | | | x | x |
| 1024 | 606 | Active and healthy | | x | x | | | | | |
| | | Coat soiled, body, oily | Slight | | | | x | x | x | x |
| | | Reduced fecal volume | | | | | | | x | x |
| 1009 | 607 | Active and healthy | | x | | | | | | |
| | | Diarrhea | | | x | x | | | | |
| | | Ano-genital staining | | | | x | x | x | x | x |
| | | Coat soiled, body, oily | Slight | | | | x | x | x | x |
| | | Reduced fecal volume | | | | | | | x | x |
| 1017 | 608 | Active and healthy | | x | x | | | | | |
| | | Coat soiled, body, oily | Slight | | | | x | x | x | x |
| | | Reduced fecal volume | | | | | | | x | x |
| 1025 | 609 | Active and healthy | | x | | x | | | | |
| | | Diarrhea | | | x | | | | | |
| | | Coat soiled, body, oily | Slight | | | | x | x | x | x |
| | | Reduced fecal volume | | | | | | | x | x |

Acclimation Period

| Animal #[11] | Ear Tag | Observation | Grade | Day of Occurrence | | | | | | |
| --- | --- | --- | --- | --- | --- | --- | --- | --- | --- | --- |
| | | | | −6 | −5 | −4 | −3 | −2 | −1 | 0 |
| 1014 | 610 | Active and healthy | | x | x | | | | | |
| | | Diarrhea | | | | x | x | | | |
| | | Coat soiled, body, oily | Slight | | | x | x | x | | |
| | | Reduced fecal volume | | | | | | | x | x |
| | | Coat soiled, body, oily | Moderate | | | | | | x | x |
| 1008 | 611 | Active and healthy | | x | x | x | | | | |
| | | Coat soiled, body, oily | Slight | | | | x | x | x | x |
| 1032 | 612 | Active and healthy | | x | x | | | | | |
| | | Diarrhea | | | | x | | | | |
| | | Coat soiled, body, oily | Slight | | | | x | x | | |
| | | Reduced fecal volume | | | | | | | x | |
| | | Coat soiled, body, oily | Moderate | | | | | | x | x |
| — | 613 | Active and healthy | | x | | | | | | |
| | | Diarrhea | | | x | x | | | | |
| | | Ano-genital staining | | | | x | | | | |
| | | Coat soiled, body, oily | Slight | | | | x | x | x | x |
| | | Reduced fecal volume | | | | | | | | x |
| 1018 | 614 | Active and healthy | | x | x | | | | | |
| | | Soft feces | | | | x | | | | |
| | | Coat soiled, body, oily | Slight | | | | x | x | x | x |
| | | Reduced fecal volume | | | | | | | x | x |

Acclimation Period

| Animal #[12] | Ear Tag | Observation | Grade | Day of Occurrence | | | | | | |
| --- | --- | --- | --- | --- | --- | --- | --- | --- | --- | --- |
| | | | | −6 | −5 | −4 | −3 | −2 | −1 | 0 |
| 1007 | 615 | Active and healthy | | x | x | x | | | | |
| | | Coat soiled, body, oily | Slight | | | | x | x | | |
| | | Reduced fecal volume | | | | | | | x | x |
| | | Coat soiled, body, oily | Moderate | | | | | | x | x |
| 1040 | 616 | Active and healthy | | x | | | | | | |
| | | Ano-genital staining | | | x | | | | | |
| | | Reduced fecal volume | | | | x | | | x | x |
| | | Diarrhea | | | | x | | | | |
| | | Coat soiled, body, oily | Slight | | | | x | x | x | x |

TABLE 4-continued

| | | INDIVIDUAL IN-LIFE OBSERVATIONS | | | | | | | |
|---|---|---|---|---|---|---|---|---|---|
| 1019 | 617 | Active and healthy | | x | x | | | | |
| | | Reduced fecal volume | | | | x | | | x |
| | | Coat soiled, body, oily | Slight | | | | x | x | x | x |
| 1023 | 618 | Active and healthy | | x | | | | | |
| | | Diarrhea | | | x | | | | |
| | | Coat soiled, body, oily | Slight | | | | x | x | x | |
| | | Reduced fecal volume | | | | | | | x | |
| | | Coat soiled, body, oily | Moderate | | | | | | x | x |
| 1031 | 619 | Active and healthy | | x | x | | | | |
| | | Reduced fecal volume | | | | | x | | x | x |
| | | Coat soiled, body, oily | Slight | | | | x | x | x | x |

Acclimation Period

| Animal | | | | Day of Occurrence | | | | | | |
|---|---|---|---|---|---|---|---|---|---|---|
| #[13] | Ear Tag | Observation | Grade | −6 | −5 | −4 | −3 | −2 | −1 | 0 |
| 1006 | 620 | Active and healthy | | x | | | | | | |
| | | Diarrhea | | | x | x | | | | |
| | | Ano-genital staining | | | x | x | | | | |
| | | Reduced fecal volume | | | | x | | | | x |
| | | Coat soiled, body, oily | Slight | | | | x | x | x | |
| | | Coat soiled, body, oily | Moderate | | | | | | | x |
| — | 621 | Active and healthy | | x | | | | | | |
| | | Diarrhea | | | x | x | | | | |
| | | Ano-genital staining | | | x | x | | | | |
| | | Coat soiled, body, oily | Slight | | | | x | | x | x |
| | | Coat soiled, body, oily | Moderate | | | | | x | | |
| | | Reduced fecal volume | | | | | | | x | x |
| 1022 | 622 | Active and healthy | | x | x | x | | | | |
| | | Coat soiled, body, oily | Slight | | | | x | x | x | x |
| | | Reduced fecal volume | | | | | | | x | |
| 1027 | 623 | Active and healthy | | x | x | | | | | |
| | | Reduced fecal volume | | | | | x | | x | x |
| | | Coat soiled, body, oily | Slight | | | | x | x | x | x |
| 1029 | 624 | Active and healthy | | x | | | | | | |
| | | Soft feces | | | x | x | | | | |
| | | Coat soiled, body, oily | Slight | | | | x | x | x | x |
| | | Reduced fecal volume | | | | | | | x | x |

Acclimation Period

| Animal | | | | Day of Occurrence | | | | | | |
|---|---|---|---|---|---|---|---|---|---|---|
| #[14] | Ear Tag | Observation | Grade | −6 | −5 | −4 | −3 | −2 | −1 | 0 |
| 1021 | 625 | Active and healthy | | x | x | | | | | |
| | | Reduced fecal volume | | | | x | | | x | x |
| | | Coat soiled, body, oily | Slight | | | | x | x | x | x |
| 1026 | 626 | Active and healthy | | x | | | | | | |
| | | Diarrhea | | | | x | | | | |
| | | Ano-genital staining | | | | x | | | | |
| | | Reduced fecal volume | | | | x | | | x | x |
| | | Coat soiled, body, oily | Slight | | | | x | x | x | x |
| 1015 | 627 | Active and healthy | | x | | | | | | |
| | | Ano-genital staining | | | x | x | | | | |
| | | Diarrhea | | | | x | | | | |
| | | Coat soiled, body, oily | Slight | | | | x | x | x | x |
| | | Reduced fecal volume | | | | | | | | x |
| 1013 | 628 | Active and healthy | | x | | | | | | |
| | | Diarrhea | | | x | x | | | | |
| | | Coat soiled, body, oily | Slight | | | | x | x | x | x |
| | | Reduced fecal volume | | | | | | | x | x |
| 1020 | 629 | Active and healthy | | x | x | x | | | | |
| | | Coat soiled, body, oily | Slight | | | | x | x | x | x |

Acclimation Period

| Animal | | | | Day of Occurrence | | | | | | |
|---|---|---|---|---|---|---|---|---|---|---|
| #[15] | Ear Tag | Observation | Grade | −6 | −5 | −4 | −3 | −2 | −1 | 0 |
| 1002 | 630 | Active and healthy | | x | | | | | | |
| | | Diarrhea | | | x | | | | | |
| | | Reduced fecal volume | | | | x | | | x | x |
| | | Coat soiled, body, oily | Slight | | | | x | x | x | x |

TABLE 4-continued

INDIVIDUAL IN-LIFE OBSERVATIONS

| | | | | -6 | -5 | -4 | -3 | -2 | -1 | 0 |
|---|---|---|---|---|---|---|---|---|---|---|
| 1028 | 631 | Active and healthy | | x | x | x | | | | |
| | | Coat soiled, body, oily | Slight | | | | x | x | x | x |
| | | Reduced fecal volume | | | | | | | x | x |
| | | Soft feces | | | | | | | x | |
| 1030 | 632 | Active and healthy | | x | | | | | | |
| | | Ano-genital staining | | | x | x | x | | | |
| | | Coat soiled, body, oily | Slight | | | x | x | | | |
| | | Coat soiled, body, oily | Moderate | | | | | x | x | x |
| 1005 | 633 | Active and healthy | | x | | | | | | |
| | | Diarrhea | | | x | | | | | |
| | | Reduced fecal volume | | | | | x | | x | x |
| | | Coat soiled, body, oily | Slight | | | | x | x | x | x |
| 1037 | 634 | Active and healthy | | x | x | | | | | |
| | | Coat soiled, body, oily | Slight | | | x | x | x | x | x |
| | | Active and healthy | | x | x | x | | | | |
| 1003 | 635 | Coat soiled, body, oily | Slight | | | | x | | | |
| | | Coat soiled, body, oily | Moderate | | | | | x | x | x |
| | | Reduced fecal volume | | | | | | x | x | x |

Acclimation Period

| Animal #[16] | Ear Tag | Observation | Grade | -6 | -5 | -4 | -3 | -2 | -1 | 0 |
|---|---|---|---|---|---|---|---|---|---|---|
| 1035 | 636 | Active and healthy | | x | | | | | | |
| | | Soft feces | | | x | x | | | | |
| | | Coat soiled, body, oily | Slight | | | | x | x | | |
| | | Coat soiled, body, oily | Moderate | | | | | | x | x |
| 1033 | 637 | Active and healthy | | x | | | | | | |
| | | Diarrhea | | | x | | | | | |
| | | Reduced fecal volume | | | | x | x | x | | |
| | | Coat soiled, body, oily | Slight | | | | x | x | x | x |
| — | 638 | Active and healthy | | x | x | | | | | |
| | | Reduced fecal volume | | | | x | x | x | x | |
| | | Coat soiled, body, oily | Slight | | | | x | x | x | x |

Group 1

| Animal Numbe | Animal Sex | Observation | Grade | 0 | 1 | 2 | 3 | 4 | 5 | 6 | 7 | 8 | 9 | 1 | 1 | 1 | 1 | 1 |
|---|---|---|---|---|---|---|---|---|---|---|---|---|---|---|---|---|---|---|
| 1001 | M | Reduced | | x | x | | x | x | x | x | x | | | | | | | |
| | | Coat soiled, | Moderat Slight | x | x | x | x | x | x | x | | | | | | | | |
| | | Active and | | | | | | | | | | x | x | x | x | x | x | |
| 1002 | M | Reduced | | x | | | | | | | | | | | x | | | |
| | | Coat Diarrhea | Slight | x | x | x | x | x | x | | | | | | | | | |
| | | Active and | | | | | | | x | x | x | x | x | x | x | x | | |
| | | Soft feces | | | | | | | | | | | | | | | | x |
| 1003 | M | Reduced | | x | | | | | | | | | | | x | | | |
| | | Coat soiled, | Moderat Slight | x | x | x | | | | | | | | | | | | |
| | | Active and | | | | | x | x | x | x | x | x | x | x | x | | | x |
| 1004 | M | Reduced | | x | | | x | x | x | x | | | | | | | | |
| | | Coat | Slight | x | x | x | | | | x | x | x | x | x | x | x | | |
| | | Soft feces | | | | | | | | | | | | | | | | x |
| 1005 | M | Reduced | | x | | | | | | | x | x | | | | | | |
| | | Coat | Slight | x | x | | | | | | | | | | | | | |
| | | Active and | | | | x | x | x | x | x | | x | x | x | x | x | | |

Group 1

| Animal Numbe | Animal Sex | Observation | Grade | 0 | 1 | 2 | 3 | 4 | 5 | 6 | 7 | 8 | 9 | 1 | 1 | 1 | 1 | 1 |
|---|---|---|---|---|---|---|---|---|---|---|---|---|---|---|---|---|---|---|
| 1006 | M | Reduced | | x | | | | | | | | | | | | | | |
| | | Coat Diarrhea | Moderat | x | x | x | | | | | | | | | | | | |
| | | | | | x | x | | | | | | | | | | | | |
| | | Coat | Slight | | | | | x | x | x | x | x | x | x | x | x | x | x |
| | | Soft feces | | | | | | | | | | | | | | | | x |
| 1007 | M | Reduced | | x | x | x | x | x | x | | x | x | | | | | | |
| | | Coat soiled, | Moderat Slight | x | x | x | x | | | | | | | | | | | |
| | | Active and | | | | | | | | | x | | x | x | x | x | | |

TABLE 4-continued

INDIVIDUAL IN-LIFE OBSERVATIONS

| 1008 | M | Coat | Slight | x | | | | | | | | x | x | x | x | x | x | | x | x |
|---|---|---|---|---|---|---|---|---|---|---|---|---|---|---|---|---|---|---|---|---|
| | | Active and | | | x | x | | | | | | | | | | | | | | |
| | | Reduced | | | | | x | x | x | x | | | | | | | | | | |
| 1009 | M | Reduced | | | x | x | x | x | x | x | x | | | | | | | | | |
| | | Ano- | | | x | x | x | | | | | | | | | | | | | |
| | | Coat | Slight | x | x | x | x | x | x | x | x | | | | | | | | | |
| | | Active and | | | | | | | | | | x | x | x | x | x | | x | x |
| 1010 | M | Reduced | | | x | x | x | x | x | x | x | | | | | | | | | |
| | | Coat | Slight | x | x | x | | | | | | | | | | | | | | |
| | | Active and | | | | | | | | | | x | x | x | x | x | x | | x | x |

Group 1

| | Animal | | | Day of Occurrence | | | | | | | | | | | | | |
|---|---|---|---|---|---|---|---|---|---|---|---|---|---|---|---|---|---|
| Animal | Sex | Observation | Grade | 1 | 1 | 1 | 1 | 1 | 2 | 2 | 2 | 2 | 2 | 2 | 2 | 2 | 2 |
| 1001 | M | Reduced | | x | x | | | | | | | | | | | | |
| | | Ano- | | | x | | | | | | | | | | | | |
| | | Active and | | | | x | x | x | x | | | | x | | | x | x |
| | | Diarrhea | | | | | | | x | | | | | | | | |
| | | Soft feces | | | | | | | | x | x | | x | x | | | |
| 1002 | M | Soft feces | | x | x | x | x | x | x | x | | x | | | | x | x |
| | | Ano- | | | x | | | | | | | | | | | | |
| | | Active and | | | | | | | | x | | x | x | x | | | |
| 1003 | M | Active and | | x | x | x | x | x | x | x | x | x | x | x | x | x | x |
| 1004 | M | Soft feces | | x | | x | x | x | x | x | x | x | | | | | x |
| | | Coat | Sligh | x | x | | | | | | | | | | | | |
| | | Active and | | | | | | | | | | | x | x | | | |
| | | Reduced | | | | | | | | | | | | | x | | |
| 1005 | M | Active and | | x | x | x | x | x | x | x | x | x | x | x | | x | x |
| 1006 | M | Soft feces | | x | x | x | x | x | x | | | | x | x | | | |
| | | Coat | Sligh | x | x | x | x | x | | | | | | | | | |
| | | Ano- | | | x | | | | | | | | | | | | |
| | | Active and | | | | | | | | x | x | x | | | | x | x |
| 1007 | M | Active and | | x | | x | x | x | x | x | x | x | x | x | x | x | x |
| | | Soft feces | | | x | | | | | | | | | | | | |

Group 1

| Animal | Animal | | Day of Occurrence | | | | | | | | | | | | |
|---|---|---|---|---|---|---|---|---|---|---|---|---|---|---|---|
| Number | Sex | Observation | 15 | 16 | 17 | 18 | 19 | 20 | 21 | 22 | 23 | 24 | 25 | 26 | 27 | 28 |
| 1008 | M | Active and | x | x | x | x | x | x | x | | | | x | x | x | x |
| | | Reduced | | | | | | | | x | x | x | | | | |
| 1009 | M | Active and | x | | x | x | x | x | x | x | x | x | x | x | x | x |
| | | Soft feces | | x | | | | | | | | | | | | |
| 1010 | M | Active and | x | x | x | x | x | x | x | x | x | x | | | | |
| | | Soft feces | | | | | | | | | | | x | | | |
| | | Diarrhea | | | | | | | | | | | | x | x | x |

Group 2

| | | | | Day of Occurrence | | | | | | | | | | | | | | |
|---|---|---|---|---|---|---|---|---|---|---|---|---|---|---|---|---|---|---|
| Animal | Anima | Observatio | Grade | 0 | 1 | 2 | 3 | 4 | 5 | 6 | 7 | 8 | 9 | 1 | 1 | 1 | 1 | 1 |
| 1011 | M | Coat | Slight | x | | | | | | | | | | | | | x | x |
| | | Coat | Moderat | | x | x | x | x | x | x | x | x | x | x | x | x | | |
| 1012 | M | Coat | Moderat | x | x | x | | | | | | | | | | | x | x |
| | | soiled, | Extreme | | | | x | x | x | x | x | x | x | x | x | x | | |
| | | Reduced | | | | | x | | | | | | | | | | | |
| 1013 | M | Reduced | | x | x | | | | | | | | | | | | | |
| | | Coat | Slight | x | x | x | x | x | x | x | x | | | x | x | x | x | x |
| | | Coat | Moderat | | | | | | | | | x | x | | | | | |
| 1014 | M | Reduced | | x | x | | | | | | | | | | | | | |
| | | Coat | Moderat | x | x | x | | | | | | | | | | | | |
| | | Coat | Slight | | | | | x | x | x | x | x | x | x | x | x | x | x |
| 1015 | M | Reduced | | x | | | | | | | | | | | | | | |
| | | Coat | Slight | x | x | x | x | x | x | x | x | x | x | x | x | x | x | x |
| 1016 | M | Reduced | | x | x | x | | | | | | | | | | | | |
| | | Active and | | | | | | x | x | x | x | x | x | x | x | x | x | x |
| 1017 | M | Reduced | | x | x | | | | | | | | | | | | | |
| | | Coat | Slight | x | | | | | | | | | | | | | | |
| | | Coat | Moderat | | x | x | x | x | x | x | x | x | x | x | x | x | x | x |

TABLE 4-continued

INDIVIDUAL IN-LIFE OBSERVATIONS

Group 2

| Animal Number | Animal Sex | Observation | Grade | \multicolumn{15}{c}{Day of Occurrence} |
|---|---|---|---|---|---|---|---|---|---|---|---|---|---|---|---|---|---|---|
| | | | | 0 | 1 | 2 | 3 | 4 | 5 | 6 | 7 | 8 | 9 | 1 | 1 | 1 | 1 | 1 |
| 1018 | M | Reduced | | x | | | | | | | | | | | | | | |
| | | Coat | Slight | x | x | x | | | | | | | | | | | | |
| | | Coat | Moderat | | | | x | x | x | x | x | x | x | x | x | x | x | x |
| 1019 | M | Reduced | | x | | | | | | | | | | | | | | |
| | | Coat | Slight | x | x | x | x | x | x | x | x | x | x | x | x | x | x | x |
| 1020 | M | Coat | Slight | x | x | x | x | x | x | x | | | | | | | x | x |
| | | Coat | Moderat | | | | | | | | x | x | x | x | x | x | | |

Group 2

| Animal Number | Animal Sex | Observation | Grade | \multicolumn{14}{c}{Day of Occurrence} |
|---|---|---|---|---|---|---|---|---|---|---|---|---|---|---|---|---|---|
| | | | | 1 | 1 | 1 | 1 | 1 | 2 | 2 | 2 | 2 | 2 | 2 | 2 | 2 | 2 |
| 1011 | M | Coat | Slight | x | x | | | | | | | | | | | | |
| | | Active | | | | x | x | x | x | x | x | x | x | x | x | x | x |
| 1012 | M | Coat soiled, | Moder Slight | x | x | | | | | | | | | | | | |
| | | Active | | | | x | x | x | x | x | x | x | x | x | | x | x |
| 1013 | M | Coat | Slight | x | x | | | | | | | | | | | | |
| | | Active | | | | x | x | x | x | x | x | x | x | x | x | x | x |
| 1014 | M | Coat | Slight | x | x | x | x | x | x | x | x | | | | | | |
| | | Active | | | | | | | | | | x | x | x | x | x | x |
| 1015 | M | Active | | x | x | x | x | x | x | x | x | x | x | x | x | x | x |
| 1016 | M | Active | | x | x | x | x | x | x | x | x | x | x | x | x | x | x |
| 1017 | M | Coat | Moder | x | x | | | | | | | | | | | | |
| | | Coat | Slight | | | x | x | x | x | x | x | x | x | x | x | x | x |
| 1018 | M | Coat soiled, | Moder Slight | x | x | | | | | | | | | | | | |
| | | Active | | | | x | x | x | x | x | x | | | | | | |
| | | Active | | | | | | | | | | x | x | x | x | x | x |
| 1019 | M | Coat | Slight | x | x | x | x | x | x | x | | | | | | | |
| | | Active | | | | | | | | | x | x | x | x | x | x | |
| 1020 | M | Coat | Slight | x | x | x | x | x | x | x | x | | | | | | |
| | | Active | | | | | | | | | | x | x | x | x | x | x |

Group 3

| Animal Number | Animal Sex | Observation | Grade | \multicolumn{15}{c}{Day of Occurrence} |
|---|---|---|---|---|---|---|---|---|---|---|---|---|---|---|---|---|---|---|
| | | | | 0 | 1 | 2 | 3 | 4 | 5 | 6 | 7 | 8 | 9 | 1 | 1 | 1 | 1 | 1 |
| 1021 | M | Reduced | | x | | | | | | | | | | | | | | |
| | | Coat | Slight | x | x | x | x | | | | | | | | | | | |
| | | Active and | | | | | | x | x | x | x | x | x | x | x | x | x | x |
| 1022 | M | Coat | Slight | x | x | x | x | x | x | x | | | | | | | | |
| | | Active and | | | | | | | | | x | x | x | x | x | x | x | x |
| 1023 | M | Coat soiled, | Moderat Slight | x | x | x | | | | | | | | | | | | |
| | | | | | | | x | x | x | x | | | | | | | | |
| | | Active and | | | | | | | | | x | x | x | x | x | x | x | x |
| 1024 | M | Reduced | | x | | | | | | | | | | | | | | |
| | | Coat | Slight | x | x | x | | | | | | | | | | | | |
| | | Active and | | | | | | x | x | x | x | x | x | x | x | x | x | x |
| 1025 | M | Reduced | | x | | | | | | | | | | | | | | |
| | | Coat | Slight | x | x | | | | | | | | | | | | | |
| | | Active and | | | | x | x | x | x | x | x | x | x | x | x | x | x | x |
| 1026 | M | Reduced | | x | | | | | | | | | | | | | | |
| | | Coat | Slight | x | x | x | x | x | x | | | | | | | | | |
| | | Active and | | | | | | | | x | x | x | x | x | x | x | x | x |
| 1027 | M | Reduced | | x | | | | | | | | | | | | | | |
| | | Coat | Slight | x | | | | | | | | | | | | | | |
| | | Active and | | | x | x | x | x | x | x | x | x | x | x | x | x | x | x |

Group 3

| Animal Number | Animal Sex | Observation | Grade | \multicolumn{15}{c}{Day of Occurrence} |
|---|---|---|---|---|---|---|---|---|---|---|---|---|---|---|---|---|---|---|
| | | | | 0 | 1 | 2 | 3 | 4 | 5 | 6 | 7 | 8 | 9 | 1 | 1 | 1 | 1 | 1 |
| 1028 | M | Reduced | | x | | | | | | | | | | x | x | | | |
| | | Coat | Slight | x | x | x | x | x | x | x | | | | | | | | |
| | | Active and | | | | | | | | | x | x | x | | x | | | |
| | | Dead | | | | | | | | | | | | | | | | |

TABLE 4-continued

INDIVIDUAL IN-LIFE OBSERVATIONS

| Animal Number | Animal Sex | Observation | Grade | | | | | | | | | | | | | | |
|---|---|---|---|---|---|---|---|---|---|---|---|---|---|---|---|---|---|
| 1029 | M | Reduced Coat | Slight | x | x | | | | | | | | | | | | |
| | | Active and | | | | x | x | x | x | x | x | x | x | x | x | x | x |
| 1030 | M | Coat soiled, | Moderat Slight | x | x | x | x | x | x | x | | | | | | | |
| | | Active and | | | | | | | | | x | x | x | x | x | x | x |

Group 3

| Animal Number | Animal Sex | Observation | Day of Occurrence | | | | | | | | | | | | |
|---|---|---|---|---|---|---|---|---|---|---|---|---|---|---|---|
| | | | 15 | 16 | 17 | 18 | 19 | 20 | 21 | 22 | 23 | 24 | 25 | 26 | 27 | 28 |
| 1021 | M | Active and | x | x | x | x | x | x | x | x | x | x | x | x | x | x |
| 1022 | M | Active and | x | x | x | x | x | x | x | x | x | x | x | x | x | x |
| 1023 | M | Active and | x | x | x | x | x | x | x | x | x | x | x | x | x | x |
| 1024 | M | Active and | x | x | x | x | x | x | x | x | x | x | x | x | x | x |
| 1025 | M | Active and | x | x | x | x | x | x | x | x | x | x | x | x | x | x |
| 1026 | M | Active and | x | x | x | x | x | x | x | x | x | x | x | x | x | x |
| 1027 | M | Active and | x | x | x | x | x | x | x | x | x | x | x | x | x | x |
| 1029 | M | Active and | x | x | x | x | x | x | x | x | x | x | x | x | x | x |
| 1030 | M | Active and | x | x | x | x | x | x | x | x | x | x | x | x | x | x |

Group 4

| Animal Numbe | Animal Sex | Observation | Grade | Day of Occurrence | | | | | | | | | | | | | |
|---|---|---|---|---|---|---|---|---|---|---|---|---|---|---|---|---|---|
| | | | | 0 | 1 | 2 | 3 | 4 | 5 | 6 | 7 | 8 | 9 | 1 | 1 | 1 | 1 | 1 |
| 1031 | M | Reduced Coat | Slight | x | x | x | | | | | | | | | | | |
| | | | | x | x | x | x | | | | | | | | | | |
| | | Active and | | | | | | x | x | x | x | x | x | x | x | x | x |
| 1032 | M | Coat | Moderat | x | x | x | | | | | | | | | | | |
| | | Reduced Coat | Slight | | x | x | | x | x | x | x | x | x | x | x | x | x |
| | | Diarrhea | | | | | | | | | x | | | | | | |
| | | Soft feces | | | | | | | | | | x | x | x | x | x | x |
| | | Ano- | | | | | | | | | | x | x | x | x | x | x |
| 1033 | M | Coat | Slight | x | x | x | | | | | x | | | | | x | x |
| | | Active and | | | | | x | x | x | x | | | | | | | |
| | | Reduced | | | | | | | | | x | x | x | | | | |
| | | Ano- | | | | | | | | | | x | x | x | x | x | x |
| | | Soft feces | | | | | | | | | | | x | x | x | x | x |
| 1034 | M | Coat | Moderat | x | x | x | x | x | x | x | x | x | | | | x | |
| | | Reduced | | | | | | x | x | x | | x | | | | x | |
| | | Diarrhea | | | | | | | | x | x | | | | | | |
| | | Ano- | | | | | | | | | x | x | x | x | x | x | x |
| | | Coat | Slight | | | | | | | | | x | x | x | x | x | x |
| | | Soft feces | | | | | | | | | | | x | x | x | x | x |
| 1035 | M | Coat | Moderat | x | x | x | | | | | | | | | | | |
| | | Reduced | | | x | | x | x | x | x | x | | x | x | x | | |
| | | Coat | Slight | | | | x | x | x | x | x | x | x | x | x | x | x |
| | | Diarrhea | | | | | | | | | | x | | | | | x |
| | | Ano- | | | | | | | | | | x | x | x | x | x | x |
| | | Soft feces | | | | | | | | | | | | | | x | |
| 1036 | M | Reduced Coat | Slight | x | x | x | x | | | | | | | x | x | x | x |
| | | Active and | | | | | x | x | x | x | x | | | | | | |
| | | Ano- | | | | | | | | | | | x | x | x | x | |
| | | Diarrhea | | | | | | | | | | | | x | x | | |
| | | Soft feces | | | | | | | | | | | | | | x | x |
| 1037 | M | Coat | Slight | x | x | x | x | x | x | | | | | | | | |
| | | Reduced | | | x | x | x | x | x | x | | | | | | | |
| | | Coat | Moderat | | | | | | | | x | x | x | x | x | x | x |
| | | Ano- | | | | | | | | | | | x | | | | |
| | | Soft feces | | | | | | | | | | | | | | | x |
| 1038 | M | Reduced Coat | Slight | x | x | x | x | x | x | x | x | | | | | | |
| | | | | | x | x | x | | | | | | | | | | |
| | | Diarrhea | | | | x | | | | | | | | | | | |
| | | Active and | | | | | | | | | | | x | x | x | x | |
| | | Soft feces | | | | | | | | | | | | | | x | x |
| | | Ano- | | | | | | | | | | | | | | | x |

TABLE 4-continued

INDIVIDUAL IN-LIFE OBSERVATIONS

Group 4

| Animal Number | Animal Sex | Observation | Grade | \multicolumn{15}{c}{Day of Occurrence} |
|---|---|---|---|---|---|---|---|---|---|---|---|---|---|---|---|---|---|---|
| | | | | 0 | 1 | 2 | 3 | 4 | 5 | 6 | 7 | 8 | 9 | 10 | 11 | 12 | 13 | 14 |
| 1039 | M | Reduced | | x | x | | | | | | x | x | | | | | | |
| | | Coat soiled, Diarrhea | Slight | x | x | x | x | x | x | x | x | x | x | x | x | x | x | x |
| | | | | | | | | | | | x | | | | | | | |
| | | Soft feces | | | | | | | | | | | x | x | x | x | x | x |
| | | Ano-genital | | | | | | | | | | | x | x | x | x | x | x |
| 1040 | M | Reduced | | x | x | | | | | | x | x | x | | | | x | x |
| | | Coat soiled, Active and | Slight | x | x | x | x | | x | x | x | | x | x | x | x | x | x |
| | | Soft feces | | | | | | | | | | | x | x | x | x | | x |
| | | Ano-genital | | | | | | | | | | | x | | | | | |

Group 4

| Animal | Animal Sex | Observation | Grade | \multicolumn{14}{c}{Day of Occurrence} |
|---|---|---|---|---|---|---|---|---|---|---|---|---|---|---|---|---|---|
| | | | | 1 | 1 | 1 | 1 | 1 | 2 | 2 | 2 | 2 | 2 | 2 | 2 | 2 | 2 |
| 1031 | M | Active | | x | x | x | x | x | x | x | x | x | x | x | | | |
| | | Soft feces | | | | | | | | | | | | | x | x | x |
| 1032 | M | Soft feces | | x | x | | | | | | x | x | | | | | |
| | | Coat | Slight | x | x | x | x | x | x | x | x | | | | | | |
| | | Ano- | | x | x | x | x | x | | | | | | | | | |
| | | Reduced | | | | x | x | x | | | | | | | | | |
| | | Active | | | | | | | | | | | | x | x | x | x |
| 1033 | M | Soft feces | | x | x | x | x | x | | | | | | | | | |
| | | Coat | Slight | x | x | x | x | x | | | | | | | | | |
| | | Active | | | | | | | x | x | x | x | x | x | x | x | x |
| 1034 | M | Soft feces | | x | x | x | x | x | x | x | | x | x | x | x | x | x |
| | | Coat | Slight | x | | x | x | x | x | | x | x | x | x | x | x | x |
| | | Ano- | | x | x | | | | | | | x | | | | x | x |
| | | Coat | Modera | | x | | | | | | | | | | | | |
| | | Diarrhea | | | | | | | | | | x | | x | x | x | |
| 1035 | M | Coat | Slight | x | x | x | x | x | x | x | x | | | | | | |
| | | Ano- | | x | x | | | | | | | | | | | | |
| | | Soft feces | | | x | | | | | | | | | | | | |
| | | Active | | | | | | | | | | x | x | x | x | x | x |
| 1036 | M | Reduced | | x | | | | | | | | | | | | | |
| | | Coat | Slight | x | x | x | x | x | x | x | x | x | | | | | |
| | | Active | | | | | | | | | | | x | x | | | |
| | | Soft feces | | | | | | | | | | | | | x | | x |
| | | Diarrhea | | | | | | | | | | | | | x | | |
| 1037 | M | Soft feces | | x | x | | | | | | | | | | | | |
| | | Coat soiled, | Modera Slight | x | x | x | x | x | x | x | x | x | | | | | |
| | | Active | | | | | | | | | | | x | x | x | x | x |
| | | Soft feces | | x | x | x | x | x | x | | | | | x | x | x | |
| 1038 | M | Ano- | | x | | | | | | | | | | | | | |
| | | Diarrhea | | | | | | | | x | | | | | | | |
| | | Active | | | | | | | | | x | x | x | x | | | |
| 1039 | M | Soft feces | | x | | x | x | x | x | x | x | x | x | x | x | x | |
| | | Coat | Slight | x | x | x | x | x | x | | | | | | | | |
| | | Ano- | | x | x | | | | | | | | | | | | |
| | | Diarrhea | | | x | x | | | | | | | | | | | |
| 1040 | M | Soft feces | | x | x | | | | | x | x | x | x | x | x | x | |
| | | Coat | Slight | x | | x | x | x | x | x | | | | | | | |
| | | Ano- | | | x | | | | | | | | | | | | |
| | | Coat | Modera | | x | | | | | | | | | | | | |

[8] Animals not assigned to individual groups, prior to randomization were identified by their ear tag ID number. Once selected for test, animals were assigned an animal number.
[9] Animals not assigned to individual groups, prior to randomization were identified by their ear tag ID number. Once selected for test, animals were assigned an animal number.
[10] Animals not assigned to individual groups, prior to randomization were identified by their ear tag ID number. Once selected for test, animals were assigned an animal number.
[11] Animals not assigned to individual groups, prior to randomization were identified by their ear tag ID number. Once selected for test, animals were assigned an animal number.
[12] Animals not assigned to individual groups, prior to randomization were identified by their ear tag ID number. Once selected for test, animals were assigned an animal number.
[13] Animals not assigned to individual groups, prior to randomization were identified by their ear tag ID number. Once selected for test, animals were assigned an animal number.
[14] Animals not assigned to individual groups, prior to randomization were identified by their ear tag ID number. Once selected for test, animals were assigned an animal number.
[15] Animals not assigned to individual groups, prior to randomization were identified by their ear tag ID number. Once selected for test, animals were assigned an animal number.
[16] Animals not assigned to individual groups, prior to randomization were identified by their ear tag ID number. Once selected for test, animals were assigned an animal number.

APPENDIX B1: DIET ANALYSES RESULTS

| | | Analytical Results | | | |
|---|---|---|---|---|---|
| Analysis | Unit | Group 1 Test Article Diet | Group 2 Modified Casein Control Diet | Group 3 Standard Casein Control Diet | Group 3 Enfamil ® Comparison Test Diet |
| Protein (average) | % | 9.92 | 9.90 | 10.04 | 9.88 |
| Moisture | % | 6.24 | 6.06 | 8.94 | 5.21 |
| Ash | % | 2.56 | 2.58 | 2.57 | 2.54 |
| Crude Fiber | % | 0.312 | 0.526 | 0.514 | 0.129 |
| Fat | % | 19.9 | 19.3 | 8 | 25.6 |
| Lactose | % | 32.3 | 18.5 | <0.1 | 34.4 |
| Zinc | PPM | 38.5 | 54.0 | 45.1 | 57.8 |
| Riboflavin | MCG/G | 8.64 | 10.1 | 5.79 | 6.36 |

Example 3. Clinical Study for the Growth and Safety Study ° Fan Exemplary Infant Formulator Healthy Term Infants Protocol Synopsis The purpose of this study is to demonstrate that this formulation meets nutritional requirements and supports age appropriate growth of healthy term infants.

Objectives:

The primary efficacy objective is to compare the growth of infants randomized to a commercially available term infant formula (Brand Formula) versus growth of infants randomized to two experimental infant formulas for term infants (FORMULA-001 w/OPN Formula and FORMULA-102 w/o OPN).

The secondary efficacy objective is to compare formula intake volume between formula groups.

The exploratory objective is to compare serum markers of inflammation between formula groups.

The primary safety objective is to compare the frequency of adverse events (AEs) between the formula groups.

The secondary safety objective is to compare the gastrointestinal tolerance (stool composition, bowel movements, stool consistency, gas, fussiness, and ICQ scales) between formula groups.

Analyses between cohorts (Brand Formula, FORMULA-001 w/ OPN Formula, and FORMULA-102 w/o OPN) will occur separately depending on finalization of Generally Recognized as Safe (GRAS) approval of specific ingredients in FORMULA-001 w/ OPN Formula.

Study Design:

This study is a randomized, controlled, double-blind study of healthy term formula-fed (FF) infants.

The first phase of the study, infants will receive either a new infant formula formulated for healthy term infants (FORMULA-001 w/ OPN Formula) or a commercially available infant formula for healthy term infants (Brand Formula) in a 1:1 ratio.

After completion of the first phase, in a second phase of the study, infants are randomized to receive either Brand Formula or FORMULA-102 w/o OPN in a 1:8 ratio.

In both study arms, infants will consume the study formula for a total of 16 weeks. Throughout the study, infant growth and tolerance to the formulas are assessed.

Criteria for Inclusion:

Infants are eligible to participate if they meet all of the following conditions:

At Birth the Infant Must be:
1. Healthy, term (early term/no less than 37 weeks, 0 days through late term/no greater than 41 weeks, 6 days), singleton infant
2. Have a birth weight of ≥2500 grams At the Time of the Baseline/Enrollment Visit, Infants Must be:
3. Designated as healthy by a physician
4. ≤14 days post-natal age (Date of Birth=Day 0)
5. Weight for age ≥5th and ≤95th percentile for age according to sex-specific World Health Organization (WHO) growth charts for infants and children ages 0 to 2 years of age
6. Length for age ≥5th and ≤95th percentile for age according to sex-specific charts World Health Organization (WHO) growth charts for infants and children ages 0 to 2 years of age
7. Head circumference for age ≥5th and ≤95th percentile for age according to sex-specific World Health Organization (WHO) growth charts for infants and children ages 0 to 2 years of age
8. Weight for length for age ≥5th and ≤95th percentile for age according to sex-specific World Health Organization (WHO) growth charts for infants and children ages 0 to 2 years of age
9. Exclusively consuming and tolerating a cow's milk infant formula at time of enrollment; only infants whose parent(s) or legal guardian(s) have decided to feed infant formula as the sole source of nutrition are approached for potential study enrollment
10. Have parent(s) or legal guardian(s) who agree to feed the study formula to the study subject as his/her sole source of nutrition for the duration of the study
11. Have parent(s) or legal guardian(s) who have read and voluntarily signed an Informed Consent form approved by the Institutional Review Board prior to any participation in the study Criteria for Exclusion:

Infants are ineligible if they have any of the following conditions that are judged by a physician to interfere with the infant's normal growth, development, and/or tolerance to an infant formula:
1. Show evidence of anatomic and physiologic defects of the respiratory tract, or other congenital defects (as determined by the clinician)
2. Show evidence of chronic hepatic, gastrointestinal, renal, cardiac, pulmonary, or neurological diseases 3. Have a maternal history with known adverse effects on the fetus and/or the newborn infant, such as diabetes (gestational diabetes is acceptable if infant's birth weight is <4300 g), active tuberculosis, perinatal infection, or substance abuse
4. Have a family history of cow's milk protein intolerance/allergy
5. Are an infant from a multiple birth (twin, triplet, etc.)

Investigational Product, Dose, and Mode of Administration:

Infants will consume ad libitum per day one of the following formulas:

Brand Formula: A commercially available infant formula for term infants; 100 kcal/5 fl. oz, 2 g protein/100 kcal (Enfamil Infant 0-12 months by Mead Johnson Nutrition, LLC)

FORMULA-001 w/ OPN Formula: An infant formula for term infants containing alpha-lactalbumin enriched whey, OPO Sn-2 oil, osteopontin, lactoferrin, pre-biotics (PD, FOS, GOS), lutein, microencapsulated DHA/ARA; 100 kcal/5 fl. oz, 2.2 g protein/100 kcal (Manufactured by Building Block Nutritionals, LLC)

FORMULA-102 w/o OPN: An infant formula for term infants containing alpha-lactalbumin enriched whey, OPO Sn-2 oil, lactoferrin, pre-biotics (FOS, GOS), lutein, DHA/ARA; 100 kcal/5 fl. oz, 2.5 g protein/100 kcal (Manufactured by Building Block Nutritionals, LLC)

Primary Efficacy and Safety Evaluations:

Weight gain velocity (g/d)

Adverse Events are collected throughout the 16-week study

Statistical Methods:

For phase one of the study, sample size estimation is based on a test for non-inferiority between Brand Formula and FORMULA-001 w/ OPN Formula. The criterion for non-inferiority in weight gain is that the difference in the two formula-fed groups' (Brand Formula and B) mean weight gain velocity (g/d) is significantly less than 3 g/d. Assuming a standard deviation in weight gain of 5.6 g/d (Nelson et al., 1989) and 80% power, 90 subjects per group (180 subjects total) are sufficient to demonstrate non-inferiority (one sided alpha=0.025). Assuming a 25% attrition rate, a total 256 subjects are enrolled in the Brand Formula and FORMULA-001 w/ OPN Formula groups.

For phase two of the study, sample size estimation is based on the primary endpoint, weight gain velocity (g/d) over a 16-week study period. Weight gain velocity are compared between Brand Formula and FORMULA-102 w/o OPN using a non-inferiority margin of 3 g/d. A blinded interim analysis of 81 subjects who completed 16 weeks of the study was performed in phase one of the study to estimate the standard deviation of weight gain. Based on this analysis, it is assumed that the standard deviation in weight gain velocity is 6.0 g/d.

Assuming this standard deviation in weight gain of 6.0 g/d and approximately 90% power, approximately 168 subjects (104 in the Brand Formula group and 64 in the FORMULA-102 w/o OPN group) are sufficient to demonstrate non-inferiority (one-sided alpha=0.025). Assuming a 25% attrition rate, a total of approximately 96 subjects are enrolled in phase two.

The plan is to use the 129 subjects randomized to Brand Formula in the first phase of the study, assuming a 25% attrition rate and 96 subjects meet the Per Protocol population criteria. This data has and will remain blinded through the enrollment of the study. In phase two of the study, infants are randomized to Brand Formula or FORMULA-102 w/o OPN in a 1:8 ratio. Assuming a 25% attrition rate and to obtain approximately 90% power, approximately 10 subjects randomized to Brand Formula and 86 subjects randomized to FORMULA-102 w/o OPN are enrolled in phase two of the study. With the addition of the 129 subjects from phase one of the study, there are approximately a total of 139 subjects enrolled in the Brand Formula group and 86 subjects enrolled in the FORMULA-102 w/o OPN group. Infants are stratified by sex to achieve balance of males and females within each formula group.

LIST OF APPENDICES

Appendix 1A—Anthropometry Data Collection Procedures
Appendix 1B—Formula Composition
Appendix 1C—Formula Ingredients
Appendix 1F—Standardized Definitions for Common Adverse Events
Appendix 1G—Formula Preparation Instructions List of Abbreviations AE Adverse event
ARA Arachidonic acid
BBN Building Block Nutritionals, LLC
bLF bovine lactoferrin
CFR Code of Federal Regulations
CI confidence interval
Cm centimeter
CRF Case report form
CRO Clinical research organization
CSA Clinical study agreement
CSR Clinical study report
DHA Docosahexaenoic acid
eCRF Electronic case report form
FDA Food and Drug Administration
FF formula-fed
fl oz fluid ounce
Formula A Experimental Formula A (Building Block Nutritionals, LLC)
Formula B Commercially Available Milk Infant Formula (Enfamil Infant 0-12 months)
Formula C Experimental Formula C (Building Block Nutritionals, LLC)
FOS Fructo-oligosaccharide
g gram
GCP Good Clinical Practice
GERD Gastroesophageal Reflux Disease
GI Gastrointestinal
GOS Galacto-oligosaccharide
GRAS Generally recognized as safe
HM Human milk
HMO Human milk oligosaccharide
ICF Informed Consent Form
ICQ Infant Characteristics Questionnaire
IEC Independent ethics committee
IP Investigational product
IRB Institutional Review Board
ITT Intent to treat
kcal kilocalorie
kg kilogram
L liter
LCPFUA long chain polyunsaturated fatty acid
LOS lactulose
mcg microgram
MedDRA Medical Dictionary for Drug Regulatory Affairs mg milligram
OFC occipital frontal circumference
OPN Osteopontin
oz ounce
PP Per protocol
PWD Powder
RTSM Randomization and Trial Supply Management
SAE Serious adverse event
SDV Source document verification interleukin 2 receptor, interleukin 1 beta, and interferon gamma) between the formula groups.

Primary Safety Objective:

To compare the frequency of adverse events (AEs) between the formula groups.

Secondary Safety Objective:

To compare the gastrointestinal tolerance (stool composition, bowel movements, stool consistency, gas, fussiness, and ICQ scales) between the formula groups.

STUDY FLOWCHART

| | \*1 | 2\* | 3\* | 4 | 5\* | 6 | 7\* | 8 | 9\* |
|---|---|---|---|---|---|---|---|---|---|
| | | | | | Study Day | | | | |
| | 0 | 15 ± 3 days | 30 ± 3 days | 45 ± 3 days | 60 ± 3 days | 75 ± 3 days | 90 ± 3 days | 105 ± 3 days | 120 ± 3 days |
| Informed consent | X | | | | | | | | |
| Inclusion/Exclusion criteria | X | | | | | | | | |
| Demography | X | | | | | | | | |
| Randomization | X | | | | | | | | |
| Infant feeding history | X | | | | | | | | |
| Physical exam | X | | | | | | | | |
| Medical history | X | | | | | | | | |
| Maternal smoking history | X | | | | | | | | |
| Anthropometry[1] | X | X | X | | X | | X | | X |
| Stool Characteristics and Tolerance Questionnaire | X | X | X | X | X | X | X | X | X |
| Infant Characteristics Questionnaire (ICQ) | X | X | X | | X | | X | | X |
| 3-day Formula/Diet Record[2] | X | X | X | | X | | X | | X |
| Blood Collection[3] | | | | | | | | | X |
| Dispense stool collection kit[4] | | | | | | | X | | |
| Stool collection[4] | | | | | | | | | X |
| Telephone contact[5] | X | | | X | | X | | X | |
| Concomitant medications | X | X | X | X | X | X | X | X | X |
| Adverse events | X | X | X | X | X | X | X | X | X |
| Dispense study formula | X | X | X | | X | | X | | |
| Collect unused study formula | | | | | | | | | X |

Columns with a "\*" indicate visit occurs at study site
[1]Anthropometry includes assessment of weight, length, and head circumference (see Appendix A for procedure details).
[2]Initial 3-day Formula/Diet Record are recorded for 3 days following the first study visit. Remainder of 3-day Formula/Diet Records are recorded for 3 days prior to each subsequent scheduled study visit.
[3]Blood collection to assess markers of inflammation (tumor necrosis factor-alpha, interleukin 2, 4, 5, 6, 8, 10, 12, 13, & 17; interleukin 2 receptor, interleukin 1 beta, and interferon gamma).
[4]Stool collection to assess stool composition. Stool collection supplies are distributed to parents at Visit 7 for collection of all stools in the 3 days just before Visit 9. The stool collection kit is returned at Visit 9.
[5]Initial telephone contact will occur 3 days after enrollment to check compliance with study feeding and inquire about subject well-being. Remainder of telephone contacts will occur mid-way between clinic visits. Telephone contact notes are recorded in the study subject's medical record. In the event a 3-day telephone contact falls on a holiday or weekend, the contact are made on the next available business day.

Clinical Study Background Information and Rationale

If an infant cannot be breastfed, the American Academy of Pediatrics recommends infant formula as the next best feeding alternative. This study is designed to evaluate the ability of FORMULA-001 w/ osteopontin (OPN) and FORMULA-102 w/o OPN to support age appropriate growth in healthy term infants.

Objectives

Primary Efficacy Objective:

Compare the growth of infants randomized to a commercially available term infant formula (Brand Formula) versus growth of infants randomized to the experimental infant formula for term infants (FORMULA-001 w/ OPN or FORMULA-102 w/o OPN).

Secondary Efficacy Objective:

Compare the formula intake volume between the formula groups.

Exploratory Objective:

Compare the markers of inflammation (tumor necrosis factor-alpha, interleukin 2, 4, 5, 6, 8, 10, 12, 13, & 17;

Study Design

Approximate Duration of Subject Participation

Subjects participate in the study for 16 weeks.

Approximate Number of Subjects

In phase one, approximately 256 healthy term infants (128 per group, 64 per gender per group) are enrolled to complete a minimum of 180 evaluable infants (90 per group, 45 per gender per group).

In phase two, approximately 96 healthy term infants (10 in the Brand Formula group and 86 in the FORMULA-102 w/o OPN group are enrolled. The 129 subjects randomized to Brand Formula in the phase one of the study are combined with the Brand Formula subjects in phase two to have a minimum of 139 infants in Brand Formula and 86 in FORMULA-102 w/o OPN. Infants are stratified by sex to achieve balance of males and females within each formula group.

Inclusion Criteria

Infants are eligible to participate if they meet all of the following conditions. At birth the infant must be:
1. Healthy, term (no less than 37 weeks, 0 days and no greater than 42 weeks, 0 days), singleton infant
2. Have a birth weight of ≥2500 grams At the time of the baseline/enrollment visit, infants must be:

3. Designated as healthy by a physician
4. ≤14 days post-natal age (Date of Birth=Day 0)
5. Weight for age ≥5th and ≤95th percentile for age according to World Health Organization (WHO) growth charts for infants and children ages 0 to 2 years of age
6. Length for age ≥5th and ≤95th percentile for age according to World Health Organization (WHO) growth charts for infants and children ages 0 to 2 years of age
7. Head circumference for age ≥5th and ≤95th percentile for age according to World Health Organization (WHO) growth charts for infants and children ages 0 to 2 years of age
8. Weight for length for age ≥5th and ≤95th percentile for age according to World Health Organization (WHO) growth charts for infants and children ages 0 to 2 years of age
9. Exclusively consuming and tolerating a cow's milk infant formula at time of enrollment; only infants whose parent(s) or legal guardian(s) have decided to feed infant formula as sole source of nutrition are approached for potential study enrollment
10. Have parent(s) or legal guardian(s) who agree to feed the study formula as the sole source of nutrition for the duration of the study
11. Have parent(s) or legal guardian(s) who have read and voluntarily signed an Informed Consent form approved by the Institutional Review Board prior to any participation in the study.
12. Infants may be considered for enrollment again with a new baseline evaluation.

Exclusion Criteria

Infants are ineligible if they have any of the following conditions that are judged by a physician to interfere with the infant's normal growth, development, and/or tolerance to an infant formula:
1. Show evidence of anatomic and physiologic defects of the respiratory tract, or other congenital defects (as determined by the clinician)
2. Show evidence of chronic hepatic, gastrointestinal, renal, cardiac, pulmonary, or neurological diseases
3. Have a maternal history with known adverse effects on the fetus and/or the newborn infant, such as diabetes (gestational diabetes is acceptable if infant's birth weight is <4300 g), active tuberculosis, perinatal infection, or substance abuse
4. Have a family history of cow's milk protein intolerance/allergy
5. Are an infant from a multiple birth (twin, triplet, etc.)

Prior and Concomitant Medication and Treatment

Infants who were previously breastfed can be enrolled provided they have discontinued breastfeeding at study entry, and parents agree that they have voluntarily chosen to exclusively formula-feed the study subject during the study. If formula-fed, infants must be currently receiving and tolerating cow's milk formula. At each study visit, site personnel will interview parent(s)/guardian(s) to obtain information about all concomitant therapy that was administered since the previous study visit. Concomitant medications include prescription medications, over-the-counter medications, and herbal supplements. Routine childhood immunizations will not be recorded as concomitant medications. This information is recorded in the subject's medical record. If the infant was administered medication or treatment for a condition that may have an effect on the infants' growth and formula tolerance, the Investigator or medical staff must assess the potential medical implications to determine whether the study subject remains eligible to continue in the study. Use of an investigational product (i.e., therapeutic drug or vaccine) during a patient's participation in the study is prohibited. Participation in an observational or non-pharmaceutical/non-interventional trial (i.e. device trial) is allowed.

If a study subject was fed a formula other than the assigned study formula, this variation from protocol must be noted on the Protocol Deviation Log.

Procedures

Screening

Each infant is screened for all inclusion and exclusion criteria. If an infant complies with all inclusion and exclusion criteria and the parent(s)/guardian(s) sign the IRB-approved ICF, the infant is randomized to receive a study formula and assigned a unique subject number. If the infant does not comply with one or more of the inclusion or exclusion criteria, the infant is defined as a screen failure.

Study Visit Procedures

Visit 1 (Day 0)
Informed consent process
Inclusion/Exclusion criteria
Demography
Randomization
Infant feeding history
Physical exam
Medical history
Maternal smoking history
Anthropometry (see Appendix 1A for data collection procedures)
Stool Characteristics and Tolerance Questionnaire
Infant Characteristics Questionnaire (ICQ)
3-day Formula/Diet Record
Telephone contact
Medications
Adverse events
Dispensing of study formula Visit 2 (Day 15±3 Days)
Medical History
Anthropometry
Stool Characteristics and Tolerance Questionnaire
Infant Characteristics Questionnaire
3-day Formula/Diet Record
Medication
Adverse events
Dispensing of study formula Visit 3 (Day 30±3 Days)
Medical history
Anthropometry
Stool Characteristics and Tolerance Questionnaire
Infant Characteristics Questionnaire
3-day Formula/Diet Record
Medication
Adverse events
Dispensing of study formula Visit 4: Telephone Contact (Day 45±3 Days)
Stool Characteristics and Tolerance Questionnaire
Medication
Adverse events
Visit 5 (Day 60±3 Days)
Medical history
Anthropometry
Stool Characteristics and Tolerance Questionnaire
Infant Characteristics Questionnaire
3-day Formula/Diet Record
Medication
Adverse event
Dispensing of study formula
Visit 6: Telephone Contact (Day 75±3 Days)
Stool Characteristics and Tolerance Questionnaire
Medication
Adverse events
Visit 7 (Day 90±3 Days)
Medical history
Anthropometry
Stool Characteristics and Tolerance Questionnaire
Infant Characteristics Questionnaire
3-day Formula/Diet Record
Dispense stool collection kit
Medication
Adverse events
Dispensing of study formula
Visit 8: Telephone Contact (Day 105±3 Days)
Stool Characteristics and Tolerance Questionnaire
Medication
Adverse events
Visit 9 (Day 120±3 Days)
Medical history
Anthropometry
Stool Characteristics and Tolerance Questionnaire
Infant Characteristics Questionnaire
3-day Formula/Diet Record
Blood Collection
Stool collection
Medication
Adverse events
Collection of all unused/partially used study formula
Investigational Product and Administration
Study Formulas
  Infants will consume ad libitum per day one of the following:
  1. Brand Formula: A commercially available infant formula for term infants; 100 kcal/5 fl. oz, 2 g protein/100 kcal (Enfamil Infant 0-12 months by Mead Johnson Nutrition, LLC)
  2. FORMULA-001 w/ OPN: An infant formula for term infants containing alpha-lactalbumin enriched whey, OPO Sn-2 oil, osteopontin, lactoferrin, pre-biotics (PD, GOS, FOS), lutein, microencapsulated DHA/ARA; 100 kcal/5 fl. oz, 2.2 g protein/100 kcal (Manufactured by Building Block Nutritionals, LLC)
  3. FORMULA-102 w/o OPN: An infant formula for term infants containing alpha-lactalbumin enriched whey, Sn-2 oil, lactoferrin, pre-biotics (GOS, FOS), lutein, DHA/ARA; 100 kcal/5 fl. oz, 2.5 g protein/100 kcal (Manufactured by Building Block Nutritionals, LLC)
  See Appendix 1B for details of formula nutrient composition and Appendix 1C for formula ingredients.
Type and Amount
  Each infant will consume either Brand Formula, FORMULA-001 w/ OPN, or FORMULA-102 w/o OPN ad libitum for 16 weeks. Parent(s) or guardian(s) are discouraged from feeding their infant any foods other than the assigned study formula.
Administration
  The study formula is provided in powder form. Each of the infant formulas are packaged in composite cans. Cans are labeled with a unique clinical product number to mask the identity of each clinical product. Study personnel will not be aware of the identity of the products. Nutrient and stability testing are conducted to ensure that each formula meets strict quality requirements for release.
  Instructions for mixing the formula to 20 kcal/oz are given to the parent(s)/guardian(s).
Formula Storage by Investigator
  Formula are labeled for clinical trial use only and kept dry, protected from sunlight, and at room temperature (60-85° F., 16-29° C.). The Principal Investigator is responsible for keeping all unassigned and returned formula in a locked storage room with controlled staff access.
Formula Storage by Parent/Guardian
  The parent(s)/guardian(s) are instructed to handle formula with clean hands. Prior to opening, the can should be cleaned. Formula may be consumed at room temperature. The parent(s)/guardian(s) are instructed to never microwave or freeze formula. Prepared formula may be warmed in a bowl of warm water. Parents are instructed that prepared formula not consumed by the infant can be stored in the refrigerator for no more than 24 hours, and then should be thrown away.
  Parents are instructed to return all unopened cans of formula at the completion of the study.
Subject Compliance
  Compliance with study feedings is monitored approximately every two weeks throughout the study. A standard set of interview questions is administered at each clinic visit and during telephone follow-up between clinic visits to inquire about consumption of study formula and all other feedings including other formulas.
Safety
  Safety assessments will involve the monitoring and recording of all AEs and serious adverse events (SAEs), stool composition, gastrointestinal tolerance, periodic anthropometric measurements, and physical assessments. Additional safety evaluations may be performed when medically indicated in the opinion of the Investigator.
Efficacy
a. Primary Efficacy Endpoint
  Mean daily weight gain (g/d) over 16 weeks.
b. Secondary Efficacy Endpoints
  Anthropometric measurements (head circumference gain velocity, length gain velocity) and Z-scores (weight for age, length for age, weight for length for age, head circumference for age)
  Formula intake volume
c. Exploratory Endpoint
  Markers of inflammation (tumor necrosis factor-alpha, interleukin 2, 4, 5, 6, 8, 10, 12, 13, & 17; interleukin 2 receptor, interleukin 1 beta, and interferon gamma).
Laboratory Determinations
  Central laboratories are used for all laboratory determinations unless a special test or emergency testing is required. The central laboratories that have been contracted to perform these tasks adhere to Good Clinical Practices and will provide supplies and shipping materials for all laboratory determinations. Refer to the central laboratory manual(s) for additional information.

d. Biological Samples

A single blood sample (1.0 milliliters) is collected from each subject via heel stick at the last study visit (visit 9) to assess markers of inflammation (tumor necrosis factor-alpha, interleukin 2, 4, 5, 6, 8, 10, 12, 13, & 17; interleukin 2 receptor, interleukin 1 beta, and interferon gamma). Stool samples will also be collected at the last study visit (visit 9) to assess stool composition (soap fatty acids).

Biological samples are used exclusively for the purposes outlined in this protocol and for no other purpose.

Statistics

Statistical Methods

Analyses between cohorts (Brand Formula, FORMULA-001 w/ OPN, and FORMULA-102 w/o OPN) will occur separately depending on finalization of Generally Recognized as Safe (GRAS) approval of specific ingredients in FORMULA-001 w/ OPN formula.

Primary Efficacy Endpoint

The primary efficacy endpoint, mean daily weight gain (g/d) over a 16-week study period, are compared between formula groups by the calculation of the 95% two-sided confidence interval on the difference between the two means. Non-inferiority is determined if the lower limit of the two-sided 95% CI for the formula difference is greater than −3, assuming a non-inferiority margin of 3 mg/d.

Infant growth will also be descriptively summarized on the basis of the following sex-specific z-scores based on World Health Organization growth charts for infants and children ages 0 to 2 years of age: weight-for age, weight-for-length, length-for-age, and head circumference-for-age z-scores. For each subject, a line listing of all raw measures of weight, length, head circumference, and all z-scores (weight-for-age z-score, length-for-age z-score, weight-for-length z-score, and head circumference-for-age z-score) is provided. Descriptive statistics are used to summarize weight (kg), length (cm), and head circumference (cm) and all z-score data (weight-for age, weight-for-length, length-for-age, and head circumference-for-age) by formula group for each visit. A test for non-inferiority will also be performed for length gain (cm/d) velocity and head circumference gain (cm/d) velocity.

Safety Endpoints

A line listing of each subject with an adverse event is generated. At the group level, the number and percentage of subjects having each AE are summarized for each formula group. Secondary endpoints including stool characteristics, GI tolerance, and infant characteristics are summarized using descriptive statistics and qualitatively compared to age appropriate reference values when appropriate.

General Methods

Continuous variables are summarized using the appropriate descriptive statistics: n, mean, standard deviation, median, minimum, and maximum. The geometric mean is presented for log-transformed variables. Frequency and percentage of observed values are reported for categorical measures. A line listing of all data, sorted by subject and when appropriate by time, is generated.

Analysis Populations

Intent to Treat (ITT): Subjects who are randomized to one of the formula feeding groups.

Per Protocol (PP): A subset of the ITT population. It will consist of all subjects who complete the feeding protocol without major protocol violations and who consume a single non-study formula feeding no more than 10 times during the duration of 16-week study as documented on the Other Than Formula Feeding Log. Additionally, subjects who consume more than 3 complete days of non-study formula, defined as greater than 50% of the number of feedings in a 24-hour period from non-study formula, will also be excluded from the PP population.

Safety Population: The safety population is comprised of any subjects who are randomized and consume at least one feeding of the assigned formula.

Classification into ITT or PP populations is conducted prior to the database lock. All listings are provided for the ITT population. A separate listing is included on the set of subjects who are randomized but never take any feeding formula before discontinuing from the study.

Since this study has a primary aim at demonstrating non-inferiority, the PP population will represent the primary analysis population to evaluate the treatment groups in terms of "efficacy". All clinical outcomes (primary and secondary) are subject to analyses using both the PP and ITT population.

Statistical Power and Sample Size Considerations

In phase one, assuming a standard deviation in weight gain of 5.6 g/d (Nelson et al., 1989) and 80% power, 90 subjects per group (180 total) is sufficient to demonstrate non-inferiority (one sided alpha=0.025). Assuming a 25% attrition rate, a total of 256 subjects are enrolled in this trial. Within each formula group, infants are balanced by sex (equal number of males and females in each formula group). At the conclusion of the study, a post-hoc power analysis on weight gain is conducted.

In phase two, the sample size for this study is based on a non-inferiority test comparing weight gain velocity between Brand Formula and FORMULA-102 w/o OPN at Week 16. A non-inferiority margin of 3 g/d is set for the difference in weight gain for the two formula-fed groups (FORMULA-001 w/ OPN and FORMULA-102 w/o OPN).

A blinded interim analysis of 81 subjects who completed 16 weeks of the study was performed in phase one of the study to estimate the standard deviation of weight gain. Based on this analysis, it is assumed that the standard deviation in weight gain is 6.0 g/d. Assuming this standard deviation in weight gain of 6.0 g/d and approximately 90% power, approximately 168 (104 in the Brand Formula group and 64 in the FORMULA-102 w/o OPN group) is sufficient to demonstrate non-inferiority (one-sided alpha=0.025). Assuming a 25% attrition rate, approximately a total of 96 subjects are enrolled in phase two of this trial.

The plan is to use the 129 subjects randomized to Brand Formula in phase one of the study, assuming a 25% attrition rate and 96 subjects meet the Per Protocol population criteria. This data has and will remain blinded through the enrollment of phase two of the study. In phase two of the study infants are randomized to Brand Formula or FORMULA-102 w/o OPN in a 1:8 ratio. Assuming a 25% attrition rate and to obtain approximately 90% power, approximately 10 subjects randomized to Brand Formula and 86 subjects randomized to FORMULA-102 w/o OPN are enrolled in phase two of the study. With the addition of the 129 subjects from phase one of the study, there are approximately a total of 139 subjects enrolled in the Brand Formula group and 86 subjects enrolled in the FORMULA-102 w/o OPN group. Infants are stratified by sex to achieve balance of males and females within each formula group.

Interim Analyses and Data Monitoring

In phase one, an interim analysis is conducted in a blinded manner when 128 infants (50% of the total goal sample size) had enrolled and completed Visit 5. Weight gain velocity (g/d) for all infants were reported descriptively (minimum, maximum, mean, median, standard deviation, first and third quartiles) for the following time intervals: enrollment to Visit 3, enrollment to Visit 5, Visit 3 to Visit 5. The purpose of the interim analysis was to determine whether or not the assumed standard deviation in weight gain velocity (5.6 g/d) based on reference data by Nelson et al., 1989, was appropriate for our study population. No unblinding or inferential statistics are performed at the interim; as such, no alpha spending procedures were required.

An interim analysis will not be performed for phase two of the study.

Subject Identification

Subjects are randomized and assigned a unique subject number. A subject number will never be reassigned or reused for any reason. The Investigator will maintain a master log linking the subject number to the subject's name. The Investigator will follow all applicable privacy laws in order to protect a subject's privacy and confidentiality. Information that could identify a subject is masked on study material.

Randomization

Formula-fed infants are randomly allocated to one of the three study formulas (FORMULA-001 w/OPN, Brand Formula, and FORMULA-102 w/o OPN) via RTSM (Randomization and Trial Supply Management) System. Randomization is blocked by formula group and stratified by infant sex to achieve balance of males and females in each formula group.

Adverse Events

Definitions

An adverse event (AE) is any untoward, undesired, or unplanned event in the form of signs, symptoms, disease, or laboratory or physiologic observations occurring in a person administered an investigational product in a clinical study. The event does not need to be causally related to an investigational product or participation in the clinical study. Any illness that a study subject develops during the study must be recorded on the AE case report form. Whenever possible, an illness should be recorded as a diagnosis rather than a series of symptoms.

Standardized definitions for stooling, spit-up, and crying (agreed upon by the Investigators and Medical Monitor; see Appendix 1F) are used to report such symptoms.

All AEs must be assigned one of the following intensity scores:

Mild: Transient or mild discomfort (<48 hours); no medical intervention/therapy required Moderate: Mild to moderate limitation in activity, some assistance may be needed; no or minimal medical intervention/therapy required Severe: Marked limitation in activity, some assistance usually required; medical intervention/therapy required, hospitalization possible Serious: please see section 19.0.

All AEs must be assigned causality. The site PI or his/her designee will make a determination about the causality or relatedness of an AE to the investigational product (i.e. study formula) using the following categories:

Related: An adverse event (AE) that has a clear temporal association with investigational product administration (e.g., within 24 hours) and there is clear evidence of a causal relationship between the investigational product and the event.

Possibly Related: An AE with a temporal association with the investigational product, but other etiologies are possible. There is a reasonable possibility that the investigational product caused the event.

Unlikely Related: An AE with a temporal association with the investigational product, but other etiologies are more likely. Relatedness to the investigational product cannot definitely be ruled out, but there is less probability that the investigational product caused the event.

Not Related: An AE with no temporal association with the investigational product or one clearly related to other etiologies such as concomitant medications or conditions, or the subject's known clinical state.

As a guideline for determining if an adverse event is related to the investigational product (investigational product related), the following questions should be considered:

Does a reasonable causal relationship exist between the AE and the investigational product based on clinical judgment and knowledge of the treatment?

Is there a temporal relationship between the investigational product and the appearance of the AE?

Is there biologic plausibility for a relationship between the AE and the investigational product?

Does the subject have an underlying medical condition or is the subject taking concomitant therapies or medications that could contribute to the AE?

Where applicable, does the AE abate on discontinuation of the investigational product (dechallenge)?

Where applicable, does the AE reappear on repeat exposure to the investigational product (rechallenge)?

A protocol-related adverse event is an AE occurring during a clinical study that is not related to the investigational product, but is considered by the Investigator or the Medical Monitor (or designee) to be related to the research conditions, (i.e., related to the fact that a subject is participating in the study).

Serious Adverse Events

A serious adverse event (SAE) is defined as an AE that:
Results in Death

Is life-threatening, i.e., the subject was, in the opinion of the Investigator, at immediate risk of death from the event as it occurred (it does not include an event that, had it occurred in a more severe form, might have caused death)

Results in a significant, persistent or permanent change, impairment, damage, or disruption in the subject's body function/structure, physical activities, and/or quality of life Requires in-subject hospitalization or prolongs hospitalization Is another medically significant event that, based upon appropriate medical judgment, may jeopardize the subject and may require medical or surgical intervention to prevent one of the outcomes listed above (e.g., allergic bronchospasm requiring intensive treatment in an emergency department or home, blood dyscrasias, or convulsions that do not result in hospitalization, or the development of drug dependency or drug abuse)

Adverse Event and Serious Adverse Event Recording and Reporting

Determination of AEs should be based on the signs or symptoms detected during the physical examination and on clinical evaluation of the subject. Adverse events (AEs) are coded using the Medical Dictionary for Drug Regulatory Affairs (MedDRA).

AEs and SAEs are collected from the signing of the informed consent form to the end of study visit 9. The Investigator will instruct the subject to report AEs and SAEs during this time period.

During the time period specified above, the Investigator will:

Record all AEs and SAEs in the subject's medical record.

Record all AEs, SAEs, and the treatment of the AE/SAE on a case report form.

Report all SAEs to the Study Sponsor as directed and to the IRB as appropriate.

An AE/SAE's causal relationship to the product has no bearing on its reportability. The Investigator must follow up on all AEs and SAEs until the events have subsided, until values have returned to baseline, or, in case of permanent impairment, until the condition has stabilized to a level acceptable to the Sponsor/Investigator.

All SAEs and follow-up information must be reported to the Study Sponsor and clinical research organization (CRO) Medical Monitor within 24 hours after learning of the event and per instructions as included in the Investigator Site File.

A listing of AEs and SAEs by subject is provided in the clinical study report (CSR).

Subject Discontinuation or Withdrawal

A study subject may withdraw or discontinue the study at any time and for any reason. Reasons why a subject may discontinue or be withdrawn from the study include, but are not limited to, AE, parent(s)/guardian(s) request, investigator request, etc. When a subject discontinues or is withdrawn from the study, the Investigator will complete all procedures designated for Visit 9 and notify the Sponsor.

APPENDIX 1A: ANTHROPOMETRY DATA COLLECTION PROCEDURES

All sites are trained on standardized techniques for the measure of weight, length, and head circumference (Lohman, 1988).

Weight

Two people are involved with infant weight measures. One measurer will weigh the infant and read the weight as it is obtained. The other measurer will immediately note the measurement in the infant's chart.

The infant's clothing and diaper are removed. The infant should be positioned in the center of the scale tray. Infants should be weighed to the nearest 10 grams on a calibrated scale. Record the weight as soon as it is completed. Then the infant should be re-positioned and the weight measurement repeated and noted in writing. After the infant is removed from the scale tray, the weights should be compared, and they should agree within 10 grams. If the difference between the weights exceeds the tolerance limit of 10 grams, the infant should be re-positioned and reweighed a third time. The two weights that are within 10 grams of one another should be recorded. If there are NOT two weights within 10 grams of one another, instrument error may be influencing the measure; the Investigator should calibrate the scale, check the position of the scale and infant, etc. and then re-weigh the infant.

Summary

Remove infant's clothing and diaper
Center infant on the scale tray
Weigh infant to nearest 10 grams
Write the weight on the infant's chart
Reposition and repeat weighing infant
Compare weights
Weight should agree within 10 grams (tolerance of the measure)

Length

Length is measured in the recumbent position with a calibrated lengthboard. The lengthboard must have 1) a fixed headpiece and 2) a moveable foot piece, which is perpendicular to the surface of the table that the length board is on.

Length measurements for infants should be obtained while the infant is dressed in light underclothing or a diaper. The infant's shoes must be removed. Hair ornaments should be removed from the top of the head.

The infant should be placed on his/her back in the center of the lengthboard so that the infant is lying straight and his/her shoulders and buttocks are flat against the measuring surface. The infant's eyes should be looking straight up. Both legs should be fully extended and the toes should be pointing upward with feet flat against the foot piece.

Two people must be involved with infant length measures. One measurer holds the infant's head, with the infant looking vertically upward and the crown of the head in contact with the headpiece in the Frankfort Horizontal Plane. The head of the infant is firmly but gently held in position. The measurer gently cups the infant's ears while holding the head in proper alignment. Make sure the infant's chin is not tucked in against his chest or stretched too far back.

While one measurer holds the infant's head in the proper position, the second measurer aligns the infant's trunk and legs, extends both legs, and brings the footpiece firmly against the heels. The measurer places one hand gently but firmly on the infant's knees to maintain full extension of the legs. The infant's toes are pointing upward with the soles of the feet perpendicular to the horizontal backpiece of the measuring device. It is imperative that both legs are fully extended for an accurate and reproducible length measurement.

The measurer at the feet should read aloud to the recorder the length measurement to the nearest cm. The length should be recorded on the data form as soon as it is completed. Then the infant should be repositioned and the length measurement repeated and noted in writing. After the infant is removed from the lengthboard, the length measurements should be compared and they should agree within 0.5 cm.

If the difference between the two length measures exceeds 0.5 cm, the infant should be repositioned and remeasured a third time. The third measure of length should be within 0.5 cm of either the first or second length measure; and the two measures within 0.5 cm should be recorded. If there are NOT two measures of length within 0.5 cm of one another, instrument error may be influencing the infantometer; the Investigator should calibrate the infantometer, re-position the infant and re-measure the infant. The two measures that are within 0.5 cm of one another should be recorded.

SUMMARY

Use a calibrated lengthboard with a fixed headpiece and movable footpiece which is perpendicular to the surface of the table
Measure infant without shoes and wearing light underclothing or diaper
Measure length to 0.1 cm
Record measurement on chart
Reposition and remeasure infant
Measurements should agree to 0.5 cm Head Circumference The goal of the head circumference measure is to locate the maximum circumference of the head. Head circumference or OFC (occipital frontal circumference) is measured over the most prominent part on the back of the head (occiput) and just above the eyebrows (supraorbital ridges), i.e. the largest circumference of the head. Any braids, barrettes, or other hair decorations that will interfere with the measurement should be removed. The infant may be held in the arms or on the lap of the parent/guardian if they prefer.

The tape is positioned across the frontal bones just above the eyebrows, above the ears, and around the biggest part of the back of the head (the occiput). The goal is to locate the maximum tissues. The measurement is read to the nearest 0.1 cm and recorded on the chart. The tape should be repositioned and the head circumference re-measured. The measures should agree within 0.2 cm. If the difference between the measures exceeds 0.2 cm, the infant should be repositioned and re-measured a third time. The two measures that are within 0.2 cm of one another should be recorded.

Summary

Use a flexible, non-stretchable tape
The goal is to locate the maximum circumference of the head
Position the tape just above the eyebrows on the supra-orbital ridge, above the ears, and around the biggest part on the back of the head (the occiput)
Pull tape snugly to compress the hair
Read the measurement to the nearest 0.1 cm
Write measurement on the chart
Reposition tape and re-measure the head circumference
Measures should agree within 0.2 cm

APPENDIX 1B: FORMULA COMPOSITION

|  | Enfamil Infant 0-12 months (Brand Formula) | Building Block Nutritionals (FORMULA-001 w/OPN) | Building Block Nutritionals (FORMULA-102 w/o OPN) |
|---|---|---|---|
| Nutrients/100 calories |  |  |  |
| Protein, g | 2 | 2.2 | 2.5 |
| Fat, g | 5.3 | 5.4 | 5.1 |
| OPO Sn-2 oil | * | 0.7 | 0.7 |
| Carbohydrate, g | 11.3 | 10.7 | 10.5 |
| Dietary Fiber, mg | ** | 130.2 | 330 |
| Galactoligosaccharide, mg | * | 29.5 | 300 |
| Polydextrose, mg | ** | 30 | * |
| Fructoligosaccharide, mg | * | 70.7 | 30 |
| Linoleic Acid, mg | 780 | 850 | 850 |
| Vitamins: |  |  |  |
| Vitamin A, IU | 300 | 300 | 300 |
| Vitamin D, IU | 60 | 60 | 60 |
| Vitamin E, IU | 2 | 2 | 2 |
| Vitamin K, mcg | 9 | 9 | 9 |
| Vitamin B1, mcg | 80 | 80 | 80 |
| Vitamin B2, mcg | 140 | 140 | 140 |
| Vitamin B3, mcg | 1000 | 1000 | 1000 |
| Vitamin B6, mcg | 60 | 60 | 60 |
| Vitamin B12, mcg | 0.3 | 0.3 | 0.3 |
| Folic acid, mcg | 16 | 16 | 16 |
| Pantothenic Acid, mcg | 500 | 600 | 600 |
| Biotin, mcg | 3 | 3 | 3 |
| Vitamin C, mg | 12 | 12 | 12 |
| Minerals: |  |  |  |
| Calcium, mg | 78 | 78 | 78 |
| Phosphorus, mg | 43 | 43 | 43 |
| Magnesium, mg | 8 | 8 | 8 |
| Iron, mg | 1.8 | 1.8 | 1.8 |
| Zinc, mg | 1 | 1.0 | 1 |
| Manganese, mcg | 15 | 15 | 15 |
| Copper, mg | 75 | 75 | 75 |
| Iodine, mcg | 15 | 10 | 15 |
| Sodium, mg | 27 | 27 | 27 |
| Potassium, mg | 108 | 108 | 108 |
| Chloride, mg | 63 | 63 | 63 |
| Selenium, mcg | 2.8 | 2.8 | 2.8 |
| Other: |  |  |  |
| Choline, mg | 24 | 24 | 24 |
| Inositol, mg | 6 | 6 | 6 |
| B-carotene, mcg | * | 19 | 19 |
| Lutein, mcg | * | 18 | 10 |
| Nucleotides, mg | ** | 3.9 | 4 |
| L-Carnitine, mg | ** | 1.4 | 1.3 |
| Taurine, mg | ** | 5.8 | 6 |
| Lactoferrin, mg | * | 18 | 9 |
| Docosahexaenoic acid (DHA) mg | ** | 7.8 | 9.6 |
| Arachidonic acid (ARA) mg | ** | 9.7 | 19 |

Data from Enfamil™ Can Label Lot Number: ZP9L4H Expiration: 1 Jun. 2021
*Not Added to Formula
**Nutritional Information not available

APPENDIX 1C: FORMULA INGREDIENTS

Brand Formula
Nonfat Milk, Lactose, Vegetable Oil (Palm Olein, Coconut, Soy and High Oleic Sunflower Oils), Whey protein concentrate and and less than 2%: Galactoligosaccharides*, Polydextrose*, *Mortierella alpina* Oil, *Schizochytrium* Sp. Oil, Calcium Carbonate, Calcium Phosphate, Potassium citrate, Ferrous sulfate, Potassium chloride, Magnesium oxide, Sodium chloride, Zinc sulfate, Cupric Sulfate, Manganese sulfate, Potassium Iodide, Sodium Selenite, Soy lecithin, Choline chloride, Ascorbic acid, Niacinamide, Calcium Pantothenate, Vitamin A palmitate, Vitamin B12, Vitamin D3, Riboflavin, Thiamin Hydrochloride, Vitamin B6 Hydrochloride, Folic acid, Vitamin K1, Biotin, Inositol, Vitamin E acetate, Taurine and L-Carnitine.

*A Type of Prebiotic
**A Source of Arachidonic acid (ARA)
**A Source of Docosahexaenoic acid (DHA)

Formula-001 w/ OPN
Nonfat Milk, Lactose, Vegetable Oil (OPO Sn-2 Oil, Coconut, Soy and High Oleic Sunflower Oils), Demineralized Whey, Whey protein concentrate, Alpha lactlbumin, and less than 1% Polydextrose*, Galactoligosaccharides*, Fructooligosaccharides*, *Mortierella alpina* Oil Powder** *Crypthecodinium Cohnii* Oil Powder** Calcium Carbonate, Dicalcium Phosphate, Potassium citrate, Ferrous sulfate, Potassium chloride, Potassium Iodide, Magnesium chloride, DiMagnesium phosphate, Sodium citrate, Zinc sulfate, Copper Sulfate, Manganese sulfate, Sodium Selenite, Soy lecithin, L-Choline bitartrate, Ascorbic acid, Niacinamide, Calcium Pantothenate, Vitmin A palmitate, Vitamin B12, Vitamin D3, Riboflavin, Thiamin Hydrochloride, Vitamin B6 Hydrochloride, Folic acid, Vitamin K1, Biotin, Inositol, Vitamin E acetate, Nucleotides (Cytidine 5'-monophosphate, Disodium Uridine 5'-monophosphate, Adenosine 5'-monophosphate, Disodium Guanosine 5'-monophosphate), Beta carotene, Lutein, Osteopontin, Lactoferrin, Taurine and L-Carnitine

*A Type of Prebiotic
**A Source of Arachidonic acid (ARA)
**A Source of Docosahexaenoic acid (DHA)

Formula-102 w/o OPN

Nonfat Milk, Lactose, Vegetable Oil (OPO Sn-2 Oil, Coconut, Soy and High Oleic Sunflower Oils), Demineralized Whey, Whey protein concentrate, Alpha lactlbumin, and less than 1%; Galactoligosaccharides*, Fructooligosaccharides*, *Mortierella alpina***, *Crypthecodinium Cohnii**** Calcium Carbonate, Calcium Phosphate, Potassium citrate, Ferrous sulfate, Potassium chloride, Potassium Iodide, Magnesium chloride, Magnesium phosphate, Sodium citrate, Zinc sulfate, Copper Sulfate, Manganese sulfate, Sodium Selenite, Soy lecithin, Choline bitartrate, Ascorbic acid, Niacinamide, Calcium Pantothenate, Vitamin A palmitate, Vitamin B12, Vitamin D3, Riboflavin, Thiamin Hydrochloride, Vitamin B6 Hydrochloride, Folic acid, Vitamin K1, Biotin, Inositol, Vitamin E acetate, Maltodextrin, Nucleotides (Cytidine 5'-monophosphate, Disodium Uridine 5'-monophosphate, Adenosine 5'-monophosphate, Disodium Guanosine 5'-monophosphate), Beta carotene, Lutein, Lactoferrin, Taurine and L-Carnitine

*A Type of Prebiotic
**A Source of Arachidonic acid (ARA)
***A Source of Docosahexaenoic acid (DHA)

APPENDIX 1F: STANDARDIZED DEFINITIONS FOR COMMON ADVERSE EVENTS

These AEs may or may not be related to formula tolerance (stooling, spit-up, crying, skin issues).

All AEs must be assigned an intensity score and causality (related or not related to the investigational product; see section 18.1 for details).

| ADVERSE EVENT | DEFINITION |
|---|---|
| Stooling Issues | |
| Difficulty having bowel movement | Crying, fussing, or turning red when having a bowel movement |
| Hard stools | Healthcare professional diagnosis; pellet or hard rock-like stools |
| Constipation | Less than 3 bowel movements in 7 days |
| Acute diarrhea | Runny or watery stools for less than 2 weeks |
| Chronic diarrhea | Runny or watery stools for more than 2 weeks or 3 separate episodes of acute diarrhea in 2 weeks |
| Spit-up, Vomiting, GERD issues | |
| Regurgitation | Milk comes up into mouth but never out of mouth AND infant DOES NOT: arch his/her back as if in pain, stop drinking even if hungry, or cry, wheeze, or cough related to feedings |
| Infantile spit up | Milk comes out of the mouth after feeding (typically non-forceful), and the amount that comes out is less than half of the feeding volume; non- projectile |
| Vomiting | Milk comes out of the mouth after feeding (typically forceful), and the amount that comes out is more than half of the feeding volume |
| Gastroesophageal Reflux Disease (GERD) | Baby arches his/her back as if in pain, stops drinking even if hungry, or cries, wheezes or coughs related to feedings (with or without milk coming up into mouth) |
| Crying issues | |
| Crying/Neonatal abnormal crying | Infant cries for 3 or more hours per day |
| Infantile colic/Infant colic | Infant cries inconsolably for 3 or more hours per day, at least 3 days per week, AND for at least 3 weeks |
| Skin issues | |
| Diaper rash | Contact/irritant dermatitis in the diaper area, with erythema and/or skin breakdown on the exposed convex skin surface (rate as Mild, Moderate, Severe using definitions outlined below) Mild: Baby has an area of pinkness in the diaper area Moderate: Baby has definite pinkness in a large area with some small areas of definite redness Severe: Baby has intense redness over a large area of the perianal region, or any area of redness with skin breakdown in the diaper area |
| Atopic dermatitis/Eczema | Any new skin lesions, not in the diaper area. Score for any erythema, edema/papulation, and/or excoriation on scale from 0-3 each (9 points max). For each item, 0 = none, 1 = mild, 2 = moderate, 3 = severe. Mild: 1 or 2 points Moderate: 3 to 5 points Severe: 6 to 9 points |

APPENDIX 1G: EXEMPLARY FORMULA PREPARATION INSTRUCTIONS

This formula preparation instruction is appropriate for all Study Infant Formulas.

Proper hygiene, study formula preparation, dilution, use and storage are important to the well-being of your baby.

Ask your baby's doctor about the need to use cooled, boiled water when preparing the study formula and whether you need to boil utensils, bottles, nipples and rings in water before each use. If you are concerned about lead or other harmful substances in your water, talk to your healthcare professional before making study formula with tap water.

How to Mix Formula-001 Study Infant Formulas:

For proper mixing, follow these steps:
1. Wash your hands thoroughly with soap and warm water.
2. Following the measurement guidelines below, add the appropriate amount of water and scoops of study formula powder to the bottle:

| Measure water | Add scoop(s) of unpacked level powder using enclosed scoop | Finished bottle (approx.) |
|---|---|---|
| 2 fl oz | 1 scoop | 2 fl oz |
| 4 fl oz | 2 scoops | 4 fl oz |
| 6 fl oz | 3 scoops | 6 fl oz |
| 8 fl oz | 4 scoops | 8 fl oz |

3. Put the cap on the bottle and shake.
4. Feed prepared study formula immediately (within 2 hours of preparation) or cover and store in the refrigerator for no longer than 24 hours.

Expected Results

Administration of the nutritional formulas (e.g., prepared via Examples 1, 1A, 1B, 2-1, 2-2, 2-3, 3) is expected to show one or more of the following advantages, as compared to prior infant formulas: a) Increased weight gain (grams/day) over 16 weeks of administration; b) Increased volume of infant formula intake (amount) over time; c) Increased infant growth: increased anthropometric measurements (head circumference gain velocity, length gain velocity) and Z-scores (weight for age, length for age, weight for length for age, head circumference for age); d) Reduced markers of inflammation (tumor necrosis factor-alpha, interleukin 2, 4, 5, 6, 8, 10, 12, 13, & 17; interleukin 2 receptor, interleukin 1 beta, and interferon gamma); e) Improved gastrointestinal tolerance (improved digestion, stool composition, bowel movements, stool consistency, gas, reduced fussiness, supported development of flora in GI tract); f) Decreased adverse events; g) improved calcium absorption, improved immunity, improved bone strength, healthy gut microbiome, better sleep; h) supported development of brain, eye, and/or heart.

REFERENCES

1. National Research Council. (2011). *Guide for the Care and Use of Laboratory Animals* (8$^{th}$ ed.). Washington, D C: The National Academies Press.
2. Benevenga, N. J., Gahl, M. J., Crenshaw, T. D., & Finke, M. D. (1994). Protein and Amino Acid Requirements for Maintenance and Amino Acid Requirements for Growth of Laboratory Rats. *The Journal of Nutrition*, 124(3), 451-453. https://doi.org/10.1093/jn/124.3.451.
3. Boye, J., Wijesinha-Bettoni, R., & Burlingame, B. (2012). Protein quality evaluation twenty years after the introduction of the protein digestibility corrected amino acid score method. *British Journal of Nutrition*, 108(SUPPL. 2). https://doi.org/10.1017/S0007114512002309.
4. Finke, M. D., DeFoliart, G. R., & Benevenga, N. J. (1987). Use of simultaneous curve fitting and a four-parameter logistic model to evaluate the nutritional quality of protein sources at growth rates of rats from maintenance to maximum gain. *Journal of Nutrition*, 117(10), 1681-1688. https://doi.org/10.1093/jn/117.10.1681.
5. Gahl, M. J., Finke, M. D., Crenshaw, T. D., & Benevenga, N. J. (1991). Use of a four-parameter logistic equation to evaluate the response of growing rats to ten levels of each indispensable amino acid. *Journal of Nutrition*, 121(11), 1720-1729. https://doi.org/10.1093/jn/121.11.1720.
6. Innis, S. M. (2011). Dietary Triacylglycerol Structure and Its Role in Infant Nutrition. *Advances in Nutrition*, 2(3), 275-283. https://doi.org/10.3945/an.111.000448.
7. Lien, E. L. (1994). The role of fatty acid composition and positional distribution in fat absorption in infants. *The Journal of Pediatrics*, 125(5 PART 2). https://doi.org/10.1016/S0022-3476(06)$_{80738}$-9.
8. Lien, E. L., Boyle, F. G., Yuhas, R., Tomarelli, R. M., & Quinlan, P. (1997). The effect of triglyceride positional distribution on fatty acid absorption in rats. *Journal of Pediatric Gastroenterology and Nutrition*, 25(2).
9. Mercer, L. P., May, H. E., & Dodds, S. J. (1989). The Determination of Nutritional Requirements in Rats: Mathematical Modeling of Sigmoidal, Inhibited Nutrient-Response Curves. *The Journal of Nutrition*, 119(10), 1465-1471. https://doi.org/10.1093/jn/119.10.1465.
10. Mitchell, G. V., & Jenkins, M. Y. (1985). Assessment of protein quality methodology for infant formulas. *Journal of the Association of Official Analytical Chemists*, 68(4), 680-683.
11. Mitchell, Geraldine V., Jenkins, M. Y., & Grundel, E. (1989). Protein efficiency ratios and net protein ratios of selected protein foods. *Plant Foods for Human Nutrition*, 39(1), 53-58. https://doi.org/10.1007/BF01092401.
12. NRC. (1995). Nutrient Requirements of Laboratory Animals: Fourth Revised Edition. Retrieved from National Research Council website: https://www.ncbi.nlm.nih.gov/books/NBK231925/.
13. Osborne, T., Mendel, L., Perry, E. (1919). A method of expressing numerically the growth promoting value of proteins. *Journal of Biol Chem*, 37, 223-229.
14. Shannon, B. M., Howe, J. M., & Clark, H. E. (1972). Interrelationships between Dietary Methionine and Cystine as Reflected by Growth, Certain Hepatic Enzymes and Liver Composition of Weanling Rats. *The Journal of Nutrition*, 102(4), 557-562. https://doi.org/10.1093/jn/102.4.557.
15. Tadesse, K. (1990). The effect of continued feeding of physiological amounts of lactose on the level of intestinal lactase and other disaccharidase enzyme activities in the rat. *Experimental Physiology*, 75, 231-238.
16. Van de Heijning, B. J. M., Kegler, D., Schipper, L., Voogd, E., Oosting, A., & van der Beek, E. M. (2015). Acute and chronic effects of dietary lactose in adult rats are not explained by residual intestinal lactase activity. *Nutrients*, 7(7), 5542-5555. https://doi.org/10.3390/nu7075237.
17. Agostoni C, Trojan S, Bellú R, Riva E, Giovannini M. Neurodevelopmental quotient of healthy term infants at 4 months and feeding practice: the role of long-chain polyunsaturated fatty acids. *Pediatr Res*. 1995; 38(2):262-266.

18. Auestad N, Montalto M B, Hall R T, et al. Visual acuity, erythrocyte fatty acid composition, and growth in term infants fed formulas with long chain polyunsaturated fatty acids for one year.
19. Ross Pediatric Lipid Study. Pediatr Res. 1997; 41(1):1-10.
20. Ballard 0 and Morrow, A. Human mik composition: Nutrient and bioactive factors. Pediatr Clin North Am. 2013; 60(1):49-74.
21. Birch E E, Garfield S, Hoffman D R, Uauy R, Birch D G. A randomized controlled trial of early dietary supply of long-chain polyunsaturated fatty acids and mental development in term infants. Dev Med Child Neurol. 2000; 42(3):174-181.
22. Bode L. Human milk oligosaccharides: every baby needs a sugar mama. Glycobiology 2012; 22:1147-62.
23. Brenna J T, Varamini B, Jensen R G, Diersen-Schade D A, Boettcher J A, Arterburn L M. Docosahexaenoic and arachidonic acid concentrations in human breast milk worldwide. *Am J Clin Nutr.* 2007; 85(6):1457-64.
24. Brodbeck U, Denton W L, Tanahashi N, Ebner K E. The isolation and identification of the B protein of lactose synthetase as alpha-lactalbumin. *J Biol Chem.* 1967; 242: 1391-1397.
25. Canfield L M, Clandinin M T, Davies D P, Fernandez M C, Jackson J, Hawkes J, Goldman W J, Pramuk K, Reyes H, Sablan B, Sonobe T, Bo X. Multinational study of major breast milk carotenoids of healthy mothers. *Eur J Nutr.* 2003; 42(3):133-41.
26. Capeding R, Gepanayao C P, Calimon N, Lebumfacil J, Davis A M, Stouffer N, Harris B J. Lutein-fortified infant formula fed to healthy term infants: evaluation of growth effects and safety. Nutr J. 2010; 21; 9:22.
27. Cheng J B, Wang J Q, Bu D P, Liu G L, Zhang C G, Wei H Y, et al. Factors affecting the lactoferrin concentration in bovine milk. J Dairy Sci. 2008; 91(3):970-6.
28. Clandinin M, Chappell J, Leong S. Intrauterine fatty acid accretion rates in human brain: implication for fatty acid requirements. Early Hum Dev. 1980; 4:121-130.
29. Clandinin M, Chappell J, Leong S. Extrauterine fatty acid accretion rates in human brain: implication for fatty acid requirements. Early Hum Dev. 1980; 4:131-138.
30. Coppa G V, Pierani P, Zampini L, Carloni I, Carlucci A, Gabrielli O. Oligosaccharides in human milk during different phases of lactation. Acta Paediatr. 1999; 88(430): 589-594.
31. Davidson B, Meinzen-Derr J K, Wagner C L, Newburg D S, Morrow A L. Fucosylated oligosaccharides in human milk in relation to gestational age and stage of lactation. Adv Exp Med Biol. 2004; 5540:427-30.
32. DHHS. (2000a, May 11, 2004). Growth chart training module. Accurately Weighing and Measuring Infants, Children and Adolescents: Technique. Health Resources and Services Agency, Maternal and Child Health Bureau. Retrieved Feb. 3, 2017, from the World Wide Web: http://www.cdc.govinccdphp/dnpa/growthcharts/training/modules/modules.htm
33. Dupont C, Rivero M, Grillon C, Belaroussi N, Kalindjian A, Marin V. Eur J Clin Nutr. 2010 July; 64(7): 765-7.
34. Fleisler S, Anderson R E. Chemistry and metabolism of lipids in the vertebrate retina. Prog Lipid Res. 1983; 22:79-131.
35. Innis SM1, Dyer R, Nelson C M. Evidence that palmitic acid is absorbed as sn-2 monacylglycerol from human milk by breast-fed infants. Lipids. 1994; 29(8):541-5.
36. Jackson J G, Janszen D B, Lonnerdal B, Lien E L, Pramuk K P, Kuhlman C F. A multinational study of alpha-lactalbumin concentration in human milk. J Nutr Biochem. 2004; 15: 517-521.
37. Johnston W H, Ashley C, Yeiser M, Harris C L, Stolz S I, Wampler J L, Wittke A, and Cooper T A. Growth and tolerance of formula with lactoferrin in infants through one year of age: double-blind, randomized, controlled trial. BMC Pediatr. 2015; 15: 173.
38. Kennedy K I, Fewtrell M S, Morley R, Abbott R, Quinlan P T, Wells J C, Bindels J G, Lucas A. Double-blind, randomized trial of a synthetic triacylglycerol in formula-fed term infants: effect on stool biochemistry, stool characteristics, and bone mineralization. Am J Clin Nutr. 1999 November; 70(5):920-7.
39. King J, Cummings G, Guo N, Trivedi L, Readmond B, Keane V, et al. A double-blind, placebo-controlled, pilot study of bovine lactoferrin supplementation in bottle-fed infants. J Pediatr Gastroentrol Nutr. 2007; 44:245-51.
40. Krinsky N I, Johnson E J. Carotenoid actions and their relation to health and disease. Mol Aspects Med. 2005; 26(6):459-516.
41. Landrum J T, Bone R A. Lutein, zeaxanthin, and the macular pigment. Arch Biochem Biophys. 2001.1; 385 (1):28-40.
42. Lien E L. The role of fatty acid composition and positional distribution in fat absorption in infants. J Pediatr. 1994; 125:S62-8.
43. Lien E L, Davis A M, and Multicenter group. Growth and Safety of a reduced protein formula enriched with bovine alpha-lactalbumin in term infants. 2004; J Pediatr Gastroenterol Nutr. 170-176.
44. Litmanovitz I, Bar-Yoseph F, Lifshitz Y, Davidson K, Eliakim A, Regev R H, Nemet D. Reduced crying in term infants fed high beta-palmitate formula: a double-blind randomized clinical trial. BMC Pediatr. 2014 Jun. 19; 14:152.
45. Lohman T, Roche A F, Martorell R. Anthropometric standardization reference manual. Champaign, Ill.: Human Kinetics Books; 1988.
46. Lonnerdal B. Digestibility and absorption of protein in infants. In: Protein Metabolism During Infancy, ed. Raiha NCR. Vevey: Raven Press. 1994; 53-65.
47. Lonnerdal B. Infant formula and infant nutrition: bioactive proteins of human milk and implications for composition of infant formulas. Am J Clin Nutr. 2014; 99(3): 7125-75.
48. Makrides M, Neumann M A, Simmer K, Gibson R A. A critical appraisal of the role of dietary long-chain poly-unsaturated fatty acids on neural indices of term infants: a randomized, controlled trial. Pediatrics. 2000; 105(1 pt 1):32-38.
49. Manzoni P, Stolfi I, Messner H, Cattani S, Laforgia N, Romeo M G, Bollani L, Rinaldi M, Gallo E, Quercia M, Maule M, Mostert M, Decembrino L, Magaldi R, Mosca F, Vagnarelli F, Memo L, Betta P M, Stronati M, Farina D, Italian Task Force for the Study and Prevention of Neo-natal Fungal Infections—the Italian Society of Neonatology. Bovine lactoferrin prevents invasive fungal infections in very low birth weight infants: a randomized controlled trial. Pediatrics. 2012 January; 129(1):116-23.
50. Moro G, Minoli I, Mosca M, Fanaro S, Jelinek J, Stahl B, Boehm G. Dose-related bifidogenic effects of galacto- and fructo-oligosaccharides in formula-fed term infants. J Pediatr Gastroenterol Nutr. 2002 March; 34(3):291-5.

51. Nelson S E, Rogers R R, Ziegler E E, Fomon S J: Gain in weight and length during early infancy. Early Human Development. 1989; 19 (4):223-239.
52. Neuringer M, Connor W, Lin D, Barstad L, Luck S. Biochemical and functional effects of prenatal and postnatal ω-3 fatty acid deficiency on retina and brain in rhesus monkeys. Proc Natl Acad Sci. 1989; 83:285-294.
53. Ochoa T J, Cleary T G. Effect of lactoferrin on enteric pathogens. Biochimie. 2009; 91(1):30-34.
54. O'Connor D L, Hall R, Adamkin D, et al. Ross Preterm Lipid Study Growth and development in preterm infants fed long-chain polyunsaturated fatty acids: a prospective, randomized controlled trial. Pediatrics. 2001; 108(2):359-371
55. Roberfroid M. Prebiotics: the concept revisited. J Nutr. 2007; 137(3 Suppl 2):8305-8375.
56. Scalabrin D M, Mitmesser S H, Welling G W, Harris C L, Marunycz J D, Walker D C, Bos N A, Tölkkö S, Salminen S, Vanderhoof J A. New prebiotic blend of polydextrose and galacto-oligosaccharides has bifidogenic effect in young infants. J Pediatr Gastroenterol Nutr. 2012; 54(3):343-52.
57. Schack L, Lange A, Kelsen J, Agnholt J, Christensen B, Petersen T E, et al. Considerable variation in the concentration of osteopontin in human milk, bovine milk, and infant formulas Journal of Dairy Science. 2009; 92:5378-5385.
58. Smilowitz J T, Lebrilla C B, Mills D A, German J B, Freeman S L. Breast milk oligosaccharides: structure-function relationships in the neonate. Ann Rev Nutr. 2014; 34: 143-169.
59. Trabulsi J, Capeding R, Lebumfacil J, Ramanujam K, Feng P, McSweeney S, Harris B, DeRusso
60. P. Effect of an α-lactalbumin-enriched infant formula with lower protein on growth. Eur J Clin Nutr. 2011; 65(2):167-74.
61. Yao M, Lien E L, Capeding MRZ, Fitzgerald M, Ramanujam K, Yuhas R, Northington R, Lebumfacil J, Wang L, DeRusso P A. Effects of term infant formulas containing high sn-2 palmitate with and without oligofructose on stool composition, stool characteristics, and bifidogenicity. J Pediatr Gastroenterol Nutr. 2014; 59(4): 440-448.
62. Ziegler E I, Vanderhoof J A, Petschow B, Mitmesser S H, Stolz S I, Harris C L, Berseth C L. Term infants fed formula supplemented with selected blends of prebiotic grow normally and have soft stools similar to those reported in breast-fed infants. J Pediatr Gastroenterol Nutr. 2007 March; 44(3):359-64.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention and/or present disclosure includes embodiments in which exactly one member of the group is present in, employed in, or otherwise relevant to a given product or process. The invention and/or present disclosure includes embodiments in which more than one, or all of the group members are present in, employed in, or otherwise relevant to a given product or process.

Furthermore, the invention and/or present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention and/or present disclosure, or aspects of the invention and/or present disclosure, is/are referred to as comprising particular elements and/or features, certain embodiments of the invention and/or present disclosure or aspects of the invention and/or present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention and/or present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention and/or present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention and/or present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention and/or present disclosure, as defined in the following claims.

What is claimed is:

1. A reconstituted, ready-to-use nutritional formula comprising:
   a) approximately 0.25 grams to approximately 5.0 grams of alpha-lactalbumin enriched whey protein concentrate per L of reconstituted, ready-to-use nutritional formula, wherein the reconstituted, ready-to-use nutritional formula comprises at least 30% alpha-lactalbumin by weight of the alpha-lactalbumin enriched whey protein concentrate;
   b) approximately 0.02 grams to approximately 1.0 grams of lactoferrin per L of reconstituted, ready-to-use nutritional formula;

c) approximately 1.0 grams to approximately 14.0 grams of oleic acid-palmitic acid-oleic acid triglyceride (OPO triglyceride) per L of reconstituted, ready-to-use nutritional formula, wherein palmitic acid is at the SN-2 position of the glycerol backbone of the OPO triglyceride;

d) approximately 35 grams to approximately 80 grams of lactose per L of the reconstituted, ready-to-use nutritional formula;

e) approximately 60 micrograms to approximately 0.05 grams of lutein per L of the reconstituted, ready-to-use nutritional formula;

f) docosahexanoic acid;

g) approximately 0.1 grams to approximately 1.0 grams of arachidonic acid per L of the reconstituted, ready-to-use nutritional formula;

h) approximately 2.0 grams to approximately 5.0 grams of galactooligosaccharides per L of the reconstituted, ready-to-use nutritional formula; and i) approximately 0.1 grams to approximately 0.5 grams of fructooligosaccharides per L of the reconstituted, ready-to-use nutritional formula;

wherein the reconstituted, ready-to-use nutritional formula does not comprise polydextrose.

2. The reconstituted, ready-to-use nutritional formula of claim 1 further comprising linoleic acid.

3. The reconstituted, ready-to-use nutritional formula of claim 1 further comprising alpha-linolenic acid.

4. The reconstituted, ready-to-use nutritional formula of claim 1 further comprising vitamins, minerals, nucleotides, or a combination thereof.

5. The reconstituted, ready-to-use nutritional formula of claim 1 further comprising L-choline bitartrate, L-carnitine, or a combination thereof.

6. The reconstituted, ready-to-use nutritional formula of claim 1 further comprising soya lecithin.

7. The reconstituted, ready-to-use nutritional formula of claim 1 further comprising beta-carotene, taurine, or a combination thereof.

8. The reconstituted, ready-to-use nutritional formula of claim 4, wherein the nucleotides are selected from the group consisting of adenosine 5'-monophosphate, cytidine 5'-monophosphate, guanosine 5'-monophosphate, uridine 5'-monophosphate, or a combination thereof.

9. The reconstituted, ready-to-use nutritional formula of claim 1, wherein the reconstituted, ready-to-use nutritional formula comprises approximately 0.5 grams to approximately 4.2 grams of alpha-lactalbumin enriched whey protein concentrate per L of reconstituted, ready-to-use nutritional formula.

10. The reconstituted, ready-to-use nutritional formula of claim 1, wherein the reconstituted, ready-to-use nutritional formula comprises approximately 0.02 grams to approximately 0.10 grams of lactoferrin per L of reconstituted, ready-to-use nutritional formula.

11. The reconstituted, ready-to-use nutritional formula of claim 1, wherein the reconstituted, ready-to-use nutritional formula comprises approximately 3.0 grams to approximately 7.0 grams of the oleic acid-palmitic acid-oleic acid triglyceride per L of reconstituted, ready-to-use nutritional formula.

12. The reconstituted, ready-to-use nutritional formula of claim 1, wherein the reconstituted, ready-to-use nutritional formula comprises approximately 0.00006 grams to approximately 0.021 grams of lutein per L of reconstituted, ready-to-use nutritional formula.

13. The reconstituted, ready-to-use nutritional formula of claim 1, wherein the reconstituted, ready-to-use nutritional formula comprises approximately 0.05 grams to approximately 0.09 grams of docosahexanoic acid per L of reconstituted, ready-to-use nutritional formula.

14. The reconstituted, ready-to-use nutritional formula of claim 1, wherein the reconstituted, ready-to-use nutritional formula comprises approximately 0.1 grams to approximately 0.50 grams of arachidonic acid per L of reconstituted, ready-to-use nutritional formula.

15. The reconstituted, ready-to-use nutritional formula of claim 1, wherein the reconstituted, ready-to-use nutritional formula comprises approximately 2.0 grams to approximately 4.1 grams of galactooligosaccharides per L of reconstituted, ready-to-use nutritional formula.

16. The reconstituted, ready-to-use nutritional formula of claim 1, wherein the reconstituted, ready-to-use nutritional formula comprises approximately 0.2 grams to approximately 0.4 grams of fructooligosaccharides per L of reconstituted, ready-to-use nutritional formula.

17. The reconstituted, ready-to-use nutritional formula of claim 1, wherein the reconstituted, ready-to-use nutritional formula comprises approximately 2.2 grams to approximately 4.5 grams of prebiotics per L of reconstituted, ready-to-use nutritional formula, wherein the prebiotics comprise galactooligosaccharides, fructooligosaccharides, or a combination thereof.

18. The reconstituted, ready-to-use nutritional formula of claim 1 wherein the reconstituted, ready-to-use nutritional formula comprises approximately 65 grams to approximately 80 grams of lactose per L of reconstituted, ready-to-use nutritional formula.

19. The reconstituted, ready-to-use nutritional formula of claim 2, wherein the reconstituted, ready-to-use nutritional formula comprises approximately 5.3 grams to approximately 6.3 grams of linoleic acid per L of reconstituted, ready-to-use nutritional formula.

20. A dehydrated powder form of a nutritional formula comprising:

a) approximately 0.18 grams to approximately 3.7 grams of alpha-lactalbumin enriched whey protein concentrate per 100 grams of the dehydrated powder form of the nutritional formula, wherein the dehydrated powder form of the nutritional formula comprises at least 30% alpha-lactalbumin by weight of the alpha-lactalbumin enriched whey protein concentrate;

b) approximately 0.015 grams to approximately 0.74 grams of lactoferrin per 100 grams of the dehydrated powder form of nutritional formula;

c) approximately 0.74 grams to approximately 10.4 grams of oleic acid-palmitic acid-oleic acid triglyceride (OPO triglyceride) per 100 grams of the dehydrated powder form of the nutritional formula, wherein palmitic acid is at the SN-2 position of the glycerol backbone of the OPO triglyceride;

d) approximately 26 grams to approximately 59 grams of lactose per 100 grams of the dehydrated powder form of the nutritional formula;

e) approximately 44 micrograms to approximately 0.037 grams of lutein per 100 grams of the dehydrated powder form of the nutritional formula;

f) docosahexanoic acid;

g) approximately 0.074 grams to approximately 0.74 grams of arachidonic acid per 100 grams of the dehydrated powder form of the nutritional formula;

h) approximately 1.5 grams to approximately 3.7 grams of galactooligosaccharides per 100 grams of the dehydrated powder form of the nutritional formula; and i) approximately 0.074 grams to approximately 0.37 grams of fructooligosaccharides per 100 grams of the dehydrated powder form of the nutritional formula;

wherein the dehydrated powder form of the nutritional formula does not comprise polydextrose.

21. The reconstituted, ready-to-use nutritional formula of claim 1 comprising the following weight ranges, in grams per liter (g/L) of reconstituted, ready-to-use nutritional formula:

a) approximately 3 grams to approximately 10 grams whey protein concentrate that is not alpha-lactalbumin enriched, per L of the reconstituted, ready-to-use nutritional formula;

b) approximately 2.5 grams to approximately 3.0 grams of alpha-lactalbumin enriched whey protein concentrate per L of the reconstituted, ready-to-use nutritional formula;

c) approximately 20.0 grams to approximately 30.0 grams of demineralized whey per L of the reconstituted, ready-to-use nutritional formula;

d) approximately 16.5 grams to approximately 18.5 grams of skimmed milk powder per L of the reconstituted, ready-to-use nutritional formula;

e) approximately 0.02 grams to approximately 0.17 grams of lactoferrin per L of the reconstituted, ready-to-use nutritional formula;

f) approximately 30.0 grams to approximately 42.0 grams of a vegetable oil blend comprising the oleic acid-palmitic acid-oleic acid triglyceride; in which approximately 3.0 grams to approximately 7.0 grams of the vegetable oil blend is oleic acid-palmitic acid-oleic acid triglyceride per L of the reconstituted, ready-to-use nutritional formula;

g) approximately 65 grams to approximately 80 grams of lactose per L of the reconstituted, ready-to-use nutritional formula;

h) approximately 0.00006 grams to approximately 0.025 grams of lutein per L of the reconstituted, ready-to-use nutritional formula;

i) approximately 0.05 grams to approximately 0.09 grams of docosahexanoic acid per L of the reconstituted, ready-to-use nutritional formula;

j) approximately 0.1 grams to approximately 0.5 grams of arachidonic acid per L of the reconstituted, ready-to-use nutritional formula;

k) approximately 5 grams to approximately 6.2 grams linoleic acid per L of the reconstituted, ready-to-use nutritional formula;

l) approximately 0.25 grams to approximately 0.6 grams alpha-linolenic acid per L of the reconstituted, ready-to-use nutritional formula;

m) approximately 2.0 grams to approximately 5.0 grams of galactooligosaccharides per L of the reconstituted, ready-to-use nutritional formula;

n) approximately 0.10 grams to approximately 0.50 grams of fructooligosaccharides per L of the reconstituted, ready-to-use nutritional formula;

o) approximately 0.05 grams to approximately 0.15 grams of Vitamin C per L of the reconstituted, ready-to-use nutritional formula; approximately 0.001 grams to approximately 0.05 grams of Vitamin E per L of the reconstituted, ready-to-use nutritional formula; approximately 0.01 grams to approximately 0.05 grams of inositol per L of the reconstituted, ready-to-use nutritional formula; approximately 0.0005 grams to approximately 0.02 grams of Vitamin A per L of the reconstituted, ready-to-use nutritional formula approximately 0.005 grams to approximately 0.009 grams of niacin per L of the reconstituted, ready-to-use nutritional formula; approximately 0.00001 grams to approximately 0.006 grams of Vitamin D3 per L of the reconstituted, ready-to-use nutritional formula; approximately 0.001 grams to approximately 0.005 grams of pantothenic acid per L of the reconstituted, ready-to-use nutritional formula; approximately 0.0005 grams to approximately 0.0015 grams of Vitamin K1 per L of the reconstituted, ready-to-use nutritional formula; approximately 0.0005 grams to approximately 0.0015 grams of Vitamin B1 per L of the reconstituted, ready-to-use nutritional formula; approximately 0.00001 grams to approximately 0.001 grams of Vitamin B2 per L of the reconstituted, ready-to-use nutritional formula; approximately 0.0001 grams to approximately 0.0008 grams of Vitamin B6 per L of the reconstituted, ready-to-use nutritional formula; approximately 0.0001 grams to approximately 0.002 grams of folic acid per L of the reconstituted, ready-to-use nutritional formula; approximately 0.00001 grams to approximately 0.004 grams of biotin per L of the reconstituted, ready-to-use nutritional formula; and approximately 0.000001 grams to approximately 0.0005 grams of Vitamin B12 per L of the reconstituted, ready-to-use nutritional formula;

p) approximately 0.5 grams to approximately 0.8 grams of dicalcium phosphate per L of the reconstituted, ready-to-use nutritional formula; approximately 0.3 grams to approximately 0.8 grams of calcium carbonate per L of the reconstituted, ready-to-use nutritional formula; approximately 0.3 grams to approximately 0.5 grams of potassium chloride per L of the reconstituted, ready-to-use nutritional formula; approximately 0.4 grams to approximately 0.7 grams of tripotassium citrate monohydrate per L of the reconstituted, ready-to-use nutritional formula; approximately 0.3 grams to approximately 0.5 grams of sodium citrate per L of the reconstituted, ready-to-use nutritional formula; approximately 0.2 grams to approximately 0.5 grams of trisodium citrate dihydrate per L of the reconstituted, ready-to-use nutritional formula; approximately 0.002 grams to approximately 0.006 grams of dimagnesium phosphate per L of the reconstituted, ready-to-use nutritional formula; approximately 0.00002 grams to approximately 0.00005 grams of sodium selenite per L of the reconstituted, ready-to-use nutritional formula; approximately 0.02 grams to approximately 0.06 grams of iron (II) sulfate per L of the reconstituted, ready-to-use nutritional formula; approximately 0.01 grams to approximately 0.03 grams of zinc sulfate per L of the reconstituted, ready-to-use nutritional formula; approximately 0.001 grams to approximately 0.004 grams of copper sulfate per L of the reconstituted, ready-to-use nutritional formula; and approximately 0.001 grams to approximately 0.0045 grams of manganese (II) sulfate per L of the reconstituted, ready-to-use nutritional formula;

q) approximately 0.05 grams to approximately 0.1 grams of adenosine 5'-monophosphate per L of the reconstituted, ready-to-use nutritional formula; approximately 0.01 grams to approximately 0.03 grams of cytidine 5'-monophosphate per L of the reconstituted, ready-to-use nutritional formula; approximately 0.001 grams to approximately 0.006 grams of guanosine 5'-monophosphate per L of the reconstituted, ready-to-use nutritional formula; and approximately 0.01 grams to approximately 0.03 grams of uridine 5'-monophosphate per L of the reconstituted, ready-to-use nutritional formula;

r) approximately 0.1 grams to approximately 0.5 grams of L-choline bitartrate per L of the reconstituted, ready-to-use nutritional formula; approximately 0.005 grams to approximately 0.03 grams of L-carnitine per L of the reconstituted, ready-to-use nutritional formula;

s) approximately 0.0001 grams to approximately 0.0007 grams of beta-carotene per L of the reconstituted, ready-to-use nutritional formula; approximately 0.03 grams to approximately 0.07 grams of taurine per L of the reconstituted, ready-to-use nutritional formula; and t) approximately 0.3 grams to approximately 0.5 grams of soya lecithin per L of the reconstituted, ready-to-use nutritional formula.

22. A method of providing nutrition to a subject, wherein the method comprises:
   administering the reconstituted, ready-to-use nutritional formula of claim 1 to the subject.

23. A method of providing nutrition to a subject, wherein the method comprises:
   i. reconstituting the dehydrated powder form of the nutritional formula of claim 20 with water to form a reconstituted, ready-to-use nutritional formula; and
   ii. administering the reconstituted, ready-to-use nutritional formula to the subject.

24. A kit comprising:
   i. one or more packages of the dehydrated powder form of the nutritional formula of claim 20; and
   ii. instructions for reconstituting the nutritional formula by adding water and administering the nutritional formula to a subject.

25. The reconstituted, ready-to-use nutritional formula of claim 1, comprising:
   a) approximately 2.7 grams of alpha-lactalbumin enriched whey protein concentrate per L of reconstituted, ready-to-use nutritional formula;
   b) approximately 63 milligrams of lactoferrin per L of reconstituted, ready-to-use nutritional formula;
   c) approximately 4.8 grams of oleic acid-palmitic acid-oleic acid triglyceride (OPO triglyceride) per L of reconstituted, ready-to-use nutritional formula;
   d) approximately 66 grams of lactose per L of the reconstituted, ready-to-use nutritional formula;
   e) approximately 70 micrograms of lutein per L of the reconstituted, ready-to-use nutritional formula;
   f) approximately 68 milligrams of docosahexanoic acid per L of the reconstituted, ready-to-use nutritional formula;
   g) approximately 135 milligrams of arachidonic acid per L of the reconstituted, ready-to-use nutritional formula;
   h) approximately 2.1 grams of galactooligosaccharides per L of the reconstituted, ready-to-use nutritional formula; and
   i) approximately 211 milligrams of fructooligosaccharides per L of the reconstituted, ready-to-use nutritional formula.

26. The dehydrated powder form of the nutritional formula of claim 20, comprising:
   a) approximately 2.0 grams of alpha-lactalbumin enriched whey protein concentrate per 100 grams of the dehydrated powder form of the nutritional formula;
   b) approximately 47 milligrams of lactoferrin per 100 grams of the dehydrated powder form of nutritional formula;
   c) approximately 3.6 grams of oleic acid-palmitic acid-oleic acid triglyceride (OPO triglyceride) per 100 grams of the dehydrated powder form of the nutritional formula;
   d) approximately 49 grams of lactose per 100 grams of the dehydrated powder form of the nutritional formula;
   e) approximately 52 micrograms of lutein per 100 grams of the dehydrated powder form of the nutritional formula;
   f) approximately 50 milligrams of docosahexanoic acid per 100 grams of the dehydrated powder form of the nutritional formula;
   g) approximately 100 milligrams of arachidonic acid per 100 grams of the dehydrated powder form of the nutritional formula;
   h) approximately 1.56 grams of galactooligosaccharides per 100 grams of the dehydrated powder form of the nutritional formula; and
   i) approximately 156 milligrams of fructooligosaccharides per 100 grams of the dehydrated powder form of the nutritional formula.

27. The reconstituted, ready-to-use nutritional formula of claim 1, wherein the reconstituted, ready-to-use nutritional formula comprises approximately 0.001 grams to approximately 0.12 grams of docosahexanoic acid per L of reconstituted, ready-to-use nutritional formula.

28. The reconstituted, ready-to-use nutritional formula of claim 21 comprising approximately 0.00001 grams to approximately 0.00005 grams of maltodextrin per L of the reconstituted, ready-to-use nutritional formula.

* * * * *

UNITED STATES PATENT AND TRADEMARK OFFICE
CERTIFICATE OF CORRECTION

PATENT NO. : 11,606,966 B2
APPLICATION NO. : 17/347977
DATED : March 21, 2023
INVENTOR(S) : James W. McGrath, Jr. et al.

It is certified that error appears in the above-identified patent and that said Letters Patent is hereby corrected as shown below:

In the Claims

In Claim 8, at Column 165, Lines 43-45:
"5 '-monophosphate, cytidine 5'-monophosphate, guanosine 5 '-monophosphate, uridine 5'-monophosphate, or a combination thereof."

Is replaced with:
--5'-monophosphate, cytidine 5'-monophosphate, guanosine 5'-monophosphate, uridine 5'-monophosphate, or a combination thereof.--.

In Claim 21, at Column 168, Lines 3-4:
"ready-to-use nutritional formula approximately"

Is replaced with:
--ready-to-use nutritional formula; approximately--.

Signed and Sealed this
Fifth Day of September, 2023

Katherine Kelly Vidal
*Director of the United States Patent and Trademark Office*